(12) United States Patent
Iliopoulos et al.

(10) Patent No.: US 10,881,656 B2
(45) Date of Patent: *Jan. 5, 2021

(54) HIF INHIBITORS AND USE THEREOF

(71) Applicant: The General Hospital Corporation, Boston, MA (US)

(72) Inventors: Othon Iliopoulos, Cambridge, MA (US); Michael Albert Zimmer, Arlington, MA (US)

(73) Assignee: THE GENERAL HOSPITAL CORPORATION, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/431,967

(22) Filed: Feb. 14, 2017

(65) Prior Publication Data
US 2017/0157111 A1 Jun. 8, 2017

Related U.S. Application Data

(63) Continuation of application No. 14/186,294, filed on Feb. 21, 2014, which is a continuation of application No. 13/139,058, filed as application No. PCT/US2009/067555 on Dec. 10, 2009, now Pat. No. 8,691,866.

(60) Provisional application No. 61/121,350, filed on Dec. 10, 2008.

(51) Int. Cl.

| | |
|---|---|
| *A61K 31/381* | (2006.01) |
| *A61K 31/38* | (2006.01) |
| *A61K 31/473* | (2006.01) |
| *A61K 31/138* | (2006.01) |
| *A61K 31/166* | (2006.01) |
| *A61K 31/167* | (2006.01) |
| *A61K 31/366* | (2006.01) |
| *A61K 31/382* | (2006.01) |
| *A61K 31/5575* | (2006.01) |
| *A61K 45/06* | (2006.01) |
| *C07C 225/16* | (2006.01) |
| *C07C 235/38* | (2006.01) |
| *C07C 237/46* | (2006.01) |
| *C07D 219/14* | (2006.01) |
| *C07D 309/38* | (2006.01) |
| *C07D 333/22* | (2006.01) |
| *C07D 333/38* | (2006.01) |
| *C07D 335/02* | (2006.01) |
| *A61K 31/137* | (2006.01) |

(52) U.S. Cl.
CPC .......... *A61K 31/473* (2013.01); *A61K 31/137* (2013.01); *A61K 31/138* (2013.01); *A61K 31/166* (2013.01); *A61K 31/167* (2013.01); *A61K 31/366* (2013.01); *A61K 31/38* (2013.01); *A61K 31/381* (2013.01); *A61K 31/382* (2013.01); *A61K 31/5575* (2013.01); *A61K 45/06* (2013.01); *C07C 225/16* (2013.01); *C07C 235/38* (2013.01); *C07C 237/46* (2013.01); *C07D 219/14* (2013.01); *C07D 309/38* (2013.01); *C07D 333/22* (2013.01); *C07D 333/38* (2013.01); *C07D 335/02* (2013.01)

(58) Field of Classification Search
None
See application file for complete search history.

(56) References Cited

U.S. PATENT DOCUMENTS

| | | | | |
|---|---|---|---|---|
| 3,076,817 | A * | 2/1963 | Fiesselmann | C07D 333/44 549/68 |
| 4,176,198 | A | 11/1979 | Nuss | |
| 4,187,317 | A | 2/1980 | Nuss | |
| 4,198,349 | A | 4/1980 | Nuss | |
| 4,200,684 | A | 4/1980 | Bro | |
| 4,230,727 | A | 10/1980 | Nuss | |
| 4,235,929 | A | 11/1980 | Nuss | |
| 4,400,380 | A | 8/1983 | Ritter | |
| 5,986,965 | A | 11/1999 | Lee | |
| 2002/0002152 | A1* | 1/2002 | Craig | C07C 243/34 514/159 |
| 2005/0272644 | A1 | 12/2005 | Chung | |
| 2007/0190022 | A1 | 8/2007 | Bacooulos | |
| 2008/0226622 | A1 | 9/2008 | Van Meir | |

FOREIGN PATENT DOCUMENTS

| | | |
|---|---|---|
| EP | 0609032 A | 8/1994 |
| JP | 2006-335666 A | 12/2006 |
| WO | 1991/011994 A1 | 8/1991 |
| WO | 1993/014081 A1 | 7/1993 |
| WO | 1993/016036 A1 | 8/1993 |
| WO | 1995/000507 A1 | 1/1995 |
| WO | 1996/022989 A1 | 8/1996 |
| WO | 1996/032383 A1 | 10/1996 |
| WO | 1998/009960 A1 | 3/1998 |
| WO | 1999/024420 A1 | 5/1999 |

(Continued)

OTHER PUBLICATIONS

Zimmer et al., "Small-molecule inhibitors of HIF-2a translation link its 5'UTR iron-responsive element to oxygen sensing", Mol Cell 32(6) 838-848 (2008).

Zundel et al., "Loss of PTEN facilitates HIF-1-mediated gene expression", Genes Dev 14(4) 391-396 (2000).

Arsham et al., "A novel hypoxia-inducible factor-independent hypoxic response regulating mammalian target of rapamycin and its targets", J Biol Chem 278(32) 29655-29660 (2003).

(Continued)

*Primary Examiner* — Nissa M Westerberg
(74) *Attorney, Agent, or Firm* — Nixon Peabody LLP; David S. Resnick; Francis De Rege

(57) ABSTRACT

The present invention is directed to HIF inhibitors and methods of preventing cell proliferation, reducing inflammation, and treating an angiogenic disease or disorders.

6 Claims, 49 Drawing Sheets

Specification includes a Sequence Listing.

(56) References Cited

FOREIGN PATENT DOCUMENTS

| WO | 1999/028464 A2 | 6/1999 | |
|---|---|---|---|
| WO | 2000/023426 A1 | 4/2000 | |
| WO | WO-0047194 A2 * | 8/2000 | ........... A61K 31/427 |
| WO | 2001/044473 A2 | 6/2001 | |
| WO | 2002/055017 A2 | 7/2002 | |
| WO | 2003/010159 A1 | 2/2003 | |
| WO | 2003/028663 A2 | 4/2003 | |
| WO | 2003/035842 A2 | 5/2003 | |
| WO | 2006/070023 A2 | 7/2006 | |
| WO | WO-2006116713 A1 * | 11/2006 | ........... C07D 401/12 |
| WO | 2009/043093 A1 | 4/2009 | |

OTHER PUBLICATIONS

Bert et al., "Assessing IRES activity in the HIF-1alpha and other cellular 5' UTRs", RNA 12(6) 1074-1083 (2006).

Blais et al., "Activating transcription factor 4 is translationally regulated by hypoxic stress", Mol Cell Biol 24(17) 7469-7482 (2004).

Brody et al., "Impaired pentose phosphate shunt and decreased glycolytic activity in lymphocytes of chronic lymphocytic leukemia. Metabolic pathway", Blood 34(4) 421-429 (1969).

Brugaroles et al., "Regulation of mTOR function in response to hypoxia by REDD1 and the TSC1/TSC2 tumor suppressor complex", Genes Dev 18(23) 2893-2904 (2004).

Brugaroles et al., "TSC2 regulates VEGF through mTOR-dependent and-independent pathways", Cancer Cell 4 (2) 147-158 (2003).

Bruick et al., "A conserved family of prolyl-4-hydroxylases that modify HIF", Science 294(5545) 1337-1340 (2001).

Cramer et al., "HIF-1alpha is essential for myeloid cell-mediated inflammation", Cell 112(5) 645-657 (2003).

Epstein et al., "C. elegans EGL-9 and mammalian homologs define a family of dioxygenases that regulate HIF by prolyl hydroxylation", Cell 107(1) 43-54 (2001).

Gordan et al., "Hypoxia-inducible factors: central regulators of the tumor phenotype", Curr Opin Genet Dev 17(1) 71-77 (2007).

Hanahan et al., "Patterns and emerging mechanisms of the angiogenic switch during tumorigenesis", Cell 86(3) 353-364 (1996).

Hudson et al., "Regulation of hypoxia-inducible factor 1alpha expression and function by the mammalian target of rapamycin", Mol Cell Biol 22(20) 7004-7014 (2002).

De Young et al., "Hypoxia regulates TSC1/2-mTOR signaling and tumor suppression through REDD1-mediated 14-3-3 shuttling" Genes Dev 22(2) 239-251 (2008).

Ivan et al., "HIFalpha targeted for VHL-mediated destruction by proline hydroxylation: implications for O2 sensing", Science 292(5516) 464-468 (2001).

Jaakkola et al., "Targeting of HIF-alpha to the von Hippel-Lindau ubiquitylation complex by O2-regulated prolyl hydroxylation", Science 292(5516) 468-472 (2001).

Ke et al., "Loops and bulge/loops in iron-responsive element isoforms influence iron regulatory protein binding. Fine-tuning of mRNA regulation?", J Biol Chem 273(37) 23637-23640 (1998).

Keen et al., "A novel histone deacetylase inhibitor, scriptaid, enhances expression of functional estrogen receptor alpha (ER) in ER negative human breast cancer cells in combination with 5-aza 2'-deoxycytidine", Breast Cancer Res Treat 81(3) 177-186 (2003).

Kim et al., "Role of VHL gene mutation in human cancer", J Clin Oncol 22(24) 4991-5004 (2004).

King et al., "Succinate dehydrogenase and fumarate hydratase: linking mitochondrial dysfunction and cancer", Oncogene 25(34) 4675-4682 (2006).

Kondo et al., "Inhibition of HIF is necessary for tumor suppression by the von Hippel-Lindau protein", Cancer Cell 1 (3) 237-246 (2002).

Kondo et al., "Inhibition of HIF2alpha is sufficient to suppress pVHL-defective tumor growth", PLoS Biol 1(3) E83 (2003).

Lando et al., "Asparagine hydroxylation of the HIF transactivation domain a hypoxic switch", Science 295(5556) 858-861 (2002).

Lando et al., "FIH-1 is an asparaginyl hydroxylase enzyme that regulates the transcriptional activity of hypoxia-inducible factor", Genes Dev 16(12) 1466-1471 (2002).

Lang et al., "Hypoxia-inducible factor-1alpha mRNA contains an internal ribosome entry site that allows efficient translation during normoxia and hypoxia", Mol Biol Cell 13(5) 1792-1801 (2002).

Laughner et al., "HER2 (neu) signaling increases the rate of hypoxia-inducible factor 1alpha (HIF-1alpha) synthesis: novel mechanism for HIF-1-mediated vascular endothelial growth factor", Mol Cell Biol 21(12) 3995-4004 (2001).

Liu et al., "Hypoxia-induced energy stress regulates mRNA translation and cell growth", Mol Cell 21(4) 521-531 (2006).

Liu et al., "Regulation of transcription and translation by hypoxia", Cancer Biol Ther 3(6) 492-497 (2004).

Mahon et al., "FIH-1: a novel protein that interacts with HIF-1alpha and VHL to mediate repression of HIF-1 transcriptional activity", Genes Dev 15(20) 2675-2686 (2001).

Majumder et al., "mTOR inhibition reverses Akt-dependent prostate intraepithelial neoplasia through regulation of apoptotic and HIF-1-dependent pathways", Nat Med 10(6) 594-601 (2004).

Maranchie et al., "The contribution of VHL substrate binding and HIF1-alpha to the phenotype of VHL loss in renal cell carcinoma", Cancer Cell 1(3) 247-255 (2002).

Maxwell et al., "Activation of the HIF pathway in cancer", Curr Opin Genet Dev 11(3) 293-299 (2001).

Maxwell et al., "The tumour suppressor protein VHL targets hypoxia-inducible factors for oxygen-dependent proteolysis", Nature 399(6733) 271-275 (1999).

Mootha et al., "PGC-1alpha-responsive genes involved in oxidative phosphorylation are coordinately downregulated in human diabetes", Nat Genet 34(3) 267-273 (2003).

Ohh et al., "Ubiquitination of hypoxia-inducible factor requires direct binding to the beta-domain of the von Hippel-Lindau protein", Nat Cell Biol 2(7) 423-427 (2000).

Punnonen et al., "Antioxidant enzyme activities and oxidative stress in human breast cancer", J Cancer Res Clin Oncol 120(6) 374-377 (1994).

Raval et al., "Contrasting properties of hypoxia-inducible factor 1 (HIF-1) and HIF-2 in von Hippel-Lindau-associated renal cell carcinoma", Mol Cell Biol 25(13) 5675-5685 (2005).

Rouault et al., "The role of iron regulatory proteins in mammalian iron homeostasis and disease", Nat Chem Biol 2 (8) 406-414 (2006).

Sahasrabudhe et al., "Inhibition of tumour growth by interference of hexose mono-phosphate pathway. Synthesis and anticancer properties of thiophene 2 : 5 dicarboxylic acid", Br J Cancer 14: 547-554 (1960).

Sambrook et al., "Molecular Cloning: A Laboratory Manual", University of Texas South Western Medical Center, No. Ed 2 (1989).

Sanchez et al., "Iron-regulatory proteins limit hypoxia-inducible factor-2alpha expression in iron deficiency", Nat Struct Mol Biol 14(5) 420-426 (2007).

Schepens et al., "The polypyrimidine tract-binding protein stimulates HIF-1alpha IRES-mediated translation during hypoxia", Nucleic Acids Res 33(21) 6884-6894 (2005).

Schofield et al., "Oxygen sensing by HIF hydroxylases", Nat Rev Mol Cell Biol 5(5) 343-354 (2004).

Semenza et al., "HIF-1: mediator of physiological and pathophysiological responses to hypoxia", J Appl Physiol (1985) 88(4) 1474-1480 (2000).

Spicher et al., "Highly conserved RNA sequences that are sensors of environmental stress", Mol Cell Biol 18(21) 7371-7382 (1998).

Takai et al., "A novel histone deacetylase inhibitor, Scriptaid, induces growth inhibition, cell cycle arrest and apoptosis in human endometrial cancer and ovarian cancer cells", Int J Mol Med 17(2) 323-329 (2006).

Thomas et al., "Identification of mRNAs that continue to associate with polysomes during hypoxia", RNA 13(7) 1116-1131 (2007).

Wang et al., "Excess capacity of the iron regulatory protein system", J Biol Chem 282(34) 24650-24659 (2007).

(56) References Cited

OTHER PUBLICATIONS

Wouters et al., "Control of the hypoxic response through regulation of mRNA translation", Semin Cell Dev Biol 16(4-5) 487-501 (2005).

Yang et al., "A novel function of the MA-3 domains in transformation and translation suppressor Pdcd4 is essential for its binding to eukaryotic translation initiation factor 4A", Mol Cell Biol 24(9) 3894-3906 (2004).

Zimmer et al., "Inhibition of hypoxia-inducible factor is sufficient for growth suppression of VHL-/- tumors", Mol Cancer Res 2(2) 89-95 (2004).

\* cited by examiner

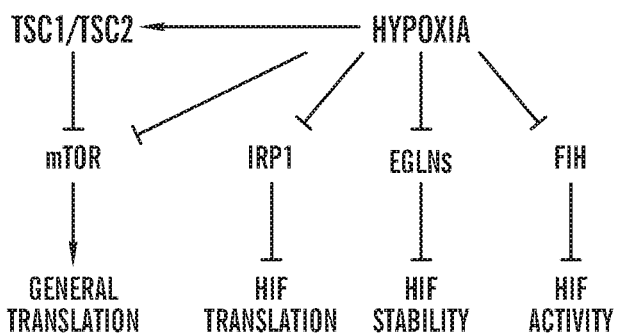
FIG. 7F
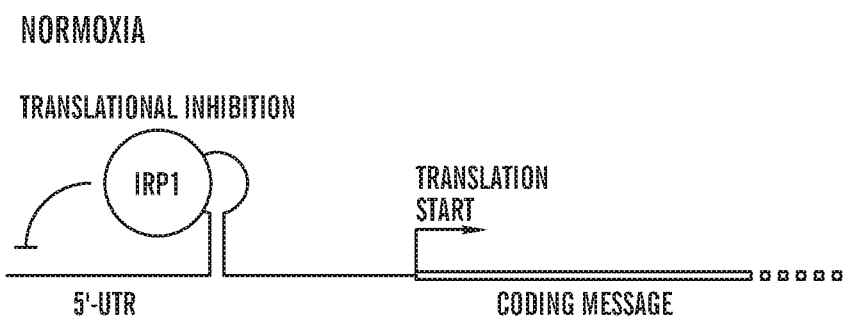
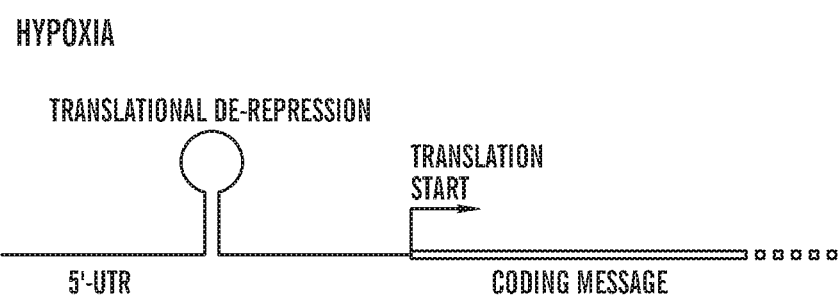
FIG. 7G

COMPOUND 40: ↑61 ↓60 GENES

| RANK | PERTURBAGEN [id] | DOSE | CELL | SCORE |
|---|---|---|---|---|
| 504 | DEFEROXAMINE [3936] | 6 μM | MCF7 | 0.497 |
| 1704 | DEFEROXAMINE [460] | 100 μM | PC3 | 0.292 |
| 2969 | DEFEROXAMINE [485] | 100 μM | MCF7 | 0 |
| 3701 | DEFEROXAMINE [573] | 100 μM | MCF7 | 0 |
| 3878 | DEFEROXAMINE [3417] | 6 μM | MCF7 | 0 |
| 4247 | DEFEROXAMINE [3842] | 6 μM | MCF7 | 0 |
| 4387 | DEFEROXAMINE [4317] | 6 μM | PC3 | 0 |
| 4691 | DEFEROXAMINE [3760] | 6 μM | PC3 | 0 |

*FIG. 13A*

COMPOUND 41: ↑70 ↓53 GENES

| RANK | PERTURBAGEN [id] | DOSE | CELL | SCORE |
|---|---|---|---|---|
| 2368 | DEFEROXAMINE [4317] | 6 μM | PC3 | 0 |
| 4202 | DEFEROXAMINE [3936] | 6 μM | MCF7 | 0 |
| 4210 | DEFEROXAMINE [3842] | 6 μM | MCF7 | 0 |
| 4384 | DEFEROXAMINE [3760] | 6 μM | PC3 | 0 |
| 5490 | DEFEROXAMINE [573] | 100 μM | MCF7 | -0.590 |
| 5957 | DEFEROXAMINE [460] | 100 μM | PC3 | -0.735 |
| 5962 | DEFEROXAMINE [485] | 100 μM | MCF7 | -0.736 |
| 5963 | DEFEROXAMINE [3417] | 6 μM | MCF7 | -0.736 |

*FIG. 13B*

COMPOUND 76: ↑70 ↓65 GENES

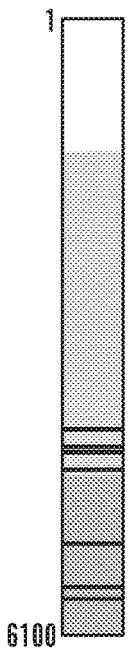

| RANK | PERTURBAGEN [id]   | DOSE   | CELL | SCORE  |
|------|--------------------|--------|------|--------|
| 4063 | DEFEROXAMINE [3936]| 6 μM   | MCF7 | 0      |
| 4246 | DEFEROXAMINE [3760]| 6 μM   | PC3  | 0      |
| 4301 | DEFEROXAMINE [4317]| 6 μM   | PC3  | 0      |
| 4459 | DEFEROXAMINE [3842]| 6 μM   | MCF7 | 0      |
| 5197 | DEFEROXAMINE [573] | 100 μM | MCF7 | -0.488 |
| 5204 | DEFEROXAMINE [485] | 100 μM | MCF7 | -0.489 |
| 5616 | DEFEROXAMINE [460] | 100 μM | PC3  | -0.580 |
| 5755 | DEFEROXAMINE [3417]| 6 μM   | MCF7 | -0.612 |

*FIG. 13C*

COMPOUND 77: ↑69 ↓67 GENES

| RANK | PERTURBAGEN [id]   | DOSE   | CELL | SCORE  |
|------|--------------------|--------|------|--------|
| 1069 | DEFEROXAMINE [3417]| 6 μM   | MCF7 | 0.308  |
| 2425 | DEFEROXAMINE [573] | 100 μM | MCF7 | 0      |
| 3477 | DEFEROXAMINE [3936]| 6 μM   | MCF7 | 0      |
| 3684 | DEFEROXAMINE [3842]| 6 μM   | MCF7 | 0      |
| 4328 | DEFEROXAMINE [4317]| 6 μM   | PC3  | 0      |
| 5593 | DEFEROXAMINE [485] | 100 μM | MCF7 | -0.550 |
| 5656 | DEFEROXAMINE [3760]| 6 μM   | PC3  | -0.568 |
| 5661 | DEFEROXAMINE [460] | 100 μM | PC3  | -0.572 |

*FIG. 13D*

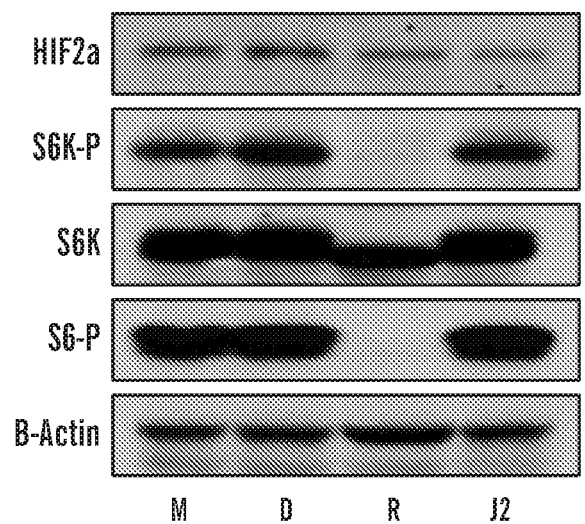
*FIG. 16C*
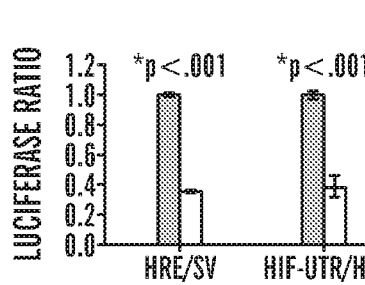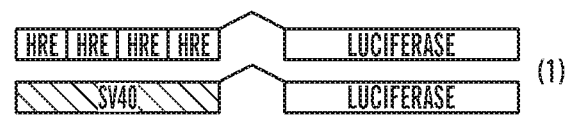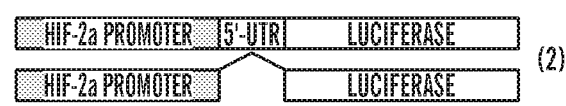
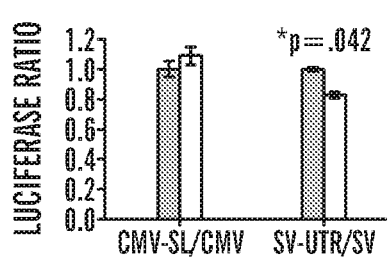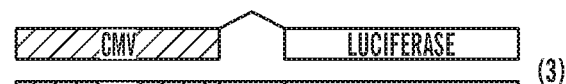
*FIG. 16D*

PHOSPHOMIMETIC S138E MUTANT FAILS TO DISSOCIATE FROM HIF-2a IRE IN HYPOXIA

HIF INHIBITORS AND USE THEREOF

RELATED APPLICATIONS

This application is a continuation application of U.S. Ser. No. 14/186,294 filed Feb. 21, 2014, which is a continuation application of U.S. Ser. No. 13/139,058, filed Aug. 24, 2011, now U.S. Pat. No. 8,691,866, which is a 35 U.S.C. § 371 National Phase Entry Application of International Application No. PCT/US2009/067555 filed Dec. 10, 2009, which designates the U.S., and which claims benefit under 35 U.S.C. § 119(e) to U.S. Provisional Application 61/121,350 filed Dec. 10, 2008, the contents of which are herein incorporated by reference in their entirety.

GOVERNMENT SUPPORT

This invention was made in part with U.S. Government support from the National Institutes of Health grant 5R01CA104574 and the National Cancer Institute's Initiative for Chemical Genetics N01-CO-12400. The U.S. Government has certain rights in this application.

SEQUENCE LISTING

The instant application contains a Sequence Listing which has been submitted in ASCII format via EFS-Web and is hereby incorporated by reference in its entirety. Said ASCII copy, created on Feb. 21, 2014, is named Sequence_Listing.txt and is 6,491 bytes in size.

FIELD OF THE INVENTION

This invention relates to HIF inhibitors and methods of preventing cell proliferation, reducing inflammation, and treating an angiogenic disease or disorders.

BACKGROUND OF THE INVENTION

Cells activate specific signaling pathways in order to transiently adapt to and eventually correct hypoxic stress (Gordan and Simon, 2007; Liu and Simon, 2004). Solid tumors depend on neovascularization for maintained growth (Hanahan and Folkman, 1996) and tumor cells secrete a number of growth and angiogenic factors that stimulate endothelial cell proliferation and, ultimately, the formation of new tumor-associated blood vessels. The Hypoxia Inducible transcription Factor (HIF) is a central regulator of the cellular response to hypoxia (Semenza, 2000) and secreted growth and angiogenic factors, including vascular endothelial growth factor (VEGF), platelet derived growth factor (PDFG), transforming growth factor (TGFa) and angiopoetins are bona fide HIF target genes (Maxwell et al., 2001).

HIF is a heterodimeric transcription factor consisting of hypoxia-regulated (HIF-a) and a constitutively expressed (HIF-1b) subunits (Semenza, 2000). There are two transactivating HIF-a isoforms, HIF-1a and HIF-2a, whose cellular activity is tightly regulated by oxygen (Gordan and Simon, 2007; Raval et al., 2005). In well-oxygenated cells, the tumor suppressor protein pVHL targets HIF-a for ubiquitination and proteasomal degradation (Maxwell et al., 1999; Ohh et al., 2000). This interaction requires hydroxylation of HIF-a proline by cellular HIF prolylhydroxylases, termed EGLN1, 2 and 3 (Epstein et al., 2001; Ivan et al., 2001; Jaakkola et al., 2001). EGLNs are non-heme, Fe(II) and 2-oxoglurarate dependent dioxygenases (Epstein et al., 2001; Schofield and Ratcliffe, 2004). A decline in intracellular oxygen prevents HIF-a prolyl hydroxylation and disrupts HIF-pVHL interaction. Stabilized HIF-a subunits enter the nucleus, heterodimerize with HIF-1b and bind to DNA sequences termed Hypoxia Response Elements (HREs) to transactivate a large number of hypoxia inducible genes. HIF's transcriptional activity is similarly attenuated by Factor Inhibiting HIF (FIH), a second Fe(II) and 2-oxoglurarate-dependent dioxygenase that hydroxylates a conserved asparagine residue in the transactivation domain of HIF (Bruick and McKnight, 2001; Lando et al., 2002a; Lando et al., 2002b; Mahon et al., 2001). Hypoxia therefore promotes both the stability and transcriptional activity of HIF.

Mutations in cellular proteins that regulate HIF stability and transactivation have been causally linked to cancer development. Inactivation of the tumor suppressor protein pVHL leads to constitutive HIF overexpression, which is both necessary and sufficient for growth of VHL deficient tumors (Kondo et al., 2003; Kondo et al., 2002; Maranchie et al., 2002; Zimmer et al., 2004). Mutations that activate the phosphatidylinositol 3-kinase (PI3K) signaling pathway result in enhanced mTOR activity (Brugarolas et al., 2004; Hudson et al., 2002; Majumder et al., 2004). This likely explains the observation that loss-of-function mutations in PTEN and TSC1/2 genes or Her2/neu overexpression lead to increased HIF expression in normoxic and hypoxic conditions (Brugarolas et al., 2003; Laughner et al., 2001; Zundel et al., 2000).

Part of the adaptive response to the hypoxia in healthy cells is to conserve energy when oxidative phosphorylation is restricted via a global decrease in protein translation (Arsham et al., 2003; Bert et al., 2006; Lang et al., 2002; Liu et al., 2006; Schepens et al., 2005). This is, at least in part, mediated by Reddl, itself a HIF target gene, inhibiting mTOR via the tuberous sclerosis (TSC1/2) complex (DeYoung et al., 2008). However, specific messages that are required to synthesize proteins that allow cells to cope with the hypoxic environment are spared this translational repression (Blais et al., 1994; Liu and Simon, 2004; Spicher et al., 1998; Thomas and Johannes, 2007; Wouters et al., 2005). The mechanisms for selectively supporting translation of certain messages in conditions of hypoxia are under investigation.

The present invention is directed to overcoming these and other deficiencies in the art.

SUMMARY OF THE INVENTION

In one aspect, the invention provides a method of inhibiting HIF-2a activity in a cell comprising: contacting the cell with a HIF inhibitor described herein.

In some embodiments of this and other aspects of the invention described herein, the HIF inhibitor is 3-(2,5-diethoxyphenyl)-1-(2-thienyl)-2-propen-1-one, $N^2$-(4-bromo-3-nitrobenzoyl)leucinamide, 2-bromo-N-(2-methoxyphenyl)propanamide, 6-(1,3-dioxo-1H-benzo[de]isoquinolin-2(3H)-yl-N-hydroxyhexanamide, 15-deoxy-$\Delta^{12,14}$-prostaglandin $J_2$ (PGJ$_2$),

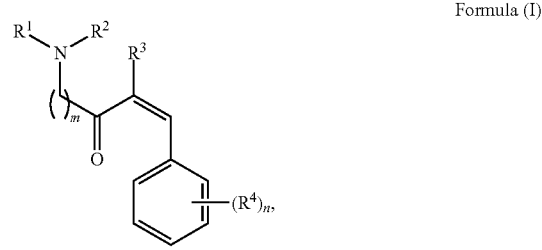

Formula (I)

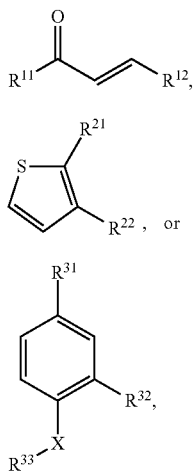

Formula (II)

Formula (III)

Formula (IV)

wherein:

$R^1$ and $R^2$ are each independently H, alkyl, alkenyl, alkynyl, or taken together with the N atom to which they are attached form a 5-8 membered heterocyclyl or heteroaryl, each of which can be optionally substituted;

$R^3$ is H, alkyl, alkenyl, or alkynyl, each of which can be optionally substituted;

$R^4$ is independently for each occurrence halogen, alkyl, alkenyl, alkynyl, alkoxy, $CF_3$, $NO_2$, $N(R^5)_2$, CN, OH, $SR^5$, $SO_2R^5$, or two $R^4$ taken together form an optionally substituted 3,4-methylenedioxy, each of which can be optionally substituted;

$R^5$ is independently for each occurrence H, alkyl, alkenyl, or alkynyl, each of which can be optionally substituted;

m is 1, 2, 3, 4 or 5;

n is 0, 1, 2, or 3;

$R^{11}$ is optionally substituted aryl, optionally substituted heteroaryl, optionally substituted cyclyl or optionally substituted heterocyclyl;

$R^{12}$ is optionally substituted aryl or optionally substituted heteroaryl;

$R^{21}$ is halogen, alkyl, alkenyl, alkynyl, alkoxy, aryl, heteroaryl, cyclyl, heterocyclyl, $CF_3$, $NO_2$, $N(R^{23})_2$, CN, OH, $SR^{23}$, $SO_2R^{23}$, or $C(O)R^{24}$, each of which can be optionally substituted;

$R^{22}$ is alkoxy, halogen, alkyl, alkenyl, alkynyl, alkoxy, aryl, heteroaryl, cyclyl, heterocyclyl, $CF_3$, $NO_2$, $N(R^{25})_2$, CN, OH, $SR^{23}$, or $SO_2R^{23}$, each of which can be optionally substituted;

$R^{23}$ is independently for each occurrence H, alkyl, alkenyl or alkynyl, each of which can be optionally substituted;

$R^{24}$ is alkyl, alkenyl, alkynyl, alkoxy, aryl, heteroaryl, cyclyl or heterocyclyl, each of which can be optionally substituted;

$R^{25}$ is independently for each occurrence alkyl, alkenyl, alkynyl, $N(R^{23})_2$ or $N=R^{26}$, each of which can be optionally substituted;

$R^{26}$ is independently for each occurrence H, alkyl, alkenyl or alkynyl, each of which can be optionally substituted;

X is S, O, or NH;

$R^{31}$ and $R^{32}$ are each independently halogen, alkyl, alkenyl, alkynyl, alkoxy, $CF_3$, $NO_2$, $N(R^{34})_2$, CN, OH, $SR^{34}$, or $SO_2R^{34}$, each of which can be optionally substituted;

$R^{33}$ is alkyl, alkenyl, alkynyl, aryl, heteroaryl, cyclyl, or heterocyclyl, each of which can be optionally substituted;

$R^{34}$ is independently for each occurrence H, alkyl, alkenyl, or alkynyl, each of which can be optionally substituted; and pharmaceutically acceptable salts and combinations thereof.

In some embodiments of this and other aspects described herein, HIF inhibitor is selected from the group consisting of 5-(dimethylamino)-2-methyl-1-phenyl-1-penten-3-one, 4-hydroxy-3-(3-(2-hydroxy-5-methoxyphenyl)acryloyl)-6-methyl-2H-pyran-2-one, methyl 3-{2-[cyano(methylsulfonyl)methyle]hydrazine]thiophene-2-carboxylate, 4-[(2,2-dimethyl-4-oxo-3,4-dihydro-2H-thinn-6-yl)thio]-3-nitrobenzonitrile, $PGJ_2$, and pharmaceutically acceptable salts and combinations thereof.

In another aspect the invention provides methods of preventing cell proliferation. The methods include contacting a cell with a HIF inhibitor described herein.

In yet another aspect the invention provides methods of treating an angiogenic disease or disorder in a subject in need thereof. The methods include administering a HIF inhibitor described herein to the subject.

In yet still another aspect the invention provide methods inhibiting angiogenesis in a mammal having an angiogenic disease. The methods include administering a HIF inhibitor described herein to the subject.

Another aspect of the invention is directed to pharmaceutical compositions for inhibiting angiogenesis comprising a HIF inhibitor described herein.

Yet another aspect of the present invention is directed to articles of manufacture comprising packaging material and a pharmaceutical composition contained within said packaging material, wherein said pharmaceutical composition is capable of treating an angiogenic disorder or disease, wherein said packaging material comprises a label which indicates that said pharmaceutical composition can be used for treating an angiogenic disorder or disease, and wherein said pharmaceutical composition comprises a HIF inhibitor described herein.

Yet another aspect of the present invention is directed to articles of manufacture comprising packaging material and a pharmaceutical composition contained within said packaging material, wherein said pharmaceutical composition is capable of reducing inflammation, wherein said packaging material comprises a label which indicates that said pharmaceutical composition can be used for reducing inflammation, and wherein said pharmaceutical composition comprises a HIF inhibitor described herein.

BRIEF DESCRIPTION OF THE DRAWINGS

FIG. 2A shows the identified compounds 40, 41, 76 and 77 coordinately downregulate HIF target genes. The genes illustrated are the top 50 markers of 786-O derived vector only (P for PRC3) cells relative to matched isogenic VHL-reconstituted (W for WT8) cells, which are also downregulated by the HIF-2a-targeting shRNA (R for pTR) cells relative to an empty vector control (V for pTV) cells. FIG. 2B shows hierarchical clustering of samples and genes reveals similarities between the activities of compounds. Samples were clustered in the space of 800 genes comprised of the 100 genes most powerfully upregulated and the 100 genes most powerfully downregulated in cells treated with compounds, and in PRC3 versus WT8 cells.

FIG. 3A shows that HIF inhibitors 40, 41, 76 and 77 decrease the angiogenic activity of renal carcinoma cell supernatant. HUVEC proliferation after incubation with conditioned tissue culture supernatant from control or compound-treated 786-O cells. Conditioned supernatant from identically treated VHL-reconstituted WT8 (W) and vector-only PRC3 (P) cells were used as positive controls. P-values were determined using a Student's paired t-Test, with a two-tailed distribution. FIG. 3B shows the effect of compounds 40, 41, 76 and 77 on endogenous HIF-2a and Glut-1 protein expression. HIF-2a, Glut-1 and B-Actin expression was analyzed by Western blot. FIG. 3C shows the effect of compounds 40, 41, 76 and 77 on VHL-reconstituted WT8 cells. Western blot for HIF-2a and B-Actin in which WT8 cells were cultured in the presence of compound, plus or minus 24 hours hypoxia. FIG. 3D shows the effect of compounds 40, 41, 76 and 77 on HIF-2a in matched isogenic PRC3 cells. Western blot on PRC3 cells were performed as described above. FIG. 3E shows the effect of compounds 40, 41, 76 and 77 on secreted VEGF and IGFBP3 expression. The concentration of VEGF and IGFBP3, secreted HIF target genes, were determined in tissue culture supernatant from the above cells, as measured by ELISA. FIG. 3F shows that compounds 40, 41, 76 and 77 do not effect HIF-2a mRNA expression. Quantitative RT-PCR was performed on matched 7 86-O derived vector-only (pTV) or HIF-2a-targeting shRNA expressing (pTR), PRC3 or WT8 clones, as well as medium only, DMSO and compound treated 7H4 cells. Data shows relative expression of both the nascent (unspliced, gray bars) and processed (spliced, white bars) HIF-2a message normalized to B-2-microglobulin (B2M) for control. FIG. 3G shows the effect of 40, 41, 76 and 77 compounds of HRE-luciferase reporter activity. In parallel with the qRT-PCR analysis, luciferase activity was measured from identically treated 7SV (gray bars) and 7H4 (white bars) cell lysates.

FIG. 4A shows compounds 40, 41, 76 and 77 decrease HIF-2a mRNA translation. Compound treated 786-O cells were subjected to 35S-methionine pulse label followed by immunoprecipitation (IP) as described in Experimental Procedures. (−) indicates anti-HA control IP, (+) indicates IP with anti-HIF-2a antibody. Loading control is a 1 : 1000 dilution of the lysate. Quantification of $^{35}$S incorporation into the radiolabeled HIF-2a protein was determined by densitometry relative to control lanes and the resulting graph is shown (top). FIG. 4B shows the effect of the compounds 40, 41, 76 and 77 is mTOR independent. 786-O cells were treated with D, DMSO; Rap, rapamycin, or the indicated compounds. HIF-2a, total p70S6K, phospho-T389 p70S6K and phospho-S235/6 S6 expression and B-Actin was analyzed by Western blot.

FIG. 5A shows the effect of compounds 40, 41, 76 and 77 is dependent upon presence of 5'-UTR. FIG. 5B shows the effect of 5'-UTR is heterologously transferable. Gray bars, ratio of cells expressing CMV-luciferase with a synthetic RNA helicase reporter 5'-UTR stem loop over those expressing luciferase from the CMV promoter alone; white bars, ratio of cells expressing SV40-luciferase with the HIF-2a 5'-UTR over those expressing luciferase from the SV40 promoter alone. Shown are p-values determined using the Student's unpaired homoscedastic t-Test with a two-tailed distribution, comparing the ratios of SV40 driven luciferase with the HIF-2a 5'-UTR over promoter alone versus CMV-driven luciferase with a synthetic stem loop over promoter alone. FIG. 5C shows the effect of compound 76 localizes to IRE element within the 5'-UTR of the HIF-2a message. A series of 5'-UTR deletion mutants were engineered into the HIF promoter driving luciferase. Shown is the normalized ratio of cells treated with 10 µM 76 over DMSO only control for each reporter relative to the construct without any 5'-UTR element. The 50 nucleotide sequence with an "x" denotes mutated IRE. FIG. 5D show All compounds 40, 41, 76 and 77 work via the Iron-Responsive Element (IRE). The effect of all compounds was tested on luciferase reporter lines containing wild-type or mutant 5'-UTR IRE element. FIG. 5E shows hypoxia mediates translational de-repression of the HIF-2a message via the 5'-UTR IRE. Mutant or wild-type HIF-2a IRE luciferase reporter lines were plated in duplicate and treated with medium only, 10 Mm DFO, 100 µM hematin, or both, as indicated and subjected to 24 hours normoxia (gray bars) or hypoxia (white bars). All data were normalized to the normoxic wild-type IRE reporter line treated with medium only. FIG. 5F shows that compounds 40, 41, 76 and 77 increase expression of Transferrin Receptor 1 mRNA. Quantitative RT-PCR was performed on WT8, PCR3, pTR, and pTV lines as well as compound treated 786-O cells. FIG. 5G shows compounds 40, 41, 76 and 77 are not iron chelators. Displacement of iron from ethyl-3,4-dihydroxybenzoate (EDHB) complex was measured as a decrease in absorbance at 500 nm in the presence compounds as well as EDTA and DFO. FIG. 5H shows that compound 76 decreases TfR1 mRNA stability. Quantitative RT-PCR showing normalized TfR1 mRNA expression in DMSO versus compound 76 treated 786-O cells following the addition of Actinomycin D. For all panels 5A-5H: P, PRC3; W, WT8; V, pTV; R, pTR, or parental 786-O cells treated with M, medium only; D, DMSO; or compounds, as indicated. Experiments were done in triplicate and error bars represent standard error of the mean (SEM).

FIG. 6A shows the effect of IRP1 and IRP2 reduction on HIF-2a. 786-O cells expressing wild-type HIF-2a IRE luciferase reporter, were infected with lentiviral shRNAs targeting IRP1, IRP2 or both. FIG. 6B shows that inhibition of IRP1 is sufficient to prevent hypoxic de-repression of HIF-2a translation. Luciferase counts were normalized to vector only (v.o.) in normoxia. The number in parentheses is the fold induction by hypoxia for each cell line. FIG. 6C shows that inhibition of IRP1 is sufficient to block effect of compounds on HIF-2a activity. qRT-PCR was performed on the HIF-2a target gene EGLN3 in the above IRP knock down lines treated with D, DMSO, 76 or 77. All measurements were done in triplicate and error bars represent standard error of the mean (SEM).

FIGS. 7A-7G show that compounds 40, 41, 76 and 77 enhance binding of IRP1 to the HIF-2a IRE. FIG. 7A shows that compounds 40, 41, 76 and 77 enhance wild-type but not mutant HIF-2a IRE probe gel shift. FIG. 7B shows IRP1 is the major species binding to HIF-2a IRE. EMSA was performed on the 786-O derived IRP knock down lines using the wild-type HIF-2a IRE probe, as indicated. FIG. 7C shows that binding of IRP1 to HIF-2a IRE decreases in hypoxia. EMSA was performed on lysates from 786-O cells subjected to 24 hours normoxia versus hypoxia. Lysates were mixed with wild-type HIF-2a IRE probe and incubated with no antibody (No Ab), control antibody (−), IRP1 polyclonal or IRP2 monoclonal antibodies. Control for IRP 1 was preimmune sera. Control for IRP2 was purified B-Actin monoclonal. FIG. 7D shows compound 76 enhances binding of IRP1 to wild-type HIF-2a probe in hypoxia. 786-O cells were treated with DMSO (D) or 76 and subjected to 24 hours normoxia (N) versus hypoxia (H). EMSA was performed on the resulting lysates following incubation with control, IRP1 or IRP2 antibodies. FIG. 7E shows IRP2 does not bind to the HIF-2a IRE. EMSA was performed on 786-O lysates treated with D, DMSO, 10 μM 76 or 150 μM DFO in normoxia or hypoxia using either the Ferritin L or HIF-2a IRE radiolabeled probe and supershifted with either control of anti-IRP2 (2 μL UT29) antibody. FIG. 7F shows cchematic of the effect of hypoxia on HIF and global translation. FIG. 7G shows a model for IRP1 mediated hypoxic de-repression of HIF-2a translation.

FIG. 8A shows a schematic of HRE luciferase reporter constructs. FIG. 8B shows the fold induction of pGL3::HRE reporter constructs by cobalt chloride and desferrioxamine. pGL3 derived reporter constructs were transiently transfected into U2OS cells and cobalt chloride (CoCl2, 150 μM) or desferrioxamine (DFO, 150 μM) was added after 16 hours. Cells were harvested at 24 hours and measured for normalized luciferase activity. Shown is the fold increase over baseline for each reporter construct. Gray bars, CoCl2; open bars, DFO. FIG. 8C shows HRE4-luciferase reporter activity is inhibited by dominant negative HIF-2a mutants. pGL3::HRE4 was transiently transfected into U2OS cells alone (lane 1) or with HIF-2a (P531A) (lanes 2-1 1), in the presence of increasing amounts of three dominant negative HIF-2a constructs, dnHIF-2a A (lanes 3-5), B (lanes 5-8) and C (lanes 9-11). FIG. 8D shows the Response of subcloned reporter constructs to hypoxia and hypoxia mimetics. U2OS cells were transiently transfected with pcDNA3.1::SV40 (gray bars) or pCDNA3.1::HRE4 (open bars) plasmids and co-transfected with HIF-2a (P531 A) mutant, stimulated by the hypoxia mimetics DFO or CoCl2 for 12 hours, or subjected to hypoxia for 24 hours. Shown is the fold increase over baseline for each reporter construct. All experiments were performed in triplicate. Error bars represent standard error of the mean (SEM).

FIG. 9A shows A498, FIG. 9B shows UOK121, FIG. 9C shows UMRC2 and FIG. 9D shows UMRC3. Gray bars, SV40-luciferase reporter plasmid; open bars, HRE4-luciferase reporter plasmid. All expressed values are normalized to DMSO-only controls for each cell line. Experiments were performed in triplicate. Error bars represent standard error of the mean (SEM). For all panels 9A-9D: M, medium only; D, DMSO; or compounds, as indicated at the following concentrations: 40, 30 μM; 41, 25 μM; 76, 10 μM; 77, 5 μM.

FIG. 10A shows the effect of compound 76 on HIF-2a protein stability. 786-O cells were treated with compound 76 for 2 days, as described for FIG. 1. De novo protein synthesis was then halted by the addition of 10 μg/mL cycloheximide (CHx) and time points taken every hour for 4 hours. Lanes 1 and 2, PRC3 (VHL-deficient) versus WT8 (VHLreconstituted) cells; lanes 3-8, control for HIF-2a expression without addition of cycloheximide (CHx) (lane 3, DMSO-only; lanes 4-8, 5 μM 76); lanes 9-14, HIF-2a expression following the addition of CHx (lane 9, DMSO-only, lanes 10-14, 5 μM 76 harvested at 0, 1, 2, 3 and 4 hours following the addition of CHx). B-Actin is shown for loading control. FIG. 10B shows HIF-2a protein stability in 786-O cells treated with DMSO-only. Identical experiment as described above without addition of compound 76. For panels A and B: P, PRC3; W, WT8; D, DMSO; 76, 5 μM 76. FIG. 10C shows HIF-2a half-life in compound-treated 786-O cells following the addition of cycloheximide. All compounds were tested analogously to 76 and the gels were quantified by gel densitometry. HIF-2a expression was corrected for B-Actin and normalized such that the band intensity in lane 10 was set at one. Closed squares, DMSO-only with no CHx (from panel B, lanes 4-8); open squares, DMSO-only with CHx (from panel B, lanes 10-14); closed diamond, 40 the presence of CHx; open diamond, 41 with CHx; closed triangles, 76 with CHx (from panel A, lanes 10-14); open triangles; 77 with CHx.

FIG. 11A shows the HIF-2a expression corrected for control and normalized such that the band intensity in all t=0 lanes was set at one. Closed squares, medium only; open squares, DMSO; closed diamond, 40; open diamond, 41; closed triangles, 76; open triangles, 77. FIG. 11B shows a bar graph of the quantification of HIF-2a immunoprecipitation shown in FIG. 11C, as determined by densitometry relative to control lanes. FIG. 11C shows the HIF-2a immunoprecipitation, where (−) indicates anti-HA control IP, (+) indicates IP with anti-HIF-2a. Control is a 1:1000 dilution of the lysate directly loaded. M, medium only; D, DMSO; compound numbers, as indicated at the experimentally determined IC50 values.

FIGS. 13A-13D show the comparison of compounds to low and high dose DFO by Connectivity Map. Gene expression signatures obtained by treating 786-O cells with compound 40 (FIG. 13A), 41 (FIG. 13B), 76 (FIG. 13C) and 77 (FIG. 13D) were analyzed using the Connectivity Map webtool to gene expression profiles of PC3 and MCF7 cell lines (as indicated) treated with low (6 µM) or high (100 µM) doses of DFO. Negative score indicates degree of negative correlation.

FIG. 14A shows a Schematic of the HIF-2a 5'-UTR Iron-responsive element (IRE) versus the putative one located in the HIF-1a 5'-UTR. The consensus sequence of the loop and the mandatory 5' cytosine bulge are highlighted with light blue circles. FIG. 14B shows the putative IRE in the HIF-1a 5'-UTR is not functional. Duplicate plates of 786-O derived lines expressing the putative wild-type or mutant HIF-1a IRE were cultured in the presence of compound as described for FIG. 1, with the exception that one set was placed at 1% oxygen for 24 hours following the first day's medium-change. Cells were treated with M, medium only; D, DMSO; or compounds, as indicated at the following concentrations: 40, 40 µM; 41, 30 µM; 76, 10 µM; 77, 5 µM. FIG. 14C shows the effect of compounds 40, 41, 76 and 77 on HIF-1a in CWR22R cells and HIF-1a and HIF-2a in Hep3B cells. CWR22R or Hep3B cells were treated with compound and subjected to hypoxia as described above. B-Actin is shown for loading control. Cells were treated with M, medium only; D, DMSO; or compounds, as indicated at the following concentrations: 40, 40 µM; 41, 30 µM; 76, 20 µM; 77, 7.5 µM.

FIG. 15A shows connectivity mapping of small molecule HIF2a inhibitors. The 'barview' is constructed from 6,100 horizontal lines, each representing an individual treatment instance, ordered by their corresponding connectivity scores with signatures produced from compounds 40, 41, 76, and 77 as indicated (+1, top; −1, bottom). All 15-delta prostaglandin J2 instances in the dataset (n=15) are shown as black bars (left). Colors applied to the remaining instances (i.e. gene expression profiles of the cells obtained with other than PGJ2 compounds) reflect the sign of their scores (top dark color, positive; middle light color, null; bottom dark color, negative). The rank, name of the perturbagen [instance id], concentration, cell line and connectivity score for each 15-delta prostaglandin J2 instance is also shown (right). Permutation p-values for the set of all 15-delta prostaglandin J2 instances are <0.00001 for compounds 40, 41 and 76, and 0.01374 for compound 77. FIG. 15B shows $PGJ_2$ decreases HRE driven luciferase activity in a dose dependent manner. 786-O cells harboring Hypoxia Response Element-driven luciferase reporter plasmid (7H4, gray bars) or the hypoxia independent, SV-40-driven luciferase reporter plasmid (7SV, white bars), were treated for 2 days with $PGJ_2$ (at the indicated micromolar concentrations), DMSO as diluent control (D) or medium only (M) application.

Relative luciferase activity is normalized to that of medium only treated cell, which was set to 1. Gray bars, SV40-luciferase; open bars, HRE-luciferase. FIG. 15C shows effect of $PGJ_2$ on HIF2a protein expression and HIF-2a target gene expression. 786-O cells were treated with the indicated concentrations of $PGJ_2$ as described above. HIF2a and Glut-1 expression was analyzed by Western blot. B-Actin is shown as loading control (upper panels). EGLN3 expression was measured by quantitative reverse transcription polymerase chain reaction (qRT-PCR), normalized to beta-2-microglobulin (B2M) (lower panel). FIG. 15D shows that $PGJ_2$ does not affect HIF2a mRNA expression. qRT-PCR was performed using RNA extracted from 786-O cells treated in parallel with $PGJ_2$. Data shows relative expression of HIF2a message, normalized to beta-2-microglobulin (B2M).

FIGS. 16A-16D show 15-deoxy-$\Delta^{12,14}$-Prostaglandin $J_2$ decreases HIF2a mRNA translation in a HIF2a 5'UTR-dependent manner. FIG. 16A shows $PGJ_2$ decreases the amount of protein translated from mRNA without decreasing the half-life of the protein. 786-O cells were treated with 10 µM $PGJ_2$ and subjected to $^{35}$S-methionine pulse-chase immunoprecipitations (IP) as described in Methods. Upper panel: autoradiography of HIF2a immunoprecipitations following the addition of excess cold methionine (chase) for the indicated time; (−) indicates anti-HA used as control antibody, (+) indicates IP with anti-HIF2a antibody1. Lower panel: loading control is a representative section of the autoradiograph in which a $\frac{1}{1000}^{th}$ of the lysate used in the IP was directly loaded. Lanes 1-4, cells treated with DMSO only; lanes 5-8, cells treated with 10 µM $PGJ_2$. FIG. 16B shows PGJ2-treated cells exhibit a normal polysome profile. Results form one of three independent experiments shown here. 786-O cells were either mock treated with DMSO, 50 nM rapamycin or 10 uM PGJ2 for 24 hours. Think black line, DMSO. Thin black line, 50 nM rapamycin. Gray line, 10 uM PGJ2. FIG. 16C shows effect of $PGJ_2$ is mTOR independent 786-O cells were treated with medium only (M), DMSO (D), 50 nM rapamycin (R), or 10 µM $PGJ_2$ (J2). HIF2a, total p70S6K (indicated as S6K), phospho-T389 p70S6K (indicated as S6K-P), and phospho-S235/6 S6 (indicated as S6-P), expression was analyzed by Western blot. B-Actin is shown for loading control. FIG. 16D shows effect of 15-deoxy-$\Delta^{12,14}$-Prostaglandin $J_2$ is dependent upon the presence of the 5'-UTR and is heterologously transferable. Stable 786-O derived polyclonal cells expressing luciferase reporters were treated with DMSO only (Gray bars) or 10 µM $PGJ_2$ (white bars). Upper panel: comparison of ratios of (1) HRE/SV40 luciferase activities to that of (2) HIF-2a promoter with the 5'-UTR over the HIF2a promoter alone. Lower panel: comparison of the ratios of (3) 7CMV-SL divided by 7CMV to that of (4) 7SV-UTR divided by 7SV. Shown are p-values determined using the Student's unpaired homoscedastic t-Test with a two-tailed distribution. No significant differences were found in a likewise comparison of $PGJ_2$ versus DMSO treated 7CMV-SL divided by 7CMV. All experiments were done in triplicate. Error bars represent standard error of the mean (SEM). Promoter-reporter constructs (1 to 4) are diagrammatically presented to the right.

FIG. 17A shows effect of $PGJ_2$ $_{on}$ on HIF2a translation is mediated through the 5'-UTR HIF2a IRE. Polyclonal 786-O cells stably expressing a luciferase reporter driven by the HIF2a promoter alone or in tandem with deletion mutants of the HIF2a 5'-UTR were treated with $PGJ_2$ for 2 days and the relative luciferase activity graphed. Mutants are shown on the left as horizontal bars spanning the corresponding UTR area, double vertical lines indicate IRE inactivating mutant ratio in the right). Luciferase activity is reported as a ratio of PGJ2 treated/DMSO treated value, normalized to the counts obtained by the reporter that contains no 5-UTR. FIG. 17B shows inhibition of IRP1 is sufficient to block the effect of PGJ2 on HIF-2a activity. 786-O cells were infected with shRNA targeting solely IRP1

(shIRP1), IRP2 (shIRP2) or with shRNAs targeting both IRP1+IRP2 isoforms (shIRP1/2). All measurements were done in triplicate and error bars represent standard error of the mean (SEM). Down regulation of IRP1 and/or IRP2 were confirmed with qRT-PCR and with Western Blot (data not show).

Figure 18A:
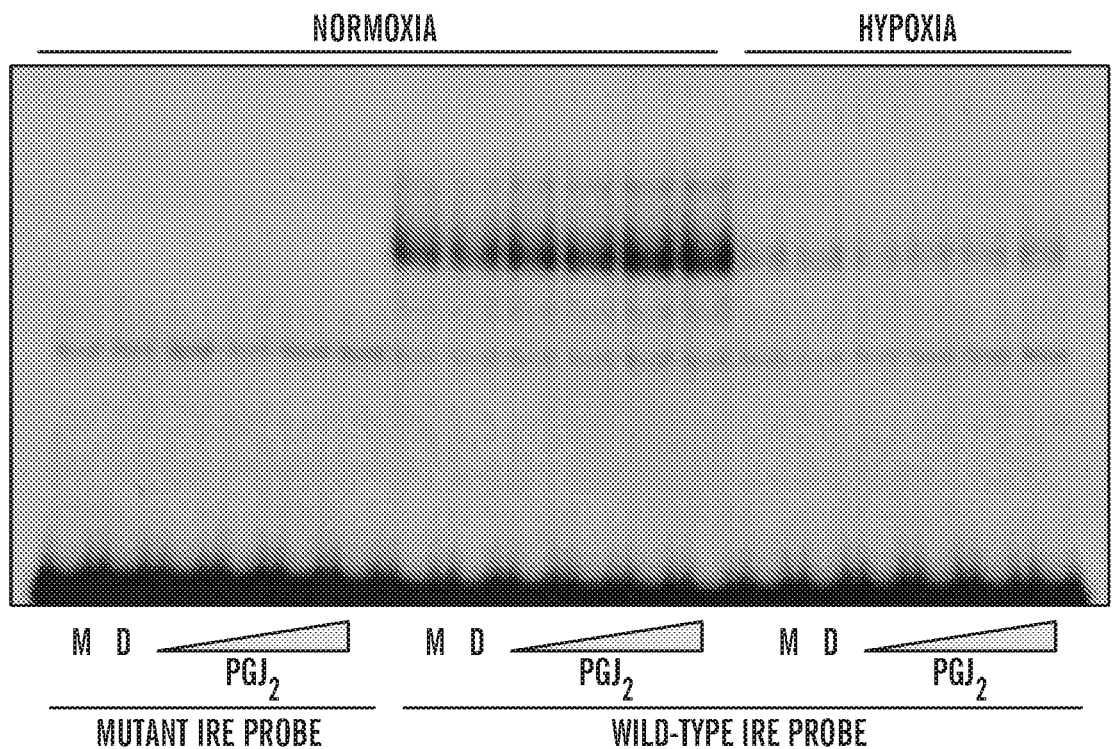
Figure 18B:
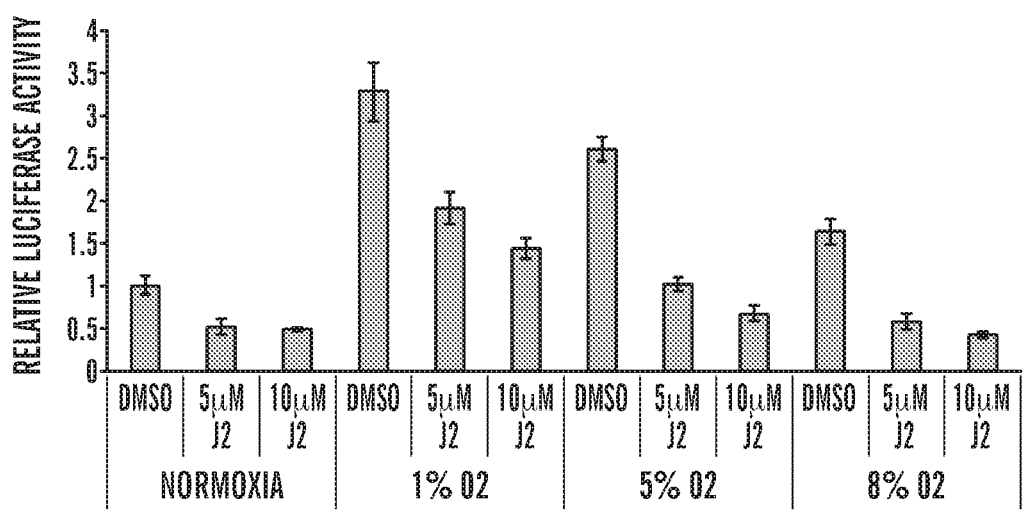

FIGS. 18A-18B show $PGJ_2$ promotes binding of IRP1 to HIF2a IRE under normoxic and hypoxic conditions. FIG. 18A shows PGJ2 promotes HIF2a IRE binding. 786-O cells were treated with medium only (M), DMSO (D) or increasing concentrations of $PGJ_2$ at 21% ambient oxygen tension (normoxia) or 1% ambient oxygen tension (hypoxia) as indicated. Equal amounts of protein lysates were tested for Iron Responsive Element (IRE) binding activity by EMSA of a wild type or mutant labeled RNA probe. The effect of $PGJ_2$ on the IRE binding activity under normoxic or hypoxic conditions is shown as indicated. FIG. 18B shows PGJ2 represses HIF2a activity under normoxic and hypoxic conditions. 786-O cells harboring Hypoxia Response Element-driven luciferase reporter plasmid were treated with DMSO as diluent control (DMSO) or PGJ2 at the indicated concentrations, for 48 hours, while cultured at a range of ambient oxygen tensions, as indicated. All luciferase values are normalized to the DMSO control under normoxic conditions. Assay was done in triplicate and the error bars represent SEM.

Figure 19:
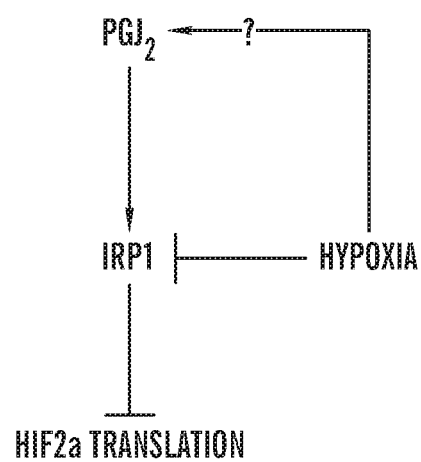

FIG. 19 is a schematic representation of the effect of hypoxia and PGJ2 on both general and IRP1-mediated translation. PGJ2 inhibits HIF2a translation by promoting Iron Regulatory Protein 1 (IRP1) activity at a wide range of ambient oxygen concentration. Hypoxia de-represses HIF2a translation by inhibiting IRP1 activity.

Figure 20A:
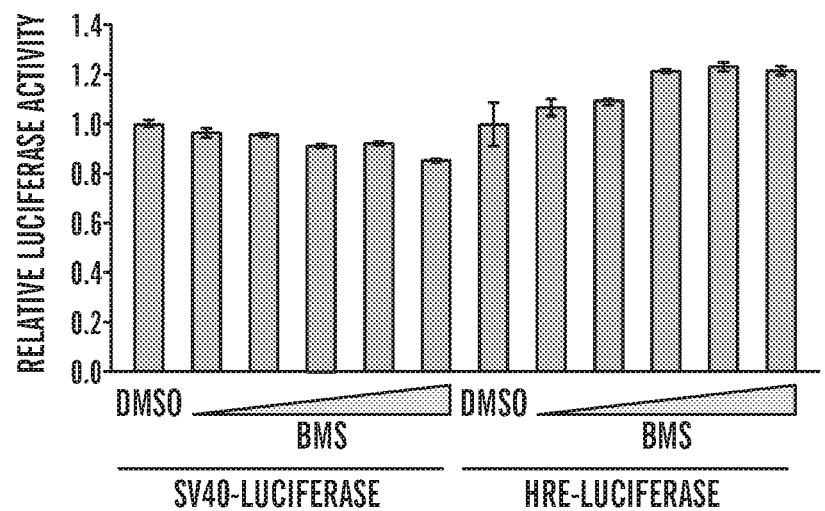
Figure 20B:
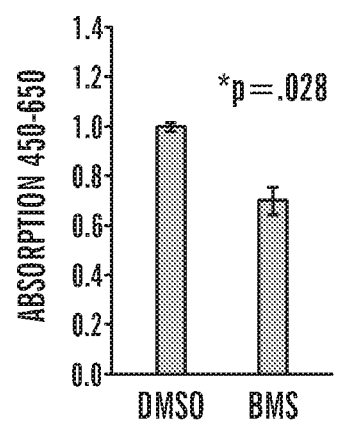

FIG. 20A-20B show NFkB inhibition does not affect activity of HIF2a. FIG. 20A shows normalized luciferase activity from stable SV40- and HRE-luciferase expressing 786-O cells, treated for 24 hours with the IKK Inhibitor, BMS-345541 at the indicated concentrations relative to DMSO-only treated control. FIG. 20B shows TransAM NFkB ELISA (Active Motif, cat.# 100627) demonstrating that basal NFkB activity is suppressed in 786-O cells when 5uM BMS-345541 is applied for 24 hours. Experiments were performed in triplicate. Error bars represent Standard Error of the Mean (SEM).

Figure 21A:
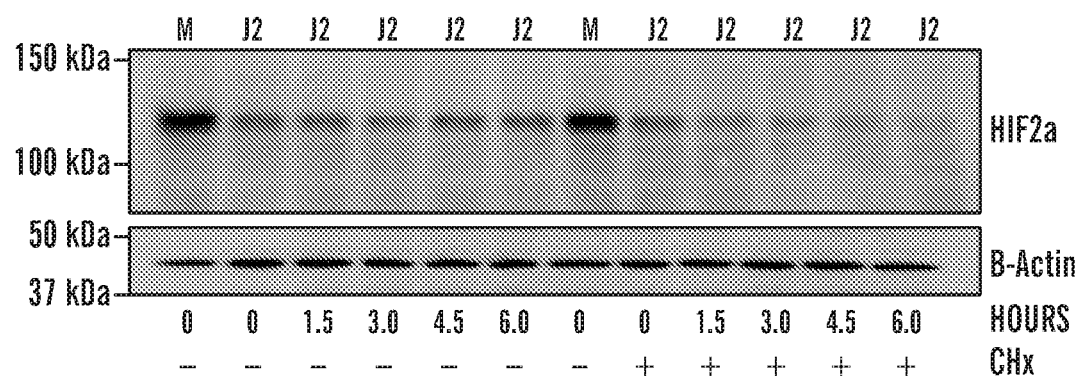
Figure 21B:
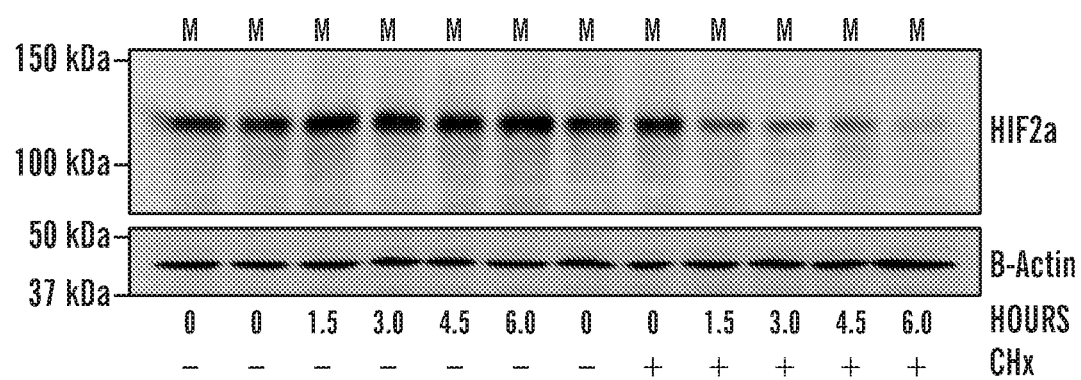

FIG. 21A-21B show PGJ2 does not affect HIF-2a stability as measured by blocking de novo protein synthesis with cyclohexamide. FIG. 21A shows effect of PGJ2 on HIF-2a protein stability. 786-O cells were treated with PGJ2 for 2 days, as described for FIG. 21b. De novo protein synthesis was then halted by the addition of 10 µg/mL cycloheximide (CHx) and time points taken every 1.5 hours for 6 hours. Lanes 1-6, control for HIF-2a expression without addition of cycloheximide (CHx) (lane 1, DMSO-only; lanes 3-6, 10 µM PGJ2); lanes 7-12, HIF-2a expression following the addition of CHx (lane 7, DMSO-only, lanes 8-12, 10 µM PGJ2 harvested at 0, 1.5, 3, 4.5 and 6 hours following the addition of CHx). B-Actin is shown for loading control. FIG. 21B shows HIF-2a protein stability in 786-O cells treated with DMSO-only. Identical experiment as described above without addition of PGJ2.

Figure 22:
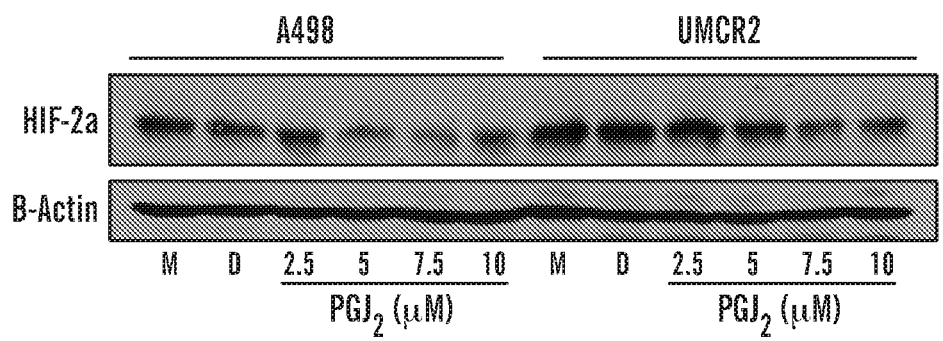

FIG. 22 shows inhibition of HIF2a expression by PGJ2 is not a cell specific phenomenon. The VHL null human renal cell carcinoma cell lines A498 and UMRC2 were treated with increasing doses of PGJ2 as indicated. HIF2a expression was analyzed by Western Blot. Beta actin loading control is shown.

Figure 23:
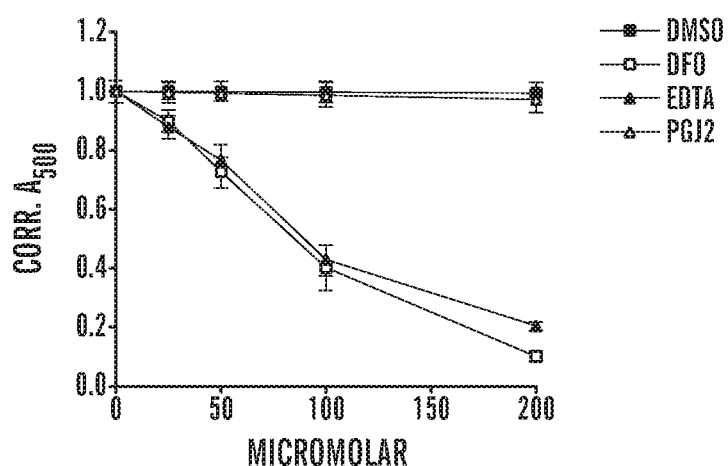

FIG. 23 shows PGJ2 is not an iron chelator. Displacement of iron from ethyl-3,4-dihydroxybenzoate (EDHB) complex was measured as a decrease in absorbance at 500 nm in the presence of PGJ2, EDTA or DFO.

Figure 24:
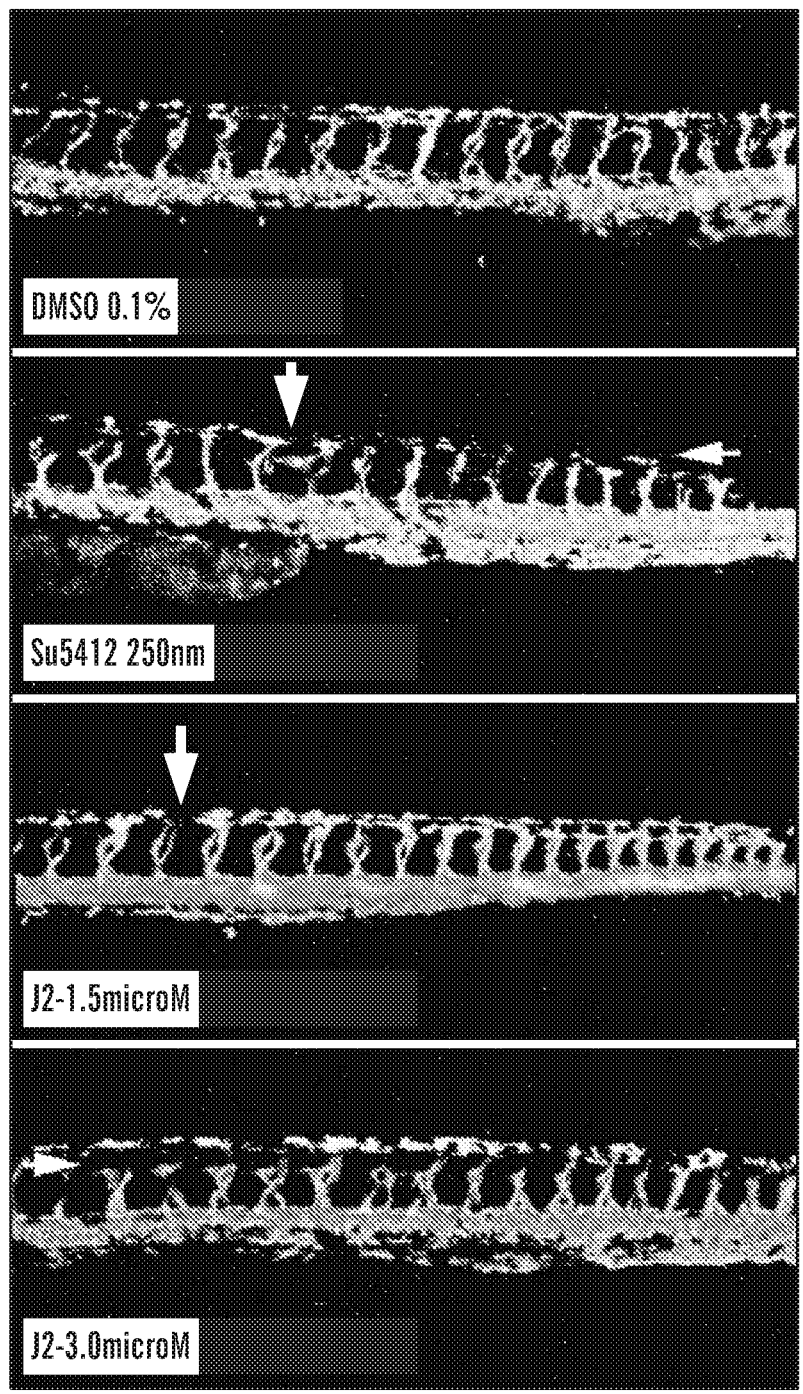

FIG. 24 shows inhibition of vascularization in fish embryo by treatment with HIF-2a inhibitor.

Figure 25A:
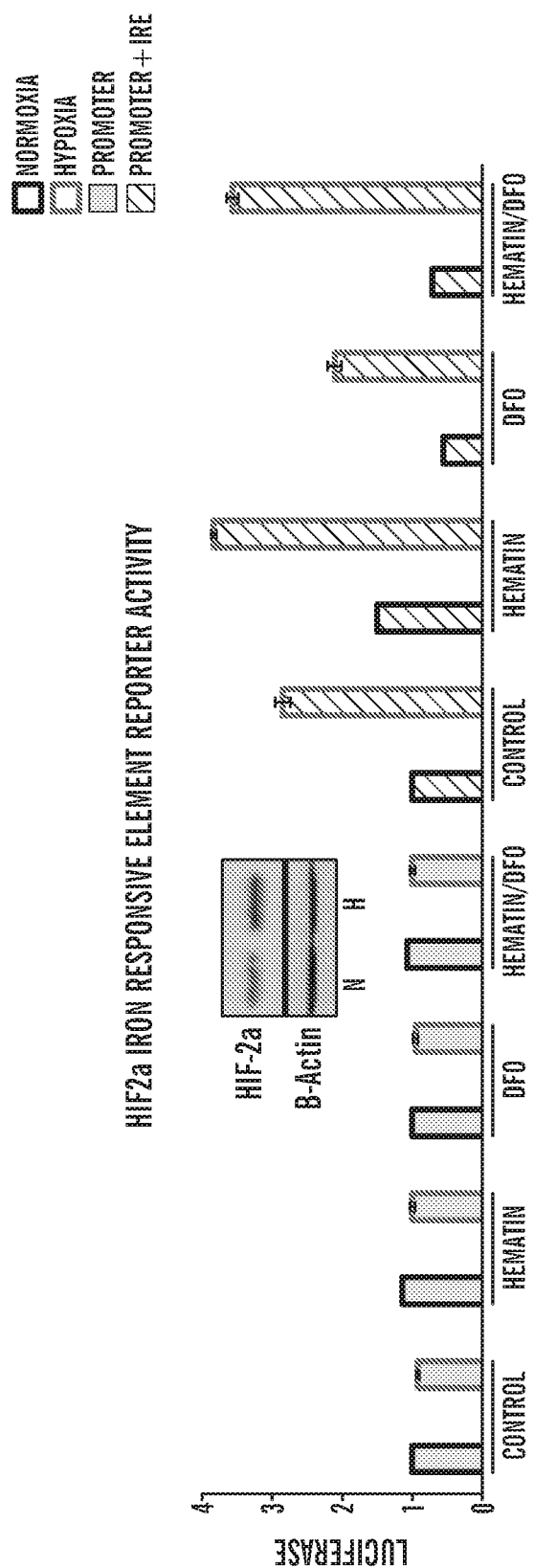
Figure 25B:
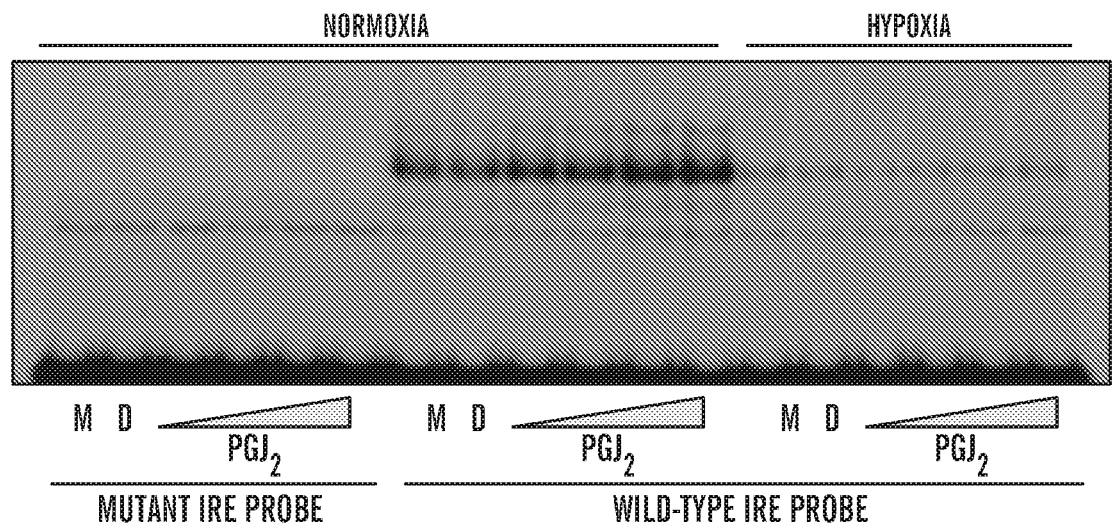
Figure 25C:
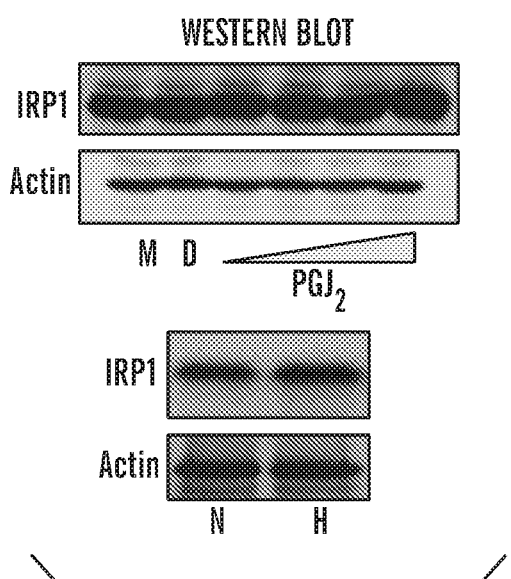

FIGS. 25A-C show compounds increase and hypoxia decreases IRP1 binding to HIF-2a IRF. FIG. 25A shows hypoxia mediates translational de-repression of HIF-2a message via the 5'-UTR IRE. FIG. 25B shows $PGJ_2$ promotes HIF-2a IRE binding. FIG. 25C shows effect of $PGJ_2$ treatment on IRP1 expression.

Figure 26A:
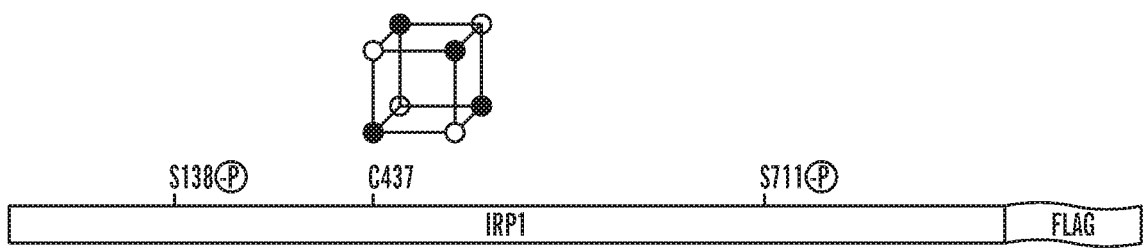
Figure 26B:
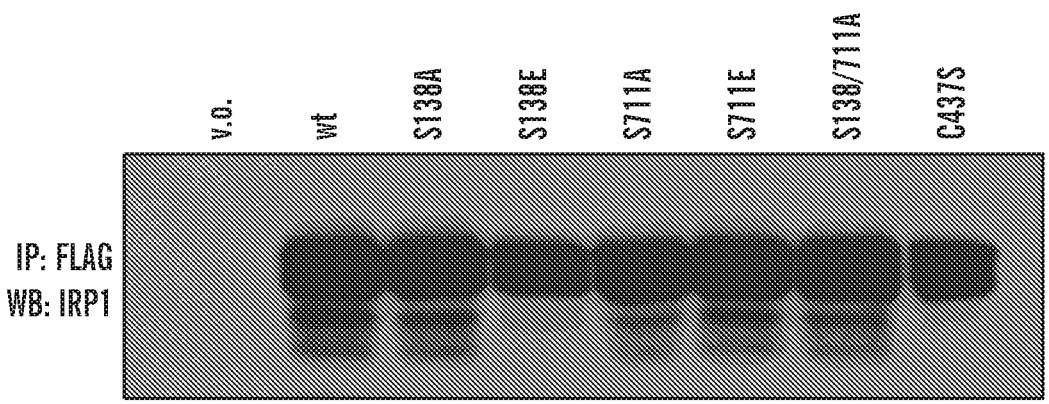

FIGS. 26A-26B show stable expression of IRP1 mutants in 786-O cells. FIG. 26A schematically shows the mutant IRP1 constructs. FIG. 26B shows expression of IRP1 mutants.

Figure 27:
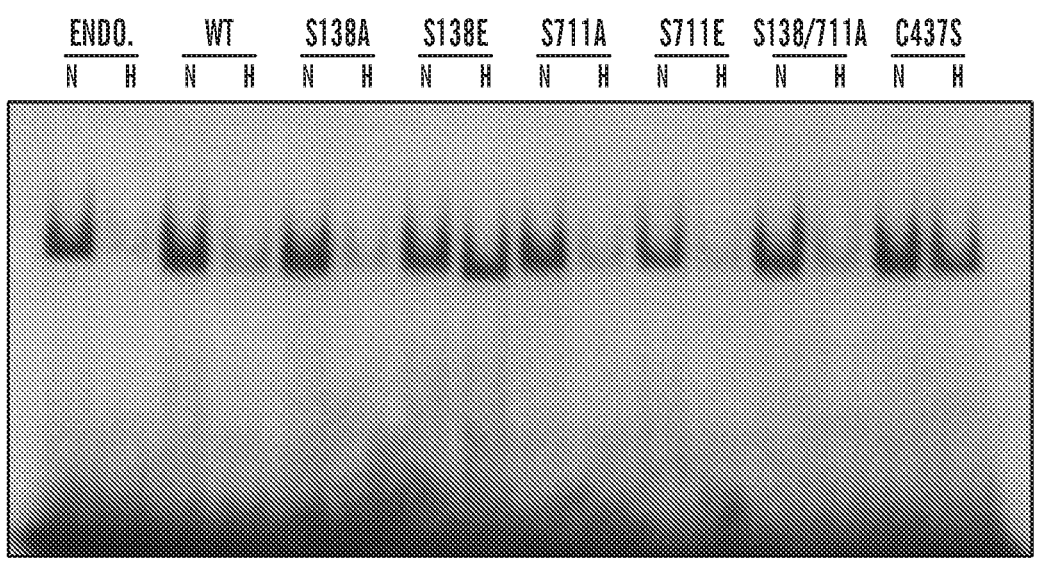

FIG. 27 shows phosphomimetic S138E mutant fails to dissociate from HIF-2a IRE in hypoxia.

Figure 28:
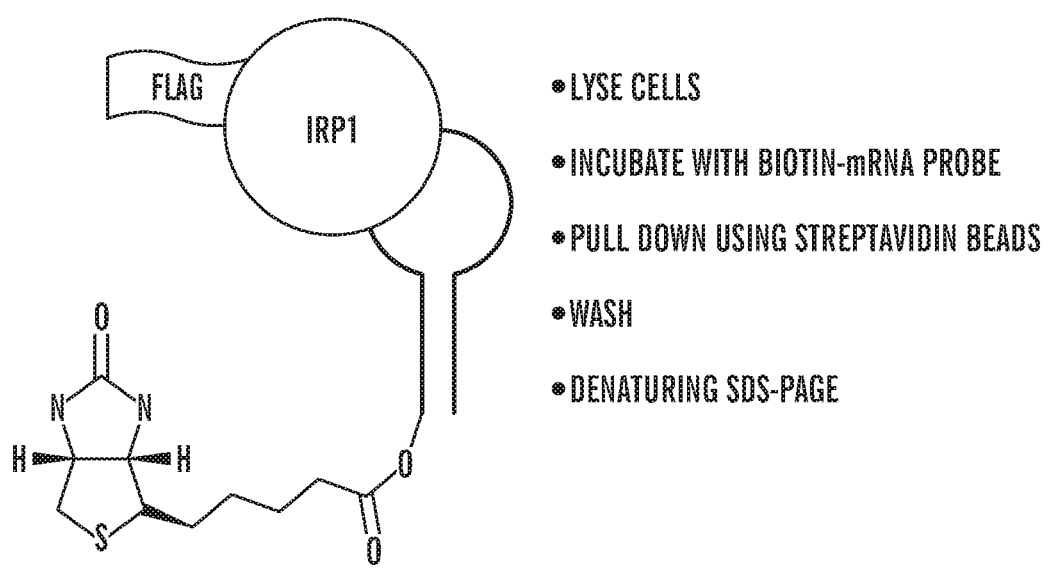

FIG. 28 is a schematic representation of biotinylated mRNA pull down assay.

Figure 29A:
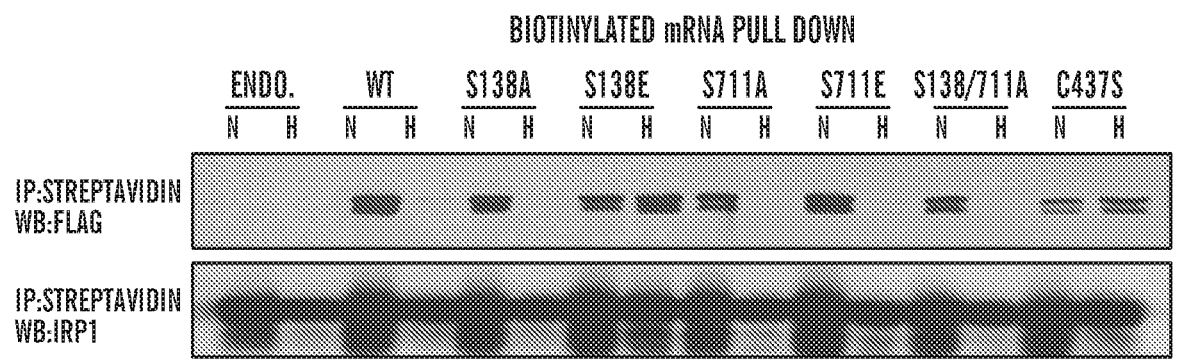
Figure 29B:
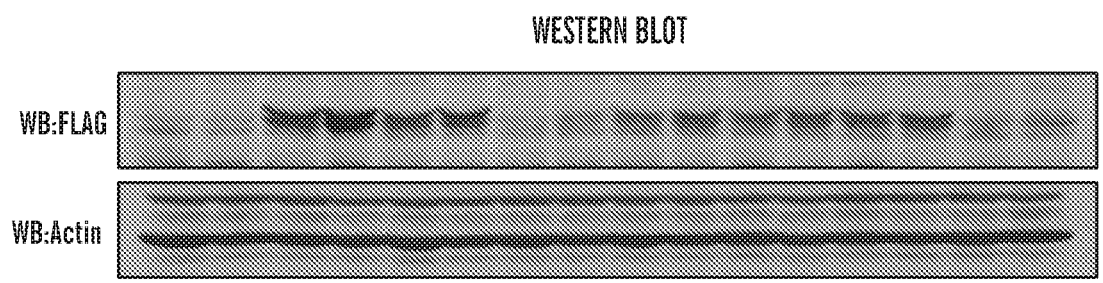

FIG. 29A-29B show phosphomimmetic S138E mutant fails to dissociate from HIF-2a IRE in hypoxia. FIG. 29A shows biotinylated mRNA pull down. FIG. 29B shows a Western blot.

Figure 30:
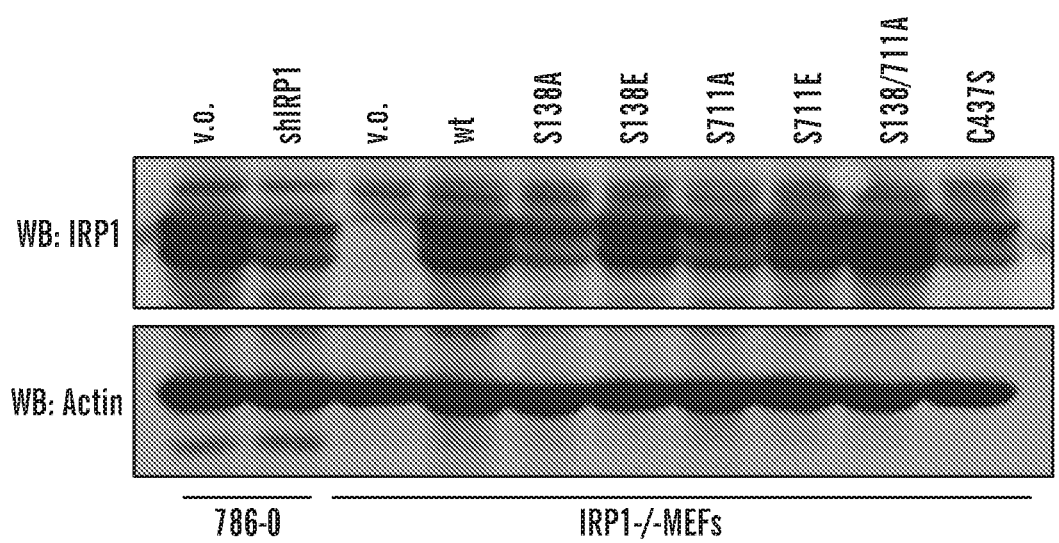

FIG. 30 shows expression of IRP1 mutants in IRP1−/− MEFs.

Figure 31A:
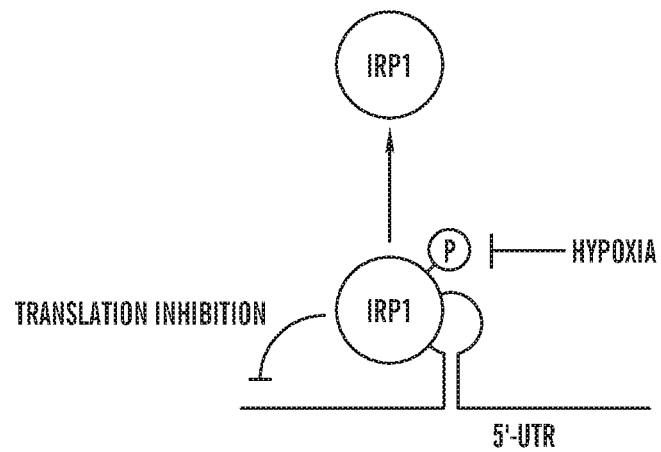
Figure 31B:
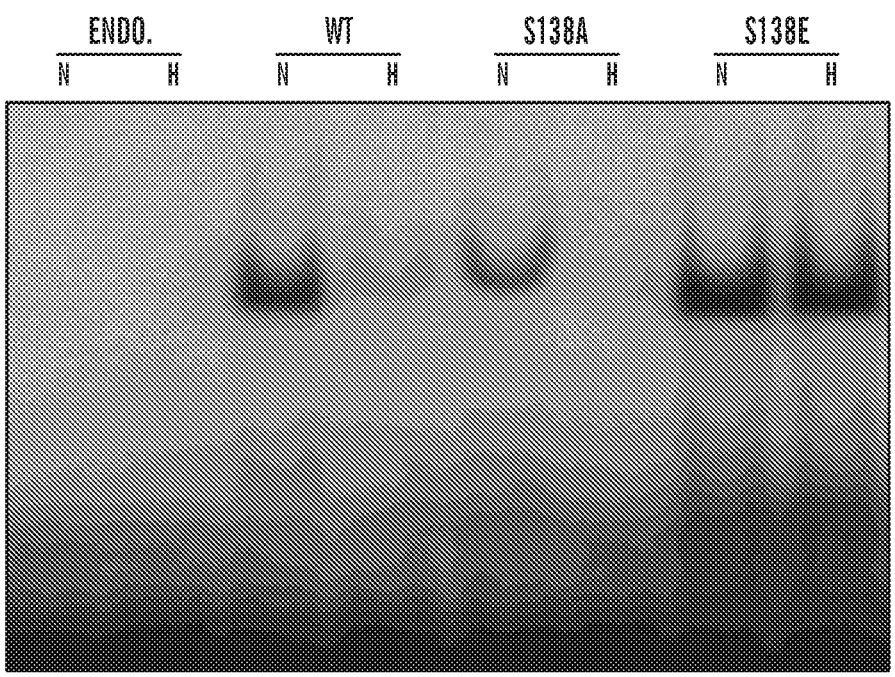

FIGS. 31A-31B show phosphomimmetic S138E mutant fails to dissociate from HIF-2a IRE in hypoxia. FIG. 31A is a schematic representation showing inhibition of dephosphorylation of IRP1 under hypoxia can lead to HIF-2a translation inhibition. FIG. 31B shows EMSA on IRP1-reconstituted IRP1−/− MEFs.

Figure 32A:
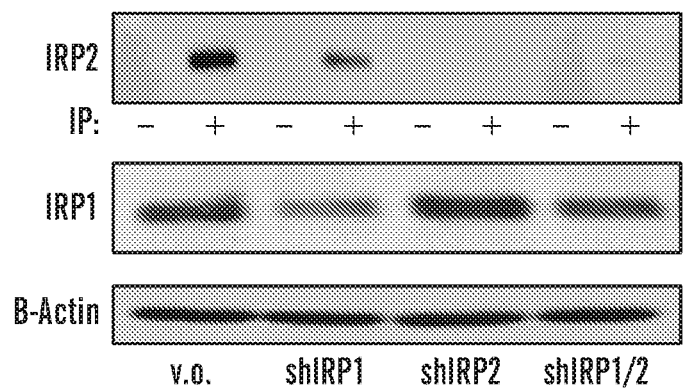
Figure 32B:
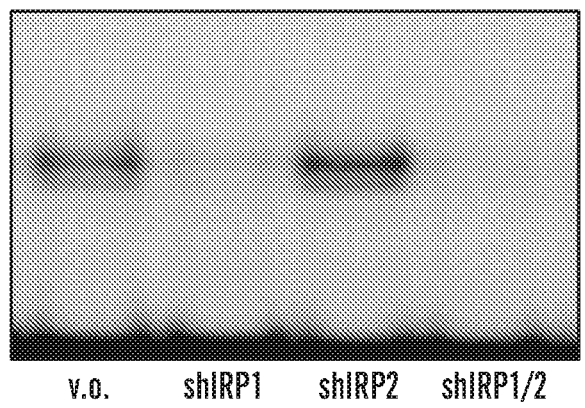
Figure 32C:
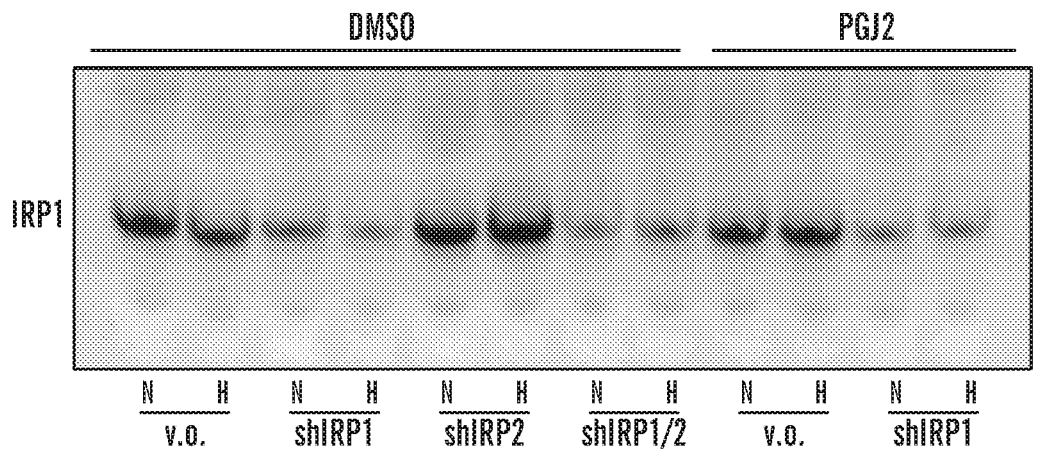
Figure 32D:
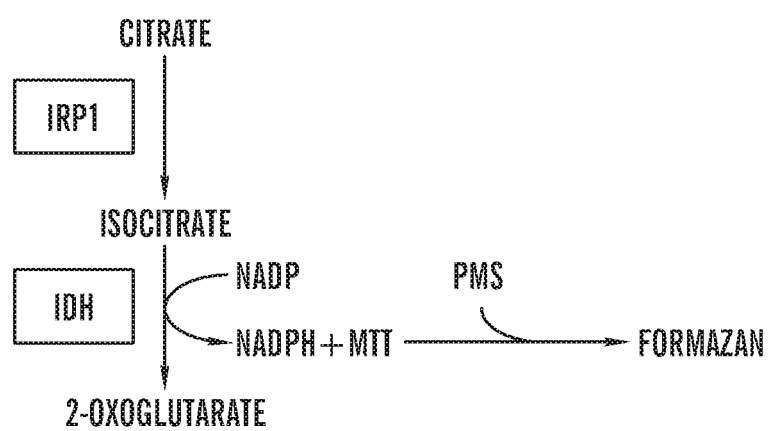

FIGS. 32A-32D show establishment of an in gel aconitase assay. FIG. 32A shows expression of IRP1 and IRP2 in IRP shRNA lines. FIG. 32B shows EMSA with IRP shRNA lines. FIG. 32C shows effect of DMSO or $PGJ_2$ on IRP1 expression with IRP1 shRNA lines. FIG. 32D shows a schematic representation of the assay.

Figure 33:
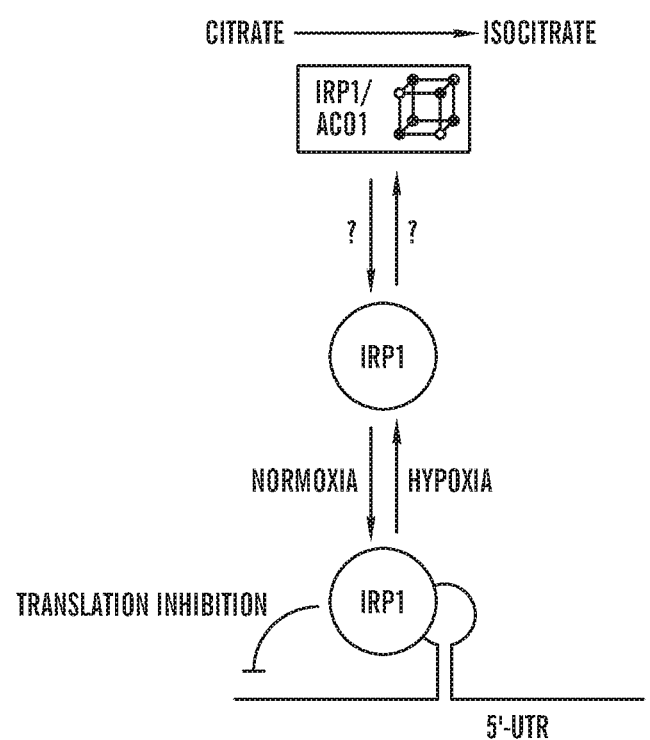

FIG. 33 shows a model for IRP1 mediated hypoxic de-repression of HIF-2a translation.

DETAILED DESCRIPTION OF THE INVENTION

In one aspect, the invention provides a method of inhibiting HIF-2a activity in a cell comprising: contacting the cell with a HIF inhibitor described herein.

In another aspect the invention provides methods of preventing cell proliferation. The methods include contacting a cell with a HIF inhibitor described herein.

In yet another aspect the invention provides methods of treating an angiogenic disease or disorder in a subject in need thereof. The methods include administering a HIF described herein inhibitor to the subject.

In yet still another aspect the invention provide methods inhibiting angiogenesis in a mammal having an angiogenic disease. The methods include administering a HIF inhibitor described herein to the subject.

Another aspect of the invention is directed to pharmaceutical compositions for inhibiting angiogenesis comprising a HIF inhibitor described herein.

Yet another aspect of the present invention is directed to articles of manufacture comprising packaging material and a pharmaceutical composition contained within said packaging material, wherein said pharmaceutical composition is capable of treating an angiogenic disorder or disease, wherein said packaging material comprises a label which indicates that said pharmaceutical composition can be used for treating an angiogenic disorder or disease, and wherein said pharmaceutical composition comprises a HIF inhibitor described herein.

Yet another aspect of the present invention is directed to articles of manufacture comprising packaging material and a pharmaceutical composition contained within said packaging material, wherein said pharmaceutical composition is capable of reducing inflammation, wherein said packaging material comprises a label which indicates that said pharmaceutical composition can be used for reducing inflammation, and wherein said pharmaceutical composition comprises a HIF inhibitor described herein.

Hypoxia Inducible Factor (HIF)

HIF is a primary transcription factor responsible for specific induction of genes in hypoxia. HIF is composed of two subunits belonging to the bHLH-PAS family: HIF-1 alpha or HIF-2alpha and aryl hydrocarbon receptor nuclear translocator (ARNT also known as HIF-1 beta). To activate transactivation of target genes, HIF alpha subunits dimerize with HIF-1 beta and bind to consensus sequences on DNA (hypoxia responsive element, HRE) in the promoter or enhancer regions of these genes. In contrast, HIF dimers containing HIF3alpha subunits are not transcriptionally active and HIF3alpha isoforms may act as dominant negative regulators. HIF modulates the expression of more than 60 genes whose products are critical to many aspects of tumor progression, including metabolic adaptation, apoptosis resistance, angiogenesis and metastasis. These include, but are not limited to, vascular endothelial growth factor (VEGF), erythropoietin, gluocose transportes, glycolytic enzymes and tyrosine hydroxylase. Additional HIF related genes are described in the following publications, all of which are incorporated herein by reference: U.S. Pat. Pub. No. 2008/0226622; Cancer Treat Rev. 2006 Aug. 2; Cardiovasc Hematol Agents Med Chem. 2006 July; 4(3): 199-218; Cardiovasc Hematol Agents Med Chem. 2006 July; 4(3): 189-97; Curr Pharm Des. 2006; 12(21):2673-88; Ann N Y Acad Sci. 2006 April; 1068:66-73; Circ Res. 2006 Jun. 23; 98(12):1465-7; Cardiovasc Res. 2006 Sep. 1; 71(4):642-51; Sci STKE. 2006 May 30; 2006(337):pe25; Endocr Relat Cancer. 2006 June; 13(2):415-25; Nature. 2006 May 25; 441(7092):437-43; Shock. 2006 June; 25(6):557-70; Crit Rev Oncol Hematol. 2006 July; 59(1): 15-26; Novartis Found Symp. 2006; 272:2-8; discussion 8-14, 33-6; Curr Atheroscler Rep. 2006 May; 8(3):252-60; Am J Physiol Renal Physiol. 2006 August; 291(2):F271-81; Curr Opin Neurol. 2006 April; 19(2):141-7; Kidney Blood Press Res. 2005; 28(5-6):325-40; Kidney Int. 2006 April; 69(8): 1302-7; Trends Mol Med. 2006 April; 12(4): 141-3; Int J Radiat Oncol Biol Phys. 2006 Feb. 1; 64(2):343-54; Int J Radiat Oncol Biol Phys. 2006 Feb. 1; 64(2):343-54; Z Gastroenterol. 2006 January; 44(1):67-76; EMBO Rep. 2006 January; 7(1):41-5; Curr Cancer Drug Targets. 2005 December; 5(8):595-610; and Chest. 2005 December; 128(6 Suppl): 5925-594S.

In normoxia, HIF is hydroxylated and interacts with the von Hippel Lindau protein (pVHL), an E3 ubiquintin subunit that targets HIF for degradation. In the absence of oxygen, HIF hydroxylation is inhibited, preventing binding of pVHL and leading to its intracellular accumulation. HIF-2a upregulation is found predominately in cancers with VHL gene mutations.

Tumor hypoxia increases malignant progression and metastasis by promoting angiogenesis through the induction of proangiogenic proteins such as VEGF (Schweiki, D. et al. Vascular endothelial growth factor induced by hypoxia may mediate hypoxia-induced angiogenesis. Nature 359, 843-5 (1992)).

The inhibition of HIF-mediated gene regulation can reduce tumor angiogenesis and prevent the adaptative metabolic response to hypoxia, thus suppressing tumor growth. Although not intending to be bound by theory, HIF inhibitors of the present disclosure that lead to downstream prevention of HIF/HRE interaction are expected to lead to the attenuation of hypoxia- or HIF-induced gene expression, retardation of tumor growth, and minimal toxicity towards normal tissues. Therefore, HIF inhibitors can interfere with solid tumor growth.

HIF Inhibitors

As used herein, the term "HIF inhibitor" refers to a compound, pharmaceutically acceptable salt, prodrug, or derivative thereof that inhibits the biological activity of HIF-1, HIF-2 and HIF-3; interferes with HIF-1, HIF-2, and HIF-3, signal transduction pathway; or down regulates expression or availability of HIF-1, HIF-2, and HIF-3 in a cell or organism. Without wishing to be bound by theory, HIF inhibitors reduce angiogenesis. Inhibition of angiogenesis can prevent the adaptative metabolic response to hypoxia. Inhibition of angiogenesis can also inhibit neovascularization.

A HIF inhibitor can act to inhibit the cellular production or activity of HIF by cells. In some embodiments, the HIF inhibitors inhibit HIF-2a production or activity by decreasing HIF-2a protein levels, inhibiting HIF-2a mRNA translation, and/or modulating the binding of IRP1 to HIF-2a IRE. In some embodiments, the HIF inhibitors inhibit binding of IRP 1 to HIF-2a IRE.

In some embodiments, HIF inhibitor is of structure shown in formula (I):

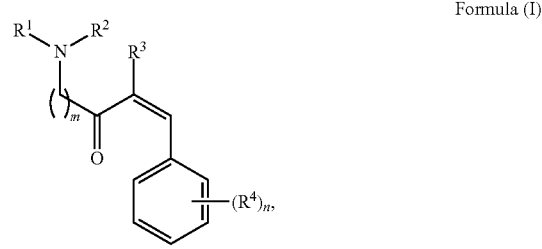

Formula (I)

wherein:

$R^1$ and $R^2$ are each independently H, alkyl, alkenyl, alkynyl, or taken together with the N atom to which they are attached form a 5-8 membered heterocyclyl or heteroaryl, each of which can be optionally substituted;

$R^3$ is H, alkyl, alkenyl, or alkynyl, each of which can be optionally substituted;

$R^4$ is independently for each occurrence halogen, alkyl, alkenyl, alkynyl, alkoxy, $CF_3$, $NO_2$, $N(R^5)_2$, CN, OH, $SR^5$, $SO_2R^5$, or two $R^4$ taken together form an optionally substituted 3,4-methylenedioxy, each of which can be optionally substituted;

$R^5$ is independently for each occurrence H, alkyl, alkenyl, or alkynyl, ach of which can be optionally substituted;

m is 1, 2, 3, 4 or 5;

n is 0, 1, 2, or 3; and pharmaceutically acceptable salts thereof.

Although, the double bond is shown in the cis configuration, both the cis and trans double bond are amenable to the invention.

In some embodiments, at least one of $R^1$ and $R^2$ is $C_1$-$C_6$ alkyl. In some further embodiments of this, both of $R^1$ and $R^2$ are $C_1$-$C_6$ alkyl. When both of $R^1$ and $R^2$ are $C_1$-$C_6$ alkyl, they can be the same or different alkyl, any combination of the two alkyl groups being suitable. In some embodiments, both of $R^1$ and $R^2$ are methyl or ethyl.

In some other embodiments, at least one of $R^1$ and $R^2$ is H. In some further embodiments of this, both of $R^1$ and $R^2$ are H.

In yet some other embodiments, $R^1$ and $R^2$ taken together with the N atom they are attached to form a 5-8 membered heterocyclyl, e.g., morphilino, piperdino, pyrrolidino or piperaznio. Preferably heterocyclyl is morphilino.

When $R^3$ is optionally substituted $C_1$-$C_6$ alkyl, $R^3$ is selected from the group consisting of methyl, ethyl, propyl, isopropyl, n-butyl, isobutyl, and t-butyl. In some embodiments, $R^3$ is methyl.

In some embodiments, m is 2.

In some embodiments, n is 0 or 1.

In general, on phenyl ring to which $R^4$ can be attached, attachment of $R^4$ at the 3- or 4-position is preferred. When n is 2, attachment of $R^4$ at the 3- and 4-positions is preferred. When m is 2 or more, all of the $R^4$ can all be the same, all different or a combination thereof.

In some embodiments, $R^4$ is halogen, OH, optionally substituted $C_1$-$C_6$ alkyl or optionally substituted $C_1$-$C_6$ alkoxy.

Some exemplary compounds of formula (I) include, 5-(4-morpholinyl)-1-phenyl-1-penten-3-one; 5-(4-morpholinyl)-1-(3,4-dichlorophenyl)-1-penten-3-one; 5-(4-morpholinyl)-1-(3-trifluoromethylpheny 1)-1-penten-3-one; 5-(4-morpholinyl)-1-(2,6-dichlorophenyl)-1-penten-3-one; 5-(4-morpholinyl)-1-(1,3-benzodioxyl-5-yl)-1-penten-3-one; 5-(4-morpholinyl)-1-(4-(methylthio)phenyl)-1-penten-3-one; 5-(4-morpholinyl)-1-(4-(methylsulfonyl)phenyl)-1-penten-3-one; 5-(4-morpholinyl)-1-(4-chlorophenyl)-1-penten-3-one; 5-(4-morpholinyl)-1-(4-cyanophenyl)-1-penten-3-one; 5-methylamino-1-phenyl-1-penten-3-one; 5-dimethylamino-1-(2-ethylphenyl)-1-penten-3-one; 5-(1-piperidino)-1-(2,4-dipropylphenyl)-1-penten-3-one; 5-(1-piperidino)-1-(2,4,6-trimethylphenyl)-1-penten-3-one; 5-(1-pyrrolidino)-1-(4-n-butoxyphenyl)-1-penten-3-one; 5-(1-piperazino)-1-(4-aininophenyl)-1-penten-3-one; 5-(4-ethylpiperazino-1-yl)-1-(4-nitrophenyl)-1-penten-3-one; 5-amino-1-(3-dim ethylaminophenyl)-1-penten-3-one; 5-(4-morpholinyl)-1-(4-hydroxyphenyl)-1-penten-3-one; and 5-(4-morpholinyl)-1-(2-methyl-4-chlorophenyl)-1-penten-3-one.

In some embodiments, the compound of formula (I) is 5-dimethylamino-2-methyl-1-phenyl-1-penten-3-one (COMPOUND 40).

In some embodiments, HIF inhibitor is of structure shown in formula (II):

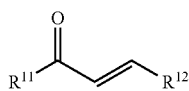

Formula (II)

wherein:
$R^{11}$ is optionally substituted aryl, optionally substituted heteroaryl, optionally substituted cyclyl or optionally substituted heterocyclyl;
$R^{12}$ is optionally substituted aryl or optionally substituted heteroaryl; and
pharmaceutically acceptable salts thereof.

Although, the double bond is shown in the trans configuration, both the cis and trans double bond are amenable to the invention.

$R^{11}$ can be substituted with a substituent selected from the group consisting of halogen, alkyl, alkenyl, alkynyl, alkoxy, aryl, heteroaryl, cyclyl, heterocyclyl, carbonyl (=O), $CF_3$, $NO_2$, $N(R^{13})_2$, CN, OH, $SR^{13}$, $SO_2R^{13}$, and combinations thereof, where each of alkyl, alkenyl, alkynyl, heterocyclyl, heteroaryl, acylcyl or heterocyclyl can be optionally substituted, and wherein $R^{13}$ is independently for each occurrence H, alkyl, alkenyl or alkynyl. In some embodiments, $R^{11}$ is substituted with 1, 2, 3, or 4 substituents. In some embodiments, $R^{11}$ is substituted with OH, alkyl and carbonyl.

In some embodiments, $R^{11}$ is an optionally substituted heterocyclyl. In some embodiments, $R^{11}$ is selected from the group consisting of pyranyl, piperazinyl, pyrrolidinyl, dioxanyl, morpholinyl, tetrahydrofuranyl, each of which cane be optionally substituted with 1 to 4 substituents. In some embomdients, $R^{11}$ is pyrane, e.g., substituted pyrane. In some embodiments, $R^{11}$ is a pyrane, wherein the pyrane is substituted with three substituents. In one embodiment, $R^{11}$ is

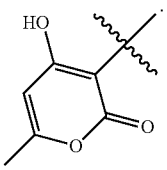 [SMILES: *c1c(O)cc(C)oc1=O]

$R^{12}$ can be substituted with a substituent selected from the group consisting of halogen, alkyl, alkenyl, alkynyl, alkoxy, aryl, heteroaryl, cyclyl, heterocyclyl, $CF_3$, $NO_2$, $N(R^{14})_2$, CN, OH, $SR^{14}$, $SO_2R^{14}$, and combinations thereof, where each of alkyl, alkenyl, alkynyl, heterocyclyl, heteroaryl, acylcyl or heterocyclyl can be optionally substituted, and wherein $R^{14}$ is independently for each occurrence H, alkyl, alkenyl or alkynyl, each of which may be optionally substituted.

In some embodiments, $R^{12}$ is substituted with 1, 2, 3, or 4 substituents. In some embodiments, $R^{12}$ is substituted with OH and alkoxy.

In some embodiments, $R^{12}$ is an optionally substituted aryl. In some embodiments, $R^{12}$ is selected from the group consisting of phenyl, naphthyl, anthracenyl, azulenyl, fluorenyl, indanyl, indenyl, and tetrahydronaphthyl, each of which can be optionally substituted with 1 to 4 substituents.

In some embodiments, $R^{12}$ is

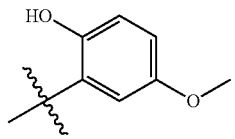

In some embodiments, the compound of formula (II) is 4-hydroxy-3-(3-(2-hydroxy-5-methoxyphenyl)acryloyl)-6-methyl-2H-pyran-2-one (COMPOUND 41).

Compounds of formula (I) and (II) can be synthesized by aldol-condensation of appropriate benzaldehydes and ketones. Synthesis of some exemplary compounds of formula (I) is described, for example in U.S. Pat. No. 4,400,380, contents of which are herein incorporated by reference in their entirety.

In some embodiments, HIF inhibitor is of structure shown in formula (III):

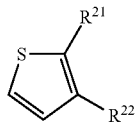

Formula (III)

wherein:

$R^{21}$ is halogen, alkyl, alkenyl, alkynyl, alkoxy, aryl, heteroaryl, cyclyl, heterocyclyl, $CF_3$, $NO_2$, $N(R^{23})_2$, CN, OH, $SR^{23}$, $SO_2R^{23}$, or $C(O)R^{24}$, each of which can be optionally substituted;

$R^{22}$ is alkoxy, halogen, alkyl, alkenyl, alkynyl, alkoxy, aryl, heteroaryl, cyclyl, heterocyclyl, $CF_3$, $NO_2$, $N(R^{25})_2$, CN, OH, $SR^{23}$, or $SO_2R^{23}$, each of which can be optionally substituted;

$R^{23}$ is independently for each occurrence H, alkyl, alkenyl or alkynyl, each of which can be optionally substituted;

$R^{24}$ is alkyl, alkenyl, alkynyl, alkoxy, aryl, heteroaryl, cyclyl or heterocyclyl, each of which can be optionally substituted;

$R^{25}$ is independently for each occurrence alkyl, alkenyl, alkynyl, $N(R^{23})_2$ or $N=R^{26}$, each of which can be optionally substituted;

$R^{26}$ is independently for each occurrence H, alkyl, alkenyl or alkynyl, each of which can be optionally substituted; and pharmaceutically acceptable salts thereof.

In some embodiments, $R^{21}$ is $C(O)R^{24}$.

In some embodiments, $R^{24}$ is an alkyl or alkoxy. In some embodiments, $R^{24}$ is an alkoxy, e.g., $C_1$-$C_6$ alkoxy.

In one embodiment, $R^{24}$ is methoxy.

In some embodiments, $R^{21}$ is $C(O)CH_3$, $C(O)CH_2CH_3$, $C(O)CH_2CH_2CH_3$, $C(O)CH(CH_2)_2$ or $C(O)C(CH_3)_3$.

In some embodiments, $R^{22}$ is $N(R^{25})_2$.

In some embodiments, at least one of $R^{25}$ is not H.

In some embodiments, $R^{25}$ is $N=R^{26}$.

In some further embodiments, $R^{26}$ is a substituted $C_1$-$C_6$ alkyl.

In some embodiments, $R^{26}$ is a $C_1$-$C_6$ alkyl, and which alkyl is substituted with $SO_2R^{23}$.

In some embodiments, $R^{26}$ is a $C_1$-$C_6$ alkyl, and which alkyl is substituted with CN.

In some embodiments, $R^{26}$ is a $C_1$-$C_6$ alkyl, and which alkyl is substituted with both $SO_2R^{23}$ and CN.

In some embodiments, $R^{26}$ is $C(SO_2R^{23})CN$.

In some embodiments, $R^{26}$ is $C(SO_2CH_3)CN$.

In some embodiments, $R^{25}$ is $N=C(SO_2CH_3)CN$.

In one embodiment, the compound of formula (III) is methyl 3-{2-[cyano(methylsulfonyl)methyle]hydrazine]thiophene-2-carboxylate (COMPOUND 76).

In some embodiments, HIF inhibitor is of structure shown in formula (IV):

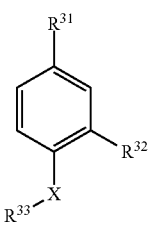

Formula (IV)

wherein:

X is S, O, or NH;

$R^{31}$ and $R^{32}$ are each independently halogen, alkyl, alkenyl, alkynyl, alkoxy, $CF_3$, $NO_2$, $N(R^{34})_2$, CN, OH, $SR^{34}$, or $SO_2R^{34}$, each of which can be optionally substituted $R^{33}$ is alkyl, alkenyl, alkynyl, aryl, heteroaryl, cyclyl, or heterocyclyl, each of which can be optionally substituted;

$R^{34}$ is independently for each occurrence H, alkyl, alkenyl, or alkynyl, each of which can be optionally substituted; and pharmaceutically acceptable salts thereof.

In some embodiments, $R^{31}$ is an optionally substituted $C_1$-$C_6$ alkyl.

In some embodiments, $R^{31}$ is an optionally substituted methyl or ethyl.

In some embodiments, $R^{31}$ is an optionally substituted alkyne.

In some embodiments, $R^{31}$ is an optionally substituted propyne.

In some embodiments, $R^{31}$ is CN.

In some embodiments, $R^{32}$ is $NO_2$ or $N(R^{34})_2$.

In some embodiments, when $R^{32}$ is $N(R^{34})_2$, both $R^{34}$ are H.

In some other embodiments, when $R^{32}$ is $N(R^{34})_2$, at least one of the $R^{34}$ is not H.

In still some other embodiments, when $R^{32}$ is $N(R^{34})_2$, at least one of the $R^{34}$ is a $C_1$-$C_6$ alkyl.

In yet still some other embodiments, $R^{32}$ is a dialkylamine.

In one preferred embodiment, $R^{31}$ is $NO_2$.

In one embodiment, $R^{33}$ is an optionally substituted heterocyclyl. In some embodiments, $R^{33}$ is selected from the group consisting of pyranyl, piperazinyl, pyrrolidinyl, dioxanyl, morpholinyl, and tetrahydrofuranyl, each of which can be optionally substituted.

In some embodiments, $R^{33}$ is an optionally substituted thiopyrane. In some embodiments, $R^{33}$ is a thiopyrane substituted with at least substituent selected from the group consisting of halogen, alkyl, alkenyl, alkynyl, alkoxy, aryl, heteroaryl, cyclyl, heterocyclyl, carbonyl (=O), $CF_3$, $NO_2$, $N(R^{35})_2$, CN, OH, $SR^{35}$, $SO_2R^{35}$, and combinations thereof, where each of alkyl, alkenyl, alkynyl, heterocyclyl, heteroaryl, acylcyl or heterocyclyl can be optionally substituted, and wherein $R^{35}$ is independently for each occurrence H, alkyl, alkenyl or alkynyl, each of which may be optionally substituted.

In some embodiments, $R^{33}$ is a mono, di, or tri substituted thiopyrane.

In some embodiments, $R^{33}$ is 2,3-dihydro-2,2-dimethyl-thiopyran-4-one.

In some embodiments, $R^{33}$ is

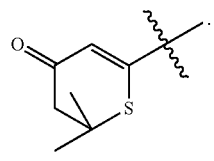

In one embodiment, the compound of formula (IV) is 4-[(2,2-dimethyl-4-oxo-3,4-dihydro-2H-thinn-6-yl)thio]-3-nitrobenzonitrile (COMPOUND 77).

In some embodiments, HIF inhibitor is selected from the group of compounds set forth in Table 1 and combinations thereof.

TABLE 1

| Name | Full Chemical Name | Structure |
|------|-------------------|-----------|
| 20 | 3-(2,5-diethoxyphenyl)-1-(2-thienyl)-2-propen-1-one | 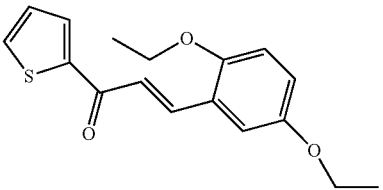 [SMILES: CCOc1ccc(OCC)c(/C=C/C(=O)c2cccs2)c1] |
| 37 | N2-(4-bromo-3-nitrobenzoyl)leucinamide | 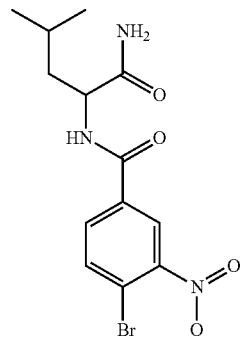 |
| 39 | 2-bromo-N-(2-methoxyphenyl)propanamide | 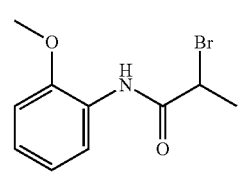 |
| 40 | 5-(dimethylamino)-2-methyl-1-phenyl-1-penten-3-one hydrochloride | 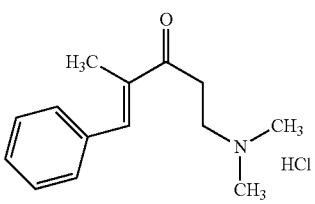 [SMILES: C/C(=C\c1ccccc1)C(=O)CCN(C)C ; Cl] |

TABLE 1-continued

| Name | Full Chemical Name | Structure |
|------|-------------------|-----------|
| 41 | 4-hydroxy-3-[3-(2-hydroxy-5-meoxyphenyl)acryloyl]-6-methyl-2H-pyran-2-one | 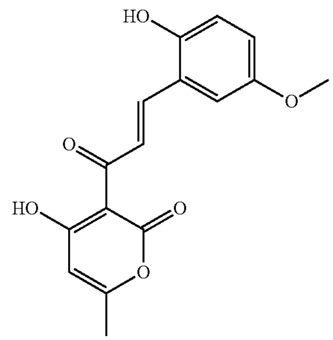 [SMILES: COc1ccc(O)c(/C=C/C(=O)c2c(O)cc(C)oc2=O)c1] |
| 42 | 6-(1,3-dioxo-1H-benzo[de]isoquinolin-2(3H)-yl)-N-hydroxyhexanamide | 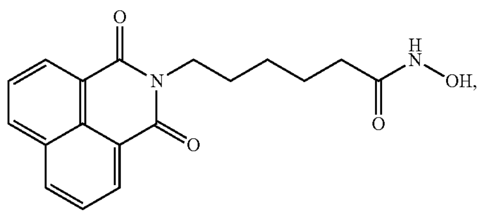 |
| | noscapine | |
| 76 | methyl 3-{2-[cyano(methylsulfonyl)methylene]hydrazino}thiophene-2-carboxylate | 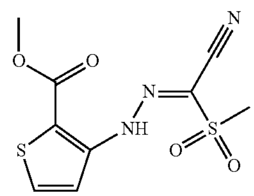 [SMILES: COC(=O)c1sccc1N/N=C(/C#N)S(C)(=O)=O] |
| 77 | 4-[(2,2-dimethyl-4-oxo-3,4-dihydro-2H-thiin-6-yl)thio]-3-nitrobenzonitrile | 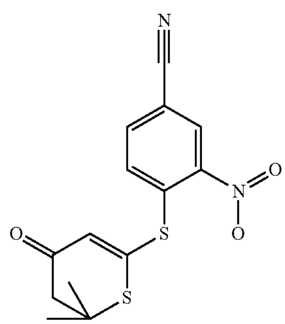 |

Contacting of Cell with HIF Inhibitors

Cells can be contacted with the HIF inhibitor in a cell culture, e.g., in vitro or ex vivo, or administrated to a subject, e.g. in vivo. In some embodiments of the invention, a HIF inhibitor described herein can be administrated to a subject to treat, and/or prevent a HIF-related pathology and/or hypoxia-related pathology.

The term "contacting" or "contact" as used herein in connection with contacting a cell includes subjecting the cell to an appropriate culture media which comprises the indicated HIF inhibitor. Where the cell is in vivo, "contacting" or "contact" includes administering the HIF inhibitor in a pharmaceutical composition to a subject via an appropriate administration route such that the HIF inhibitor contacts the cell in vivo. For in vivo methods, a therapeutically effective amount of a HIF inhibitor described herein can be administered to a subject. Methods of administering compounds to a subject are known in the art and easily available to one of skill in the art.

The term "ex vivo" refers to cells which are removed from a living organism and cultured outside the organism (e.g., in a test tube).

The term "organism" refers to any living entity comprised of at least one cell. A living organism can be as simple as, for example, a single eukaryotic cell or as complex as a mammal, including a human being.

In some embodiments, cell is a tissue where the tissue is associated with disease and neovascularization.

Diseases

There are a variety of diseases in which inhibition of angiogenesis is important, referred to as angiogenic diseases, including but not limited to, inflammatory disorders such as immune and non-immune inflammation, chronic articular rheumatism and psoriasis, disorders associated with inappropriate or inopportune invasion of vessels such as diabetic retinopathy, neovascular glaucoma, restenosis, capillary proliferation in atherosclerotic plaques, and cancer associated disorders, such as solid tumors, solid tumor metastases, angiofibromas, retrolental fibroplasia, hemangiomas and Kaposi sarcoma.

As used herein, the term "angiogenic disease or disorder" includes a disease, disorder, or condition characterized or caused by aberrant or unwanted, e.g., stimulated or suppressed, formation of blood vessels (angiogenesis). Aberrant or unwanted angiogenesis may either cause a particular disease directly or exacerbate an existing pathological condition. Examples of angiogenic diseases include ocular disorders, e.g., diabetic retinopathy, retinopathy of prematurity, corneal graft rejection, retrolental fibroplasia, neovascular glaucoma, rubeosis, retinal neovascularization due to macular degeneration, hypoxia, angiogenesis in the eye associated with infection or surgical intervention, ocular tumors and trachoma, and other abnormal neovascularization conditions of the eye, where neovascularization may lead to blindness; disorders affecting the skin, e.g., psoriasis and pyogenic granuloma; cancer, e.g., carcinomas and sarcomas, where progressive growth is dependent upon the continuous induction of angiogenesis by these tumor cells, lung cancer, brain cancer, kidney cancer, colon cancer, liver cancer, pancreatic cancer, stomach cancer, prostate cancer, breast cancer, ovarian cancer, cervical cancer, melanoma, and metastatic versions of any of the preceding cancers; pediatric disorders, e.g., angiofibroma, and hemophiliac joints; blood vessel diseases such as hemangiomas, and capillary proliferation within atherosclerotic plaques; disorders associated with surgery, e.g., hypertrophic scars, wound granulation and vascular adhesions; and autoimmune diseases such as rheumatoid, immune and degenerative arthritis, where new vessels in the joint may destroy articular cartilage and scleroderma.

The term angiogenic disease also includes diseases characterized by excessive or abnormal stimulation of endothelial cells, including but not limited to intestinal adhesions, Crohn's disease, atherosclerosis, scleroderma, and hypertrophic scars, i.e., keloids; diseases that have angiogenesis as a pathologic consequence such as cat scratch disease (*Rochele ninalia quintosa*) and ulcers (*Helicobacter pylori*). In addition, the angiogenesis inhibitor compounds of the present invention are useful as birth control agents (by virtue of their ability to inhibit the angiogenesis dependent ovulation and establishment of the placenta) and may also be used to reduce bleeding by administration to a subject prior to surgery.

Cancer is a general term for diseases in which abnormal cells divide without control. Cancer cells can invade nearby tissues and can spread through the bloodstream and lymphatic system to other parts of the body. It has been discovered that the administration of an HIF-1 inhibitor to a host, for example a mammal, inhibits or reduces cancer, tumor growth or formation, and the metastasis of tumor cells.

There are several main types of cancer, and the disclosed compositions or emthods can be used to treat any type of cancer. For example, carcinoma is cancer that begins in the skin or in tissues that line or cover internal organs. Sarcoma is cancer that begins in bone, cartilage, fat, muscle, blood vessels, or other connective or supportive tissue. Leukemia is cancer that starts in blood-forming tissue such as the bone marrow, and causes large numbers of abnormal blood cells to be produced and enter the boodstream. Lymphoma is cancer that begins in the cells of the immune system.

When normal cells lose their ability to behave as a specified, controlled and coordinated unit, a tumor is formed. Generally, a solid tumor is an abnormal mass of tissue that usually does not contain cysts or liquid areas (some brain tumors do have cysts and central necrotic areas filled with liquid). A single tumor may even have different populations of cells within it with differing processes that have gone awry. Solid tumors may be benign (not cancerous), or malignant (cancerous). Different types of solid tumors are named for the type of cells that form them. Examples of solid tumors are sarcomas, carcinomas, and lymphomas. Leukemias (cancers of the blood) generally do not form solid tumors. The compositions described herein can be used to reduce, inhibit, or diminish the proliferation of tumor cells, and thereby assist in reducing the size of a tumor. In particular, the disclosed compositions are useful for the treatment of solid tumors or pathologies in areas of hypoxia. Cancers can also have genetic alterations that lead to constitutive HIF expression independently of hypoxia.

Representative cancers that can be treated with the disclosed compositions and methods include, but are not limited to, bladder cancer, breast cancer, colorectal cancer, endometrial cancer, head & neck cancer, leukemia, lung cancer, lymphoma, melanoma, non-small-cell lung cancer, ovarian cancer, prostate cancer, testicular cancer, uterine cancer, cervical cancer, thyroid cancer, gastric cancer, brain stem glioma, cerebellar astrocytoma, cerebral astrocytoma, glioblastoma, ependymoma, Swing's sarcoma family of tumors, germ cell tumor, extracranial cancer, Hodgkin's disease, leukemia, acute lymphoblastic leukemia, acute myeloid leukemia, liver cancer, medulloblastoma, neuroblastoma, brain tumors generally, non-Hodgkin's lymphoma, osteosarcoma, malignant fibrous histiocytoma of bone, retinoblastoma, rhabdomyosarcoma, soft tissue sarcomas generally, supratentorial primitive neuroectodermal and pineal tumors, visual pathway and hypothalamic glioma, Wilms' tumor, acute lymphocytic leukemia, adult acute myeloid leukemia, adult non-Hodgkin's lymphoma, chronic lymphocytic leukemia, chronic myeloid leukemia, esophageal cancer, hairy cell leukemia, kidney cancer, multiple myeloma, oral cancer, pancreatic cancer, primary central nervous system lymphoma, skin cancer, small-cell lung cancer, among others. In some embodiments, the cancer comprises a mutation in VHL gene.

Other exemplary cancers/tumors for treatment with the present invention include VHL−/− cancers, e.g., renal cell carcinomas (RCC), hemangioblastomas (HB) and pheochromocytomas, and islet cell tumors of the pancreas, tumor overexpressing HER2/Neu, e.g., breast cancer, PTEN−/− cancers, e.g., prostate, Glioblastoma multiforme (GBM) and endometrial cancer.

A tumor can be classified as malignant or benign. In both cases, there is an abnormal aggregation and proliferation of cells. In the case of a malignant tumor, these cells behave more aggressively, acquiring properties of increased invasiveness. Ultimately, the tumor cells may even gain the ability to break away from the microscopic environment in which they originated, spread to another area of the body (with a very different environment, not normally conducive to their growth) and continue their rapid growth and division in this new location. This is called metastasis. Once malignant cells have metastasized, achieving cure is more difficult.

Benign tumors have less of a tendency to invade and are less likely to metastasize. Brain tumors spread extensively within the brain but do not usually metastasize outside the brain. Gliomas are very invasive inside the brain, even crossing hemispheres. They do divide in an uncontrolled manner, though. Depending on their location, they can be just as life threatening as malignant lesions. An example of this would be a benign tumor in the brain, which can grow and occupy space within the skull, leading to increased pressure on the brain. The compositions provided herein can be used to treat benign or malignant tumors.

Accordingly, one embodiment provides a method of modulating gene transcription, for example the transcription of VEGF, erythropoietin, glucose transporter-1, glycolytic enzymes, or tyrosine hydroxylase, in a cell, for example a tumor or cancer cell, by contacting the cell with an HIF inhibitor, pharmaceutical salts, prodrugs, or derivatives thereof.

Another embodiment provides a method of modulating gene expression in a tumor cell by contacting the tumor cell with an HIF-1 modulating amount of one or more of the disclosed compounds, compositions, pharmaceutically acceptable salts, derivatives or prodrugs thereof. The modulation of the HIF-1 pathway with the disclosed compounds and compositions can occur at transcriptional, translational and/or post-translational levels. The disclosed compounds can modulate gene transcriptions by binding to HIF-1 and preventing HIF-1 from forming complexes with other molecules including DNA and proteins. For example, the disclosed compounds and compositions can bind to HIF-1 and induce conformational changes that prevent HIF-1 from interacting with its biological targets. Alternatively, the disclosed compounds can bind HIF-1 and form aggresomes or other complexes that sequester HIF-1 or otherwise physically prevent HIF-1 from interacting with other biological molecules. Finally, the disclosed compounds and compositions can inhibit or interfere with the intracellular transport of HIF-1 including, but not limited to, the translocation of HIF-1 from the cytoplasm to the nucleus.

The present invention provides for the treatment diseases or disorders associated with increased or abnormal angiogenesis. Such diseases or disorders include, for example, cancer, solid tumors, metastases, tissues undergoing restenosis (and the like tissues), diabetic retinopathy, vascular restenosis, primary pulmonary hypertension, hereditary hemorrhagic telangiectasis, post-operative adhesion formation, fibrosis, keloids, atherosclerosis and rheumatoid arthritis.

Thus, methods which inhibit angiogenesis in a tissue associated with a disease condition ameliorate symptoms of the disease and, depending upon the disease, can contribute to cure of the disease. In one embodiment, the invention contemplates inhibition of angiogenesis, per se, in a tissue associated with a disease condition. The extent of angiogenesis in a tissue, and therefore the extent of inhibition achieved by the present methods, can be evaluated by a variety of methods.

Thus, in one embodiment, a tissue to be treated is an inflamed tissue and the angiogenesis to be inhibited is inflamed tissue angiogenesis where there is neovascularization of inflamed tissue. This particular method includes inhibition of angiogenesis in arthritic tissues, such as in a patient with chronic articular rheumatism, in immune or non-immune inflamed tissues, in psoriatic tissue, and the like.

In another embodiment, a tissue to be treated is a retinal tissue of a patient suffering from a retinal disease such as diabetic retinopathy or neovascular glaucoma and the angiogenesis to be inhibited is retinal tissue angiogenesis where there is neovascularization of retinal tissue. The present invention may also be used to treat or prevent macular degeneration.

In an additional embodiment, a tissue to be treated is a tumor tissue of a patient with a solid tumor, a metastases, a skin cancer, a breast cancer, a hemangioma or angiofibroma and the like cancer, and the angiogenesis to be inhibited is tumor tissue angiogenesis where there is neovascularization of a tumor tissue. Typical solid tumor tissues treatable by the present methods include lung, prostate, pancreas, renal, breast, colon, laryngeal, ovarian, and the like tissues. Inhibition of tumor tissue angiogenesis is a particularly preferred embodiment because of the important role neovascularization plays in tumor growth. In the absence of neovascularization of tumor tissue, the tumor tissue does not obtain the required nutrients, slows in growth, ceases additional growth, regresses and ultimately becomes necrotic resulting in killing of the tumor.

Stated in other words, the present invention provides for a method of inhibiting tumor neovascularization by inhibiting tumor angiogenesis according to the present methods. Similarly, the invention provides a method of inhibiting tumor growth by practicing the angiogenesis-inhibiting methods.

The methods are also particularly effective against the formation of metastases because (1) their formation requires vascularization of a primary tumor so that the metastatic cancer cells can exit the primary tumor and (2) their establishment in a secondary site requires neovascularization to support growth of the metastases.

Examples of tissue associated with disease and neovascularization that will benefit from inhibition of angiogenesis include cancer, rheumatoid arthritis, ocular diseases such as diabetic retinopathy, inflammatory diseases, restenosis, and the like. Where the growth of new blood vessels is required to support growth of a deleterious tissue, inhibition of angiogenesis reduces the blood supply to the tissue and thereby contributes to reduction in tissue mass based on blood supply requirements. Particularly preferred examples include growth of tumors where neovascularization is a continual requirement in order that the tumor grow beyond a few millimeters in thickness, and for the establishment of solid tumor metastases.

Insofar as the present methods apply to inhibition of tumor neovascularization, the methods can also apply to inhibition of tumor tissue growth, to inhibition of tumor metastases formation, and to regression of established tumors.

Restenosis is a process of smooth muscle cell (SMC) migration and proliferation into the tissue at the site of percutaneous transluminal coronary angioplasty which hampers the success of angioplasty. The migration and proliferation of SMC's during restenosis can be considered a process of angiogenesis which is inhibited by the present methods. Therefore, the invention also contemplates inhibition of restenosis by inhibiting angiogenesis according to the present methods in a patient following angioplasty procedures. For inhibition of restenosis, the compound is typically administered after the angioplasty procedure because the coronary vessel wall is at risk of restenosis, typically for from about 2 to about 28 days, and more typically for about the first 14 days following the procedure.

The present method for inhibiting angiogenesis in a tissue associated with a disease condition, and therefore for also practicing the methods for treatment of angiogenesis-related diseases, comprises contacting a tissue in which angiogenesis is occurring, or is at risk for occurring, with a therapeutically effective amount of a composition comprising an HIF inhibitory compound.

In some embodiments, the angiogenic disease or disorder is a solid tumor, solid tumor metastasis, or cancer.

In some embodiments, the cancer is renal cell, colon, breast, prostate, glioblastoma multiforme, or endometrial.

In some embodiments, the administering is conducted in conjunction with chemotherapy.

In someembodiments, the angiogenic disease or disorder is retinopathy, diabetic retinopathy, or macular degeneration.

In some embodiments, the administering comprises intravenous, transdermal, intrasynovial, intramuscular, or oral administration.

In some embodiments, the angiogenic disease or disorder is arthritis or rheumatoid arthritis.

Pharmaceutical Compositions

For administration to a subject, the HIF inhibitors can be provided in pharmaceutically acceptable compositions. The pharmaceutically acceptable compostions comprise a therapeutically-effective amount of one or more HIF inhibitors desccribed herein, formulated together with one or more pharmaceutically acceptable carriers (additives) and/or diluents. As described in detail below, the pharmaceutical compositions of the present invention can be specially formulated for administration in solid, liquid or gel form, including those adapted for the following: (1) oral administration, for example, drenches (aqueous or non-aqueous solutions or suspensions), lozenges, dragees, capsules, pills, tablets (e.g., those targeted for buccal, sublingual, and systemic absorption), boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) transmucosally; or (9) nasally. Additionally HIF inhibitors can be implanted into a patient or injected using a drug delivery system. See, for example, Urquhart, et al., Ann. Rev. Pharmacol. Toxicol. 24: 199-236 (1984); Lewis, ed. "Controlled Release of Pesticides and Pharmaceuticals" (Plenum Press, New York, 1981); U.S. Pat. No. 3,773,919; and U.S. Pat. No. 35 3,270,960. Examples of dosage forms include, but are not limited to: tablets; caplets; capsules, such as hard gelatin capsules and soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquids such as suspensions (e.g., aqueous or non-aqueous liquid suspensions, oil-in-water emulsions, or water-in-oil liquid emulsions), solutions, and elixirs; and sterile solids (e.g., crystalline or amorphous solids) that can be reconstituted to provide liquid dosage forms.

As used here, the term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used here, the term "pharmaceutically-acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alchols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein. In some embodiments, the carrier inhibits the degradation of HIF inhibitor present in the pharmaceutical composition.

Additionally, the HIF inhibitiors can be delivered using lipid- or polymer-based nanoparticles. See for example Allen, T. M., Cullis, P. R. Drug delivery systems: entering themainstream. Science. 303(5665): 1818-22 (2004).

The amount of HIF inhibitor which can be combined with a carrier material to produce a single dosage form will generally be that amount of the HIF inhibito which produces a therapeutic effect. Generally out of one hundred percent, this amount will range from about 0.1% to 99% of HIF inhibitor, preferably from about 5% to about 70%, most preferably from 10% to about 30%.

The phrase "therapeutically-effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment. For example, an amount of a compound administered to a subject that is sufficient to produce a statistically significant, measurable change in at least one symptom of an angiogenic disease or disorder. Determination of a therapeutically effective amount is well within the capability of those skilled in the art. Generally, a therapeutically effective amount can vary with the subject's history, age, condition, sex, as well as the severity and type of the medical condition in the subject, and administration of other pharmaceutically active agents.

In reference to cancer or pathologies related to unregulated cell division and/or lack of programmed cell death, a therapeutically effective amount refers to that amount which has the effect of (1) reducing the size of a tumor, (2) inhibiting (that is, slowing to some extent, preferably stopping) aberrant cell division, for example cancer cell division, (3) preventing or reducing the local invasion and distant metastasis of cancer cells, (4) relieving to some extent (or, preferably, eliminating) one or more symptoms associated with a pathology related to or caused in part by unregulated or aberrant cellular division, including for example, cancer, (5) prevention of the formation of cancer by application of the compound (like sun screen to protect against cancer), and/or (6) to prevent the chain of events downstream of an initial ischemic condition which leads to the pathology.

As used herein, the term "administer" refers to the placement of an HIF inhibitor into a subject by a method or route which results in at least partial localization of the HIF inhibitor at a desired site such that desired effect is produced. A compound or composition described herein can be administered by any appropriate route known in the art including, but not limited to, oral or parenteral routes, including intravenous, intramuscular, subcutaneous, transdermal, airway (aerosol), pulmonary, nasal, rectal, and topical (including buccal and sublingual) administration.

Exemplary modes of administration include, but are not limited to, injection, infusion, instillation, inhalation, or ingestion. "Injection" includes, without limitation, intravenous, intramuscular, intraarterial, intrathecal, intraventricular, intracapsular, intraorbital, intracardiac, intradermal, intraperitoneal, intratracheal, subcutaneous, subcuticular, intraarticular, sub capsular, subarachnoid, intraspinal, intracerebro spinal, and intrasternal injection and infusion. In preferred embodiments, the compositions are administered by intravenous infusion or injection.

By "treatment", "prevention" or "amelioration" of a disease or disorder is meant delaying or preventing the onset of such a disease or disorder, reversing, alleviating, ameliorating, inhibiting, slowing down or stopping the progression, aggravation or deterioration the progression or severity of a condition associated with such a disease or disorder. The term "treatment" of a disease also includes providing relief from the symptoms or side-effects of the disease (including palliative treatment). With regard to cancer, these terms simply mean that the life expectancy of an individual affected with a cancer will be increased or that one or more of the symptoms of the disease will be reduced. In one embodiment, the symptoms of a disease or disorder are alleviated by at least 5%, at least 10%, at least 20%, at least 30%, at least 40%, or at least 50%.

In methods of treatment described herein, the administration of HIF inhibitor can be for either "prophylactic" or "therapeutic" purpose. When provided prophylactically, the HIF inhibitor is provided in advance of any symptom. The prophylactic administration of the HIF inhibitor serves to prevent or inhibit any angiogenesis at a site. When provided therapeutically, the HIF inhibitor is provided at (or after) the onset of a symptom or indication of angiogenesis. Thus, HIF inhibitor can be provided either prior to the anticipated angiogenesis at a site or after the angiogenesis has begun at a site.

Toxicity and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compositions that exhibit large therapeutic indices, are preferred.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized.

The therapeutically effective dose can be estimated initially from cell culture assays. A dose may be formulated in animal models to achieve a circulating plasma concentration range that includes the IC50 (i.e., the concentration of the therapeutic which achieves a half-maximal inhibition of symptoms) as determined in cell culture. Levels in plasma may be measured, for example, by high performance liquid chromatography. The effects of any particular dosage can be monitored by a suitable bioassay.

The dosage may be determined by a physician and adjusted, as necessary, to suit observed effects of the treatment. Generally, the compositions are administered so that HIF inhibitor is given at a dose from 1 µg/kg to 150 mg/kg, 1 µg/kg to 100 mg/kg, 1 µg/kg to 50 mg/kg, 1 µg/kg to 20 mg/kg, 1 µg/kg to 10 mg/kg, 1 µg/kg to 1 mg/kg, 100 µg/kg to 100 mg/kg, 100 µg/kg to 50 mg/kg, 100 µg/kg to 20 mg/kg, 100 µg/kg to 10 mg/kg, 100 µg/kg to 1 mg/kg, 1 mg/kg to 100 mg/kg, 1 mg/kg to 50 mg/kg, 1 mg/kg to 20 mg/kg, 1 mg/kg to 10 mg/kg, 10 mg/kg to 100 mg/kg, 10 mg/kg to 50 mg/kg, 10 mg/kg to 20 mg/kg, or 0.01 pg/kg to 1 mg/kg. It is to be understood that ranges given here include all intermediate ranges, for example, the range 1 mg/kg to 10 mg/kg includes 1 mg/kg to 2 mg/kg, 1 mg/kg to 3 mg/kg, 1 mg/kg to 4 mg/kg, 1 mg/kg to 5 mg/kg, 1 mg/kg to 6 mg/kg, 1 mg/kg to 7 mg/kg, 1 mg/kg to 8 mg/kg, 1 mg/kg to 9 mg/kg, 2 mg/kg to 10 mg/kg, 3 mg/kg to 10 mg/kg, 4 mg/kg to 10 mg/kg, 5 mg/kg to 10 mg/kg, 6 mg/kg to 10 mg/kg, 7 mg/kg to 10 mg/kg, 8 mg/kg to 10 mg/kg, 9 mg/kg to 10 mg/kg, and the like. It is to be further understood that the ranges intermediate to the given above are also within the scope of this invention, for example, the range 1 mg/kg to 10 mg/kg includes dose ranges such as 2 mg/kg to 8 mg/kg, 3 mg/kg to 7 mg/kg, 4 mg/kg to 6 mg/kg, and the like. With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment or make other alteration to treatment regimen. The dosing schedule can vary from once a week to daily depending on a number of clinical factors, such as the subject's sensitivity to the polypeptides. The desired dose can be administered at one time or divided into subdoses, e.g., 2-4 subdoses and administered over a period of time, e.g., at appropriate intervals through the day or other appropriate schedule. Such sub-doses can be administered as unit dosage forms. In some embodiments, administration is chronic, e.g., one or more doses daily over a period of weeks or months. Examples of dosing schedules are administration daily, twice daily, three times daily or four or more times daily over a period of 1 week, 2 weeks, 3 weeks, 4 weeks, 1 month, 2 months, 3 months, 4 months, 5 months, or 6 months or more.

Oral Dosage Forms

Pharmaceutical HIF inhibitor compositions of the disclosure that are suitable for oral administration can be presented as discrete dosage forms, such as, but not limited to, tablets (including without limitation scored or coated tablets), pills, caplets, capsules, chewable tablets, powder packets, cachets, troches, wafers, aerosol sprays, or liquids, such as but not limited to, syrups, elixirs, solutions or suspensions in an aqueous liquid, a non-aqueous liquid, an oil-in-water emulsion, or a water-in-oil emulsion. Such compositions contain a predetermined amount of the pharmaceutically acceptable salt of the disclosed compounds, and may be prepared by methods of pharmacy well known to those skilled in the art. See generally, Remington's Pharmaceutical Sciences, 18th ed., Mack Publishing, Easton, Pa. (1990).

Typical oral dosage forms of the compositions of the disclosure are prepared by combining the pharmaceutically acceptable salt of disclosed compounds in an intimate admixture with at least one excipient according to conventional pharmaceutical compounding techniques. Excipients can take a wide variety of forms depending on the form of the composition desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, microcrystalline cellulose, kaolin, diluents, granulating agents, lubricants, binders, and disintegrating agents. Due to their ease of administration, tablets and capsules represent the most advantageous solid oral dosage unit forms, in which case solid pharmaceutical excipients are used. If desired, tablets can be coated by standard aqueous or nonaqueous techniques. These dosage forms can be prepared by any of the methods of pharmacy. In general, pharmaceutical compositions and dosage forms are prepared by uniformly and intimately admixing the active ingredient(s) with liquid carriers, finely divided solid carriers, or both, and then shaping the product into the desired presentation if necessary.

For example, a tablet can be prepared by compression or molding. Compressed tablets can be prepared by compressing in a suitable machine the active ingredient(s) in a free-flowing form, such as a powder or granules, optionally mixed with one or more excipients. Molded tablets can be made by molding in a suitable machine a mixture of the powdered compound moistened with an inert liquid diluent. Examples of excipients that can be used in oral dosage forms of the disclosure include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Suitable forms of microcrystalline cellulose include, but are not limited to, the materials sold as AVICEL-PH-101, AVICEL-PH-103 AVICEL RC-581, and AVICEL-PH-105 (available from FMC Corporation, American Viscose Division, Avicel Sales, Marcus Hook, Pa., U.S.A.), and mixtures thereof. An exemplary suitable binder is a mixture of microcrystalline cellulose and sodium carboxymethyl cellulose sold as AVICEL RC-581. Suitable anhydrous or low moisture excipients or additives include AVICEL-PH-103TM and Starch 1500 LM.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions of the disclosure is typically present in from about 50 to about 99 weight percent of the pharmaceutical composition or dosage form.

Disintegrants are used in the compositions of the disclosure to provide tablets that disintegrate when exposed to an aqueous environment. Tablets that contain too much disintegrant may swell, crack, or disintegrate in storage, while those that contain too little may be insufficient for disintegration to occur and may thus alter the rate and extent of release of the active ingredient(s) from the dosage form. Thus, a sufficient amount of disintegrant that is neither too little nor too much to detrimentally alter the release of the active ingredient(s) should be used to form solid oral dosage forms of the disclosure. The amount of disintegrant used varies based upon the type of formulation and mode of administration, and is readily discernible to those of ordinary skill in the art. Typical pharmaceutical compositions comprise from about 0.5 to about 15 weight percent of disintegrant, preferably from about 1 to about 5 weight percent of disintegrant.

Disintegrants that can be used to form pharmaceutical compositions and dosage forms of the disclosure include, but are not limited to, agar, alginic acid, calcium carbonate, microcrystalline cellulose, croscarmellose sodium, crospovidone, polacrilin potassium, sodium starch glycolate, potato or tapioca starch, other starches, pre-gelatinized starch, clays, other algins, other celluloses, gums, and mixtures thereof.

Lubricants that can be used to form pharmaceutical compositions and dosage forms of the disclosure include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL® 200, manufactured by W. R. Grace Co. of Baltimore, Md.), a coagulated aerosol of synthetic silica (marketed by Degussa Co. of Piano, Tex.), CAB-O-SIL® (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

This disclosure further encompasses lactose-free pharmaceutical compositions and dosage forms, wherein such compositions preferably contain little, if any, lactose or other mono- or di-saccharides. As used herein, the term "lactose-free" means that the amount of lactose present, if any, is insufficient to substantially increase the degradation rate of an active ingredient.

Lactose-free compositions of the disclosure can comprise excipients which are well known in the art and are listed in the USP (XXI)/NF (XVI), which is incorporated herein by reference. In general, lactose-free compositions comprise a pharmaceutically acceptable salt of an HIF inhibitor, a binder/filler, and a lubricant in pharmaceutically compatible and pharmaceutically acceptable amounts. Preferred lactose-free dosage forms comprise a pharmaceutically acceptable salt of the disclosed compounds, microcrystalline cellulose, pre-gelatinized starch, and magnesium stearate.

This disclosure further encompasses anhydrous pharmaceutical compositions and dosage forms comprising the disclosed compounds as active ingredients, since water can facilitate the degradation of some compounds. For example, the addition of water (e.g., 5%) is widely accepted in the pharmaceutical arts as a means of simulating long-term storage in order to determine characteristics such as shelf life or the stability of formulations over time. See, e.g., Jens T. Carstensen, Drug Stability: Principles & Practice, 379-80 (2nd ed., Marcel Dekker, NY, N.Y.: 1995). Water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms of the disclosure can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials) with or without desiccants, blister packs, and strip packs.

For oral administration, the dosage should contain at least at least 0.1% of HIF inhibitor. The percentage of HIF inhibitor in these compositions may, of course, be varied and may conveniently be between about 2% to about 60% of the weight of the unit. The amount of HIF inhibitor in such therapeutically useful compositions is such that a suitable dosage will be obtained. Preferred compositions according to the present invention are prepared so that an oral dosage unit contains between about 1 and 250 mg of HIF inhibitor.

Controlled and Delayed Release Dosage Forms

Pharmaceutically acceptable salts of the disclosed HIF inhibitor compounds can be administered by controlled- or delayed-release means. Controlled-release pharmaceutical products have a common goal of improving drug therapy over that achieved by their non-controlled release counterparts. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. Kim, Cherng-ju, Controlled Release Dosage Form Design, 2 (Technomic Publishing, Lancaster, Pa.: 2000).

Conventional dosage forms generally provide rapid or immediate drug release from the formulation. Depending on the pharmacology and pharmacokinetics of the drug, use of conventional dosage forms can lead to wide fluctuations in the concentrations of the drug in a patient's blood and other tissues. These fluctuations can impact a number of parameters, such as dose frequency, onset of action, duration of efficacy, maintenance of therapeutic blood levels, toxicity, side effects, and the like. Advantageously, controlled-release formulations can be used to control a drug's onset of action, duration of action, plasma levels within the therapeutic window, and peak blood levels. In particular, controlled- or extended-release dosage forms or formulations can be used to ensure that the maximum effectiveness of a drug is achieved while minimizing potential adverse effects and safety concerns, which can occur both from under-dosing a drug (i.e., going below the minimum therapeutic levels) as well as exceeding the toxicity level for the drug.

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, ionic strength, osmotic pressure, temperature, enzymes, water, and other physiological conditions or compounds.

A variety of known controlled- or extended-release dosage forms, formulations, and devices can be adapted for use with the salts and compositions of the disclosure. Examples include, but are not limited to, those described in U.S. Pat. Nos. 3,845,770; 3,916,899; 3,536,809; 3,598,123; 4,008,719; 5674,533; 5,059,595; 5,591,767; 5,120,548; 5,073,543; 5,639,476; 5,354,556; 5,733,566; and 6,365,185 B1; each of which is incorporated herein by reference. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), multilayer coatings, microparticles, liposomes, or microspheres or a combination thereof to provide the desired release profile in varying proportions. Additionally, ion exchange materials can be used to prepare immobilized, adsorbed salt forms of the disclosed compounds and thus effect controlled delivery of the drug. Examples of specific anion exchangers include, but are not limited to, Duolite® A568 and Duolite® AP143 (Rohm&Haas, Spring House, Pa. USA).

One embodiment of the disclosure encompasses a unit dosage form that includes a pharmaceutically acceptable salt of the disclosed compounds (e.g., a sodium, potassium, or lithium salt), or a polymorph, solvate, hydrate, dehydrate, co-crystal, anhydrous, or amorphous form thereof, and one or more pharmaceutically acceptable excipients or diluents, wherein the pharmaceutical composition or dosage form is formulated for controlled-release. Specific dosage forms utilize an osmotic drug delivery system.

A particular and well-known osmotic drug delivery system is referred to as OROS® (Alza Corporation, Mountain View, Calif. USA). This technology can readily be adapted for the delivery of compounds and compositions of the disclosure. Various aspects of the technology are disclosed in U.S. Pat. Nos. 6,375,978 B1; 6,368,626 B1; 6,342,249 B1; 6,333,050 B2; 6,287,295 B1; 6,283,953 B1; 6,270,787 B1; 6,245,357 B1; and 6,132,420; each of which is incorporated herein by reference. Specific adaptations of OROS® that can be used to administer compounds and compositions of the disclosure include, but are not limited to, the OROS® Push-Pull™, Delayed Push-Pull™, Multi-Layer Push-Pull™, and Push-Stick™ Systems, all of which are well known. See, e.g. worldwide website alza.com. Additional OROS® systems that can be used for the controlled oral delivery of compounds and compositions of the disclosure include OROS®-CT and L-OROS®; see, Delivery Times, vol. 11, issue II (Alza Corporation).

Conventional OROS® oral dosage forms are made by compressing a drug powder (e.g., a HIF inhibitor salt) into a hard tablet, coating the tablet with cellulose derivatives to form a semi-permeable membrane, and then drilling an orifice in the coating (e.g., with a laser). Kim, Cherng-ju, Controlled Release Dosage Form Design, 231-238 (Technomic Publishing, Lancaster, Pa.: 2000). The advantage of such dosage forms is that the delivery rate of the drug is not influenced by physiological or experimental conditions. Even a drug with a pH-dependent solubility can be delivered at a constant rate regardless of the pH of the delivery medium. But because these advantages are provided by a build-up of osmotic pressure within the dosage form after administration, conventional OROS® drug delivery systems cannot be used to effectively delivery drugs with low water solubility. Because HIF inhibitor salts and complexes of this disclosure (e.g., an HIF inhibitor sodium salt) may be far more soluble in water than an HIF inhibitor itself, they may be well suited for osmotic-based delivery to patients. This disclosure does, however, encompass the incorporation of an HIF inhibitor, and non-salt isomers and isomeric mixtures thereof, into OROS® dosage forms.

A specific dosage form of the HIF inhibitor compositions of the disclosure includes: a wall defining a cavity, the wall having an exit orifice formed or formable therein and at least a portion of the wall being semipermeable; an expandable layer located within the cavity remote from the exit orifice and in fluid communication with the semipermeable portion of the wall; a dry or substantially dry state drug layer located within the cavity adjacent the exit orifice and in direct or indirect contacting relationsnip witn tne expandable layer; and a flow-promoting layer interposed between the inner surface of the wall and at least the external surface of the drug layer located within the cavity, wherein the drug layer includes a salt of an HIF inhibitor, or a polymorph, solvate, hydrate, dehydrate, co-crystal, anhydrous, or amorphous form thereof. See U.S. Pat. No. 6,368,626, the entirety of which is incorporated herein by reference.

Another specific dosage form of the disclosure includes: a wall defining a cavity, the wall having an exit orifice formed or formable therein and at least a portion of the wall being semipermeable; an expandable layer located within the cavity remote from the exit orifice and in fluid communication with the semipermeable portion of the wall; a drug layer located within the cavity adjacent the exit orifice and in direct or indirect contacting relationship with the expandable layer; the drug layer comprising a liquid, active agent formulation absorbed in porous particles, the porous particles being adapted to resist compaction forces sufficient to form a compacted drug layer without significant exudation of the liquid, active agent formulation, the dosage form optionally having a placebo layer between the exit orifice and the drug layer, wherein the active agent formulation comprises a salt of a HIF inhibitor, or a polymorph, solvate, hydrate, dehydrate, co-crystal, anhydrous, or amorphous form thereof. See U.S. Pat. No. 6,342,249, the entirety of which is incorporated herein by reference.

In some embodiments, the HIF inhibitory compound is administered to a subject by sustained release or in pulses. Pulse therapy is not a form of discontinuous administration of the same amount of a composition over time, but comprises administration of the same dose of the composition at a reduced frequency or administration of reduced doses. Sustained release or pulse administration are particularly preferred when the angiogenesis is associated with tumor growth as it leads to regression of blood vessels feeding the tumor and ultimately to regression of the tumor itself. Each pulse dose can be reduced and the total amount of drug administered over the course of treatment to the patient is minimized.

Individual pulses can be delivered to the patient continuously over a period of several hours, such as about 2, 4, 6, 8, 10, 12, 14 or 16 hours, or several days, such as 2, 3, 4, 5, 6, or 7 days, preferably from about 1 hour to about 24 hours and more preferably from about 3 hours to about 9 hours.

The interval between pulses or the interval of no delivery is greater than 24 hours and preferably greater than 48 hours, and can be for even longer such as for 3, 4, 5, 6, 7, 8, 9 or 10 days, two, three or four weeks or even longer. As the results achieved may be surprising, the interval between pulses, when necessary, can be determined by one of ordinary skill in the art. Often, the interval between pulses can be calculated by administering another dose of the composition when the composition or the active component of the composition is no longer detectable in the patient prior to delivery of the next pulse. Intervals can also be calculated from the in vivo half-life of the composition. Intervals may be calculated as greater than the in vivo half-life, or 2, 3, 4, 5 and even 10 times greater the composition half-life.

The number of pulses in a single therapeutic regimen may be as little as two, but is typically from about 5 to 10, 10 to 20, 15 to 30 or more. In fact, patients can receive drugs for life according to the methods of this invention without the problems and inconveniences associated with current therapies. Compositions can be administered by most any means, but are preferable delivered to the patient as an injection (e.g. intravenous, subcutaneous, intraarterial), infusion or instillation. Various methods and apparatus for pulsing compositions by infusion or other forms of delivery to the patient are disclosed in U.S. Pat. Nos. 4,747,825; 4,723,958; 4,948,592; 4,965,251 and 5,403,590.

In a certain embodiments, the interval between pulses is 24 hours or greater.

In a certain embodiments, the plurality of pulses comprises from about 5 to about 10 pulses.

In a certain embodiments, the plurality of pulses comprises greater than 20 pulses.

In a certain embodiments, the interval is from 1 to about 7 days.

Sustained release may be accomplished by means of an osmotic pump. In some embodiments HIF inhibitor is administered over a period of several days, such as 2, 3, 4, 5, 6 or 7 days.

Parenteral Dosage Forms

Parenteral dosage forms can be administered to patients by various routes, including, but not limited to, subcutaneous, intravenous (including bolus injection), intramuscular, and intraarterial. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. In addition, controlled-release parenteral dosage forms can be prepared for administration of a patient, including, but not limited to, administration DUROS®-type dosage forms, and dose-dumping.

Suitable vehicles that can be used to provide parenteral dosage forms of the disclosure are well known to those skilled in the art. Examples include, without limitation: sterile water; water for injection USP; saline solution; glucose solution; aqueous vehicles such as but not limited to, sodium chloride injection, Ringer's injection, dextrose Injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate.

Compounds that alter or modify the solubility of a pharmaceutically acceptable salt of a HIF inhibitor disclosed herein can also be incorporated into the parenteral dosage forms of the disclosure, including conventional and controlled-release parenteral dosage forms.

Topical, Transdermal and Mucosal Dosage Forms

Topical dosage forms of the disclosure include, but are not limited to, creams, lotions, ointments, gels, shampoos, sprays, aerosols, solutions, emulsions, and other forms known to one of skill in the art. See, e.g., Remington's Pharmaceutical Sciences, 18th ed., Mack Publishing, Easton, Pa. (1990); and Introduction to Pharmaceutical Dosage Forms, 4th ed., Lea & Febiger, Philadelphia, Pa. (1985). For non-sprayable topical dosage forms, viscous to semi-solid or solid forms comprising a carrier or one or more excipients compatible with topical application and having a dynamic viscosity preferably greater than water are typically employed. Suitable formulations include, without limitation, solutions, suspensions, emulsions, creams, ointments, powders, liniments, salves, and the like, which are, if desired, sterilized or mixed with auxiliary agents (e.g., preservatives, stabilizers, wetting agents, buffers, or salts) for influencing various properties, such as, for example, osmotic pressure. Other suitable topical dosage forms include sprayable aerosol preparations wherein the active ingredient, preferably in combination with a solid or liquid inert carrier, is packaged in a mixture with a pressurized volatile (e.g., a gaseous propellant, such as freon), or in a squeeze bottle. Moisturizers or humectants can also be added to pharmaceutical compositions and dosage forms if desired. Examples of such additional ingredients are well known in the art. See, e.g., Remington's Pharmaceutical Sciences, 18.sup.th Ed., Mack Publishing, Easton, Pa. (1990).

Transdermal and mucosal dosage forms of the HlF inhibitor compositions of the disclosure include, but are not limited to, ophthalmic solutions, patches, sprays, aerosols, creams, lotions, suppositories, ointments, gels, solutions, emulsions, suspensions, or other forms known to one of skill in the art. See, e.g., Remington's Pharmaceutical Sciences, 18th Ed., Mack Publishing, Easton, Pa. (1990); and Introduction to Pharmaceutical Dosage Forms, 4th Ed., Lea & Febiger, Philadelphia, Pa. (1985). Dosage forms suitable for treating mucosal tissues within the oral cavity can be formulated as mouthwashes, as oral gels, or as buccal patches. Additional transdermal dosage forms include "reservoir type" or "matrix type" patches, which can be applied to the skin and worn for a specific period of time to permit the penetration of a desired amount of active ingredient.

Examples of transdermal dosage forms and methods of administration that can be used to administer the active ingredient(s) of the disclosure include, but are not limited to, those disclosed in U.S. Pat. Nos. 4,624,665; 4,655,767; 4,687,481; 4,797,284; 4,810,499; 4,834,978; 4,877,618; 4,880,633; 4,917,895; 4,927,687; 4,956,171; 5,035,894; 5,091,186; 5,163,899; 5,232,702; 5,234,690; 5,273,755; 5,273,756; 5,308,625; 5,356,632; 5,358,715; 5,372,579; 5,421,816; 5,466,465; 5,494,680; 5,505,958; 5,554,381; 5,560,922; 5,585,111; 5,656,285; 5,667,798; 5,698,217; 5,741,511; 5,747,783; 5,770,219; 5,814,599; 5,817,332; 5,833,647; 5,879,322; and 5,906,830, each of which are incorporated herein by reference in their entirety.

Suitable excipients (e.g., carriers and diluents) and other materials that can be used to provide transdermal and mucosal dosage forms encompassed by this disclosure are well known to those skilled in the pharmaceutical arts, and depend on the particular tissue or organ to which a given pharmaceutical composition or dosage form will be applied. With that fact in mind, typical excipients include, but are not limited to water, acetone, ethanol, ethylene glycol, propylene glycol, butane-1,3-diol, isopropyl myristate, isopropyl palmitate, mineral oil, and mixtures thereof, to form dosage forms that are non-toxic and pharmaceutically acceptable.

Depending on the specific tissue to be treated, additional components may be used prior to, in conjunction with, or subsequent to treatment with an HIF inhibitor of the disclosure. For example, penetration enhancers can be used to assist in delivering the active ingredients to or across the tissue. Suitable penetration enhancers include, but are not limited to: acetone; various alcohols such as ethanol, oleyl, an tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as TWEEN 80 (polysorbate 80) and SPAN 60 (sorbitan monostearate).

The pH of a pharmaceutical composition or dosage form, or of the tissue to which the pharmaceutical composition or dosage form is applied, may also be adjusted to improve delivery of the active ingredient(s). Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of the active ingredient(s) so as to improve delivery. In this regard, stearates can serve as a lipid vehicle for the formulation, as an emulsifying agent or surfactant, and as a delivery-enhancing or penetration-enhancing agent. Different hydrates, dehydrates, co-crystals, solvates, polymorphs, anhydrous, or amorphous forms of the pharmaceutically acceptable salt of an HIF inhibitor can be used to further adjust the properties of the resulting composition.

Aerosols

HIF inhibitors can be administered directly to the airways in the form of an aerosol. For use as aerosols, HIF inhibitors in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

HIF inhibitors can also be administered directly to the airways in the form of a dry powder. For use as a dry powder, HIF inhibitors can be administered by use of an inhaler. Exemplary inhalers include metered dose inhalers and dry powdered inhalers. A metered dose inhaler or "MDI" is a pressure resistant canister or container filled with a product such as a pharmaceutical composition dissolved in a liquefied propellant or micronized particles suspended in a liquefied propellant. The correct dosage of the composition is delivered to the patient. A dry powder inhaler is a system operable with a source of pressurized air to produce dry powder particles of a pharmaceutical composition that is compacted into a very small volume. For inhalation, the system has a plurality of chambers or blisters each containing a single dose of the pharmaceutical composition and a select element for releasing a single dose.

Suitable powder compositions include, by way of illustration, powdered preparations of HIF inhibitors thoroughly intermixed with lactose, or other inert powders acceptable for intrabronchial administration. The powder compositions can be administered via an aerosol dispenser or encased in a breakable capsule which may be inserted by the patient into a device that punctures the capsule and blows the powder out in a steady stream suitable for inhalation. The compositions can include propellants, surfactants, and co-solvents and may be filled into conventional aerosol containers that are closed by a suitable metering valve.

Kits

In some aspects, the invention provides kits or articles of manufacture that include a suitable container containing an HIF inhibitor, e.g., HIF inhibitor pharmaceutical composition. In addition to the formulation, the kit can include informational material. The informational material can be descriptive, instructional, marketing or other material that relates to the methods described herein and/or the use of the compound for the methods described herein. For example, the informational material describes methods for administering the formulation to a subject. The kit can also include a delivery device.

In some embodiments, the informational material can include instructions to administer the formulation in a suitable manner, e.g., in a suitable dose, dosage form, or mode of administration (e.g., a dose, dosage form, or mode of administration described herein). In some embodiments, the informational material can include instructions for identifying a suitable subject, e.g., a human, e.g., an adult human. In some embodiments, the informational material indicates the use of the HIF inhibitor contained in the kit, e.g., for treating conditions assisted by the inhibition or potentiation of angiogenesis, and the like conditions disclosed herein. In some embodiments, the informational material indicates that the HIF inhibitor pharmaceutical composition can be used for treating an angiogenic disorder or disease. In some embodiments, the informational material indicates that the HIF inhibitor pharmaceutical composition can be used for reducing inflammation.

The informational material of the kits is not limited in its form. In many cases, the informational material, e.g., instructions, is provided in printed matter, e.g., a printed text, drawing, and/or photograph, e.g., a label or printed sheet. However, the informational material can also be provided in other formats, such as Braille, computer readable material, video recording, or audio recording. In another embodiment, the informational material of the kit is a link or contact information, e.g., a physical address, email address, hyperlink, website, or telephone number, where a user of the kit can obtain substantive information about the formulation and/or its use in the methods described herein. Of course, the informational material can also be provided in any combination of formats.

In some embodiments the individual components of the formulation can be provided in one container. Alternatively, it can be desirable to provide the components of the formulation separately in two or more containers, e.g., one container for a HIF inhibitor, and at least another for a carrier compound. The different components can be combined, e.g., according to instructions provided with the kit. The components can be combined according to a method described herein, e.g., to prepare and administer a pharmaceutical composition.

In addition to the formulation, the composition of the kit can include other ingredients, such as a solvent or buffer, a stabilizer or a preservative, and/or a second agent for treating a condition or disorder described herein. Alternatively, the other ingredients can be included in the kit, but in different compositions or containers than the formulation. In such embodiments, the kit can include instructions for admixing the formulation and the other ingredients, or for using the oligonucleotide together with the other ingredients.

The HIF inhibitor formulations can be provided in any form, e.g., liquid, dried or lyophilized form. It is preferred that the formulation be substantially pure and/or sterile. When the formulation is provided in a liquid solution, the liquid solution preferably is an aqueous solution, with a sterile aqueous solution being preferred. When the formulation is provided as a dried form, reconstitution generally is by the addition of a suitable solvent. The solvent, e.g., sterile water or buffer, can optionally be provided in the kit.

In some embodiments, the kit contains separate containers, dividers or compartments for the formulation and informational material. For example, the formulation can be contained in a bottle, vial, or syringe, and the informational material can be contained in a plastic sleeve or packet. In other embodiments, the separate elements of the kit are contained within a single, undivided container. For example, the formulation is contained in a bottle, vial or syringe that has attached thereto the informational material in the form of a label.

In some embodiments, the kit includes a plurality, e.g., a pack, of individual containers, each containing one or more unit dosage forms of the formulation. For example, the kit includes a plurality of syringes, ampules, foil packets, or blister packs, each containing a single unit dose of the formulation. The containers of the kits can be air tight and/or waterproof.

Combinations

The HIF inhibitors can be administered to a subject in combination with a pharmaceutically active agent. Exemplary pharmaceutically active compound include, but are not limited to, those found in *Harrison's Principles of Internal Medicine,* 13$^{th}$ Edition, Eds. T. R. Harrison et al. McGraw-Hill N.Y., NY; Physicians Desk Reference, 50$^{th}$ Edition, 1997, Oradell New Jersey, Medical Economics Co.; Pharmacological Basis of Therapeutics, 8$^{th}$ Edition, Goodman and Gilman, 1990; United States Pharmacopeia, The National Formulary, USP XII NF XVII, 1990; current edition of Goodman and Oilman's *The Pharmacological Basis of Therapeutics*; and current edition of The Merck Index, the complete contents of all of which are incorporated herein by reference.

In some embodiments, the pharmaceutically active agent includes, but is not limited to, antibody, antibiotic, anti-inflammatory, anti-oxidant, analgesic, radioisotope, noscapine, paclitaxel, nocodazole, Busulfan (MYLERAN® or BUSULFEX IV®), lomustine (CCNU) (CEENU LOMUSTINE®), caboplatinum, cisplatinum, cyclophosphamide (CYTOXAN®), daunorubicin, Dacarbazine (DTIC), 5-fluorouracil (5-FU), fludarabine (FLUDARA®), Hydroxyurea (DROXIA®, HYDREA®), idarubicin (IDAMYCIN PFS®, IDAMYCIN®), ifosfamide (IFEX®), methotrexrate, mithramycin, mitomycin (MUTAMYCIN®), mitoxantrone (NOVANTRONE®), nitrogen mustard, vinblastine (VELBAN®), vincristine (ONCOVIN®, VINCASAR PSF®), CPT-11, cladribine (LEUSTATIN®, CLADRIBINE NOVAPLUS®), vinorebine tartrate (NAVELBIN®), rituximab (RITUXAN®), STI-571, docetaxel (TAXOTERE®, DOCEFREZ®), temozolomide (TEMODAR®), topotecan (HYCAMTIN®), capecitaine (XELODA®), ibritumomab tiuxetan (ZEVALIN®), and combinations thereof.

In some embodiments, the pharmaceutically active agent is an angiogenesis inhibiting factor. Exemplary angiogenesis inhibiting factors include, but not are limited to, platelet factor 4, thrombospondin-1, tissue inhibitors of metalloproteases (TIMP1 and TIMP2) prolactin (16-Kd fragment), angiostatin (38-Kd fragment of plasminogen), bFGF soluble receptor, transforming growth factor-beta, interferon alfa, inhibitors of VEGF receptor tyrosine kinase (RTK) activity, recombinant humanized antibody to vascular endothelial cell growth factor (e.g., Avastin), placental proliferin-related protein, PTK787, endostatin, PF4, TNP-470, caplostatin, lodamine, thrombospondin and the like.

In some embodiments, the pharmaceutically active agent is a chemotherapeutic agent. Such a therapy is particularly useful in situations in which the mammal to be treated has a large preexisting tumor mass which is well vascularized. The chemotherapeutic agent serves to reduce the tumor mass and the DBP-maf prevents or inhibits neovascularization within or surrounding the tumor mass. The chemotherapeutic agent may also be administered at lower doses than normally used and at such doses may act as an antiangiogenic agent. Examples of chemotherapeutic agents include adriamycin, taxol, fluorouricil, melphalan, cisplatin, oxaliplatin, alpha interferon, vincristine, vinblastine, angioinhibins, TNP-470, pentosan poiysulfate, platelet factor 4, angiostatin, LM-609, SU-101, CM-101, Techgalan, thalidomide, SP-PG, gancyclovir, and the like. Other chemotherapeutic agents include alkylating agents such as nitrogen mustards including mechloethamine, melphan, chlorambucil, cyclophosphamide and ifosfamide, nitrosoureas including carmustine, lomustine, semustine and streptozocin; alkyl sulfonates including busulfan (MYLERAN® or BUSULFEX IV®); triazines including dicarbazine; ethyenimines including thiotepa and hexamethylmelamine; folic acid analogues including methotrexate; pyrimidine analogues including 5-fluorouracil (5-FU), cytosine arabinoside; purine analogues including 6-mercaptopurine and 6-thioguanine; antitumour antibiotics including actinomycin D; the anthracyclines including doxorubicin, bleomycin, mitomycin C and methramycin; hormones and hormone antagonists including tamoxifen and cortiosteroids and miscellaneous agents including cisplatin and brequinar.

In some embodiments, the pharmaceutically active agent is a HIF-1 inhibitor. Exemplary HIF-1 inhibitors include those described in Int. Pub. No. WO09/043093 and U.S. Pat. Pub. No. 2008/0226622, contents of both of which are herein incorporated by reference in their entirety.

The HIF inhibitor and the pharmaceutically active agent can be administrated to the subject in the same pharmaceutical composition or in different pharmaceutical compositions (at the same time or at different times). When administrated at different times, compound of the invention and the pharmaceutically active agent can be administered within 5 minutes, 10 minutes, 20 minutes, 60 minutes, 2 hours, 3 hours, 4, hours, 8 hours, 12 hours, 24 hours of administration of the other. When HIF inhibitor and the pharmaceutically active agent are administered in different pharmaceutical compositions, routes of administration can be different. For example, an HIF inhibitor can be administered by any appropriate route known in the art including, but not limited to oral or parenteral routes, including intravenous, intramuscular, subcutaneous, transdermal, airway (aerosol), pulmonary, nasal, rectal, and topical (including buccal and sublingual) administration, and pharmaceutically active agent is administration by a different route, e.g. a route commonly used in the art for administration of said pharmaceutically active agent.

In some embodiments, the invention contemplates the practice of the methods described herein in conjunction with other therapies such as conventional chemotherapy directed against solid tumors and for control of establishment of metastases as well as other forms of antiangiogenesis therapy. The administration of angiogenesis inhibitor is typically conducted during or after chemotherapy, although it is preferably to inhibit angiogenesis after a regimen of chemotherapy at times where the tumor tissue will be responding to the toxic assault by inducing angiogenesis to recover by the provision of a blood supply and nutrients to the tumor tissue. In addition, it is preferred to administer the angiogenesis inhibition methods after surgery where solid tumors have been removed as a prophylaxis against metastases.

Discussion

To gain further insights into the regulation of HIF activity, the inventors devised a cell-based assay to screen for small molecule HIF inhibitor compounds in VHL-deficient RCC cells and identified four small molecules that, in multiple cancer cell lines, selectively inhibited translation of the HIF-2a message in an mTOR independent manner. The inventors discovered that the HIF-2a 5'-UTR is necessary and sufficient to confer compound sensitivity. Deletion analysis of the 5'-UTR revealed that the minimal region necessary and sufficient for compound efficacy mapped to a newly identified IRE within the 5'-UTR of the HIF-2a mRNA (Sanchez et al., 2007). Mutations within the conserved IRE motif abolished the effect of the compounds, as did knocking down the expression of the IRE binding protein, Iron Regulatory Protein 1 (IRP1). Electrophoretic mobility shift assays showed that the compounds directly promoted IRP1 binding to the HIF-2a IRE. Furthermore, results shown herein demonstrate that hypoxia de-repressed HIF-2a translation by impairing the IRP 1/IRE interaction. These data explain for the first time how the HIF-2a message is spared the mTOR-mediated global translational repression induced by hypoxia. The compounds identified in this work will therefore serve as chemical genetic tools by which to further study the role of IRP1 and IRP2 on translation and tumor progression.

The inventors employed a cell-based assay specific for HIF activity and identified several novel small molecule HIF inhibitors that decreased both constitutive and hypoxia-induced HIF-2a protein expression. Used as chemical genetics probes, these HIF inhibitors highlighted IRE as key regulatory components of HIF signaling pathway. Our data suggest that HIF-2a IRE preferentially engages IRP1 as a regulator of its translational response to hypoxia. IRP1 is a hypoxia sensitive regulator of HIF translation akin to EGLN- and FIH-mediated regulation of its stability and transcriptional activity, respectively. Hypoxia therefore coordinately upregulates HIF translation, stability and transcriptional activity (FIG. 7f).

These inhibitors show that IRP1 is clearly amenable to pharmacologic manipulation and may therefore be useful target for future anti-HIF drug development. Compounds that inhibit HIF activity were reported before (see Table 2). HIF translation features prominently among the mechanisms of pharmacologic HIF manipulation, indicating that it is clearly amenable to drug development. It is possible that several of these compounds may inhibit HIF translation in an IRP1-dependent manner, a hypothesis that can be tested directly.

TABLE 2

Published HIF inhibitor compounds.

| Name | Method of Identification | Mechanism of HIF inhibtion | Biological Activities | Ref. |
|---|---|---|---|---|
| Chemotin | HTS-p300-HIF interaction | p300-HIF interaction | Tumor suppression | (Kung et al., 2004) |
| Topotecan | HTS- HRE-glioma cell line | HIF translation | VEGF decrease | (Rapisarda et al., 2002) |
| 103D5R | HTS-HRE-glioma cell line | HIF translation | Decreases HIF tested target genes | (Tan et al., 2005) |
| YC-1 | Direct Testing | HIF protein levels | VEGF decrease/tumor suppression | (Yeo et al., 2003) |
| GL331 | Direct testing | Protein levels | Inhibits HUVEC proliferation | (Chang et al., 2003) |
| Geldanamycin | Direct testing | HSP90 inhibitor-HIF half life | Tumor suppression | (Mabjeesh et al., 2002) |
| 2-ME2 | Direct testing | Post-transcriptional | Inhibits HUVEC proliferation | (Mabjeesh et al., 2003) |
| Bisphenol | Direct testing | HIF degradation | No report | (Kubo et al., 2004) |
| Berberine | Direct testing | HIF degradation | No report | (Lin et al., 2004) |
| PX-478 | Thioredoxin inhibitor | Unknown | Tumor suppression | (Welsh et al., 2004) |
| PX-12 | Thioredoxin inhibitor | Unknown | Tumor suppression | (Welsh et al., 2004) |

Hypoxia globally decreases translational initiation through inhibition of mTOR and phosphorylation of the translation elongation factor eIF2. Hypoxia inhibits mTOR phosphorylation and leads to hypophosphorylation of its substrates 4E-BP1 and p70S6K. These events prevent formation of the eIF4F complex and phosphorylation of ribosomal protein S6, respectively (Arsham et al., 2003; Brugarolas et al., 2004; Liu et al., 2006). Hypoxia also phosphorylates eIF2a (Blais et al., 1994), which decreases translational elongation (Koumenis et al., 2002). These effects of hypoxia on translation may explain why tumor cells select for increased mTOR activity through various mutations in the PI3-K/PKB signaling pathway—to maintain translation during conditions of chronic hypoxia.

Figure 3A:
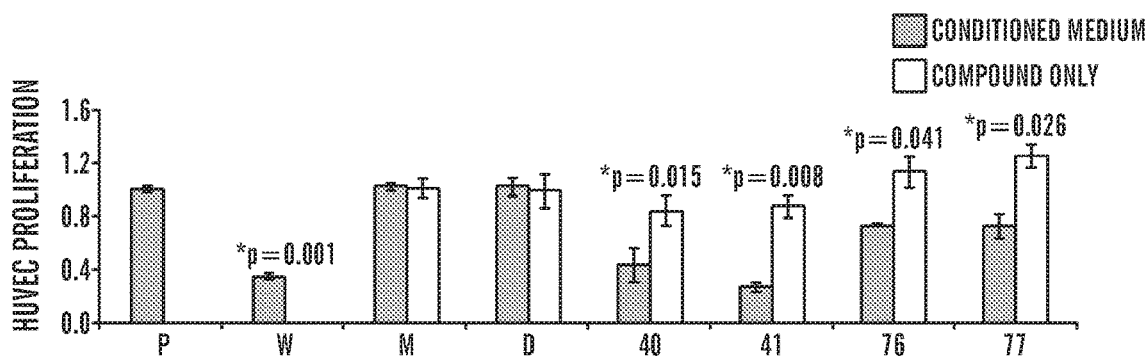
FIGS. 3A-3G show the effect of compounds on the angiogenic activity of renal carcinoma cell supernatant, the expression of endogenous HIF-2a protein, its cognate mRNA and HIF-downstream target genes. For all panels: P, PRC3; W, WT8; V, pTV; R, pTR, or parental 786-O cells treated with M, medium only; D, DMSO; or compounds, as indicated. HUVEC proliferation, ELISA, qRT-PCR and luciferase measurements were performed in triplicate. Error bars represent standard error of the mean (SEM).

In order to cope with cellular hypoxia and other forms of environmental stress, cells need to efficiently translate the appropriate stress response genes during conditions in which global mRNA translation is attenuated. In fact, the translation of several transcripts, including FGF2, VEGFB, ATF4, Glut-1, Angiopoietin-like 4, Hypoxia-inducible Gene 2, ribosomal protein S6 and many others is increased during hypoxia (Blais et al., 1994; Thomas and Johannes, 2007). It has been proposed that this selective translational specificity is mediated largely through the 5'- and 3'-UTR (Spicher et al., 1 998; Wouters et al., 2005). HIF-2a, a critical factor for repair of the hypoxic insult, conforms to this physiologic mechanism. The proposed model for how the IRP1 system works on the HIF-2a message is shown (FIG. 7G. Under normoxic conditions, IRP1 binds to the IRE of the HIF-2a 5'-UTR to repress basal translation of the HIF-2a message. This repression is roughly an order of magnitude, as the raw luciferase activity of 786-O polyclonal cells expressing the mutant IRE is 10 fold higher than those expressing the wild-type. However, this repression can be even further enhanced, as evidenced when cells are treated with iron chelators or the compounds identified here in the chemical genetic screen. Hypoxia de-represses IRE activity by mediating IRP1 post-translational changes that attenuate its binding to mRNA. This explains the observed increase in HIF-2a expression in hypoxic VHL-/- cells (FIG. 3d). The data address previously conflicting reports regarding IRE binding of IRP1 and IRP2 under hypoxic conditions (Hanson et al., 1999; Toth et al., 1999) and demonstrate that IRP1 serves as a direct or indirect hypoxia sensor.

It has been reported that hypoxia stabilizes IRP2 and enhances its binding to ferritin-L IRE. The inventors were not able to document detectable IRP2 activity on HIF-2a IRE under conditions of normoxia, hypoxia or iron depletion. In contrast, binding of IRP2 to Ferritin-L IRE was clearly detectable under the same experimental conditions and slightly enhanced by hypoxia, compound 76 and DFO. These data demonstrate that there is a differential affinity of IRP2 for slightly different IREs and that IRP 1 is the primary regulator of HIF-2a IRE. The role of IRP2 on the HIF-2a IRE it is likely indirect, since IRP2 knock down enhanced IRP1 binding to HIF-2a IRE, as detected in biochemical and reporter assays. It is of course possible that differential IRP affinity for specific IREs changes within different cell/tissue contexts. Formal comparison of such affinities in representative cell lines as well as testing in IRP-/- cell lines will help answer these questions.

Figure 14A:
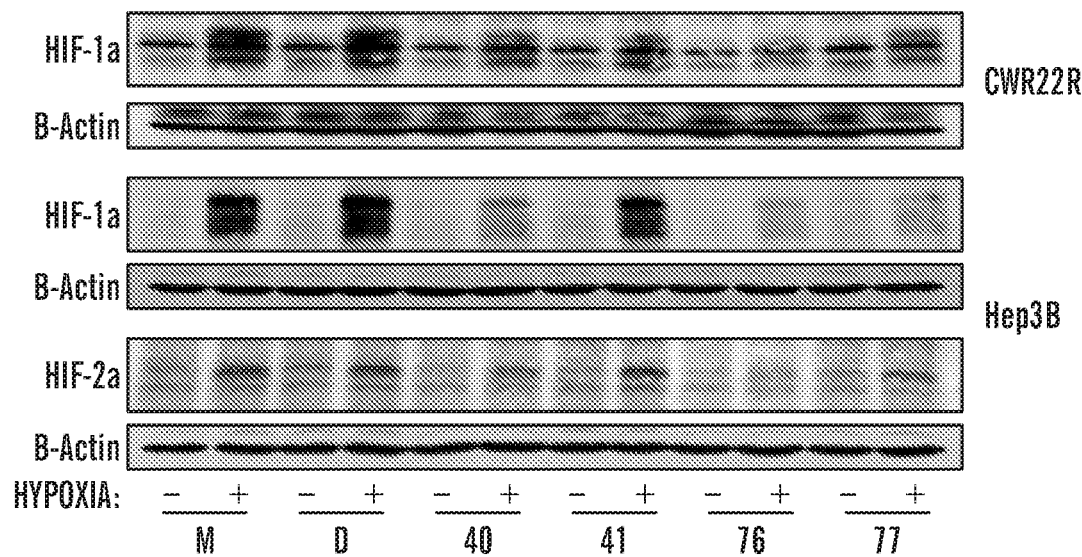
FIGS. 14A-14C show compounds 40, 41, 76 and 77 do not affect putative IRE in HIF-1a 5'-UTR yet indirectly suppress hypoxic induction of HIF-1a in multiple cell types.
Figure 14B:
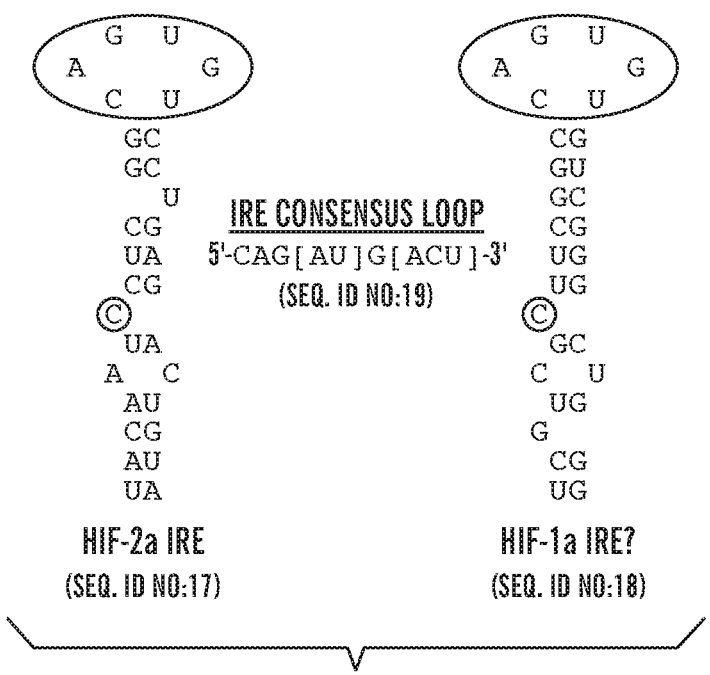

The compounds described herein also decreased the expression of HIF-1a in cell lines that express this isoform (see FIG. 14A). Scanning the 5'-UTR of the HIF-1a message suggests a putative, non-canonical consensus IRE loop (FIG. 14b). However, the inventors found that this near-consensus IRE did not confer sensitivity to the compound or responded to hypoxia (FIG. 14B). Knocking down the expression of HIF-2a in VHL-deficient UMRC2 cells did not affect the ability of the compounds to decrease expression of HIF-1a (data not shown). The inventors therefore demonstrated that the effect of the compounds on HIF-1a is indirect and independent of HIF-2a. The lack of a functional IRE in HIF-1a represents a clear dichotomy between the two HIF isoforms that allows their translation to be controlled by a different regulatory system.

To gain insight into the signaling target(s) of the compounds, the inventors utilized the Connectivity Map and linked the gene expression signature of three of these compounds to the molecular signature of $PGJ_2$, a member of the arachidonic acid signaling cascade that appears to have anti-inflammatory and potentially anti-neoplastic activities. The inventors experimentally validated this hypothesis by showing that addition of exogenous $PGJ_2$ to cells in culture inhibited translation of the HIF2a mRNA. Moreover, the inventors demonstrated that this function of $PGJ_2$ is mediated through enhanced IRP1 binding to the Iron Responsive Element (IRE) within the HIF2a 5'-UTR. This is the first report of an endogenous cellular metabolite that regulates HIF2a translation through the IRE mechanism.

Activation of the arachidonic acid cascade generates prostaglandin H2 ($PGH_2$) through the activity of COX-1 and COX-2 synthases. $PGH_2$ provides a substrate for the generation of lipid mediator products of different nature and function, catalyzed by specific synthases. One of the well-characterized metabolites of $PGH_2$ is prostaglandin E2 ($PGE_2$), which, in comparison to the results presented herein, has the ability to upregulate HIF1a activity (Liu et al., 2002; Fukuda et al., 2003). The mechanism for this might involve activation of the EGF receptor by $PGE_2$ and activation of the c-Src and ERK/MAPK pathway (Pai et al., 2002; Wang et al., 2005). In addition, $PGE_2$ promotes colonic adenomatous polyposis through PPAR delta activation (Wang et al., 2004; Sonoshita et al., 2001). It therefore appears that $PGE_2$ is the "pro-inflammatory" and "pro-proliferative" component of arachidonic acid signaling while $PGJ_2$ is part of the "anti-inflammatory" and "anti-proliferative" component.

The clinical use of COX inhibitors for prevention of APC and treatment of arthritis and other inflammatory conditions have met with increased frequency of coronary artery disease associated morbidity and mortality. A plausible explanation for this down side of COX inhibition may be that these agents restrict production of $PGD_2/PGJ_2$ products along with the pro-inflammatory prostaglandins. This may aggravate site-specific inflammation and such a process has been linked to progression of atheromatosis.

$PGJ_2$ has been recently reported to inhibit global translation of cellular proteins through binding to and inactivation of eIF4A and sequestration of TRAF2 into stress granules (Kim et al., 2007). Here the inventors employed lower concentrations of $PGJ_2$ than those associated with the formation of stress granules and inhibition of eIF4A. Moreover, the inventors did not observe any effect of $PGJ_2$ on global translation in $^{35}$S-methione labeling pulse chase experiments or polysome analysis. Apart from possible cell type differences that can account for these discrepancies, it is more likely that the first response of cells to moderate levels of $PGJ_2$ concentrations is to selectively down-regulate HIF2a mRNA translation, while higher doses are associated with a global reduction of protein translation.

Up regulation of IRP1 binding activity by $PGJ_2$ is likely to promote iron uptake and availability in sites of inflammation. Iron is essential for oxidative burst of PMNs and macrophages, and is therefore important for maintenance of the local inflammatory and immune responses (Murakawa et al., 1987; Fleming, 2008). The availability of $PGJ_2$ may be a mechanism by which the end of inflammatory phase (by inhibiting translation of the HIF2a message) is linked to restoration of iron stores in resident inflammatory and immune cells.

In cells, the majority of IRP1 functions as a cytosolic aconitase, catalyzing the conversion of citrate to isocitrate. Reduction of cellular iron stores causes a conformational change in the iron-sulfur cluster (ISC) of IRP1 protein that concomitantly decreases its aconitase activity and promotes its binding to IREs (Pantopoulos, 2004). The results presented herein indicate that conditions that change the intracellular levels of PGJ2 have the ability to similarly promote the RNA binding activity of IRP1. The exact mechanism by which PGJ2 signals to IRP1 will be the object of further studies. Currently, we have shown (Supplementary FIG. 4) that PGJ2 does not act as an iron chelator and therefore it is likely to affect IRP1 through a novel, ISC-dependent or independent mechanism.

In summary, the inventors have identified and demonstrated four small molecule inhibitors of HIF translation that work via an Iron-Responsive Element (IRE) located within the 5'-UTR of the HIF-2a message. IRP1 binding to the HIF-2a IRE represses its translation during normoxia in several cell lines. Hypoxia, however, impairs the IRP 1/IRE interaction, allowing for efficient translation of the message when translation is globally attenuated through the mTOR and eIF2a pathways. The relative abundance of HIF inhibitor compounds identified over the past few years that affect translation strongly suggests that translation is an exquisitely sensitive and pharmacologically amenable component of HIF regulation, and the compounds identified demonstrated herein in will certainly be useful molecules for inhibition of HIF2a express in methods of treatment as well as chemical genetic tools by which to further study the biochemical mechanism of how IRP1 affects hypoxia/HIF/VHL signaling.

Additionally, the inventors have provided evidence for a novel connection between cancer and inflammation in which programs involved in the resolution of inflammation may modify tumor vascularization. This connection can contribute to new strategies of cancer chemoprevention.

Furthermore, the compounds disclosed herein or derivatives thereof will be useful as clinically useful agents that can be used for treatment of cancers such as renal cell carcinoma as well as prevalent solid tumors of the prostate, breast and colon.

Definitions

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

Other than in the operating examples, or where otherwise indicated, all numbers expressing quantities of ingredients or reaction conditions used herein should be understood as modified in all instances by the term "about." The term "about" when used in connection with percentages may mean ±1%.

The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description.

Although methods and materials similar or equivalent to those described herein can be used in the practice or testing of this disclosure, suitable methods and materials are described below. The term "comprises" means "includes."

The abbreviation, "e.g." is derived from the Latin exempli gratia, and is used herein to indicate a non-limiting example. Thus, the abbreviation "e.g." is synonymous with the term "for example."

The terms "decrease", "reduced", "reduction", "decrease" or "inhibit" are all used herein generally to mean a decrease by a statistically significant amount. However, for avoidance of doubt, "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g. absent level as compared to a reference sample), or any decrease between 10-100% as compared to a reference level.

The terms "increased","increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "statistically significant" or "significantly" refers to statistical significance and generally means a two standard deviation (2SD) below normal, or lower, concentration of the marker. The term refers to statistical evidence that there is a difference. It is defined as the probability of making a decision to reject the null hypothesis when the null hypothesis is actually true. The decision is often made using the p-value.

As used herein, the term "HIF-related pathology" means a pathology that is caused in part, either directly or indirectly by altered HIF-1, HIF-2 or HIF-3 biological activity; altered HIF-1, HIF-2 or HIF-3 signal transduction; or altered HIF-1, HIF-2 or HIF-3 expression or availability.

As used herein, the term "hypoxia-related pathology" means a pathology that is caused in part, either directly or indirectly, by conditions of below typical physiological amounts of oxygen. The term "hypoxia-related pathology" also means a pathology caused by a non-hypoxic stimulus. The term includes cancer, cancer metastasis, ischemia, stroke and related conditions, diseases, or syndromes.

HIF- or hypoxia-related pathologies include inflammation and angiogenic disorders or disesases. Exemplary HIF- or hypoxia related pathologies include, but are not limited to, cancer, a solid tumor, solid tumor metastasis, inflammation, ascites, cirrhosis, pleural effusion, cerebral oedema, pulmonary oedema, cardiovascular disease, ischemic heart disease, chronic obstructive pulmonary diseasecerebrovascular disorders, macular degeneration, retinopathy, proliferative retinopathy, diabetic reinopathy, retinopathy of prematurity, psoriasis, endometriosis, arthritis such as rheumatoid arthiritis, primary pulmonary hypertension, vascul; ar rstenosis, hereditary hemorrhagic telangiectasis, post-operative adhesion formation, fibrosis, keloids, artherosclerosis, or combinations thereof.

The term "inhibiting" as used here in relation to HIF means preventing, reducing, or otherwise ameliorating HIF production or activation. For example, depending on the circumstances, including nature of the condition being treated, it may not be necessary that inhibition should mean completely blocking HIF production or activation, but reducing HIF production or activation to a sufficient degree to enable the desired effect to be achieved.

The term "prodrug" refers to an agent that is converted into a biologically active form in vivo. Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis. Harper, N.J. (1962). Drug Latentiation in Jucker, ed. Progress in Drug Research, 4:221-294; Morozowich et al. (1977). Application of Physical Organic Principles to Prodrug Design in E. B. Roche ed. Design of Biopharmaceutical Properties through Prodrugs and Analogs, APhA; Acad. Pharm. Sci.; E. B. Roche, ed. (1977). Bioreversible Carriers in Drug in Drug Design, Theory and Application, APhA; H. Bundgaard, ed. (1985) Design of Prodrugs, Elsevier; Wang et al. (1999) Prodrug approaches to the improved delivery of peptide drug, Curr. Pharm. Design. 5(4):265-287; Pauletti et al. (1997). Improvement in peptide bioavailability: Peptidomimetics and Prodrug Strategies, Adv. Drug. Delivery Rev. 27:235-256; Mizen et al. (1998). The Use of Esters as Prodrugs tor Oral Delivery of β-Lactam antibiotics, Pharm. Biotech. 11:345-365; Gaignault et al. (1996). Designing Prodrugs and Bioprecursors I. Carrier Prodrugs, Pract. Med. Chem. 671-696; M. Asgharnejad (2000). Improving Oral Drug Transport Via Prodrugs, in G. L. Amidon, P. I. Lee and E. M. Topp, Eds., Transport Processes in Pharmaceutical Systems, Marcell Dekker, p. 185-218; Balant et al. (1990) Prodrugs for the improvement of drug absorption via different routes of administration, Eur. J. Drug Metah. Pharmacokinet, 15(2): 143-53; Balimane and Sinko (1999). Involvement of multiple transporters in the oral absorption of nucleoside analogues, Adv. Drug Delivery Rev., 39(1-3):183-209; Browne (1997). Fosphenytoin (Cerebyx), Clin. Neuropharmacol. 20(1): 1-12; Bundgaard (1979). Bioreversible derivatization of drugs-principle and applicability to improve the therapeutic effects of drugs, Arch. Pharm. Chemi. 86(1): 1-39; H. Bundgaard, ed. (1985) Design of Prodrugs, New York: Elsevier; Fleisher et al. (1996). Improved oral drug delivery: solubility limitations overcome by the use of prodrugs, Adv. Drug Delivery Rev. 19(2): 115-130; Fleisher et al. (1985). Design of prodrugs for improved gastrointestinal absorption by intestinal enzyme targeting, Methods Enzymol. 112: 360-81; Farquhar D, et al. (1983). Biologically Reversible Phosphate-Protective Groups, J. Pharm. Sci., 72(3): 324-325; Han, H. K. et al. (2000). Targeted prodrug design to optimize drug delivery, AAPS PharmSci., 2(1): E6; Sadzuka Y. (2000). Effective prodrug liposome and conversion to active metabolite, Curr. Drug Metab., 1(1):31-48; D. M. Lambert (2000) Rationale and applications of lipids as prodrug carriers, Eur. J. Pharm. Sci., 11 Suppl 2:S15-27; Wang, W. et al. (1999) Prodrug approaches to the improved delivery of peptide drugs. Curr. Pharm. Des., 5(4):265-87.

As used herein, the term "topically active agents" refers to compositions of the present disclosure that elicit pharmacological responses at the site of application (contact in a topical application) to a host.

As used herein, the term "topically" refers to application of the compositions of the present disclosure to the surface of the skin and mucosal cells and tissues.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments, the subject is a mammal, e.g., a primate, e.g., a human. The terms, "patient" and "subject" are used interchangeably herein.

Preferably, the subject is a mammal. The mammal can be a human, non-human primate, mouse, rat, dog, cat, horse, or cow, but are not limited to these examples. Mammals other than humans can be advantageously used as subjects that represent animal models of HIF or hypoxia related pathologies. In addition, the methods described herein can be used to treat domesticated animals and/or pets. A subject can be male or female. A subject can be one who has been previously diagnosed with or identified as suffering from or having a HIF or hypoxia related pathology, one or more complications related to a HIF or hypoxia related pathology, and optionally, but need not have already undergone treatment for such a HIF or hypoxia related pathology.

In some embodiments, the methods of the invention further comprise selecting a subject in need of treatment of an angiogenic disease or disorder.

In some embodiments, the methods of the invention further comprise selecting a subject in need of inhibiting angiogenesis.

In some embodiments, the methods of the invention further comprise selecting a subject in need of reducing inflammation.

For simplicity, chemical moieties are defined and referred to throughout can be univalent chemical moieties (e.g., alkyl, aryl, etc.) or multivalent moieties under the appropriate structural circumstances clear to those skilled in the art. For example, an "alkyl" moiety can be referred to a monovalent radical (e.g. $CH_3$—$CH_2$—), or in other instances, a bivalent linking moiety can be "alkyl," in which case those skilled in the art will understand the alkyl to be a divalent radical (e.g., —$CH_2$—$CH_2$—), which is equivalent to the term "alkylene." Similarly, in circumstances in which divalent moieties are required and are stated as being "alkoxy", "alkylamino", "aryloxy", "alkylthio", "aryl", "heteroaryl", "heterocyclic", "alkyl" "alkenyl", "alkynyl", "aliphatic", or "cycloalkyl", those skilled in the art will understand that the terms "alkoxy", "alkylamino", "aryloxy", "alkylthio", "aryl", "heteroaryl", "heterocyclic", "alkyl", "alkenyl", "alkynyl", "aliphatic", or "cycloalkyl" refer to the corresponding divalent moiety.

The term "halo" or "halogen" refers to any radical of fluorine, chlorine, bromine or iodine.

The term "acyl" refers to an alkylcarbonyl, alkoxycarbonyl, cycloalkylcarbonyl, arylcarbonyl, heterocyclylcarbonyl, or heteroarylcarbonyl substituent, any of which may be further substituted by substituents. Exemplary acyl groups include, but are not limited to, ($C_1$-$C_6$)alkanoyl (e.g., formyl, acetyl, propionyl, butyryl, valeryl, caproyl, t-butylacetyl, etc.), ($C_3$-$C_6$)cycloalkylcarbonyl (e.g., cyclopropylcarbonyl, cyclobutylcarbonyl, cyclopentylcarbonyl, cyclohexylcarbonyl, etc.), heterocyclic carbonyl (e.g., pyrrolidinylcarbonyl, pyrrolid-2-one-5-carbonyl, piperidinylcarbonyl, piperazinylcarbonyl, tetrahydrofuranylcarbonyl, etc.), aroyl (e.g., benzoyl) and heteroaroyl (e.g., thiophenyl-2-carbonyl, thiophenyl-3-carbonyl, furanyl-2-carbonyl, furanyl-3-carbonyl, 1H-pyrroyl-2-carbonyl, 1H-pyrroyl-3-carbonyl, benzo[b] thiophenyl-2-carbonyl, etc.). In addition, the alkyl, cycloalkyl, heterocycle, aryl and heteroaryl portion of the acyl group may be any one of the groups described in the respective definitions.

The term "alkyl" refers to saturated non-aromatic hydrocarbon chains that may be a straight chain or branched chain, containing the indicated number of carbon atoms (these include without limitation propyl, allyl, or propargyl), which may be optionally inserted with N, O, or S. For example, $C_1$-$C_6$ indicates that the group may have from 1 to 6 (inclusive) carbon atoms in it.

The term "alkenyl" refers to an alkyl that comprises at least one double bond. Exemplary alkenyl groups include, but are not limited to, for example, ethenyl, propenyl, butenyl, 1-methyl-2-buten-1-yl and the like.

The term "alkynyl" refers to an alkyl that comprises at least one triple bond.

The term "alkoxy" refers to an —O-alkyl radical.

The term "aminoalkyl" refers to an alkyl substituted with an amino.

The term "mercapto" refers to an —SH radical.

The term "thioalkoxy" refers to an —S-alkyl radical.

The term "aryl" refers to monocyclic, bicyclic, or tricyclic aromatic ring system wherein 0, 1, 2, 3, or 4 atoms of each ring may be substituted by a substituent. Examplary aryl groups include, but are not limited to, phenyl, naphthyl, anthracenyl, azulenyl, fluorenyl, indanyl, indenyl, naphthyl, phenyl, tetrahydronaphthyl, and the like.

The term "arylalkyl" refers to alkyl substituted with an aryl.

The term "cyclyl" or "cycloalkyl" refers to saturated and partially unsaturated cyclic hydrocarbon groups having 3 to 12 carbons, for example, 3 to 8 carbons, and, for example, 3 to 6 carbons, wherein the cycloalkyl group additionally may be optionally substituted. Exemplary cycloalkyl groups include, but are not limited to, cyclopropyl, cyclobutyl, cyclopentyl, cyclopentenyl, cyclohexyl, cyclohexenyl, cycloheptyl, cyclooctyl, and the like.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2, 3, or 4 atoms of each ring may be substituted by a substituent. Examplary heteroaryl groups include, but are not limited to, pyridyl, furyl or furanyl, imidazolyl, benzimidazolyl, pyrimidinyl, thiophenyl or thienyl, pyridazinyl, pyrazinyl, quinolinyl, indolyl, thiazolyl, naphthyridinyl, and the like.

The term "heteroarylalkyl" refers to an alkyl substituted with a heteroaryl.

The term "heterocyclyl" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2 or 3 atoms of each ring may be substituted by a substituent. Examplary heterocyclyl groups include, but are not limited to piperazinyl, pyrrolidinyl, dioxanyl, morpholinyl, tetrahydrofuranyl, and the like.

The term "haloalkyl" refers to an alkyl group having one, two, three or more halogen atoms attached thereto. Exemplary haloalkyl groups incude, but are not limited to chloromethyl, bromoethyl, trifluoromethyl, and the like.

The term "optionally substituted" means that the specified group or moiety, such as an alkyl, alkoxy, aryl group, heteroaryl group and the like, is unsubstituted or is substituted with one or more (typically 1 to 4 substituents) independently selected from the group of substituents listed below in the definition for "substituents" or otherwise specified.

The term "substituents" refers to a group "substituted" on an alkyl, alkenyl, alkynyl, cycloalkyl, aryl, heterocyclyl, or heteroaryl group at any atom of that group. Suitable substituents include, without limitation, halo, hydroxy, oxo, nitro, haloalkyl, alkyl, alkenyl, alkynyl, alkaryl, aryl, aralkyl, alkoxy, aryloxy, amino, acylamino, alkylcarbanoyl, arylcarbanoyl, aminoalkyl, alkoxycarbonyl, carboxy, hydroxyalkyl, alkanesulfonyl, arenesulfonyl, alkanesulfonamido, arenesulfonamido, aralkylsulfonamido, alkylcarbonyl, acyloxy, cyano or ureido. In some cases, two substituents, together with the carbons to which they are attached to can form a ring.

As used herein, the term "pharmaceutically acceptable salt" refers to salts of the compounds described herein which are substantially non-toxic to living organisms. Typical pharmaceutically acceptable salts include those salts prepared by reaction of the compounds of the present invention with a pharmaceutically acceptable mineral or organic acid or an organic or inorganic base. Such salts are known as acid addition and base addition salts.

Acids commonly employed to form acid addition salts are inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of such pharmaceutically acceptable salts are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, hydrochloride, dihydrochloride, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, hydroxybenzoate, methoxybenzoate, phthalate, xylenesulfonate, phenylacetate, phenylpropionate, phenylbutyrate, citrate, lactate, y-hydroxybutyrate, glycolate, tartrate, methanesulfonate, propanesulfonate, naphthalene-1sulfonate, napthhalene-2-sulfonate, mandelate and the like. Preferred pharmaceutically acceptable acid addition salts are those formed with mineral acids such as hydrochloric acid and hydrobromic acid, and those formed with organic acids such as maleic acid and methanesulfonic acid.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like. The potassium and sodium salt forms are particularly preferred.

It should be recognized that the particular counterion forming a part of any salt of this invention is usually not of a critical nature, so long as the salt as a whole is pharmacologically acceptable and as long as the counterion does not contribute undesired qualities to the salt as a whole. It is further understood that the above salts may form hydrates or exist in a substantially anhydrous form.

The compounds described herein and their salts include asymmetric carbon atoms and may therefore exist as single stereoisomers, racemates, and as mixtures of enantiomers and diastereomers. Typically, such compounds will be prepared as a racemic mixture. If desired, however, such compounds can be prepared or isolated as pure stereoisomers, i.e., as individual enantiomers or diastereomers, or as stereoisomer-enriched mixtures. As discussed in more detail below, individual stereoisomers of compounds are prepared by synthesis from optically active starting materials containing the desired chiral centers or by preparation of mixtures of enantiomeric products followed by separation or resolution, such as conversion to a mixture of diastereomers followed by separation or recrystallization, chromatographic techniques, use of chiral resolving agents, or direct separation of the enantiomers on chiral chromatographic columns. Starting compounds of particular stereochemistry are either commercially available or are made by the methods described below and resolved by techniques well-known in the art.

As used herein, the terms "stereoisomer" or "optical isomer" mean a stable isomer that has at least one chiral atom or restricted rotation giving rise to perpendicular dissymmetric planes (e.g., certain biphenyls, allenes, and spiro compounds) and can rotate plane-polarized light. Because asymmetric centers and other chemical structure exist in the compounds described herein as suitable for use in the present invention which may give rise to stereoisomerism, the invention contemplates stereoisomers and mixtures thereof. The term "enantiomers" means a pair of stereoisomers that are non-superimposable mirror images of each other. The term "diastereoisomers" or "diastereomers" mean optical isomers which are not mirror images of each other. The term "racemic mixture" or "racemate" mean a mixture containing equal parts of individual enantiomers. The term "non-racemic mixture" means a mixture containing unequal parts of individual enantiomers.

The term "enantiomeric enrichment" as used herein refers to the increase in the amount of one enantiomer as compared to the other. A convenient method of expressing the enantiomeric enrichment achieved is the concept of enantiomeric excess, or "ee", which is found using the following equation:

$$ee = 100 \times (E^1 - E^2)/(E^1 + E^2),$$

wherein $E^1$ is the amount of the first enantiomer and $E^2$ is the amount of the second enantiomer.

In some embodiments, compound described herein have an enantiomeric excess of at least 1%, 5%, 10%, 20%, 30%, 40%, 50%, 60%, 70%, 80%, 90%, 95% or more. Generally, an ee of greater than 90% is preferred, an ee of greater than 95% is most preferred and an ee of greater than 99% is most especially preferred.

Enantiomeric enrichment is readily determined by one of ordinary skill in the art using standard techniques and procedures, such as gas or high performance liquid chromatography with a chiral column. Choice of the appropriate chiral column, eluent and conditions necessary to effect separation of the enantiomeric pair is well within the knowledge of one of ordinary skill in the art. In addition, the enantiomers of compounds can be resolved by one of ordinary skill in the art using standard techniques well known in the art, such as those described by J. Jacques, et al., "Enantiomers, Racemates, and Resolutions", John Wiley and Sons, Inc., 1981. Examples of resolutions include recrystallization techniques or chiral chromatography.

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

To the extent not already indicated, it will be understood by those of ordinary skill in the art that any one of the various embodiments herein described and illustrated may be further modified to incorporate features shown in any of the other embodiments disclosed herein.

The present invention may be defined in any of the following numbered paragraphs:

1. A method of inhibiting HIF-2a activity in a cell comprising:

contacting the cell with a HIF inhibitor, wherein said HIF inhibitor is 3-(2,5-diethoxyphenyl)-1-(2-thienyl)-2-propen-1-one, $N^2$-(4-bromo-3-nitrobenzoyl)leucinamide, 2-bromo-N-(2-methoxyphenyl)propanamide, 6-(1,3-dioxo-1H-benzo[de]isoquinolin-2(3H)-yl-N-hydroxyhexanamide, 15-deoxy-$\Delta^{12,14}$-prostaglandin $J_2$ ($PGJ_2$),

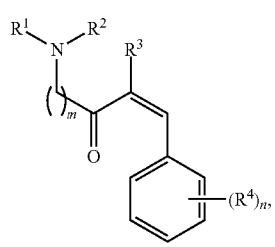

Formula (I)

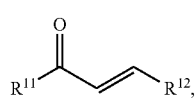

Formula (II)

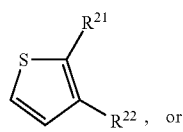

Formula (III)

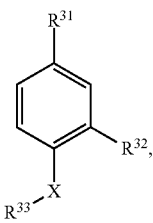

Formula (IV)

wherein:

$R^1$ and $R^2$ are each independently H, alkyl, alkenyl, alkynyl, or taken together with the N atom to which they are attached form a 5-8 membered heterocyclyl or heteroaryl, each of which can be optionally substituted;

$R^3$ is H, alkyl, alkenyl, or alkynyl, each of which can be optionally substituted;

$R^4$ is independently for each occurrence halogen, alkyl, alkenyl, alkynyl, alkoxy, $CF_3$, $NO_2$, $N(R^5)_2$, CN, OH, $SR^5$, $SO_2R^5$, or two $R^4$ taken together form an optionally substituted 3,4-methylenedioxy, each of which can be optionally substituted;

$R^5$ is independently for each occurrence H, alkyl, alkenyl, or alkynyl, each of which can be optionally substituted;

m is 1, 2, 3, 4 or 5;

n is 0, 1, 2, or 3;

$R^{11}$ is optionally substituted aryl, optionally substituted heteroaryl, optionally substituted cyclyl or optionally substituted heterocyclyl;

$R^{12}$ is optionally substituted aryl or optionally substituted heteroaryl;

$R^{21}$ is halogen, alkyl, alkenyl, alkynyl, alkoxy, aryl, heteroaryl, cyclyl, heterocyclyl, $CF_3$, $NO_2$, $N(R^{23})_2$, CN, OH, $SR^{23}$, $SO_2R^{23}$, or $C(O)R^{24}$, each of which can be optionally substituted;

$R^{22}$ is alkoxy, halogen, alkyl, alkenyl, alkynyl, alkoxy, aryl, heteroaryl, cyclyl, heterocyclyl, $CF_3$, $NO_2$, $N(R^{25})_2$, CN, OH, $SR^{23}$, or $SO_2R^{23}$, each of which can be optionally substituted;

$R^{23}$ is independently for each occurrence H, alkyl, alkenyl or alkynyl, each of which can be optionally substituted;

$R^{24}$ is alkyl, alkenyl, alkynyl, alkoxy, aryl, heteroaryl, cyclyl or heterocyclyl, each of which can be optionally substituted;

$R^{25}$ is independently for each occurrence alkyl, alkenyl, alkynyl, $N(R^{23})_2$ or $N=R^{26}$, each of which can be optionally substituted;

$R^{26}$ is independently for each occurrence H, alkyl, alkenyl or alkynyl, each of which can be optionally substituted;

X is S, O, or NH;

$R^{31}$ and $R^{32}$ are each independently halogen, alkyl, alkenyl, alkynyl, alkoxy, $CF_3$, $NO_2$, $N(R^{34})_2$, CN, OH, $SR^{34}$, or $SO_2R^{34}$, each of which can be optionally substituted $R^{33}$ is alkyl, alkenyl, alkynyl, aryl, heteroaryl, cyclyl, or heterocyclyl, each of which can be optionally substituted;

$R^{34}$ is independently for each occurrence H, alkyl, alkenyl, or alkynyl, each of which can be optionally substituted; and pharmaceutically acceptable salts and combinations thereof.

2. A method of preventing cell proliferation comprising:

contacting a cell with a HIF inhibitor, wherein said HIF inhibitor is 3-(2,5-diethoxyphenyl)-1-(2-thienyl)-2- propen-1-one, N²-(4-bromo-3-nitrobenzoyl)leucinamide, 2-bromo-N-(2-methoxyphenyl)propanamide, 6-(1,3-dioxo-1H-benzo[de]isoquinolin-2(3H)-yl-N-hydroxyhexanamide, 15-deoxy-Δ$^{12,14}$-prostaglandin J$_2$ (PGJ$_2$),

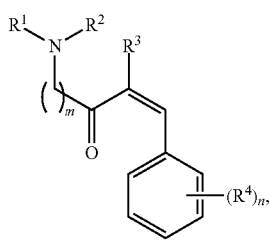

Formula (I)

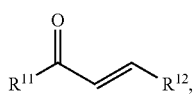

Formula (II)

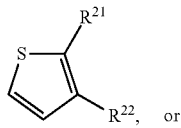

Formula (III)

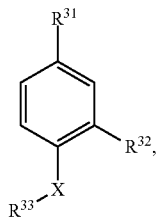

Formula (IV)

wherein:
R$^1$ and R$^2$ are each independently H, alkyl, alkenyl, alkynyl, or taken together with the N atom to which they are attached form a 5-8 membered heterocyclyl or heteroaryl, each of which can be optionally substituted;
R$^3$ is H, alkyl, alkenyl, or alkynyl, each of which can be optionally substituted;
R$^4$ is independently for each occurrence halogen, alkyl, alkenyl, alkynyl, alkoxy, CF$_3$, NO$_2$, N(R$^5$)$_2$, CN, OH, SR$^5$, SO$_2$R$^5$, or two R$^4$ taken together form an optionally substituted 3,4-methylenedioxy, each of which can be optionally substituted;
R$^5$ is independently for each occurrence H, alkyl, alkenyl, or alkynyl, each of which can be optionally substituted;
m is 1, 2, 3, 4 or 5;
n is 0, 1, 2, or 3;
R$^{11}$ is optionally substituted aryl, optionally substituted heteroaryl, optionally substituted cyclyl or optionally substituted heterocyclyl;
R$^{12}$ is optionally substituted aryl or optionally substituted heteroaryl;
R$^{21}$ is halogen, alkyl, alkenyl, alkynyl, alkoxy, aryl, heteroaryl, cyclyl, heterocyclyl, CF$_3$, NO$_2$, N(R$^{23}$)$_2$, CN, OH, SR$^{23}$, SO$_2$R$^{23}$, or C(O)R$^{24}$, each of which can be optionally substituted;
R$^{22}$ is alkoxy, halogen, alkyl, alkenyl, alkynyl, alkoxy, aryl, heteroaryl, cyclyl, heterocyclyl, CF$_3$, NO$_2$, N(R$^{25}$)$_2$, CN, OH, SR$^{23}$, or SO$_2$R$^{23}$, each of which can be optionally substituted;

R$^{23}$ is independently for each occurrence H, alkyl, alkenyl or alkynyl, each of which can be optionally substituted;
R$^{24}$ is alkyl, alkenyl, alkynyl, alkoxy, aryl, heteroaryl, cyclyl or heterocyclyl, each of which can be optionally substituted;
R$^{25}$ is independently for each occurrence alkyl, alkenyl, alkynyl, N(R$^{23}$)$_2$ or N=R$^{26}$, each of which can be optionally substituted;
R$^{26}$ is independently for each occurrence H, alkyl, alkenyl or alkynyl, each of which can be optionally substituted;
X is S, O, or NH;
R$^{31}$ and R$^{32}$ are each independently halogen, alkyl, alkenyl, alkynyl, alkoxy, CF$_3$, NO$_2$, N(R$^{34}$)$_2$, CN, OH, SR$^{34}$, or SO$_2$R$^{34}$, each of which can be optionally substituted
R$^{33}$ is alkyl, alkenyl, alkynyl, aryl, heteroaryl, cyclyl, or heterocyclyl, each of which can be optionally substituted;
R$^{34}$ is independently for each occurrence H, alkyl, alkenyl, or alkynyl, each of which can be optionally substituted; and
pharmaceutically acceptable salts and combinations thereof.

3. The method of any of paragraphs 1-2, wherein said contacting is in vitro.
4. The method of any of paragraphs 1-2, wherein said contacting is in vivo.
5. The method of paragraph 4, wherein in vivo contacting is in a mammal.
6. The method of paragraph 4, wherein in vivo contacting is in a mouse.
7. The method of paragraph 4, wherein in vivo contacting is in a human.
8. The method of paragraph 4, wherein in vivo contacting is in a subject in need of treatment or prevention of a HIF related pathology.
9. A method of reducing inflammation comprising:
selecting a subject in need of reduced inflammation; and administering to said subject a HIF inhibitor, wherein said inhibitor is 3-(2,5-diethoxyphenyl)-1-(2-thienyl)-2-propen-1-one, N²-(4-bromo-3-nitrobenzoyl)leucinamide, 2-bromo-N-(2-methoxyphenyl)propanamide, 6-(1,3-dioxo-1H-benzo[de]isoquinolin-2(3H)-yl-N-hydroxyhexanamide, 15-deoxy-Δ$^{12,14}$-prostaglandin J$_2$ (PGJ$_2$).

Formula (I)

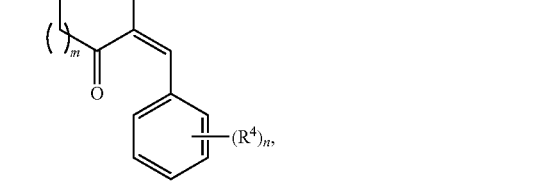

Formula (II)

Formula (III)

-continued

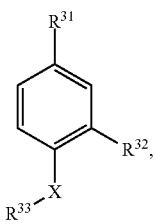

Formula (IV)

wherein:
R¹ and R² are each independently H, alkyl, alkenyl, alkynyl, or taken together with the N atom to which they are attached form a 5-8 membered heterocyclyl or heteroaryl, each of which can be optionally substituted;
R³ is H, alkyl, alkenyl, or alkynyl, each of which can be optionally substituted;
R⁴ is independently for each occurrence halogen, alkyl, alkenyl, alkynyl, alkoxy, $CF_3$, $NO_2$, $N(R^5)_2$, CN, OH, $SR^5$, $SO_2R^5$, or two R⁴ taken together form an optionally substituted 3,4-methylenedioxy, each of which can be optionally substituted;
R⁵ is independently for each occurrence H, alkyl, alkenyl, or alkynyl, each of which can be optionally substituted;
m is 1, 2, 3, 4 or 5;
n is 0, 1, 2, or 3;
R¹¹ is optionally substituted aryl, optionally substituted heteroaryl, optionally substituted cyclyl or optionally substituted heterocyclyl;
R¹² is optionally substituted aryl or optionally substituted heteroaryl;
R²¹ is halogen, alkyl, alkenyl, alkynyl, alkoxy, aryl, heteroaryl, cyclyl, heterocyclyl, $CF_3$, $NO_2$, $N(R^{23})_2$, CN, OH, $SR^{23}$, $SO_2R^{23}$, or $C(O)R^{24}$, each of which can be optionally substituted;
R²² is alkoxy, halogen, alkyl, alkenyl, alkynyl, alkoxy, aryl, heteroaryl, cyclyl, heterocyclyl, $CF_3$, $NO_2$, $N(R^{25})_2$, CN, OH, $SR^{23}$, or $SO_2R^{23}$, each of which can be optionally substituted;
R²³ is independently for each occurrence H, alkyl, alkenyl or alkynyl, each of which can be optionally substituted;
R²⁴ is alkyl, alkenyl, alkynyl, alkoxy, aryl, heteroaryl, cyclyl or heterocyclyl, each of which can be optionally substituted;
R²⁵ is independently for each occurrence alkyl, alkenyl, alkynyl, $N(R^{23})_2$ or $N=R^{26}$, each of which can be optionally substituted;
R²⁶ is independently for each occurrence H, alkyl, alkenyl or alkynyl, each of which can be optionally substituted;
X is S, O, or NH;
R³¹ and R³² are each independently halogen, alkyl, alkenyl, alkynyl, alkoxy, $CF_3$, $NO_2$, $N(R^{34})_2$, CN, OH, $SR^{34}$, or $SO_2R^{34}$, each of which can be optionally substituted
R³³ is alkyl, alkenyl, alkynyl, aryl, heteroaryl, cyclyl, or heterocyclyl, each of which can be optionally substituted;
R³⁴ is independently for each occurrence H, alkyl, alkenyl, or alkynyl, each of which can be optionally substituted; and
pharmaceutically acceptable salts and combinations thereof.

10. A method of treating an angiogenic disease or disorder in a host in need thereof, comprising administrating to said host of an effective amount of an HIF inhibitor, wherein said inhibitor is 3-(2,5-diethoxyphenyl)-1-(2-thienyl)-2-propen-1-one, $N^2$-(4-bromo-3-nitrobenzoyl)leucinamide, 2-bromo-N-(2-methoxyphenyl)propanamide, dioxo-1H-benzo[de]isoquinolin-2(3H)-yl-N-hydroxyhexanamide, 15-deoxy-$\Delta^{12,14}$-Prostaglandin $J_2$ ($PGJ_2$),

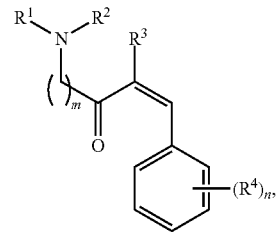

Formula (I)

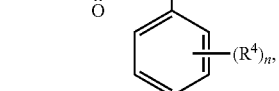

Formula (II)

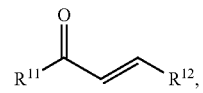

Formula (III)

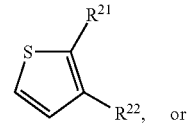

or

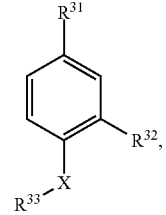

Formula (IV)

wherein:
R¹ and R² are each independently H, alkyl, alkenyl, alkynyl, or taken together with the N atom to which they are attached form a 5-8 membered heterocyclyl or heteroaryl, each of which can be optionally substituted;
R³ is H, alkyl, alkenyl, or alkynyl, each of which can be optionally substituted;
R⁴ is independently for each occurrence halogen, alkyl, alkenyl, alkynyl, alkoxy, $CF_3$, $NO_2$, $N(R^5)_2$, CN, OH, $SR^5$, $SO_2R^5$, or two R⁴ taken together form an optionally substituted 3,4-methylenedioxy, each of which can be optionally substituted;
R⁵ is independently for each occurrence H, alkyl, alkenyl, or alkynyl, each of which can be optionally substituted;
m is 1, 2, 3, 4 or 5;
n is 0, 1, 2, or 3;
R¹¹ is optionally substituted aryl, optionally substituted heteroaryl, optionally substituted cyclyl or optionally substituted heterocyclyl;
R¹² is optionally substituted aryl or optionally substituted heteroaryl;
R²¹ is halogen, alkyl, alkenyl, alkynyl, alkoxy, aryl, heteroaryl, cyclyl, heterocyclyl, $CF_3$, $NO_2$, $N(R^{23})_2$, CN, OH, $SR^{23}$, $SO_2R^{23}$, or $C(O)R^{24}$, each of which can be optionally substituted;
R²² is alkoxy, halogen, alkyl, alkenyl, alkynyl, alkoxy, aryl, heteroaryl, cyclyl, heterocyclyl, $CF_3$, $NO_2$, $N(R^{25})_2$, CN, OH, $SR^{23}$, or $SO_2R^{23}$, each of which can be optionally substituted;

$R^{23}$ is independently for each occurrence H, alkyl, alkenyl or alkynyl, each of which can be optionally substituted;

$R^{24}$ is alkyl, alkenyl, alkynyl, alkoxy, aryl, heteroaryl, cyclyl or heterocyclyl, each of which can be optionally substituted;

$R^{25}$ is independently for each occurrence alkyl, alkenyl, alkynyl, $N(R^{23})_2$ or $N=R^{26}$, each of which can be optionally substituted;

$R^{26}$ is independently for each occurrence H, alkyl, alkenyl or alkynyl, each of which can be optionally substituted;

X is S, O, or NH;

$R^{31}$ and $R^{32}$ are each independently halogen, alkyl, alkenyl, alkynyl, alkoxy, $CF_3$, $NO_2$, $N(R^{34})_2$, CN, OH, $SR^{34}$, or $SO_2R^{34}$, each of which can be optionally substituted $R^{33}$ is alkyl, alkenyl, alkynyl, aryl, heteroaryl, cyclyl, or heterocyclyl, each of which can be optionally substituted;

$R^{34}$ is independently for each occurrence H, alkyl, alkenyl, or alkynyl, each of which can be optionally substituted; and pharmaceutically acceptable salts and combinations thereof.

11. The method of paragraph 9 or 10, comprising pulsed or sustained release administration of said HIF inhibitor.

12. The method of paragraph 11, wherein interval between pulses is 24 hours or greater.

13. The method of paragraph 11, wherein a plurality of pulses comprises from about 5 to about 10 pulses.

14. The method of paragraph 11, wherein a plurality of pulses comprises greater than 20 pulses.

15. The method of any of paragraphs 9-14, comprising co-administering a second therapeutic agent.

16. The method of paragraph 15, wherein the second therapeutic agent is an antibody, antibiotic, anti-inflammatory, anti-oxidant, analgesic, radioisotope, noscapine, paclitaxel, nocodazole, buslfulan, lomustine (CCNU), caboplatinum, cisplatinum, cytoxan, daunorubicin, dacarbazine (DTIC), 5-fluorouracil (5-FU), fludarabine, hydroxyurea, idarubicin, ifosfamide, methotrextrate, mithramycin, mitomycin, mitoxantrone, nitrogen mustard, vinblastin, vincristine, CPT-11, cladribine, vinorebne tartrate, rituximab, STI-571, docetaxel, temozolomide, topotecan, capecitaine, ibritumomab tiuxetan, and combinations thereof.

17. The method of paragraph 16, wherein the second therapeutic agent is an anti-angiogenic factor.

18. The method of any of paragraphs 10-17, wherein said angiogenic disease or disorder is retinopathy, diabetic retinopathy, vascular restenosis, primary pulmonary hypertension, hereditary hemorrhagic telangiectasis, postoperative adhesion formation, fibrosis, keloids, artherosclerosis, macular degeneration, arthritis, rheumatoid arthritis, a solid tumor, solid tumor metastasis, cancer or combination thereof.

19. The method of paragraph 18, wherein said cancer is renal cell, colon, breast, prostate, glioblastoma multiform, or endometrial.

20. The method of paragraph 19, wherein said cancer comprises a VHL gene mutation.

21. The method of any of paragraphs 9-20, wherein said administering is conducted in conjunction with chemotherapy.

22. The method of any of paragraphs 9-21, wherein said administering comprises intravenous, transdermal, intrasynovial, intramuscular, or oral administration.

23. The method of any of paragraphs 9-22, wherein said HIF inhibitor inhibits angiogenesis.

24. The method of any of paragraph 9-23, wherein said HIF inhibitor inhibits neovasculization.

25. The method of any of paragraphs 1-24, wherein said HIF inhibitor is selected from the group consisting of 5-dimethylamino)-2-methyl-1-phenyl-1-penten-3-one, 4-hydroxy-3-(3-(2-hydroxy-5-methoxyphenyl)acryloyl)-6-methyl-2H-pyran-2-one, methyl 3-{2-[cyano(methyl sulfonyl)methyle]hydrazine]thiophene-2-carboxylate, 4-[(2,2-dimethyl-4-oxo-3,4-dihydro-2H-thinn-6-yl)thio]-3-nitrobenzonitrile, $PGJ_2$, and pharmaceutically acceptable salts and combinations thereof.

26. The method of any of paragraphs 1-25, wherein said HIF inhibitor decreases HIF-2a protein levels.

27. The method of any of paragraphs 1-26, wherein said HIF inhibitor inhibits HIF-2a mRNA translation.

28. The method of any of paragraphs 1-27, wherein said HIF inhibitor modulates binding of iron regulatory protein-1 (IRP1) to HIF-2a iron response element (IRE).

29. The method of paragraph 28, wherein said HIF inhibitor enhances binding of IRP1 to HIF-2a IRE.

30. A pharmaceutical composition for inhibiting angiogenesis comprising a HIF inhibitor and a pharmaceutically acceptable carrier or excipient, wherein said inhibitor is 3-(2,5-diethoxyphenyl)-1-(2-thienyl)-2-propen-1-one, $N^2$-(4-bromo-3-nitrobenzoyl)leucinamide, 2-bromo-N-(2-methoxyphenyl)propanamide, 6-(1,3-dioxo-1H-benzo[de]isoquinolin-2(3H)-yl-N-hydroxyhexanamide, 15-deoxy-$\Delta^{12,14}$-Prostaglandin $J_2$ ($PGJ_2$),

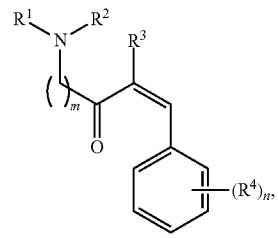

Formula (I)

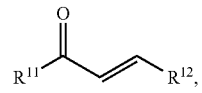

Formula (II)

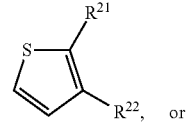

Formula (III)

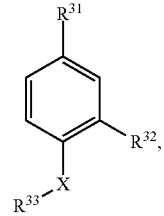

Formula (IV)

wherein:

$R^1$ and $R^2$ are each independently H, alkyl, alkenyl, alkynyl, or taken together with the N atom to which they are attached form a 5-8 membered heterocyclyl or heteroaryl, each of which can be optionally substituted;

R$^3$ is H, alkyl, alkenyl, or alkynyl, each of which can be optionally substituted;

R$^4$ is independently for each occurrence halogen, alkyl, alkenyl, alkynyl, alkoxy, CF$_3$, NO$_2$, N(R$^5$)$_2$, CN, OH, SR$^5$, SO$_2$R$^5$, or two R$^4$ taken together form an optionally substituted 3,4-methylenedioxy, each of which can be optionally substituted;

R$^5$ is independently for each occurrence H, alkyl, alkenyl, or alkynyl, each of which can be optionally substituted;

m is 1, 2, 3, 4 or 5;

n is 0, 1, 2, or 3;

R$^{11}$ is optionally substituted aryl, optionally substituted heteroaryl, optionally substituted cyclyl or optionally substituted heterocyclyl;

R$^{12}$ is optionally substituted aryl or optionally substituted heteroaryl;

R$^{21}$ is halogen, alkyl, alkenyl, alkynyl, alkoxy, aryl, heteroaryl, cyclyl, heterocyclyl, CF$_3$, NO$_2$, N(R$^{23}$)$_2$, CN, OH, SR$^{23}$, SO$_2$R$^{23}$, or C(O)R$^{24}$, each of which can be optionally substituted;

R$^{22}$ is alkoxy, halogen, alkyl, alkenyl, alkynyl, alkoxy, aryl, heteroaryl, cyclyl, heterocyclyl, CF$_3$, NO$_2$, N(R$^{25}$)$_2$, CN, OH, SR$^{23}$, or SO$_2$R$^{23}$, each of which can be optionally substituted;

R$^{23}$ is independently for each occurrence H, alkyl, alkenyl or alkynyl, each of which can be optionally substituted;

R$^{24}$ is alkyl, alkenyl, alkynyl, alkoxy, aryl, heteroaryl, cyclyl or heterocyclyl, each of which can be optionally substituted;

R$^{25}$ is independently for each occurrence alkyl, alkenyl, alkynyl, N(R$^{23}$)$_2$ or N=R$^{26}$, each of which can be optionally substituted;

R$^{26}$ is independently for each occurrence H, alkyl, alkenyl or alkynyl, each of which can be optionally substituted;

X is S, O, or NH;

R$^{31}$ and R$^{32}$ are each independently halogen, alkyl, alkenyl, alkynyl, alkoxy, CF$_3$, NO$_2$, N(R$^{34}$)$_2$, CN, OH, SR$^{34}$, or SO$_2$R$^{34}$, each of which can be optionally substituted R$^{33}$ is alkyl, alkenyl, alkynyl, aryl, heteroaryl, cyclyl, or heterocyclyl, each of which can be optionally substituted;

R$^{34}$ is independently for each occurrence H, alkyl, alkenyl, or alkynyl, each of which can be optionally substituted; and pharmaceutically acceptable salts and combinations thereof.

31. The pharmaceutical composition of paragraph 30, wherein the composition comprises two or more different HIF inhibitors.

32. An article of manufacture comprising packaging material and a pharmaceutical composition contained within said packaging material, wherein said pharmaceutical composition is capable of treating an angiogenic disorder or disease, wherein said packaging material comprises a label which indicates that said pharmaceutical composition can be used for treating an angiogenic disorder or disease, and wherein said pharmaceutical composition comprises a HIF inhibitor wherein said HIF inhibitor is 3-(2,5-diethoxyphenyl)-1-(2-thienyl)-2-propen-1-one, N$^2$-(4-bromo-3-nitrobenzoyl)leucinamide, 2-bromo-N-(2-methoxyphenyl)propanamide, 6-(1,3-dioxo-1H-benzo[de]isoquinolin-2(3H)-yl-N-hydroxyhexanamide, 15-deoxy-Δ$^{12,14}$-Prostaglandin J$_2$ (PGJ$_2$),

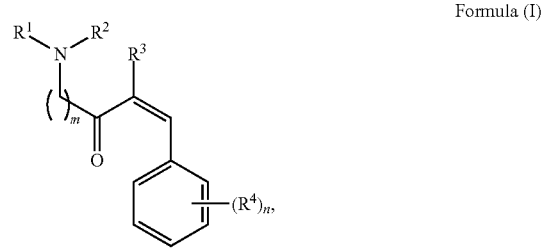

Formula (I)

Formula (II)

Formula (III)

or

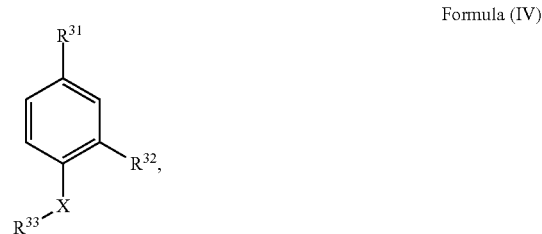

Formula (IV)

wherein:

R$^1$ and R$^2$ are each independently H, alkyl, alkenyl, alkynyl, or taken together with the N atom to which they are attached form a 5-8 membered heterocyclyl or heteroaryl, each of which can be optionally substituted;

R$^3$ is H, alkyl, alkenyl, or alkynyl, each of which can be optionally substituted;

R$^4$ is independently for each occurrence halogen, alkyl, alkenyl, alkynyl, alkoxy, CF$_3$, NO$_2$, N(R$^5$)$_2$, CN, OH, SR$^5$, SO$_2$R$^5$, or two R$^4$ taken together form an optionally substituted 3,4-methylenedioxy, each of which can be optionally substituted;

R$^5$ is independently for each occurrence H, alkyl, alkenyl, or alkynyl, each of which can be optionally substituted;

m is 1, 2, 3, 4 or 5;

n is 0, 1, 2, or 3;

R$^{11}$ is optionally substituted aryl, optionally substituted heteroaryl, optionally substituted cyclyl or optionally substituted heterocyclyl;

R$^{12}$ is optionally substituted aryl or optionally substituted heteroaryl;

R$^{21}$ is halogen, alkyl, alkenyl, alkynyl, alkoxy, aryl, heteroaryl, cyclyl, heterocyclyl, CF$_3$, NO$_2$, N(R$^{23}$)$_2$, CN, OH, SR$^{23}$, SO$_2$R$^{23}$, or C(O)R$^{24}$, each of which can be optionally substituted;

R$^{22}$ is alkoxy, halogen, alkyl, alkenyl, alkynyl, alkoxy, aryl, heteroaryl, cyclyl, heterocyclyl, CF$_3$, NO$_2$, N(R$^{25}$)$_2$, CN, OH, SR$^{23}$, or SO$_2$R$^{23}$, each of which can be optionally substituted;

R$^{23}$ is independently for each occurrence H, alkyl, alkenyl or alkynyl, each of which can be optionally substituted;

R$^{24}$ is alkyl, alkenyl, alkynyl, alkoxy, aryl, heteroaryl, cyclyl or heterocyclyl, each of which can be optionally substituted;

R$^{25}$ is independently for each occurrence alkyl, alkenyl, alkynyl, N(R$^{23}$)$_2$ or N=R$^{26}$, each of which can be optionally substituted;

$R^{26}$ is independently for each occurrence H, alkyl, alkenyl or alkynyl, each of which can be optionally substituted;

X is S, O, or NH;

$R^{31}$ and $R^{32}$ are each independently halogen, alkyl, alkenyl, alkynyl, alkoxy, $CF_3$, $NO_2$, $N(R^{34})_2$, CN, OH, $SR^{34}$, or $SO_2R^{34}$, each of which can be optionally substituted $R^{33}$ is alkyl, alkenyl, alkynyl, aryl, heteroaryl, cyclyl, or heterocyclyl, each of which can be optionally substituted;

$R^{34}$ is independently for each occurrence H, alkyl, alkenyl, or alkynyl, each of which can be optionally substituted; and pharmaceutically acceptable salts and combinations thereof.

33. An article of manufacture comprising packaging material and a pharmaceutical composition contained within said packaging material, wherein said pharmaceutical composition is capable of reducing inflammation, wherein said packaging material comprises a label which indicates that said pharmaceutical composition can be used for reducing inflammation, and wherein said pharmaceutical composition comprises a HIF inhibitor wherein said HIF inhibitor is 3-(2,5-diethoxyphenyl)-1-(2-thienyl)-2-propen-1-one, $N^2$-(4-bromo-3-nitrobenzoyl)leucinamide, 2-bromo-N-(2-methoxyphenyl)propanamide, 6-(1,3-dioxo-1H-benzo[de]isoquinolin-2(3H)-yl-N-hydroxyhexanamide, 15-deoxy-$\Delta^{12,14}$-Prostaglandin $J_2$ (PGJ$_2$),

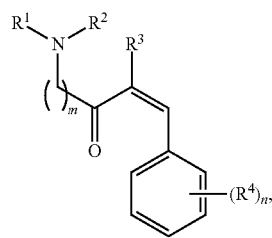

Formula (I)

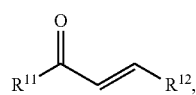

Formula (II)

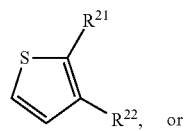

Formula (III)

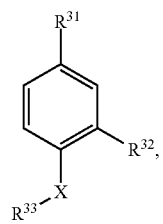

Formula (IV)

wherein:

$R^1$ and $R^2$ are each independently H, alkyl, alkenyl, alkynyl, or taken together with the N atom to which they are attached form a 5-8 membered heterocyclyl or heteroaryl, each of which can be optionally substituted;

$R^3$ is H, alkyl, alkenyl, or alkynyl, each of which can be optionally substituted;

$R^4$ is independently for each occurrence halogen, alkyl, alkenyl, alkynyl, alkoxy, $CF_3$, $NO_2$, $N(R^5)_2$, CN, OH, $SR^5$, $SO_2R^5$, or two $R^4$ taken together form an optionally substituted 3,4-methylenedioxy, each of which can be optionally substituted;

$R^5$ is independently for each occurrence H, alkyl, alkenyl, or alkynyl, each of which can be optionally substituted;

m is 1, 2, 3, 4 or 5;

n is 0, 1, 2, or 3;

$R^{11}$ is optionally substituted aryl, optionally substituted heteroaryl, optionally substituted cyclyl or optionally substituted heterocyclyl;

$R^{12}$ is optionally substituted aryl or optionally substituted heteroaryl;

$R^{21}$ is halogen, alkyl, alkenyl, alkynyl, alkoxy, aryl, heteroaryl, cyclyl, heterocyclyl, $CF_3$, $NO_2$, $N(R^{23})_2$, CN, OH, $SR^{23}$, $SO_2R^{23}$, or $C(O)R^{24}$, each of which can be optionally substituted;

$R^{22}$ is alkoxy, halogen, alkyl, alkenyl, alkynyl, alkoxy, aryl, heteroaryl, cyclyl, heterocyclyl, $CF_3$, $NO_2$, $N(R^{25})_2$, CN, OH, $SR^{23}$, or $SO_2R^{23}$, each of which can be optionally substituted;

$R^{23}$ is independently for each occurrence H, alkyl, alkenyl or alkynyl, each of which can be optionally substituted;

$R^{24}$ is alkyl, alkenyl, alkynyl, alkoxy, aryl, heteroaryl, cyclyl or heterocyclyl, each of which can be optionally substituted;

$R^{25}$ is independently for each occurrence alkyl, alkenyl, alkynyl, $N(R^{23})_2$ or $N=R^{26}$, each of which can be optionally substituted;

$R^{26}$ is independently for each occurrence H, alkyl, alkenyl or alkynyl, each of which can be optionally substituted;

X is S, O, or NH;

$R^{31}$ and $R^{32}$ are each independently halogen, alkyl, alkenyl, alkynyl, alkoxy, $CF_3$, $NO_2$, $N(R^{34})_2$, CN, OH, $SR^{34}$, or $SO_2R^{34}$, each of which can be optionally substituted $R^{33}$ is alkyl, alkenyl, alkynyl, aryl, heteroaryl, cyclyl, or heterocyclyl, each of which can be optionally substituted;

$R^{34}$ is independently for each occurrence H, alkyl, alkenyl, or alkynyl, each of which can be optionally substituted; and pharmaceutically acceptable salts and combinations thereof.

34. The article of any of paragraphs 32-33, wherein said HIF inhibitor decreases HIF-2a protein levels.

35. The article of any of paragraphs 32-34, wherein said HIF inhibitor inhibits HIF-2a mRNA translation.

36. The article of any of paragraphs 32-35, wherein said HIF inhibitor modulates binding of iron regulatory protein-1 (IRP1) to HIF-2a iron response element (IRE).

37. The article of paragraph 32-36, wherein said HIF inhibitor enhances binding of IRP1 to HIF-2a IRE.

38. The article of any of paragraphs 32-37, wherein said HIF inhibitor is selected from the group consisting of 5-dimethylamino)-2-methyl-1-phenyl-1-penten-3-one, 4-hydroxy-3-(3-(2-hydroxy-5-methoxyphenyl)acryloyl)-6-methyl-2H-pyran-2-one, methyl 3-{2-[cyano (methylsulfonyl)methyle]hydrazine]thiophene-2-carboxylate, 4-[(2,2-dimethyl-4-oxo-3,4-dihydro-2H-thinn-6-yl)thio]-3-nitrobenzonitrile, PGJ$_2$, and pharmaceutically acceptable salts and combinations thereof.

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The following examples do not in any way limit the invention.

EXAMPLES

Methods
Cell Culture and Transfections

Luciferase reporters were first made in pGL3 vector system (Promega) and then subcloned into pcDNA3.1 (In-vitrogen) such that the entire CMV promoter of the parental pcDNA3.1 vector was removed. Cells were grown on Dulbecco's Modification of Eagle's Medium (DMEM; MediaTech, 15-013-CM) supplemented with 10% Fetal Clone I (Hyclone, SH30080.03) and 1× Glutamine (Gibco, 10378-016). All standard buffers and solutions were made as described in Molecular Cloning: a Laboratory Manual (Sambrook et al., 1989) and chemicals ordered through Sigma Inc. Stable clones were generated by transfecting 786-O cells using FuGENE6 Transfection Reagent (Roche, 1 814 443) followed by selection on 1 mg/mL G418 (Gibco, 11811-031). Unless stated differently, 25% confluent cells were treated with either fresh DMEM medium, DMEM supplemented with DMSO-only or compound for 24 hours and then changed into fresh DMEM medium, DMEM supplemented with DMSO-only or compound for an additional 24 hours before harvesting at 90-100% confluence. Sets of two 25% confluent identical plates of cells were changed into fresh DMEM, DMEM containing DMSO-only or compound and incubated at 37° C., 5% $CO_2$, and ambient $O_2$, for 24 hours. Cells were then subjected to a second change into fresh DMEM, DMEM containing DMSO-only or compound. One set was kept at 37° C., 5% $CO_2$, and ambient $O_2$, while the other was placed into an ESPEC hypoxic incubator (1% $O_2$, 5% $CO_2$, 37° C.) for another 24 hours. Cells were harvested by immediately washing twice with ice cold PBS, lysed in RIPA buffer supplemented with proteinase inhibitors and immunoblotted or lysed for luciferase measurements as described above. Expression of IRP1, IRP2 or both was stably knocked down in 786-O lines expressing the IRE-luciferase reporter. Due to the excess capacity of IRP1 in cells (Wang et al., 2007), it was necessary to concomitantly use two shRNAs targeting IRP1. All cell lines used in this work were purchases from ATCC, they were aliquoted and immediately frozen and they were plated again for the purposes of these experiments within the last 9 months. All plasmids used herein have been described before (Zimmer et al., 2008) and are listed in Table 4. List of all the cell lines used herein (purchased and reporter derivatives) are provided in Table 5.

TABLE 4

Plasmids used (Table 4 discloses the "pLentiLox3.7puro::IRP1-15" oligos as SEQ ID NOS 20 and 21, the "pLentiLox3.7hygro::IRP1-14" oligos as SEQ ID NOS 22 and 23, the "pLentiLox3.7blasti::IRP2-4" oligos as SEQ ID NOS 24 and 25 and the "HRE" sequence as SEQ ID NO: 26)

| Plasmid | Description | Ref: |
|---|---|---|
| pGL3 basic | Promoterless luciferase expression vector | Promega |
| pGL3 promoter | SV40-luciferase expression vector | Promega |
| pGL3::HIF2p | 1000 nt HIF-2a promoter PCR fragment cloned into pGL3 basic vector (cut NheI/HindIII) | This work |
| pGL3::HIF2p-UTR | 1000 nt HIF-2a promoter with 5'-UTR PCR fragment cloned into pGL3 basic (cut NheI/HindIII) | This work |
| pGL3::SV-UTR | SV40-luciferase vector with HIF-2a 5'-UTR (cut NcoI and screened for orientation) | This work |
| pGL3::HRE1 | 1xHRE-luciferase made from pGLH3 basic vector (cut NheI/XhoI)a | This work |
| pGL3::HRE2 | 2xHRE-luciferase made from pGLH3 basic vector (cut MluI/XhoI)a | This work |
| pGL3::HRE3 | 3xHRE-luciferase made from pGLH3 basic vector (cut SacI/XhoI)a | This work |
| pGL3::HRE4 | 4xHRE-luciferase made from pGLH3 basic vector (cut KpnI/XhoI)a | This work |
| pGL3::HIF2p-UTR1 | 1-100 nt HIF-2a 5'-UTR PCR fragment cloned into pGL3::HIF2p (cut HindIII/NcoI) | This work |
| pGL3::HIF2p-UTR3 | 100-200 nt HIF-2a 5'-UTR PCR fragment cloned into pGL3::HIF2p (cut HindIII/NcoI) | This work |
| pGL3::HIF2p-UTR5 | 200-300 nt HIF-2a 5'-UTR PCR fragment cloned into pGL3::HIF2p (cut HindIII/NcoI) | This work |
| pGL3::HIF2p-UTR10 | 1-250 nt HIF-2a 5'-UTR PCR fragment cloned into pGL3::HIF2p (cut HindIII/NcoI) | This work |
| pGL3::HIF2p-UTR12 | 250-488 nt HIF-2a 5'-UTR PCR fragment cloned into pGL3::HIF2p (cut HindIII/NcoI) | This work |
| pGL3::HIF2p-UTR13 | 1-488 nt (full length) HIF-2a 5'-UTR PCR fragment cloned into pGL3::HIF2p (cut HindIII/Ncol) | This work |

TABLE 4-continued

Plasmids used (Table 4 discloses the "pLentiLox3.7puro::IRP1-15" oligos as SEQ ID NOS 20 and 21, the "pLentiLox3.7hygro::IRP1-14" oligos as SEQ ID NOS 22 and 23, the "pLentiLox3.7blasti::IRP2-4" oligos as SEQ ID NOS 24 and 25 and the "HRE" sequence as SEQ ID NO: 26)

| Plasmid | Description | Ref: |
| --- | --- | --- |
| pGL3::HIF2p-UTR16 | 50-100 nt HIF-2a 5'-UTR fragment generated using annealed oligos with overhaning HindIII/NcoI sites cloned into pGL3::HIF2p (cut HindIII/NcoI) | This work |
| pGL3::HIF2p-UTR17 | Mutant 50-100 nt HIF-2a 5'-UTR fragment generated using annealed oligos with overhaning HindIII/NcoI sites cloned into pGL3::HIF2p (cut HindIII/NcoI)) in which CAGTGT of the IRE stem loop is changed to CAAAGT | This work |
| pGL3::HIF2p-laUTR16 | HIF-2a promoter-UTR1-luciferase from pGL:HIF2p-UTR16 (cut BglI$^b$/XbaI) subcloned into pcDNA3.1 (cut MiuI$^b$/XbaI) | This work |
| pGL3::HIF2p-laUTR17 | HIF-2a promoter-UTR1-luciferase from pGL:HIF2p-UTR17 (cut BglI$^b$/XbaI) subcloned into pcDNA3.1 (cut MiuI$^b$/XbaI) | This work |
| pcDNA3.1 | Mammalian expression vector Invitrogen | |
| pcDNA3.1::SV40 | SV40-luciferase from pGL3 promoter (cut NotIb/XbaI) subcloned into pcDNA3.1 (cut MluIb/XbaI) | This work |
| pcDNA3.1::HRE4 | 4xHRE-luciferase from pGLH4 (cut NotIb/XbaI) subcloned into pcDNA3.1 (cut MluIb/XbaI) | This work |
| pcDNA3.1::HIF2p | HIF-2a promoter-luciferase from pGL3::HIF2p (cut NotIb/XbaI) subcloned into pcDNA3.1 (cut MluIb/XbaI) | This work |
| pcDNA3.1::HIF2p-UTR | HIF-2a promoter-UTR-luciferase from pGL3::HIF2p-UTR (cut BglIb/XbaI) subcloned into pcDNA3.1 (cut MluIb/XbaI) | This work |
| pcDNA3.1::SV40-UTR | SV40-UTR-luciferase from pGL3::SV-UTR (cut NotIb/XbaI) subcloned into pcDNA3.1 (cut MluIb/XbaI) | This work |
| pcDNA3.1::CMV | CMV-Luciferase in pcDNA3.1 | This work |
| pcDNA3.1::CMV-SL | CMV-SL-luciferase in pcDNA3.1 (SL is a synthetic 5'-UTR with a stem loop to measure RNA helicase activity) | This work |
| pcDNA3.1::HIF2p-UTR1 | HIF-2a promoter-UTR1-luciferase from pGL3::HIF2p-UTR1 (cut BglIb/XbaI) subcloned into pcDNA3.1 (cut MluIb/XbaI) | This work |
| pcDNA3.1::HIF2p-UTR3 | HIF-2a promoter-UTR1-luciferase from pGL3::HIF2p-UTR3 (cut BglIb/XbaI) subcloned into pcDNA3.1 (cut MluIb/XbaI) | This work |
| pcDNA3.1::HIF2p-UTR5 | HIF-2a promoter-UTR1-luciferase from pGL3::HIF2p-UTR5 (cut BglIb/XbaI) subcloned into pcDNA3.1 (cut MluIb/XbaI) | This work |
| pcDNA3.1::HIF2p-UTR10 | HIF-2a promoter-UTR1-luciferase from pGL3::HIF2p-UTR10 (cut BglIb/XbaI) subcloned into pcDNA3.1 (cut MluIb/XbaI) | This work |
| pcDNA3.1::HIF2p-UTR12 | HIF-2a promoter-UTR1-luciferase from pGL3::HIF2p-UTR12 (cut BglIb/XbaI) subcloned into pcDNA3.1 (cut MluIb/XbaI) | This work |
| pcDNA3.1::HIF2p-UTR16 | HIF-2a promoter-UTR1-luciferase from pGL3::HIF2p-UTR16 (cut BglIb/XbaI) subcloned into pcDNA3.1 (cut MluIb/XbaI) | This work |
| pcDNA3.1::HIF2p-UTR17 | HIF-2a promoter-UTR1-luciferase from pGL3::HIF2p-UTR17 (cut BglIb/XbaI) subcloned into pcDNA3.1 (cut MluIb/XbaI) | This work |
| pcDNA3.1::HIF2p-laUTR16 | HIF-2a promoter-UTR1-luciferase from pGL3::HIF2p-UTR16 (cut BglIb/XbaI) subcloned into pcDNA3.1 (cut MluIb/XbaI) | pcDNA3.1::HIF2p-UTR16 |
| pcDNA3.1::HIF2p-laUTR17 | HIF-2a promoter-UTR1-luciferase from pGL3::HIF2p-UTR17 (cut BglIb/XbaI) subcloned into pcDNA3.1 (cut MluIb/XbaI) | pcDNA3.1::HIF2p-UTR17 |
| pcDNA3.1::UTR16 probe | 50-100 nt HIF-2a 5'-UTR fragment generated using annealed oligos with overhaning HindIII/NcoI sites cloned into pcDNA3.1 (cut HindIII/NcoI) to maintain T7 promoter for EMSA probe | This work |
| pcDNA3.1::UTR17 probe | Mutant 50-100 nt HIF-2a 5'-UTR fragment generated using annealed oligos with overhaning HindIII/NcoI sites cloned into pcDNA3.1 (cut HindIII/NcoI)) in which CAGTGT of the IRE stem loop is changed to CAAAGT to maintain T7 promoter for EMSA probe | This work |

TABLE 4-continued

Plasmids used (Table 4 discloses the "pLentiLox3.7puro::IRP1-15" oligos as SEQ ID NOS 20 and 21, the "pLentiLox3.7hygro::IRP1-14" oligos as SEQ ID NOS 22 and 23, the "pLentiLox3.7blasti::IRP2-4" oligos as SEQ ID NOS 24 and 25 and the "HRE" sequence as SEQ ID NO: 26)

| Plasmid | Description | Ref: |
| --- | --- | --- |
| pRL-SV40 | Control SV40-Renilla luciferase construct used to normalize transient transfections | |
| pIRESpuro | Mammalian Internal Ribsomal Entry site (IRES) expression vector | BD Biosciences |
| pIRESpuro::HIF-2a(P531A0 | Degradation resistant HIF-2a(P531A) mutant | This work |
| pIREShygro | Mammalian Internal Ribosimal Entry Site (IRES) expression vector | BD Biosciences |
| pIREShygro::dnHIFA | Dominant Negative HIF-2a construct lacking transactivation domain (aa's 1-517) | This work |
| pIREShygro::dnHIFB | Dominant Negative HIF-2a construct lacking transactivation domain including N-terminus NLS sequence (aa's 1-517 fused to aa's 738-741) | This work |
| pIREShygro::dnHIFC | Dominant Negative HIF-2a construct lacking N- and C-terminal transactivation domain (aa's 1-530-628 and 828-870) | This work |
| pRC/CMV | Mammalian expression vector | (Iliopoulos et al., 1995) |
| pRC/CMV::VHL30 | VHL30 cloned into pRC/CMV | (Iliopoulos et al., 1995) |
| pTUIIa' | Stable hairpin shRNAi expression vector | |
| pUTTa'::HIF-2a | Stable hairpin shRNAi expression vector targeting HIF2-a | |
| pLentiLox3.7puro | pLentiLox3.7 vector conferring puromycin resistance | J. Rocco (unpublished) |
| pLentiLox3.7hygro | pLentiLox3.7 vector conferring hygromycin resistance | J. Rocco (unpublished) |
| pLentiLox3.7blasti | pLentiLox3.7 vector conferring blasticidin resistance | J. Rocco (unpublished) |
| pLentiLox3.7puro::IRP1-15 | The following oligos were annealed and ligated into pLentiLox3.7puro (cut XbaI/HpaI)" 5'-TGACCTTCCAGGCTGTCATGAGGTTCAAGAGACCTCATGACAGCCTGGAAGGTCTTTTTTC**** (SEQ ID NO: 20) TCGAGAAAAAAGACCTTCCAGGCTGTCATGAGGTCTCTTGAACCTCATGACAGCCTGGAAGGTCA (SEQ ID NO: 21) | This work |
| pLentiLox3.7hygro::IRP1-14 | The following oligos were annealed and ligated into pLentiLox3.7hygro (cut XbaI/HpaI)" 5'-TGCCATCACACAGGGAGACCTTGTTCAAGAGACAAGGTCTCCCTGTGTGATGGCTTTTTTC-3' (SEQ ID NO: 22); 5'-TCGAGAAAAAAGCCATCACACAGGGAGACCTTGTCTCTTGAACAAGGTCTCCCTGTGTGATGGCA-3' (SEQ ID NO: 23) | This work |
| pLentiLox3.7blasti::IRP2-4 | The following oligos were annealed and ligated into pLentiLox3.7blasti (cut XbaI/HpaI)" 5'-TGGATTCTGGGGTGGGGGGTCTCTTCACCCCCACCCCAGAATCCTTTTTTC-3' (SEQ ID NO: 24); 5'-TCGAGAAAAAAGGATTCTGGGGTGGGGGGTGAAGAGACCCCCACCCCAGAATCCA-3' (SEQ ID NO: 25) | This work |
| pMDLG/pRRE | LentiLox3.7 Helper plasmid encoding gaga/pol elements | Dull et al., 1998 |

TABLE 4-continued

Plasmids used (Table 4 discloses the "pLentiLox3.7puro::IRP1-15" oligos as SEQ ID NOS 20 and 21, the "pLentiLox3.7hygro::IRP1-14" oligos as SEQ ID NOS 22 and 23, the "pLentiLox3.7blasti::IRP2-4" oligos as SEQ ID NOS 24 and 25 and the "HRE" sequence as SEQ ID NO: 26)

| Plasmid | Description | Ref: |
|---|---|---|
| pRSV-Rev | LentiLox3.7 Helper plasmid encoding Rev | Dull et al, 1998 |
| pCVM-VSVG | LentiLox3.7 Helper plasmid encoding envelope for viral pseudotyping | Dull et al., 1998 | a HRE (5'-CCACAGTGCATACGTGGGCTCCAACAGGTCCTCTTCCCTCCCATGCA-3') (SEQ ID NO: 26) cloned into pGL3 basic vector using 4 sets of annealed oligos with overhanging KpnI, SacI, MluI, NheI or XhoI sites. Final product was KpnI-HRE4-SacI-HRE3-MluI-HRE2-NheI-HRE1-XhoI where SacI, MluI and NheI sites were destroyed.
b site blunt-ended following restriction digest using T7 polymerase

TABLE 5

Cell lines used

| Cell line | Description | Ref. |
|---|---|---|
| U2OS | Osteosarcoma cell line used for transient transfection experiments | (Ponten and Saksela, 1967) |
| Hep3B | Hepatoblastoma | (Aden et al., 1979) |
| 786-O | VHL$^{-/-}$ Renal Clear Cell Carcinoma (RCC) | (Williams et al., 1978) |
| WT8 | 786-O derived clone stably transfected with pRC/CMV::VHL30, neo$^r$ | (Iliopoulos et al., 1995) |
| PRC3 | Matched vector only control for WT8 cells, neo$^r$ | (Iliopoulos et al., 1995) |
| 7TR1 | 786-O derived clone stably transfected with pTUIIa::HIF-2a targeting shRNAi, blasti$^r$ | (Zimmer et al., 2004) |
| 7TV1 | Matched vector only control for 7TR1 cells, blasti$^r$ | (Zimmer et al., 2004) |
| 7H4 | 786-O derived clone stably transfected with pcDNA3.1::HRE4, neo$^r$ | This work |
| 7SV | 786-O derived clone stably transfected with pDNA3.1::SV40, neo$^r$ | This work |
| 7SV-UTR | 786-O derived polyclonal line stably transfected with pDNA3.1::SV40-UTR, neo$^r$ | This work |
| 7H2P2 | 786-O derived polyclonal line stably transfected with pcDNA3.1::HIF2p, neo$^r$ | This work |
| 7H2P3 | 786-O derived polyclonal line stably transfected with pcDNA3.1::HIF2p-UTR, neo$^r$ | This work |
| 7CMV | 786-O derived polyclonal line stably transfected with pcDNA3.1::CMV, neo$^r$ | (Yang et al., 2004) |
| 7H2P2-UTR1 | 786-O derived polyclonal line stably transfected with pcDNA3.1::HIF2p-UTR1, neo$^r$ | This work |
| 7H2P2-UTR3 | 786-O derived polyclonal line stably transfected with pcDNA3.1::HIF2p-UTR3, neo$^r$ | This work |
| 7H2P2-UTR5 | 786-O derived polyclonal line stably transfected with pcDNA3.1::HIF2p-UTR5, neo$^r$ | This work |
| 7H2P2-UTR10 | 786-O derived polyclonal line stably transfected with pcDNA3.1::HIF2p-UTR10, neo$^r$ | This work |
| 7H2P2-UTR12 | 786-O derived polyclonal line stably transfected with pcDNA3.1::HIF2p-UTR12 neo$^r$ | This work |
| 7H2P2-UTR13 | 786-O derived polyclonal line stably transfected with pcDNA3.1::HIF2p-UTR13 neo$^r$ | This work |
| 7H2P2-UTR16 | 786-O derived polyclonal line stably transfected with pcDNA3.1::HIF2p-UTR16, neo$^r$ | This work |
| 7H2P2-UTR17 | 786-O derived polyclonal line stably transfected with pcDNA3.1::HIF2p-UTR17, neo$^r$ | This work |
| 7H2P2-1aUTR16 | 786-O derived polyclonal line stably transfected with pcDNA3.1::HIF2p-1aUTR16, neo$^r$ | This work |
| 7H2P2-1aUTR17 | 786-O derived polyclonal line stably transfected with pcDNA3.1::HIF2p-1aUTR17, neo$^r$ | This work |
| 7CMV-SL | 786-O derived polyclonal line stably transfected with pcDNA3.1::CMV-SL, neo$^r$ | (Yang et al., 2004) |
| 7UTR16 v.o. | 7H2P2-UTR16 line infected with pLentiLox3.7puro, pLentiLox3.7hygro and pLentiLox3.7blasti | This work |
| 7UTR16 IRP1 k.d. | 7H2P2-UTR16 line infected with pLentiLox3.7puro::IRP1-15, pLentiLox3.7hygro::IRP1-14 and pLentiLox3.7blasti | This work |
| 7UTR16 IRP2 k.d. | 7H2P2-UTR16 line infected with pLentiLox3.7puro, pLentiLox3.7hygro and pLentiLox3.7blasti::IRP2-4 | This work |
| 7UTR16 IRP1/2 k.d. | 7H2P2-UTR16 line infected with pLentiLox3.7puro::IRP1-15, pLentiLox3.7hygro::IRP1-14 and pLentiLox3.7blasti::IRP2-4 | This work |
| A498 | VHL$^{-/-}$ RCC | (Giard et al., 1973) |
| A-H4 | A498 derived polyclonal line stably transfected with pcDNA3.1::HRE4, neo$^r$ | This work |
| A-SV | A498 derived polyclonal line stably transfected with pDNA3.1::SV40, neo$^r$ | This work |
| UMRC2 | VHL$^{-/-}$ RCC | (Grossman et al., 1985) |
| U2-H4 | UMRC2 derived polyclonal line stably transfected with pcDNA3.1::HRE4, neo$^r$ | This work |
| U2-SV | UMRC2 derived polyclonal line stably transfected with pDNA3.1::SV40, neo$^r$ | This work |
| UMRC3 | VHL$^{-/-}$ RCC | (Grossman et al., 1985) |
| U3-H4 | UMRC3 derived polyclonal line stably transfected with pcDNA3.1::HRE4, neo$^r$ | This work |
| U3-SV | UMRC3 derived polyclonal line stably transfected with pDNA3.1::SV40, neo$^r$ | This work |
| UOK121 | VHL$^{-/-}$ RCC | (Herman et al., 1994) |
| UK-H4 | UOK121 derived polyclonal line stably transfected with pcDNA3.1::HRE4, neo$^r$ | This work |
| UK-SV | UOK121 derived polyclonal line stably transfected with pDNA3.1::SV40, neo$^r$ | This work | neo$^r$, neomycin/G418 resistant;
blasti$^r$, blasticidin resistant

High Throughput Small Molecule Screen for HIF-2a Inhibitors

The screen for small molecule inhibitors was performed in the Institute for Chemical and Cellular biology, Harvard Medical School. 7SV or 7H4 cells were plated onto 384-well plates. The next day compounds were added robotically to the medium, to a final concentration of approximately 10 µM. 24 hours later, media was aspirated and Passive Lysis Buffer (Promega) and Luciferase Assay Reagent II (Promega) were added. Luciferase activity was measured with an Analyst plate reader (LJL Biosystems). All experiments were performed in duplicate and the identity of lead compounds was confirmed by mass spectroscopy Quantitative Real Time Polymerase Chain Reaction (qRT-PCR)

The total RNA was harvested from the cells using the phenol and guanidine thiocyanate method using TRI-Reagent LS (Molecular Research Center, TS 120). Cells were lysed in 6 mL TRI-reagent LS, the contents transferred to a 15 mL conical to which 1.2 mL of Chloroform was added. Contents were mixed by shaking and centrifuged at 3000 rpm's at 4° C. in a Beckman Coulter Allegra 6R Centrifuge. The aqueous layer was then transferred to a new 15 mL conical, mixed with an equal volume of Diethyl pyrocarbonate (DEPC) treated 75% EtOH and washed over RNeasy Mini Kit columns (Qiagen, 74104) before eluting in 50 µL DEPC treated $H_2O$. In order to remove contaminating genomic DNA so that the levels of nascent message could be measured using intron-targeting primers, the resulting RNA preparation was then mixed with 50 µL DEPC treated 2×HSB buffer (0.5M NaCl, 50 mM $MgCl_2$, 2 mM $CaCl_2$, 10 mM Tris-Cl, pH 7.4) supplemented with 5 Units of RNase-free DNaseI (Worthington) and 50 Units of RNase inhibitor (RNaseOUT, Invitrogen) and incubated at 30° C. for 1 hour. The reaction was then mixed with an equal volume of DEPC treated 75% EtOH, washed over RNeasy Mini Kit columns and again eluted in 50 µL DEPC treated $H_2O$. RNA was quantified by measuring Absorbance at 260 nM using a Beckman DU 640 spectrophotometer. 1 µg of RNA was then subjected to reverse transcription using random hexamer primers and Reverse Transcriptase III (Invitrogen) according to the manufacturer's recommendations. Polymerase chain reaction was performed on the resulting RT reactions using IQ SYBR Green Supermix (BioRad) and run on a MyIQ Single Color Real-Time PCR machine (BioRad) using the following intron-spanning primers: 5'-TTTCATCCATCCGACATTGA-3' (SEQ ID NO: 1) and 5'-ATCTTCAAACCTCCATGATG-3' (SEQ ID NO: 2) for B-2-microglobulin (B2M); 5'-GGATCAGCGCACAGAGTTC-3' (SEQ ID NO: 3) and 5'-GTACTGGGTGGCGTAGCACT-3' (SEQ ID NO: 4) for HIF-2a; 5'-AAGCGGTTCTTGGTACCAGC-3' (SEQ ID NO: 5) and 5'-GGATAATCTGTGTCCTCGCA-3' (SEQ ID NO: 6) for Transferrin Receptor 1 (TFR1); 5'-GCTACGATTGCTAACATGTG-3' (SEQ ID NO: 7) and 5'-GAGGCCTTTTGGGTCCACTA-3' (SEQ ID NO: 8) for IRP1; 5'-TGTGATTCTGGAGAACTAGG-3' (SEQ ID NO: 9) and 5'-CCCTAAACCATTCACCATCG-3' (SEQ ID NO: 10) for IRP2; 5'-ATCAGCTTCCTCCTGTCCCT-3' (SEQ ID NO: 11) and 5'-GGGCTGCACTTCGTGTGGGT-3' (SEQ ID NO: 12) for EGLN3. Nascent HIF-2a message levels were determined using primers located within the first intron of the unprocessed message: 5'-AGACGGTGGACTCCGCCA-3' (SEQ ID NO: 13) and 5'-TTAAAGGGAGGGGTACAC-3' (SEQ ID NO: 14).

Gene Expression Profiling and Connectivity Map Analysis

RNA from compound treated 786-O cells was isolated as described for qRT-PCR experiments. Labeled cRNA was prepared and hybridized to Affymetrix U133 Plus 2.0 microarrays according to the manufacturer's protocols. Scans were processed using Affymetrix MASS software and median scaled. Gene expression values less than a minimum threshold of 20 or a maximum threshold of 16000 were set to 20 and 16000, respectively. Genes with minimal variation across the dataset were discarded (maximum/minimum<3 or maximum−minimum<100). Class neighbors were identified with GenePattern software using the signal to noise metric (Golub et al., 1999). Hierarchical clustering was performed using dCHIP software. Gene set enrichment analysis was performed as described (Mootha et al., 2003) and significance was determined by permutation of the gene labels. Gene expression signatures were analyzed using the Connectivity Map webtool (build 01). Full details of the Connectivity Map dataset and analytics are provided elsewhere (Lamb et al., 2006). For $PGJ_2$ expression analysis, raw gene-expression data have GEO series accession number GSE13818 and compound signatures from which non-HG-U133A probe sets were removed (see Table 6) were used to query the Connectivity Map (build 02).

TABLE 6

Signature of HIF-2a inhibitors used for Connectivity Mapping

| 40up | 41up | 76up | 77up | 40down | 41down | 76down | 77up |
|---|---|---|---|---|---|---|---|
| 209160_at | 209160_at | 211653_x_at | 208792_s_at | 238737_at | 225660_at | 1557921_s_at | 211756_at |
| 209699_x_at | 211653_x_at | 216594_x_at | 1569577_x_at | 202833_s_at | 223449_at | 223449_at | 1556000_s_at |
| 204151_x_at | 204151_x_at | 204151_x_at | 238084_at | 1553589_a_at | 210905_x_at | 225660_at | 225660_at |
| 211653_x_at | 223333_s_at | 206561_s_at | 213988_s_at | 207184_at | 222925_at | 201313_at | 207126_x_at |
| 203889_at | 241418_at | 217678_at | 201467_s_at | 206023_at | 230746_s_at | 210905_x_at | 223449_at |
| 216594_x_at | 228824_s_at | 242775_at | 202434_s_at | 202902_s_at | 210512_s_at | 1553589_a_at | 215125_s_at |
| 201467_s_at | 208792_s_at | 228824_s_at | 209099_x_at | 222925_at | 223827_at | 215028_at | 208596_s_at |
| 214211_at | 209699_x_at | 241418_at | 1569303_s_at | 206461_x_at | 210538_s_at | 202833_s_at | 1556773_at |
| 203665_at | 217678_at | 228825_at | 205083_at | 211429_s_at | 1557921_s_at | AFFX-HUMISGF3A/M97935_MA_at | 232654_s_at |
| | 206561_s_at | 231897_at | 209699_x_at | 235085_at | 208795_s_at | AFFX-HUMISGF3A/M97935_MB_at | AFFX-HUMISGF3A/M97935_5_at | 208725_at |

TABLE 6-continued

Signature of HIF-2a inhibitors used for Connectivity Mapping

| 40up | 41up | 76up | 77up | 40down | 41down | 76down | 77up |
|---|---|---|---|---|---|---|---|
| 214307_at | 206237_s_at | 231897_at | 1563445_x_at | 218834_s_at | 205670_at | AFFX-HUMISG F3A/M97935_MB_at | 232221_x_at |
| 219874_at | 210143_at | 209160_at | 216268_s_at | 211756_at | 226907_at | 209969_s_at | 226907_at |
| 242037_at | 209921_at | 235629_at | 210224_at | 223484_at | 209969_s_at | 206023_at | 215849_x_at |
| 207528_s_at | 201467_s_at | 219475_at | 228824_s_at | 213785_at | 225681_at | 230746_s_at | 210355_at |
| 205808_at | 216594_x_at | 201467_s_at | 208791_at | 225681_at | 202687_s_at | 220454_s_at | 204845_s_at |
| 224346_at | 209101_at | 209921_at | 231897_at | 209754_s_at | 205575_at | 210538_s_at | 204532_x_at |
| 208791_at | 200800_s_at | 210143_at | 205952_at | 232596_at | AFFX-HUMISG F3A/M97935_MA_at | 206758_at | 241950_at |
| 209921_at | 224609_at | 208161_s_at | 225386_s_at | 230499_at | 221123_x_at | 202086_at | 205560_at |
| 226248_s_at | 226218_at | 208792_s_at | 211499_s_at | 226869_at | 241950_at | 202687_s_at | 206094_x_at |
| 202756_s_at | 203889_at | 204694_at | 202437_s_at | 228121_at | 1553589_a_at | 219630_at | 214890_s_at |
| 1569303_s_at | 206561_s_at | 239896_at | 217892_s_at | 242844_at | 230499_at | 235278_at | 241644_at |
| 213350_at | 228825_at | 207528_s_at | 202436_s_at | 215726_at | 235278_at | 226907_at | 235278_at |
| 210663_s_at | 229441_at | 204105_at | 236321_at | 222767_s_at | 215028_at | 1556773_at | 218149_at |
| 204341_at | 214211_at | 228062_at | 239823_at | 241950_at | 236083_at | 221538_s_at | 203710_at |
| 231735_at | 228274_at | 214211_at | 230795_at | 236277_at | 221801_x_at | 203710_at | 232004_at |
| 225252_at | 203665_at | 236140_at | 207813_s_at | 201313_at | 235144_at | 234975_at | 230746_s_at |
| 217388_s_at | 217388_s_at | 203343_at | 215071_s_at | 217165_x_at | 205302_at | 225681_at | 230352_at |
| 208792_s_at | 201107_s_at | 209457_at | 202275_at | 226278_at | 203641_s_at | 214329_x_at | 220454_s_at |
| 224559_at | 235085_at | 229879_at | 203158_s_at | 230352_at | 220454_s_at | 230352_at | 213652_at |
| 222016_s_at | 224990_at | 226462_at | 202803_s_at | 225660_at | 226438_at | 202149_at | 201313_at |
| 202017_at | 200799_at | 202053_s_at | 202284_s_at | 202430_s_at | 201313_at | 202796_at | 234924_at |
| 214701_s_at | 238084_at | 202923_s_at | 214446_at | 206936_x_at | 226436_at | 232693_s_at | 209969_s_at |
| 218246_at | 225252_at | 200748_s_at | 201601_x_at | 210117_at | 208608_s_at | 225601_at | 1557921_s_at |
| 213747_at | 210663_s_at | 218417_s_at | 1557905_s_at | 219929_at | 202688_at | 241950_at | 210095_s_at |
| 223577_x_at | 200748_s_at | 210519_s_at | 205925_at | 213169_at | 203037_s_at | 205302_at | 221916_at |
| 205606_at | 209457_at | 210896_s_at | 222457_s_at | 231872_at | 203710_at | 232004_at | 205670_at |
| 213998_s_at | 1559462_at | 225252_at | 218825_at | 226348_at | 218145_at | 227405_s_at | 218507_at |
| 227616_at | 220617_at | 203665_at | 202435_at | 202073_at | 214890_at | 222925_at | 218145_at |
| 217678_at | 208791_at | 223594_at | 201058_s_at | 206300_s_at | 238756_at | 222450_at | 202086_at |
| 235589_s_at | 210519_s_at | 203925_at | 209835_x_at | 214329_x_at | AFFX-HUMISG F3A/M97935_5_at | 225792_at | 202830_s_at |
| 225116_at | 204694_at | 202201_at | 206237_s_at | 214095_at | 223216_x_at | 205670_at | 215028_at |
| 226150_at | 203343_at | 201468_s_at | 236175_at | 228401_at | 205403_at | 209546_s_at | 224477_s_at |
| 219882_at | 207528_s_at | 201118_at | 202270_at | 210017_at | 214329_x_at | 214532_x_at | 217289_at |
| 206343_s_at | 202201_at | 202054_at | 204734_at | 215101_s_at | 244567_at | 214890_at | 239229_at |
| 212224_at | 219874_at | 216959_x_at | 202756_s_at | 229235_at | 1553986_at | 221610_s_at | 223216_x_at |
| 224568_x_at | 225386_s_at | 1569303_s_at | 202201_at | 201436_at | 236261_at | 227598_at | 227405_s_at |
| 236814_at | 201058_s_at | 242037_at | 1565772_at | 227110_at | 227812_at | 202073_at | 221801_x_at |
| 1558678_s_at | 202581_at | 229963_at | 239202_at | 225048_at | 203642_s_at | AFFX-HUMISG F3A/M97935_3_at | 206026_s_at |
| 202284_s_at | 209797_at | 202275_at | 201939_at | 210538_s_at | 222536_s_at | 212061_at | 222925_at |
| 1556959_at | 212848_s_at | 238084_at | 209806_at | 210512_s_at | 200887_s_at | 202848_s_at | 214889_at |
| 223940_x_at | 221009_s_at | 219508_at | 202755_s_at | AFFX-HUMISG F3A/M97935_3_at | 212427_at | 205575_at | 214095_at |
| 226640_at | 228205_at | 207029_at | 212014_x_at | 204972_at | 204200_s_at | 210355_at | 212170_at |
| 1568574_x_at | 205943_at | 230560_at | 1556959_at | 225421_at | 218149_s_at | 202902_s_at | 212332_at |
| 228928_x_at | 209928_s_at | 219874_at | 223541_at | 204632_x_at | 1570065_at | 219232_s_at | 221567_at |
| 202648_at | 206153_at | 233540_s_at | 214085_x_at | 212206_s_at | 202833_s_at | 223216_x_at | 222847_s_at |
| 211692_s_at | 207029_at | 202014_at | 203904_x_at | 200887_s_at | 202149_at | 226869_at | 228565_at |
| 1552944_a_at | 202923_s_at | 209135_at | 203889_at | 203276_at | 225671_at | 211756_at | 211138_s_at |
| 217117_x_at | 201468_s_at | 234986_at | 209398_at | 230746_at | 234975_at | 203128_at | 232693_s_at |
| 227510_x_at | 202053_s_at | 211124_s_at | 1552546_a_at | 230493_at | 235890_at | 210095_s_at | 209967_s_at |
| 210686_x_at | 201348_at | 219295_s_at | 230493_at | 205395_s_at | 211756_at | 222536_s_at | 210905_x_at |
| 213710_s_at | 208161_s_at | 207469_s_at | 203159_at | 202149_at | 1555788_a_at | 201295_s_at | 213506_at |
| 224966_at | 242037_at | 206153_at | 204470_at | 226189_at | 236277_at | 218149_s_at | 230958_at |
| 215388_s_at | 213139_at | 209735_at | 1559462_at | 202687_s_at | 206693_at | 227812_at | 201418_s_at |
| 204384_at | 236140_at | 203159_at | 237737_at | 218400_at | | 214889_at | 208650_s_at |
| | | | | AFFX-HUMISG F3A/M97935_MB_at | | | |
| 225118_at | 220935_s_at | 48106_at | 201107_s_at | 214974_x_at | 206025_s_at | 228126_x_at | 221123_x_at |
| 237287_at | 203925_at | 213112_s_at | 214307_at | 215177_s_at | 234725_s_at | 206026_s_at | 209426_s_at |
| 212070_at | 201108_s_at | 239001_at | 210589_s_at | 208296_x_at | 204597_x_at | 223827_at | 202848_s_at |
| 219328_at | 217841_s_at | 224990_at | 216716_at | 203642_s_at | 219630_at | 204597_x_at | 233520_s_at |

TABLE 6-continued

Signature of HIF-2a inhibitors used for Connectivity Mapping

| 40up | 41up | 76up | 77up | 40down | 41down | 76down | 77up |
|---|---|---|---|---|---|---|---|
| 214333_x_at | 210220_at | 220935_s_at | 201108_s_at | 217347_at | 205822_s_at | 209183_s_at | 205575_at |
| 211019_s_at | 211124_s_at | 228063_s_at | 229396_at | 1556773_at | 221916_at | 204152_s_at | 209424_s_at |
| 224990_at | 202017_at | 1558199_at | 239503_at | 213518_at | 211488_s_at | 221123_x_at | 209772_s_at |
| 228594_at | 242775_at | 1563445_x_at | 208579_x_at | 1558330_x_at | 226869_at | 218087_s_at | 1555788_a_at |
| 212272_at | 239896_at | 219247_s_at | 204823_at | 201044_x_at | 238423_at | 203642_s_at | 221805_at |
| 210022_at | 234986_at | 202260_s_at | 226136_at | 202688_at | 228565_at | 230499_at | 210761_s_at |
| 235659_at | 1563445_x_at | 204114_at | 206074_s_at | 201123_s_at | 206023_at | 213785_at | 205306_x_at |
| 203679_at | 201110_s_at | 220254_at | 204489_s_at | 232004_at | 237328_at | 208978_at | 205942_s_at |
| 205640_at | 235274_at | 203158_s_at | 217996_at | 223423_at | 205047_s_at | 201418_s_at | 228269_x_at |
| 222675_s_at | 225175_s_at | 232155_at | 214605_x_at | 206026_s_at | 203556_at | 222809_x_at | 240122_at |
| 204227_s_at | 219475_at | 202756_s_at | 204222_s_at | 238469_at | 231888_at | 221916_at | 214177_s_at |
| 227549_x_at | 220922_s_at | 208791_at | 212665_at | 203493_s_at | 202897_at | 1555705_a_at | 210367_s_at |
| 212274_at | 218970_s_at | 205808_at | 213338_at | 221610_s_at | 242329_at | 204200_s_at | 209496_at |
| 227617_at | 204385_at | 56256_at | 209911_x_at | 202660_at | 212810_s_at | 209558_s_at | 235309_at |
| 239067_s_at | 229879_at | 225242_s_at | 217997_at | 229427_at | 242069_at | 215849_x_at | 218309_at |
| 239208_s_at | 210589_s_at | 217996_at | 211320_s_at | 1562836_at | 202643_s_at | 205306_x_at | 1569732_at |
| 207714_s_at | 201266_at | 209797_at | 210916_s_at | 200864_s_at | 207052_at | 222934_s_at | 216366_x_at |
| 231763_at | 208997_s_at | 218000_s_at | 204490_s_at | 223449_at | 229800_at | 207556_s_at | 203126_at |
| 223578_x_at | 228346_at | 228928_x_at | 211003_x_at | 221765_at | 226722_at | 214906_x_at | 205920_at |
| 205798_at | 202054_s_at | 220994_s_at | 226218_at | 229265_at | 206758_at | 210512_s_at | 209425_at |
| 230341_x_at | 224826_at | 204058_at | 1554274_at | 240114_s_at | 213056_at | 228565_at | 205822_s_at |
| 217173_s_at | 204341_at | 202017_at | 213028_at | 224577_at | 232693_s_at | 218995_s_at | 212143_s_at |
| 201373_at | 219410_at | 210544_s_at | 204221_x_at | 213470_s_at | 232004_at | 222847_s_at | 229925_at |
| 216479_at | 203810_at | 203157_s_at | 242037_at | 207002_s_at | 210237_at | 234987_at | 218816_at |
| 212844_at | 233571_x_at | 214307_at | 206343_s_at | 235890_at | 236979_at | 213675_at | 210601_at |
| 211708_s_at | 49077_at | 223333_s_at | 223333_s_at | 226326_at | 1559638_at | 201242_s_at | 205380_at |
| 223200_s_at | 201939_at | 206237_s_at | 218843_at | 91816_f_at | 210827_s_at | 228987_at | 221246_x_at |
| 201810_s_at | 202014_at | 220253_s_at | 1560402_at | 202904_s_at | 211372_s_at | 209369_at | 213437_at |
| 212187_x_at | 237737_at | 201348_at | 214290_s_at | 233899_x_at | 215244_at | 227889_at | 207713_s_at |
| 242414_at | 208998_at | 204341_at | 203157_s_at | 209969_s_at | 227598_at | 205067_at | 222536_s_at |
| 225254_at | 212977_at | 218970_s_at | 209803_s_at | 215436_at | 222934_s_at | 206300_s_at | 228302_x_at |
| 208962_s_at | 239001_at | 226258_at | 231577_s_at | 235940_at | 227907_at | 210367_s_at | 210827_s_at |

HUVEC Proliferation Assay

HUVEC cells were plated in a 96 well plate in HUVEC minimal medium (Chembrex, EBM-2). 24 hours later, medium was replaced with a 1:4 mix of tissue culture medium that had been conditioned from compound or DMSO-only treated 786-O cells and HUVEC minimal medium. HUVEC proliferation was quantified by a colorimetric proliferation assay (WST-1, Roche, Germany).

Western Blots

Western Blot were performed as described previously (Zimmer et al., 2004). For protein detection we used monoclonal anti-HIF-2a (Novus, NB100-132), polyclonal anti-HIF-2a (Novus, NB100-122), monoclonal anti-HIF-1a (BD Biosciences, 610958), polyclonal Glut-1 (Alpha Diagnostics, GT-1 1-A), polyclonal anti-p70S6K (Cell Signaling Technologies, 9202), polyclonal anti-phospho T389 p70S6K (Cell Signaling Technologies, 9205S), polyclonal anti-phospho S235/6 S6 (Cell Signaling Technologies, 22115), monoclonal IRP2 (Santa Cruz, sc-33680) or monoclonal anti-B-Actin (Novus, ab8226). The polyclonal IRP1 antibody and the polyclonal IRP2 antibodies (UT29 and UT30) were generous gifts from Drs K. Pantopoulos and B. Leibold, correspondingly. Secondary, HRP-conjugated antibodies to mouse or rabbit immunoglobulin G were purchased from Pierce (31432, 31462). Primary antibodies were used at 1:1000 dilution. Hypoxia induction: Two identical plates of cells were changed into fresh medium and incubated at 37° C., 5% CO2, and ambient O2, for 24 hours. After 24 hours, one set was kept at 37° C., 5% CO2, and ambient O2, while the other was placed into an ESPEC hypoxic incubator (1% O2, 5% CO2, 37° C.) for another 24 hours. Cells were harvested and immunoblotted as described above.

Enzyme-Linked Immunosorbent Assay (ELISA)

VEGF or IGFBP3 ELISA was performed on the conditioned supernatant using Quantikine immunoassay kits (R&D Systems, DVE00 for VEGF, DGB300 for IGFBP3).

Cycloheximide Experiments

Cells were treated with medium only, DMSO, or compound as described for western blots. Following the second day of compound incubation, 10 µg/mL cycloheximide (CHx) was added to halt de novo protein synthesis and time points were taken. Protein quantification and Western blots were performed as described.

In Vivo $^{35}$S-Methionine Pulse-Label Experiments

Cells were treated with medium only, DMSO, or compound as described for western blots. Following the second day of treatment, cells were washed twice in PBS and then placed into medium only, DMSO, or labeling medium (methionine minus DMEM supplemented with 1× glutamine and 5% dialyzed FBS) and pulse-labeled for 30 minutes at 37° C. with 0.5 mCi $^{35}$S-Methionine (New England Nuclear) per p100 plate. Cells were washed twice in PBS and lysed with RIPA buffer supplemented with protease inhibitors. Protein concentration was determined using the Bradford assay and 500 µg lysate was immunoprecipitated with 2 polyclonal anti-HIF2a (Novus, NB100-122) or control polyclonal anti-HA Y-11 (Santa Cruz, sc-805) antibodies using Protein A sepharose CL-4B beads (GE Healthcare). In the case of the pulse-chase experiment, two identically treated plates were placed into chasing medium (DMEM supplemented with 10% Fetal Clone I, 1× Glutamine and 3 mg/mL methionine), placed back into the 37° C. incubator and harvested after 1.5 and 3 hours. Immunoprecipitated samples were subjected to SDS-PAGE, enhanced in sodium salicylate, dried and exposed for 2-3 days before the film was quantified by densitometry.

Electrophoretic Mobility Shift Assays (EMSAs)

EMSAs were performed as described previously (Fillebeen et al., 2003). Briefly, 50 µg lysate from 786-O cells treated with medium only, DMSO, or compounds were incubated with 25,000 cpm wild-type or mutant radiolabeled HIF-2a IRE probe for 20 minutes at room temperature before loading onto non-denaturing acrylamide gels. Supershifts were performed identically, save that 0.2 µg control, IRP1 or IRP2 antibodies were also added. Total protein content was estimated by Bradford Assay (BioRad, 500-0006), and even loading for all experiments was confirmed by Western blot for B-Actin.

In Vitro Iron Competition Assay

This assay was performed similarly to that described previously (Wang et al., 2002). Briefly, displacement of iron from ethyl-3,4-dihydroxybenzoate (EDHB) complex was measured as a decrease in absorbance at 500 nm. Ferric iron, prepared as a 5 mM stock solution of FeCl3 in 100 mM sodium citrate, was diluted to 25 µM in the presence of 750 µM EDHB. 1 ml aliquots of this solution were then mixed with 0, 25, 50, 100 or 200 micromolars of compounds 40, 41, 76, and 77 as well as EDTA and DFO for controls. With the exception of compound 41, only the Fe-(EDHB)$_3$ complex absorbed significantly at 500 nm. The self absorbance of compound 41 in a matched solution lacking Fe-(EDHB)$_3$ was subtracted from the A500 value obtained in the presence of the Fe-(EDHB)$_3$ complex.

Luciferase Assays

Luciferase assays were performed using the Promega's Dual-luciferase Assay Reporter System (Promega, E1910) according to the manufacturer's instructions. Counts obtained from transient transfections were normalized for co-transfected *Renilla luciferase*. Stable clones were normalized to medium only treated wells.

Polysome Analysis

DMSO-, rapamycin- or PGJ2-treated 786-O cells were harvested from 10 cm plates for each polysomal analysis. Confluent cells were harvested and lysed in 300 µL of RSB [10 mmol/L NaCl, 10 mmol/L Tris-HCl (pH 7.4), 15 mmol/L MgCl$_2$] containing 100 µg/mL heparin, 1.2% Triton X-100, and 0.12% deoxycholate. Nuclei were pelleted for 3 min in a microcentrifuge at 4° C. The 300-µL extract was layered over 11.5 mL of a 15% to 45% (wt/wt) sucrose gradient with a 0.5-mL cushion of 45% sucrose. The gradients were centrifuged at 37,000 rpm for 2.5 h in an SW 41 (Beckman) rotor at 4° C. After centrifugation, the $A_{260}$ was continuously monitored and recorded across the gradient using a Foxy Jr. Density Gradient fractionation system and UA-6 UV/VIS Detector (ISCO, Inc.).

Gel Densitometry

Western blot and autoradiograph images were scanned and optical density of bands determined using a UVP BioImaging System and LabWorks Image Acquisition and Analysis Software (UVP, Inc.).

Example 1

High-Throughput Screen for Small Molecule HIF-2a Inhibitors

Figure 8A:
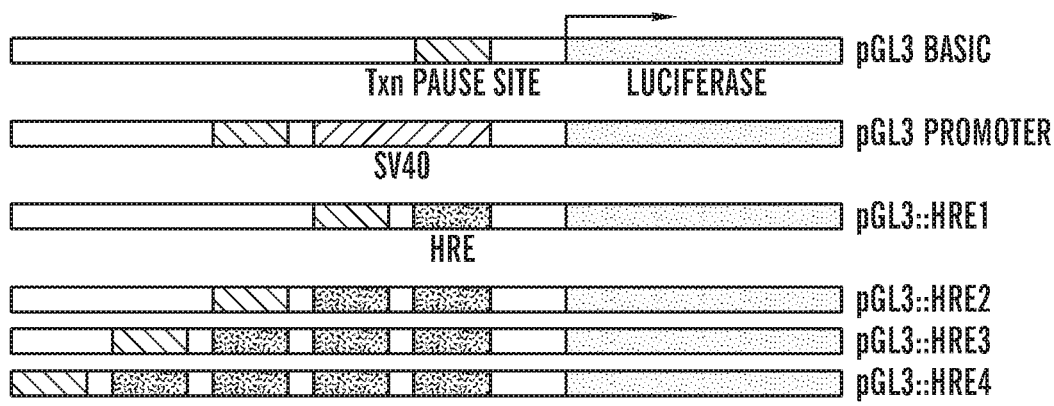
FIGS. 8A-8D show data to validate the luciferase reporter constructs.
Figure 8B:
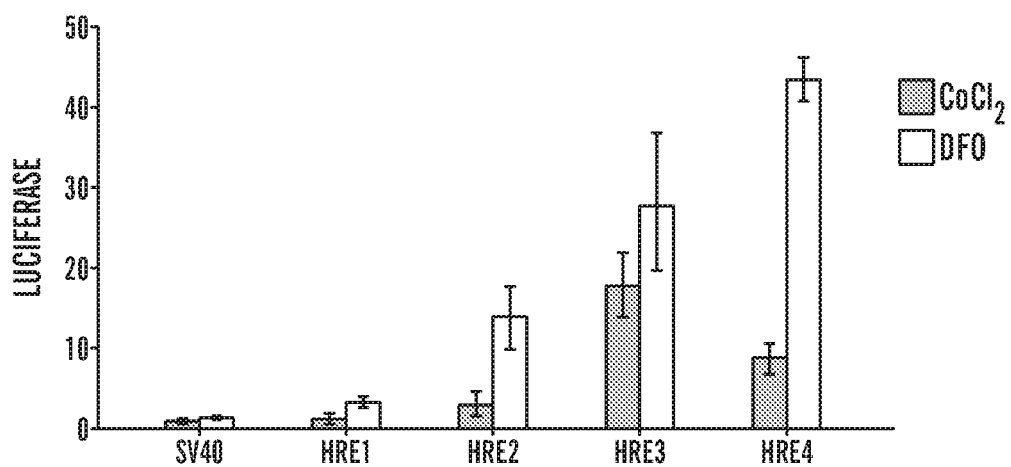
Figure 8C:
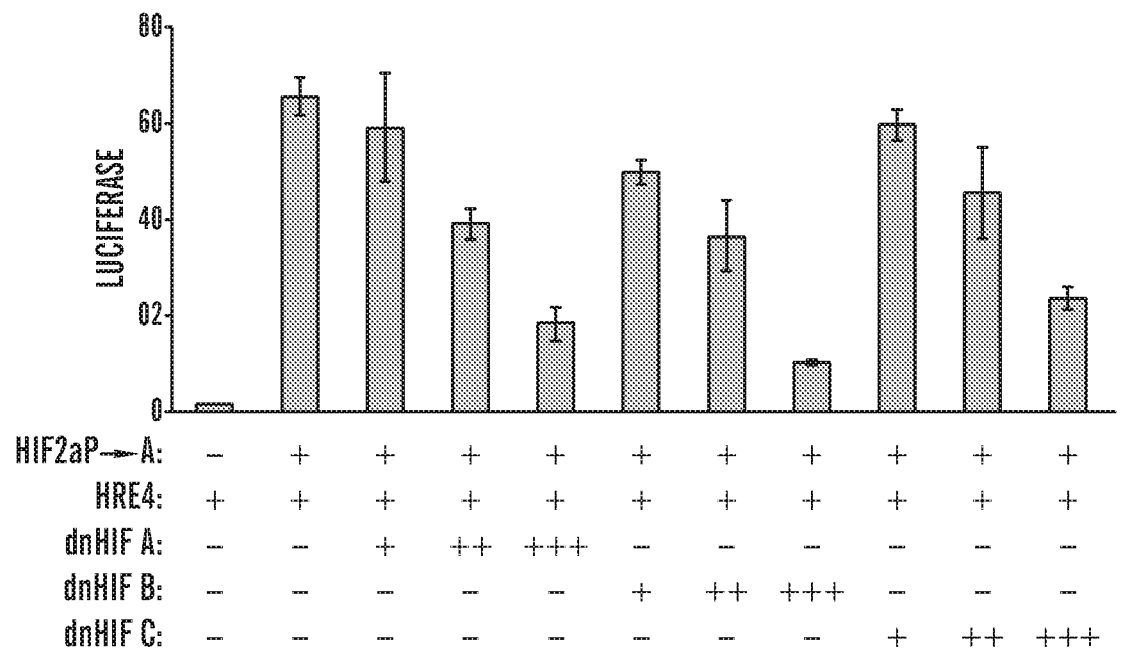
Figure 8D:
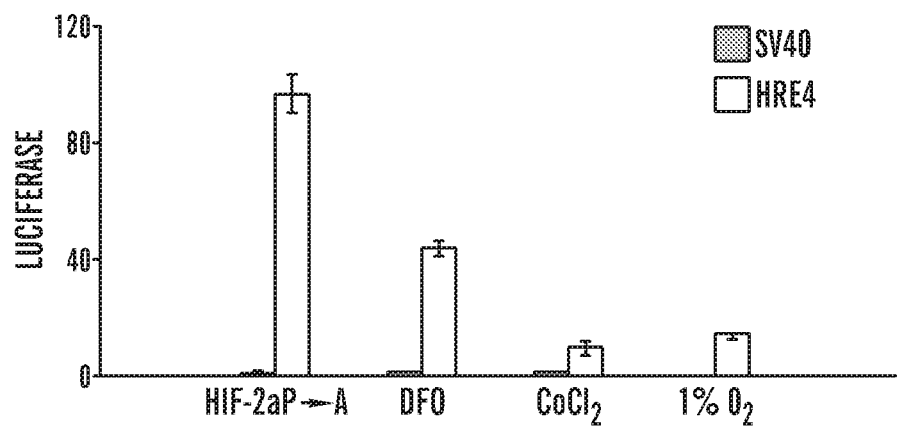
Figure 9A:
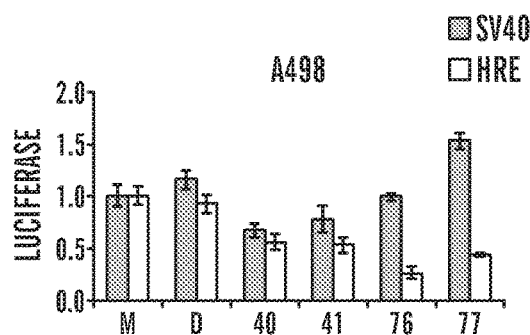
FIGS. 9A-9D show compounds A498, UOK121, UMRC2 and UMRC3 affect multiple RCC cell lines. Compounds were tested on stable polyclonal versions of VHL-defective lines expressing either the SV40- or HRE-luciferase reporter constructs.
Figure 9B:
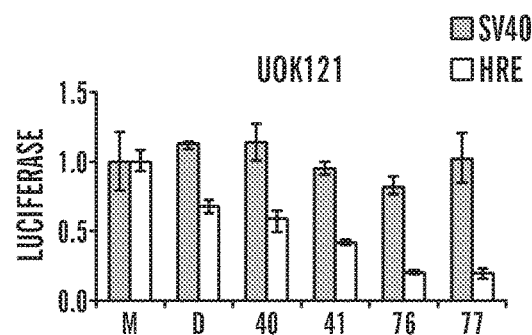
Figure 9C:
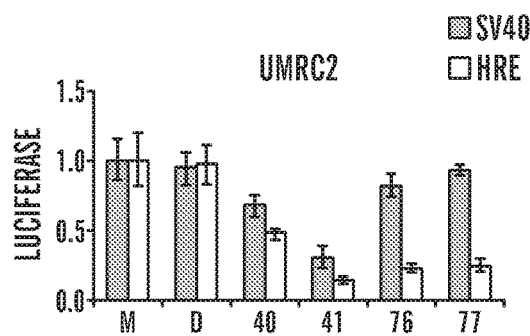
Figure 9D:
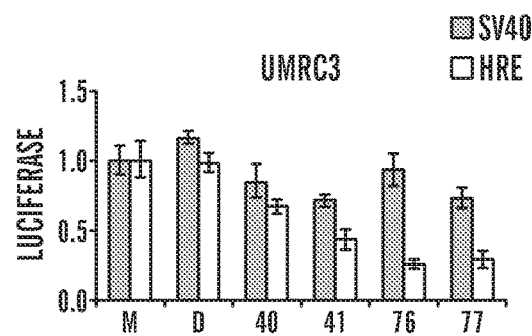

Functionally validated HRE and control SV40 luciferase reporter constructs were stably introduced into VHL-deficient 786-O cells to generate 7H4 and 7SV lines, respectively (see FIG. 8A). These lines were used to screen five commercial small molecule libraries (NCI Diversity Set, Chembridge, Maybridge, CEREP and Peakdale) and the ICCB Diversity-Oriented Synthesis (DOS) Diversity Set 2 (DDS2) and serine-derived peptidomimetic (SDP1) collections, totaling 58,000 compounds. Eight compounds were identified that reproducibly decreased luciferase activity by greater than 80% when applied to 7H4 cells, while having little or no affect on the corresponding 7SV cells and worked on multiple RCC cell types when stably transfected with the same luciferase reporters (see FIGS. 9A-9D).

Example 2

Dose Response Curves of Selected Inhibitors

786-O cells were untreated (M, for medium only), mock-treated (D, for DMSO) or treated with compounds for two days before assaying for normalized luciferase activity. The resulting dose response curves are shown along with the compound structures in FIGS. 1A-1H. The full chemical name of the compounds is listed in Table 1. Compounds exhibited apparent IC50 values ranging from 2.5-40 µM. Based on the potency of the compounds and comparative lack of cellular toxicity at IC50 concentrations we chose to focus our mechanistic analysis on compounds 40, 41, 76 and 77.

Example 3

Figure 1A:
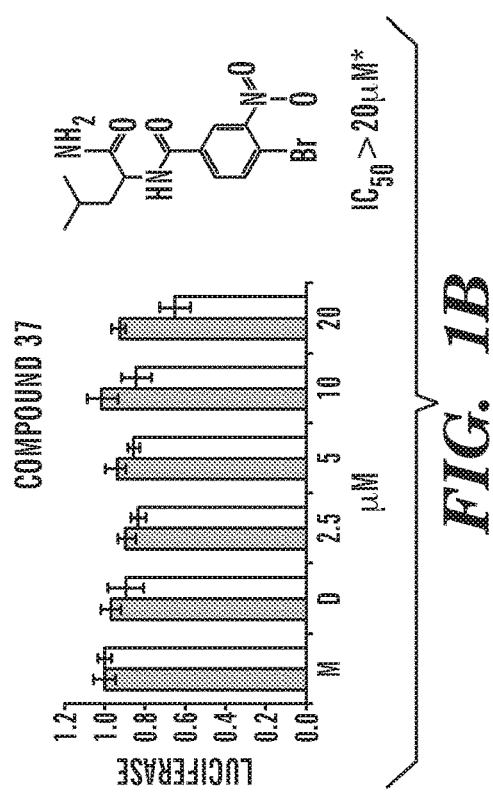
FIGS. 1A-1H show the structure and dose response of HIF inhibitor compounds 20, 37, 39, 40, 41, 42, 76, and 77. All compounds were added at the indicated concentrations for two days prior to measuring normalized luciferase activity. Gray bars, 7SV (SV40-luciferase) cells; white bars, 7H4 (HRE-luciferase) cells. All experiments were performed in triplicate. Error bars represent standard error of the mean (SEM).
Figure 1B:
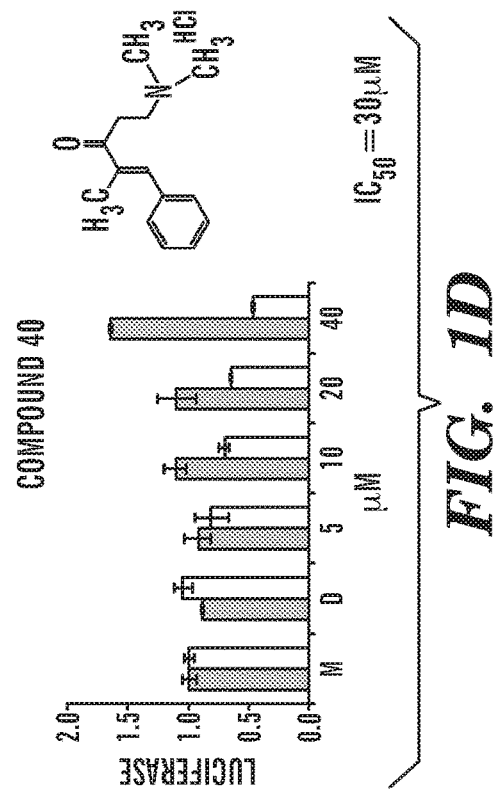
Figure 1C:
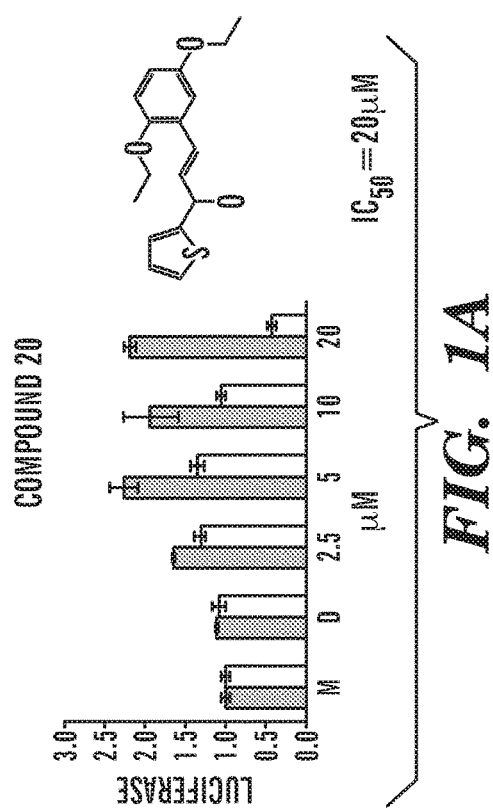
Figure 1D:
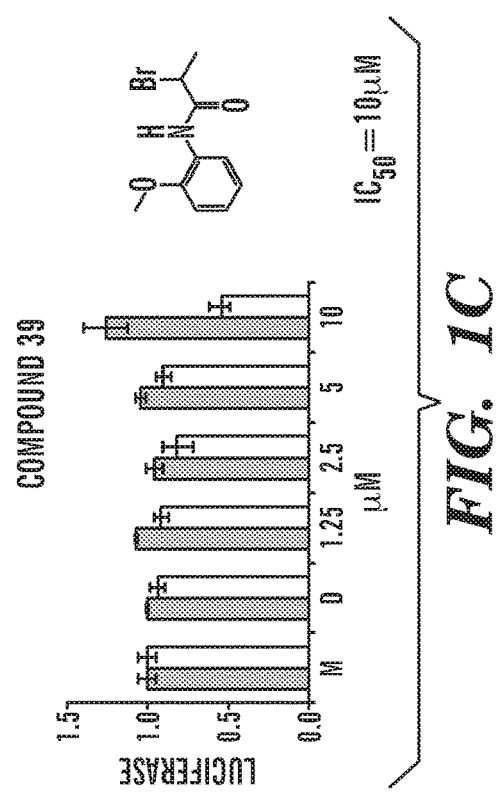
Figure 1E:
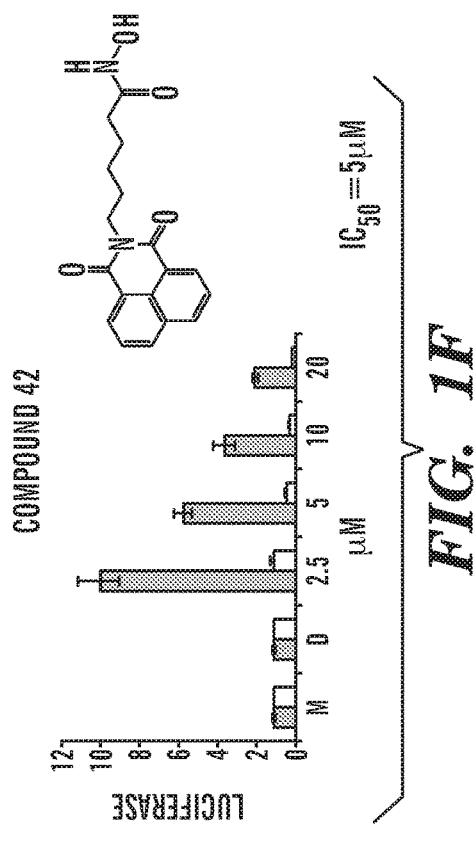
Figure 1F:
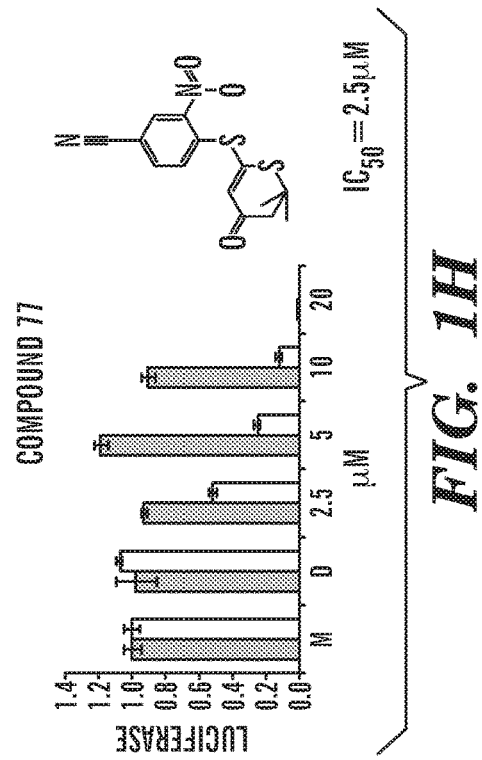
Figure 1G:
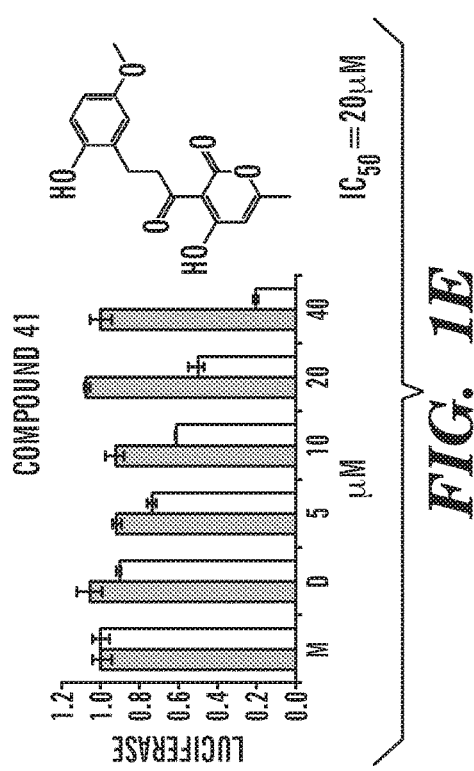
Figure 1H:
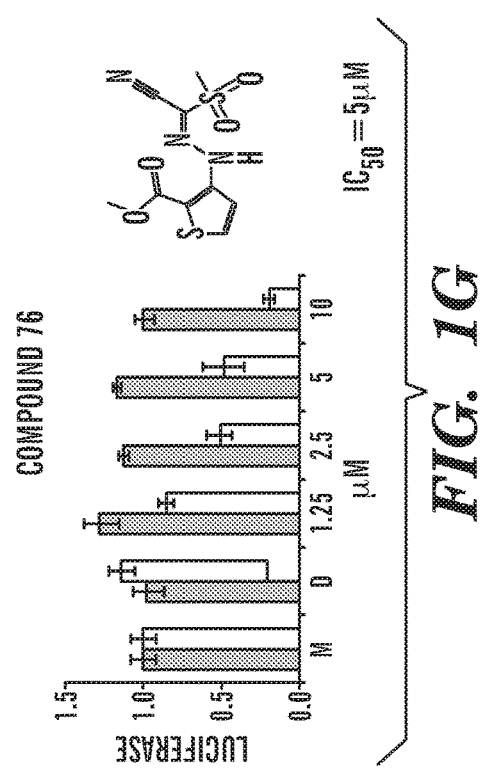
Figure 2A:
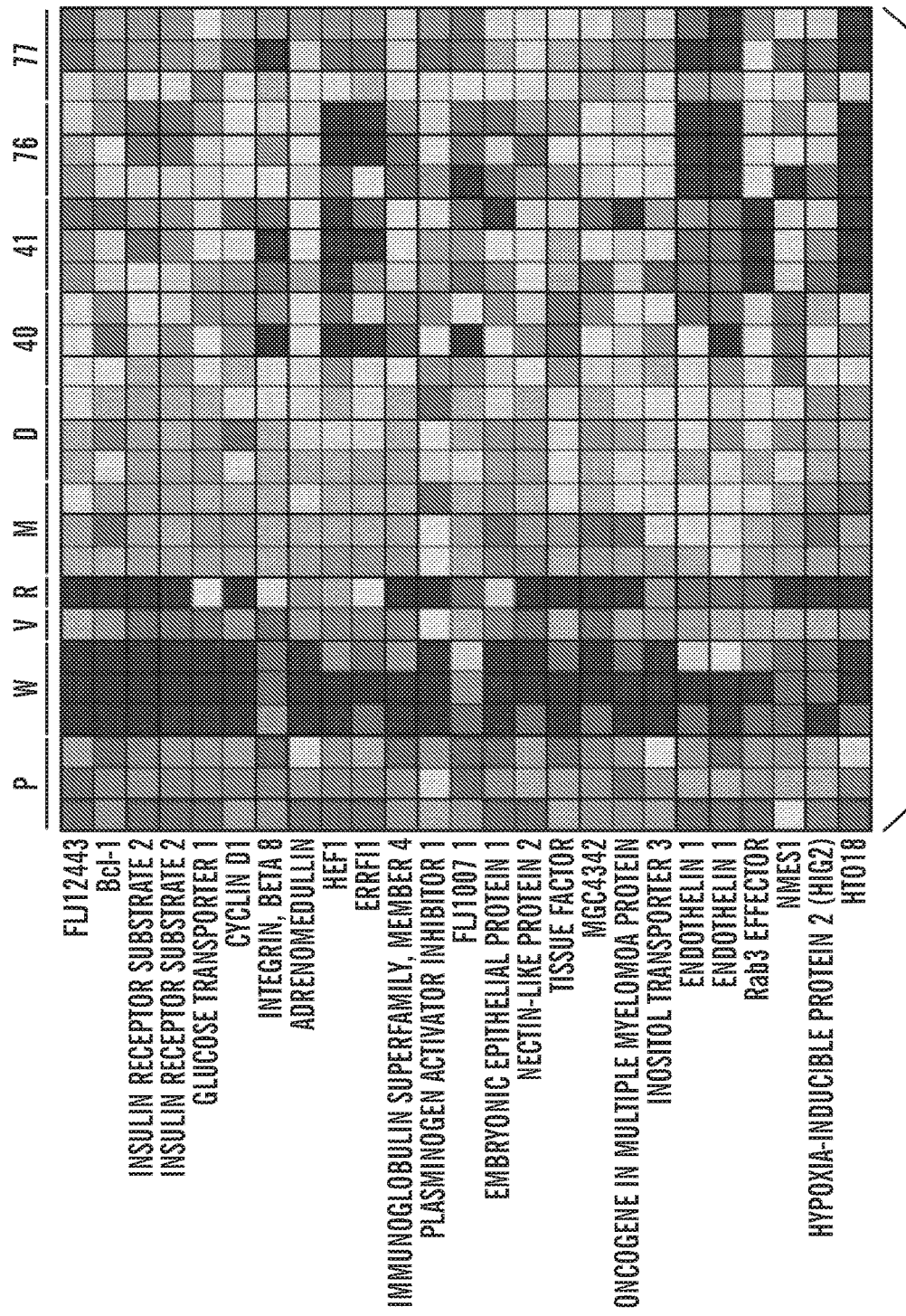
FIGS. 2A-2B show the gene expression profile of compound treated 786-O cells. For all panels, the cell lines used were: P, PRC3; W, WT8; V, pTV; R, pTR; or parental 786-O cells treated with M, medium only; D, DMSO; or compounds 40, 41, 76 and 77 as indicated, at the experimentally determined IC50 concentrations.
Figure 2A:
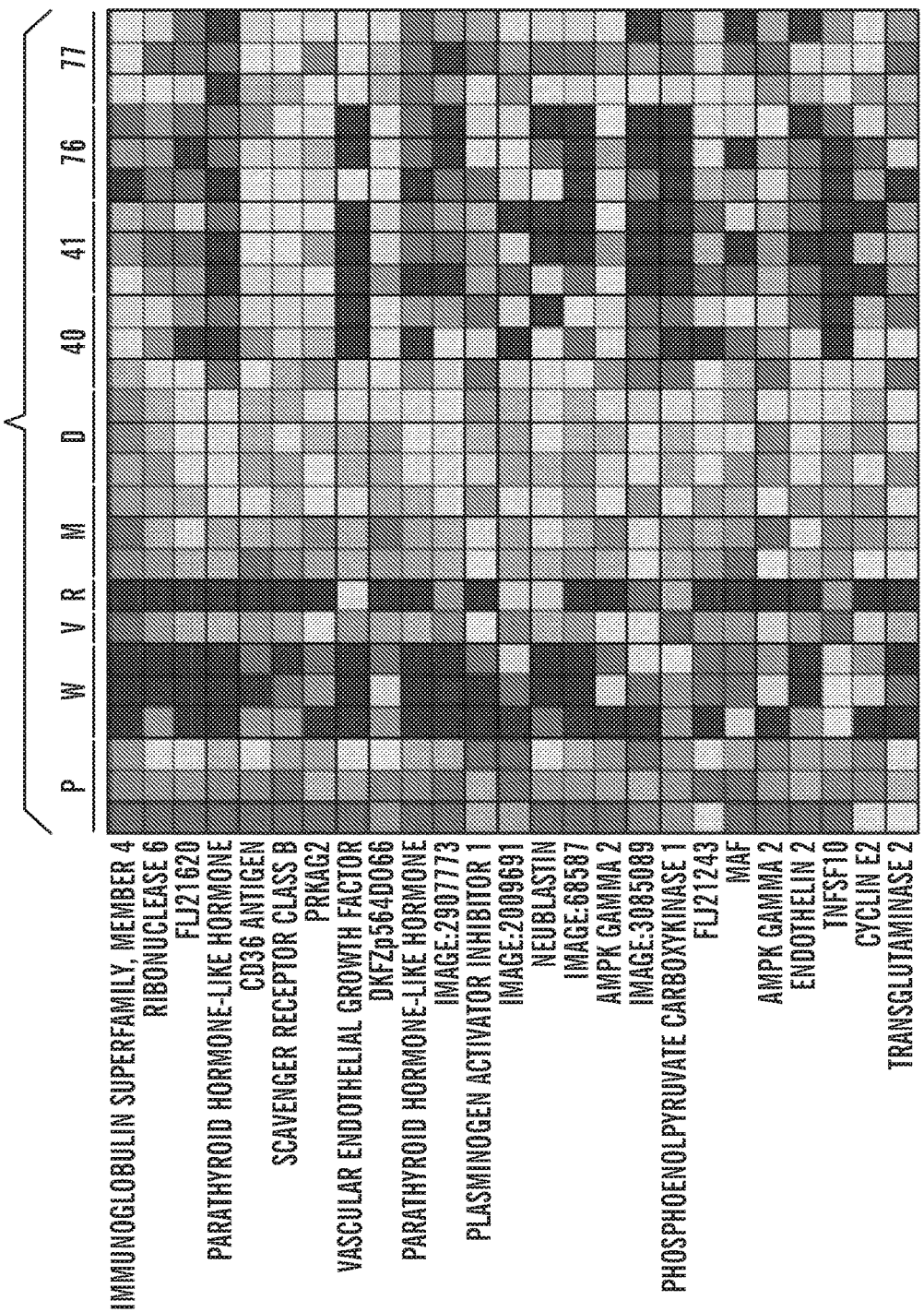

Gene Expression Profiling Suggests Compounds Preferentially Affect HIF Target Gene Expression Total RNA was extracted from stable 786-O derived VHL-reconstituted (WT8), HIF-2a knock down (pTR) and their respective vector only control (PRC3 and pTV) cells and labeled cRNA was hybridized to oligonucleotide arrays. Comparison of WT8 to PRC3 shows genes that were downregulated by pVHL while comparison of pTR to pTV identifies direct HIF-2a target genes since 786-O cells express only the HIF-2a isoform. Compound-treated parental 786-O cells were subjected to the same analysis. Overall, genes downregulated by either VHL-reconstitution or HIF-2a-targeting shRNA expression were also coordinately downregulated by exposure to compounds 40, 41, 76 and 77 in parental 786-O cells (FIG. 2A). The gene set enrichment analysis (GSEA) algorithm was used to investigate whether the compounds affected the expression of genes identified as VHL and HIF targets in other cell types (Mootha et al., 2003). The inventors discovered that genes that were upregulated in VHL or HIF gene sets were downregulated by compounds 40, 41, 76 and 77; and genes that were downregulated in the VHL gene set were upregulated by compounds 41, 76 and 77 (see Table 3).

TABLE 3

Regulation of HIF and VHL target genes by identified compounds.

| Gene set | Description | 40 | 41 | 76 | 77 |
|---|---|---|---|---|---|
| PRC3, VHL null | Markers of PRC3 cells compared to WT8 cells | NES: −3.50 p < .001 | NES*: −2.98 p < .001 | NES: −3.15 p < .001 | NES: −3.15 p < .001 |
| Staller, VHL null | Markers of VHL null cells compared to VHL WT cells | NES: −2.48 p < .001 | NES: −2.42 p < .001 | NES: −2.45 p < .001 | NES: −2.45 p < .001 |
| Schofield, HIF | Validated HIF-regulated genes as reviewed by Schofield et al. | NES: −1.65 p < .001 | NES: −1.62 p = .005 | NES: −1.78 p = .002 | NES: −1.78 p = .002 |
| WT8, VHL WT | Markers of WT8 cells compared to PRC3 cells | NES: −1.86 p < .001 | NES: 1.58 p < .007 | NES: 1.88 p < .001 | NES: 1.88 p < .001 |
| Staller, VHL WT | Markers of VHL WT cells compared to VHL null cells | NES: −1.75 p < .001 | NES: 1.62 p < .001 | NES: 1.53 p = .002 | NES: 1.53 p = .002 |

*Using the GSEA algorithm, normalized enrichment scores (NES) was calculated for each gene set. A negative NES indicates downregulation of the set of genes by the compound, and a positive score indicates upregulation. Statistical significance was determined by permutation testing. Gene sets are listed in the supplementary materials.

Figure 2B:
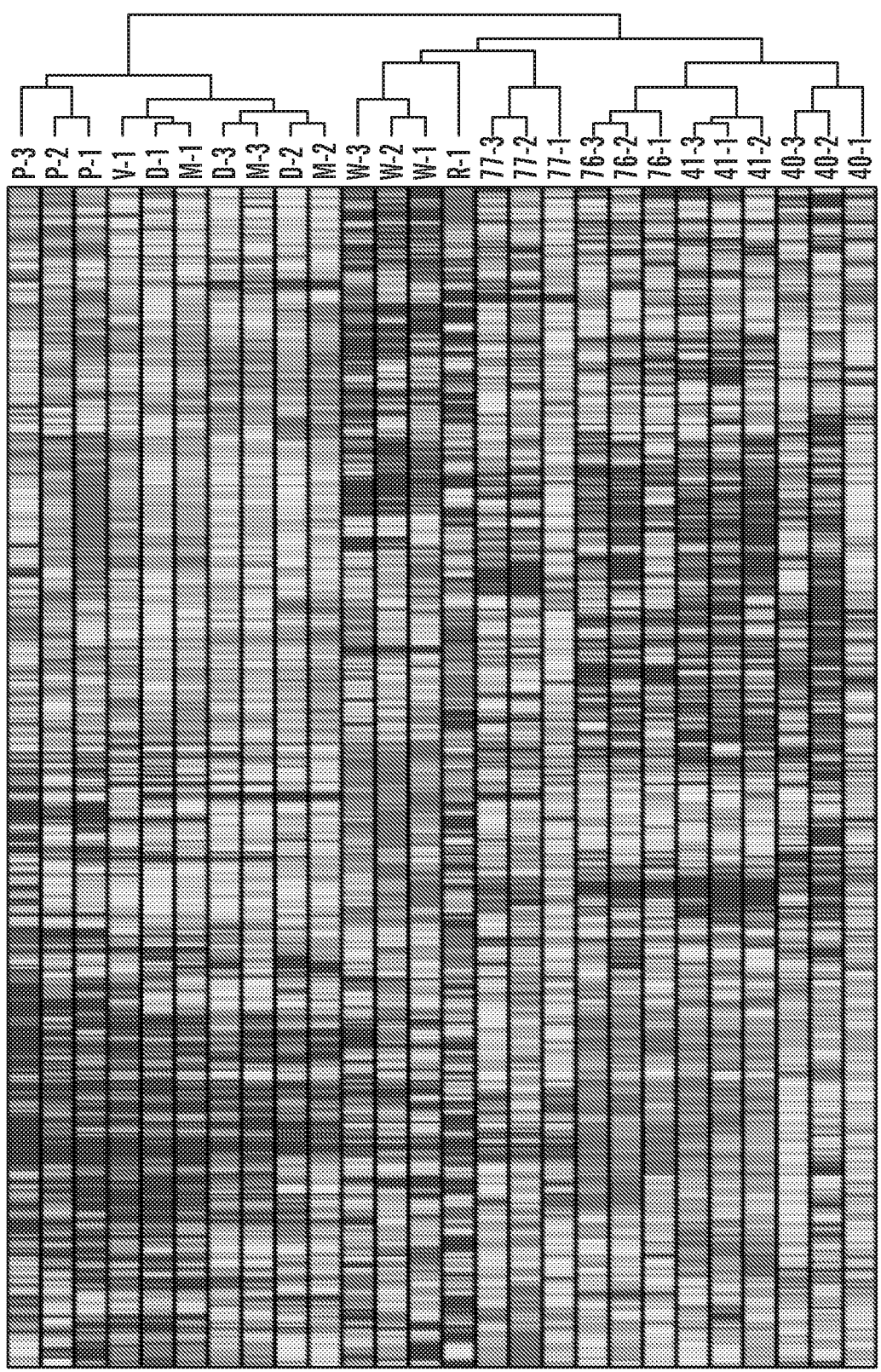

Hierarchical clustering reveals one tight cluster formed by samples in which HIF is constitutively active, including PRC3 and pTV cells, and 786-O cells that were untreated or mock treated with DMSO. A separate cluster included samples with inactive HIF, including WT8 and pTR cells, and 786-O cells treated with the identified compounds. Independent, replicate experiments clustered together, demonstrating the distinctive and highly reproducible gene expression profiles associated with each compound. Compounds 41 and 76 have highly similar molecular profiles (FIGS. 2A and 2B).

Example 4

Conditioned Medium from Compound Treated Cells Suppress HUVEC Growth In Vitro

Conditioned tissue culture medium from compound-treated 786-O cells was tested for its ability to induce human umbilical vein endothelial cell (HUVEC) proliferation. Compound application decreased the ability of conditioned tissue culture medium to sustain HUVEC proliferation while the compounds themselves exhibited no significant affect on HUVEC proliferation when applied directly at the same concentrations (FIG. 3A).

Example 5

Figure 3B:
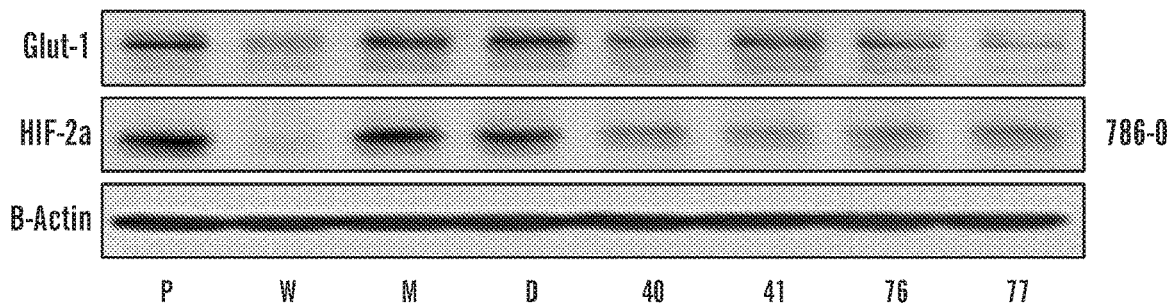
Figure 3C:
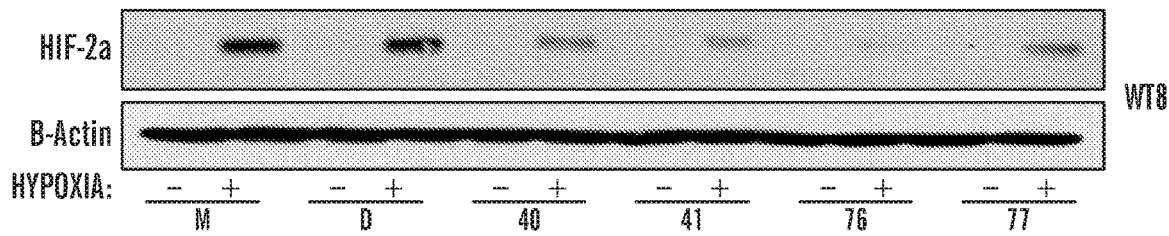
Figure 3D:
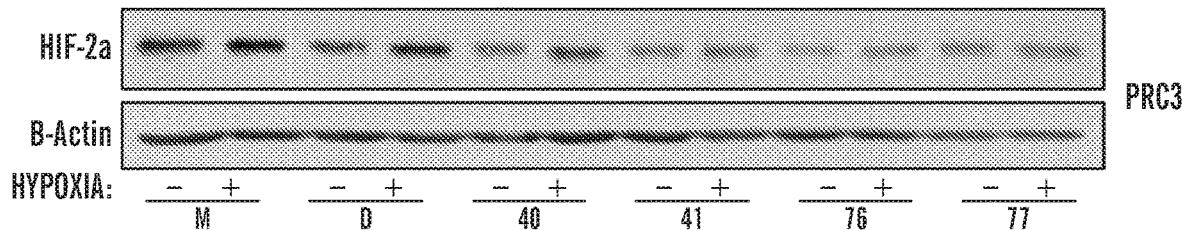
Figure 3E:
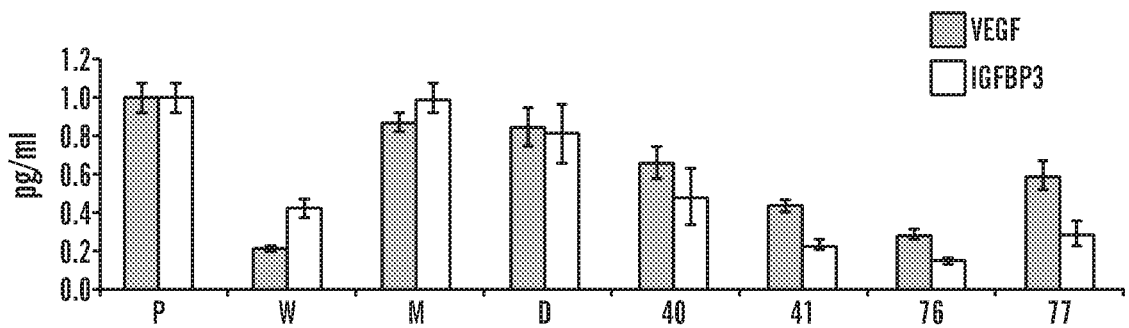
Figure 14C:
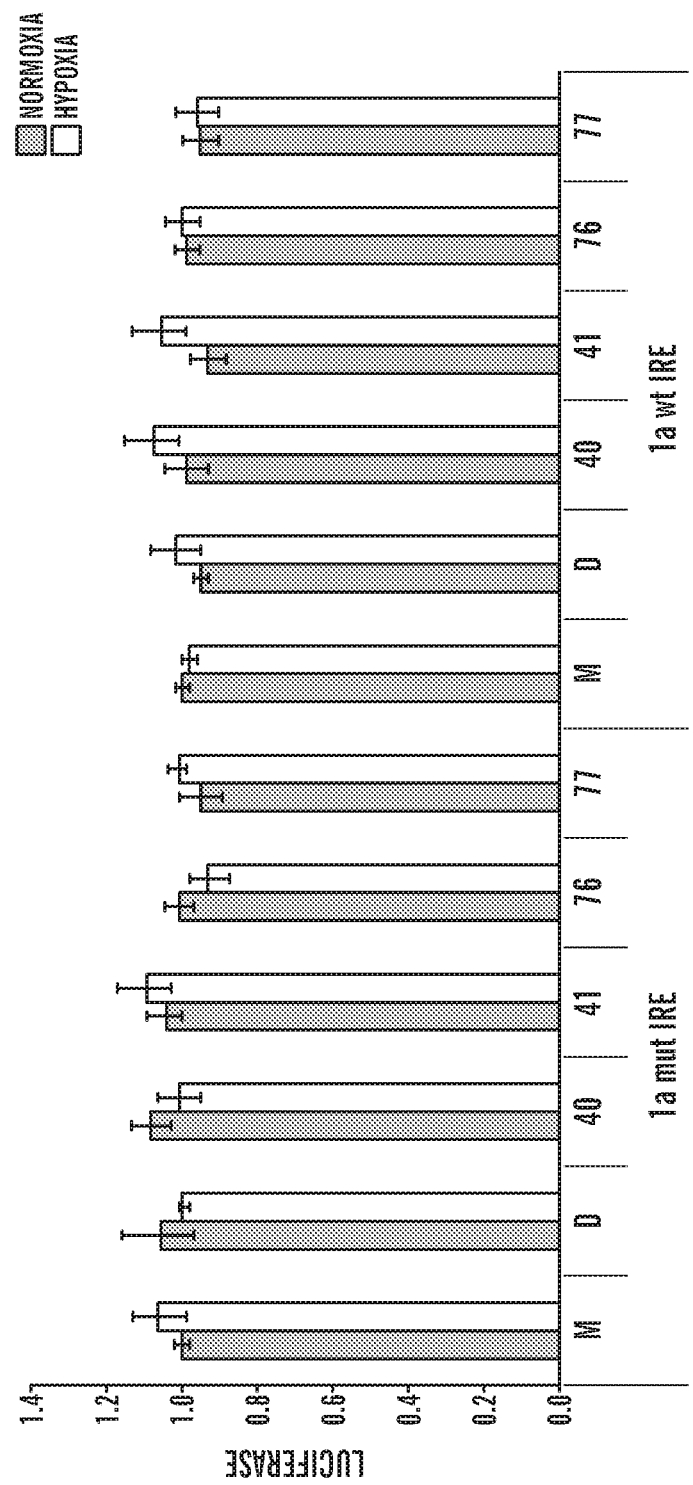

Compounds Decrease Endogenous HIF-2a Protein Expression and Inhibit Endogenous HIF-2a Target Gene Expression in Normoxia and Hypoxia All compounds decreased endogenous HIF-2a protein expression (FIG. 3B). Hypoxia stabilized HIF-2a in VHL-reconstituted WT8 cells, but treatment with compounds diminished hypoxia-induced HIF-2a expression (FIG. 3C). Normoxic HIF-2a expression was similarly decreased in VHL-deficient PRC3 cells (FIG. 3D). The expression of known HIF-2a target genes, Glut-1, VEGF and IGFBP3, was also concomitantly decreased in compound treated 786-O cells (FIGS. 3B and 3E). Compound treatment decreased also HIF-1a levels in cells expressing both HIF-1a and HIF-2a isoforms (FIG. 14).

Example 6

Compounds Decrease Neither HIF-2a mRNA Expression Nor HIF-2a Protein Stability

Figure 3F:
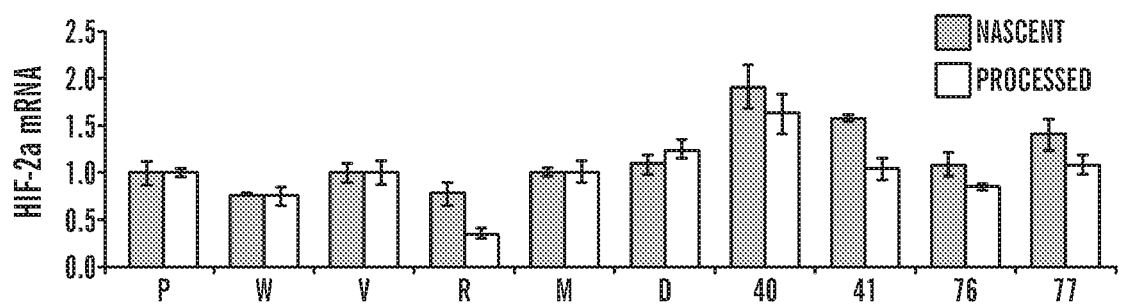
Figure 3G:
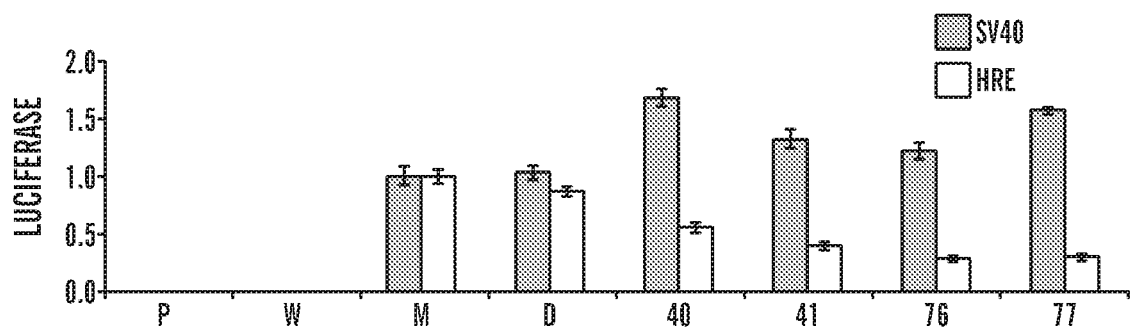
Figure 10A:
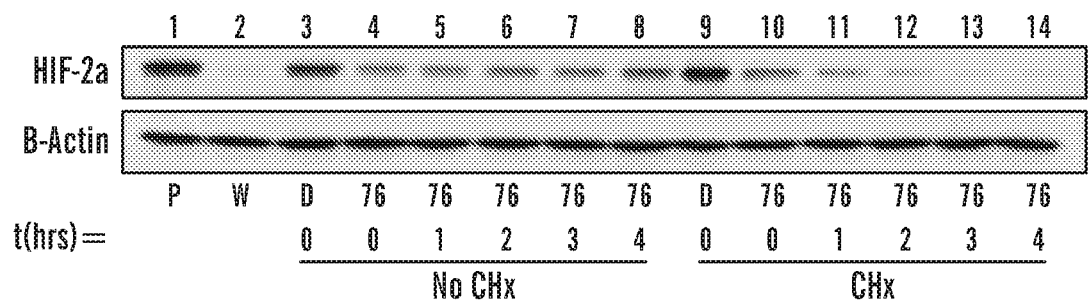
FIGS. 10A-10C show no compound of 40, 41, 76 and 77 significantly affects HIF-2a stability as measured by blocking de novo protein synthesis with cycloheximide.
Figure 10B:
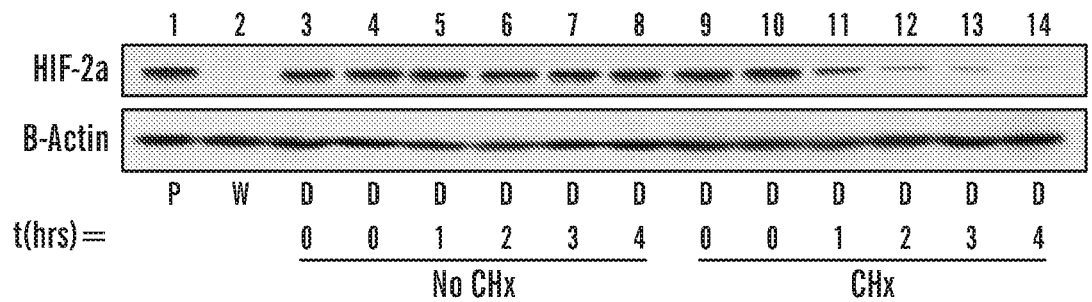
Figure 10C:
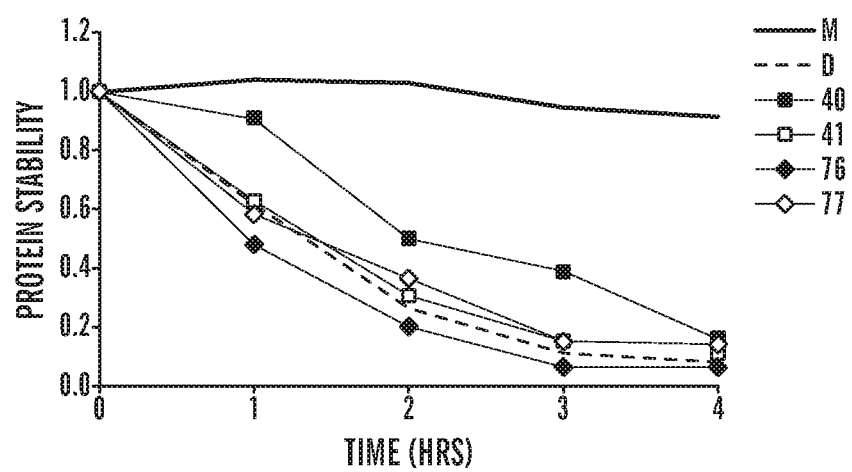

Quantitative RT-PCR was performed on total RNA harvested from 7H4 cells treated with medium only, DMSO or compound. In no case was the expression of nascent (unspliced) or processed (spliced) HIF-2a mRNA decreased, while a luciferase assay performed in parallel show that the compounds were active (FIG. 3f and g). To test whether the compounds alter HIF-2a stability, the inventors assessed protein half-life following the addition of cycloheximide in compound versus DMSO-only treated cells (see FIG. 10). These experiments provided no evidence to demonstrate that any of the compounds affected HIF-2a protein stability.

Example 7

Compounds Decrease HIF-2a mRNA Translation in an mTOR Independent Manner

Figure 4A:
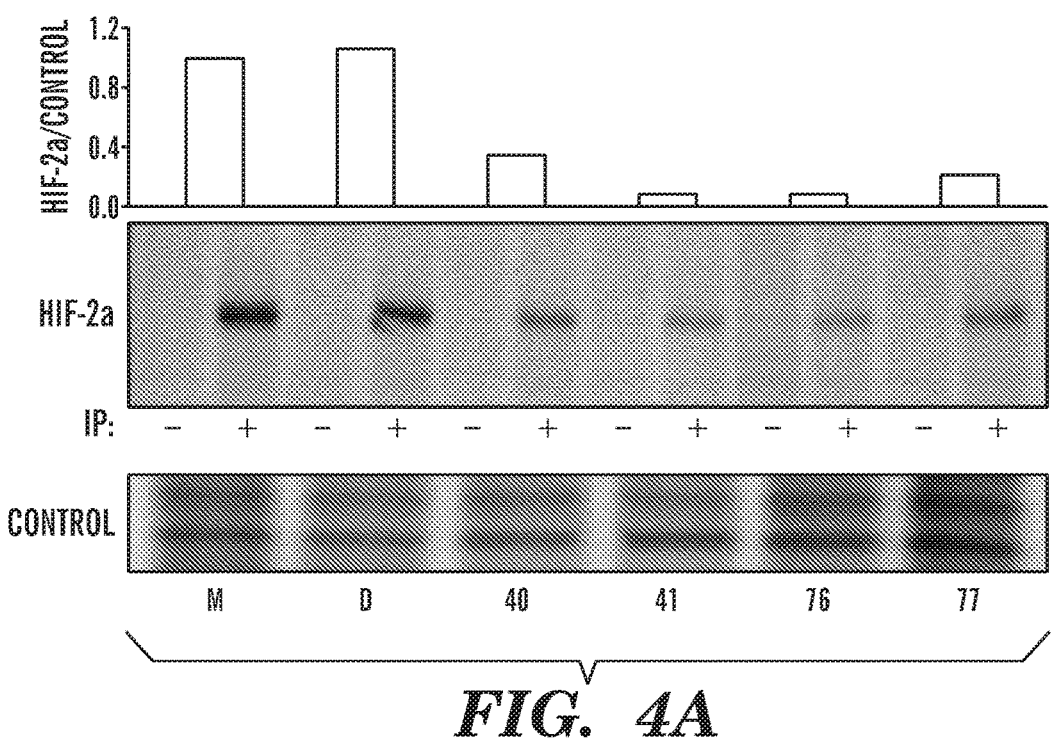
FIGS. 4A-4B show that compounds 40, 41, 76 and 77 decrease HIF-2a mRNA translation in an mTOR independent manner.
Figure 11A:
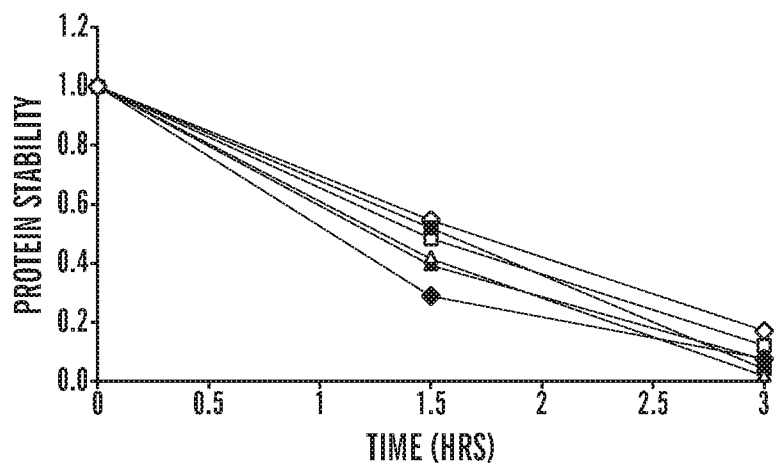
FIGS. 11A-11C show compounds 40, 41, 76 and 77 have no affect on HIF-2a protein stability as measured by $^{35}$S-methionine pulse chase. Cells were treated as described in FIG. 1 and $^{35}$S-methionine pulse-chase and immunoprecipitations were performed as described in Experimental Procedures.
Figure 11B:
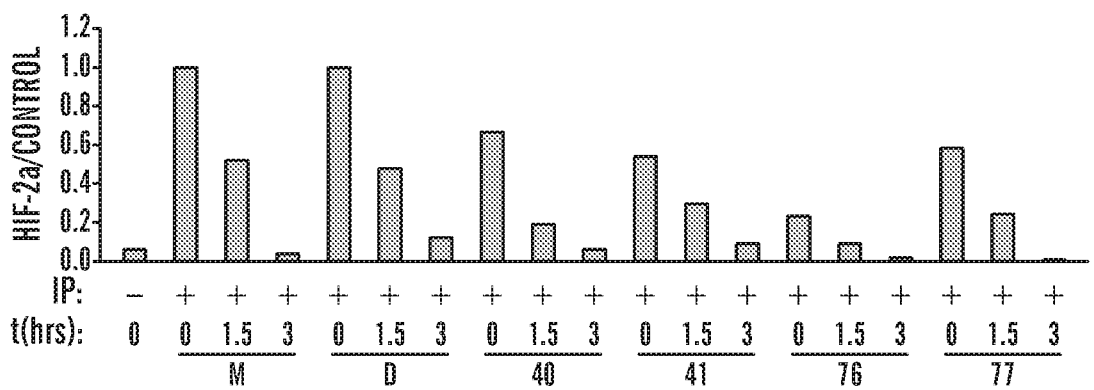
Figure 11C:
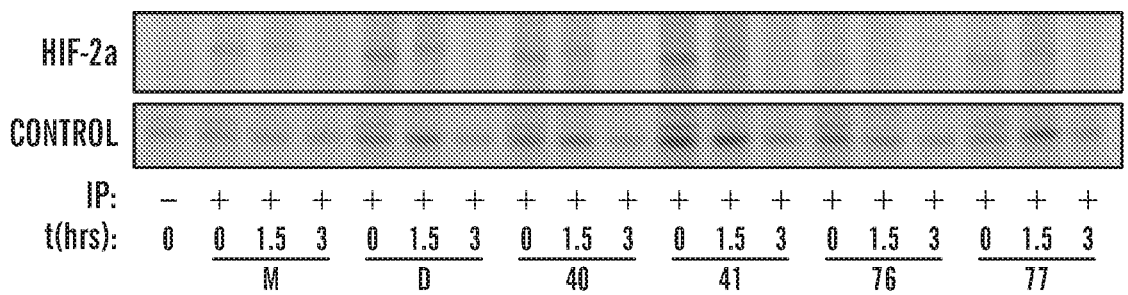
Figure 12:
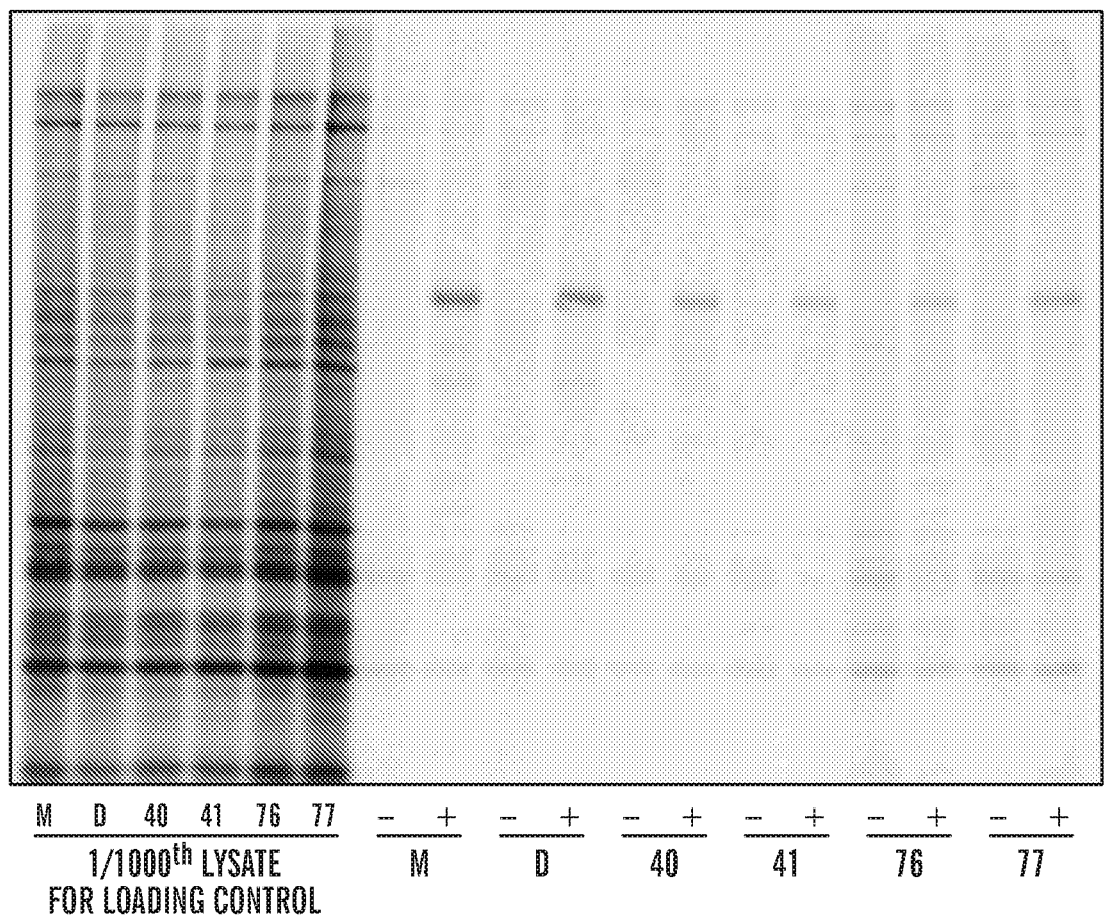
FIG. 12 shows compounds 40, 41, 76 and 77 decrease HIF-2a mRNA translation (presentation of the whole gel). Cells were treated with compound as described in FIG. 1 and $^{35}$S-methionine pulse label immunoprecipitation was performed as described in Experimental Procedures. For HIF-2a immunoprecipitations, (−) indicates anti-HA control IP, (+) indicates IP with anti-HIF-2a antibody. Loading control is a representative section of the autoradiograph in which a 1:1000 dilution of the lysate was directly loaded. M, medium only; D, DMSO; compound numbers, as indicated at the following concentrations: 40, 30 μM; 41, 25 μM; 76, 10 μM; 77, 5 μM.

The effect of HIF inhibitors on protein translation was determined by $^{35}$S-methionine pulse labeling DMSO or compound treated cells. All compounds significantly decreased the amount of newly synthesized HIF-2a protein (FIGS. 4A and 11). Pulse chase experiments confirm that this decrease is not attributable to any effect on the protein half-life (see FIG. 11).

Figure 4B:
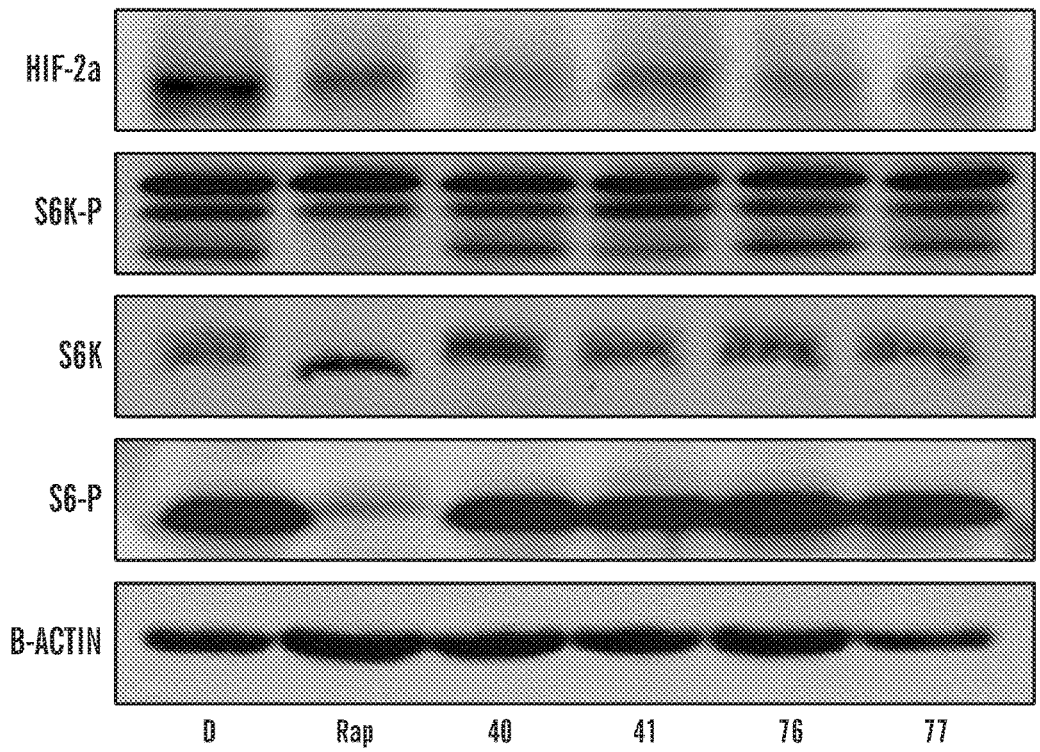

Any effect on translation suggests that the compounds might inhibit mTOR activity (Brugarolas et al., 2004; Hudson et al., 2002; Majumder et al., 2004). The inventors then compared the effects of compound versus rapamycin treated 786-O cells on HIF-2a, phospho-S6, p70S6K and phospho-p70S6K expression, as measured by Western blot using total or phospho-specific antibodies. As is the case for HIF-1a, HIF-2a protein expression was decreased by rapamycin. This was also the case for HRE-luciferase reporter activity (data not shown). However, only rapamycin appeared to have any effect on p70S6K and S6 phosphorylation (FIG. 4B).

Example 8

Figure 5A:
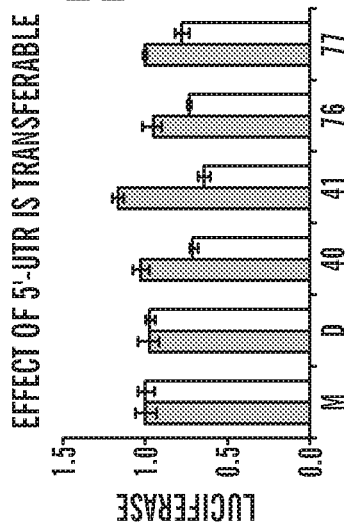
FIGS. 5A-5H show that the HIF-2a IRE is necessary and sufficient for mediating the effect of HIF inhibitors and it is de-repressed by hypoxia.

Effect of Compounds is Dependent Upon the Presence of the 5'-UTR and is Heterologously Transferable The inventors generated stable 786-O derived clones expressing luciferase reporter constructs driven by the endogenous HIF-2a promoter alone or the promoter with the 5'-UTR. The compounds exhibited little effect on luciferase activity when driven by the HIF-2a promoter alone. However, the same luciferase reporter containing the 5'-UTR recapitulated the effect of the compounds on HIRE-driven luciferase reporter activity (FIG. 5A).

Figure 5B:
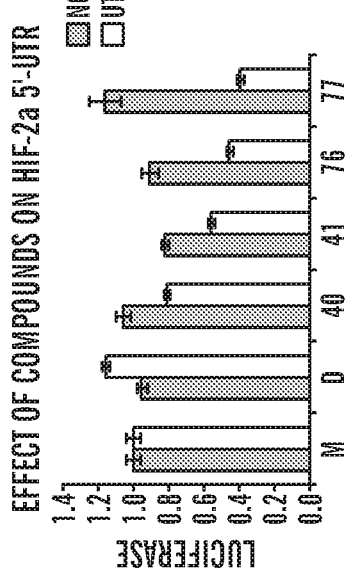

The inventors next stably transfected 786-O cells with luciferase reporter constructs driven by the HIF independent SV40 promoter with or without the presence of the HIF-2a 5'-UTR (FIG. 5B). To control for general RNA helicase activity, the inventors also stably transfected 786-O cells with luciferase reporters, with or without a synthetic 5'-UTR stem loop, driven by the CMV promoter (Yang et al., 2004). The inventors demonstrated that the 5'-UTR is sufficient to confer compound sensitivity and that this effect was independent of RNA helicase activity.

Example 9

Figure 5C:
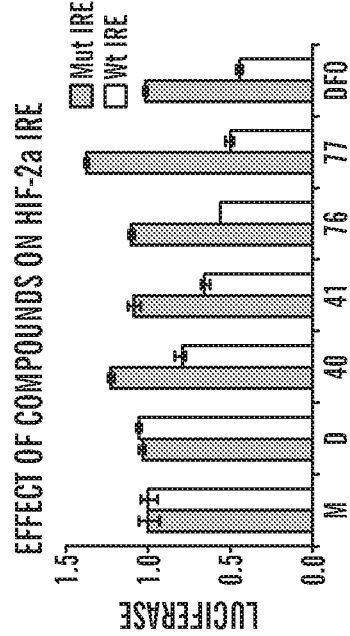
Figure 5D:
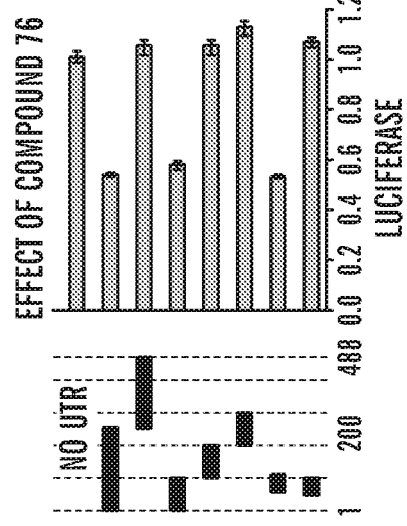

The Iron-Responsive Element (IRE) Within the 5'-UTR of HIF-2a is Necessary and Sufficient for Compound Sensitivity A series of 5'-UTR deletions were engineered into the HIF promoter-luciferase construct. The inventors discovered that nucleotides 50-100 of the HIF-2a 5-UTR were necessary and sufficient for mediating the effect of our HIF inhibitors (FIG. 5C. This region contains a near consensus Iron-Responsive Element (IRE) that was recently shown to interact with IRP1 (Sanchez et al., 2007). Point mutations within the consensus loop, in which the 5'-CAGUGU-3' (SEQ ID NO: 15) is changed to 5'-CAAAGU-3' (SEQ ID NO: 16), ablated the effect of all compounds and DFO (FIG. 5D).

Example 10

Hypoxia Upregulates HIF-2a Translation Via the 5'-UTR IRE

Figure 5E:
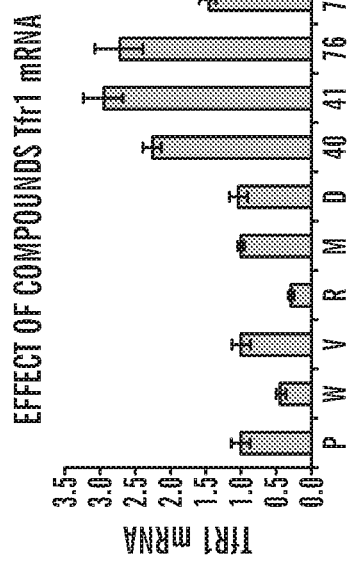

The luciferase reporter containing the wild-type, but not mutant, IRE was significantly activated under hypoxic conditions. Luciferase activity was approximately 10-fold higher in cells harboring the mutant reporter (data not shown), suggesting that IRP1/2 binding to the IRE is capable of repressing basal translation by an order of magnitude in well-oxygenated cells. Addition of exogenous iron, as a positive control for IRE-reporter activity, promoted translation and synergized with the effect of hypoxia. Low concentration (10 µM) of the iron chelator DFO repressed reporter activity and diminished the effect of hypoxia (FIG. 5E).

Example 11

Compounds Promote Stability of Transferrin Receptor 1 (TfR1) mRNA

Figure 5F:
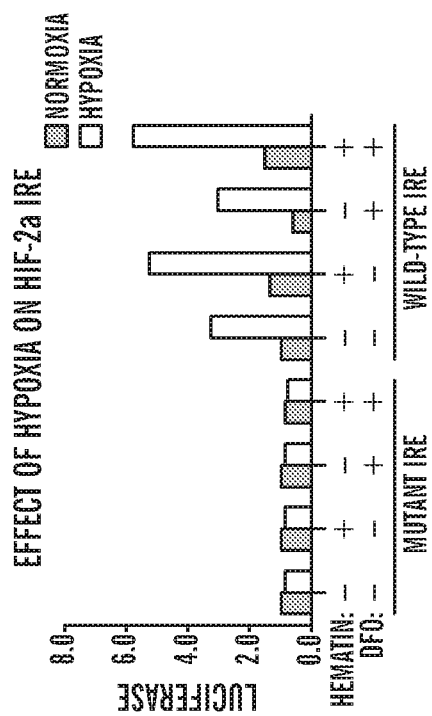
Figure 5G:
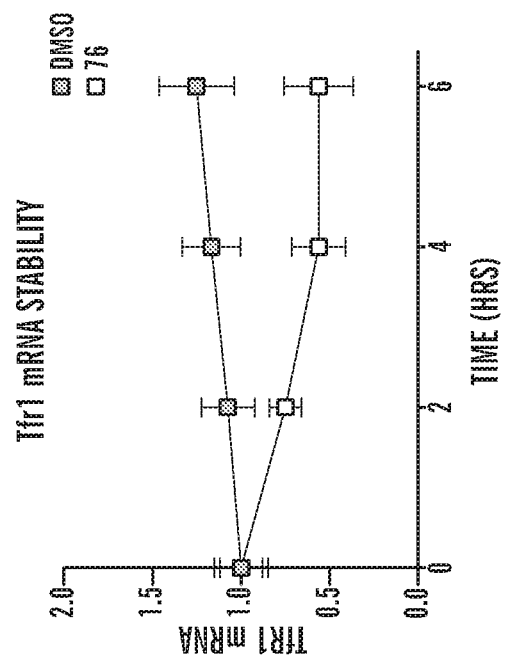
Figure 5H:
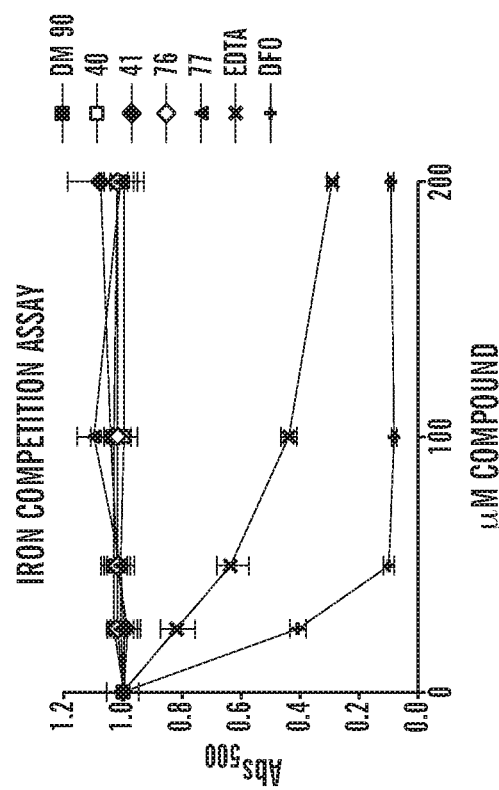

Transferrin Receptor 1 (TfR1) has multiple IREs located in the 3'-UTR whose function is to sterically block riboendonuclease cleavage sites upon IRP binding. The inventors discovered that expression of TfR1 mRNA is increased in compound treated cells relative to medium or DMSO only treated control cells (FIG. 5F). TfR1 has been reported to be a HIF-1a target gene and our data indicate that it appears to be also a HIF-2a, since TfR1 message is indeed decreased in VHL-reconstituted or HIF-2a shRNA targeting 786-O cells. The fact that net mRNA is increased by the compounds is therefore very likely due to an affect on mRNA stability. To directly support this, the inventors demonstrated that the stability of TfR1 mRNA in compound 76 treated 786-O cells is decreased following the addition of Actinomycin D. (FIG. 5H).

Example 12

Compounds Do Not Act by Iron Chelation

The inventors next directly tested whether the compounds bind iron by performing a competition assay in which the displacement of iron from ethyl-3,4-dihydroxybenzoate (EDHB), a weakly chelating ester, was measured as a decrease in absorbance at 500 nm. The inventors discovered that even at concentrations as high as 200 µM, there was no evidence of any compound binding to iron, whereas the iron chelators EDTA and DFO readily displaced iron from EDHB (FIG. 5G). In addition, the inventors utilized the Connectivity Map to look for similarities between the induced gene expression signatures of low and high dose DFO and compound treated cells (Lamb et al., 2006). Using this bioinformatic approach, the inventors discovered no significant similarity between the gene expression profile of the compounds and low (chelating) DFO dose, while there was a negative correlation between compound effect and high (HIF stabilizing) DFO dose (see FIG. 13).

Example 13

IRP1 is Solely Responsible for Hypoxic De-Repression of HIF-2a Translation

Figure 6A:
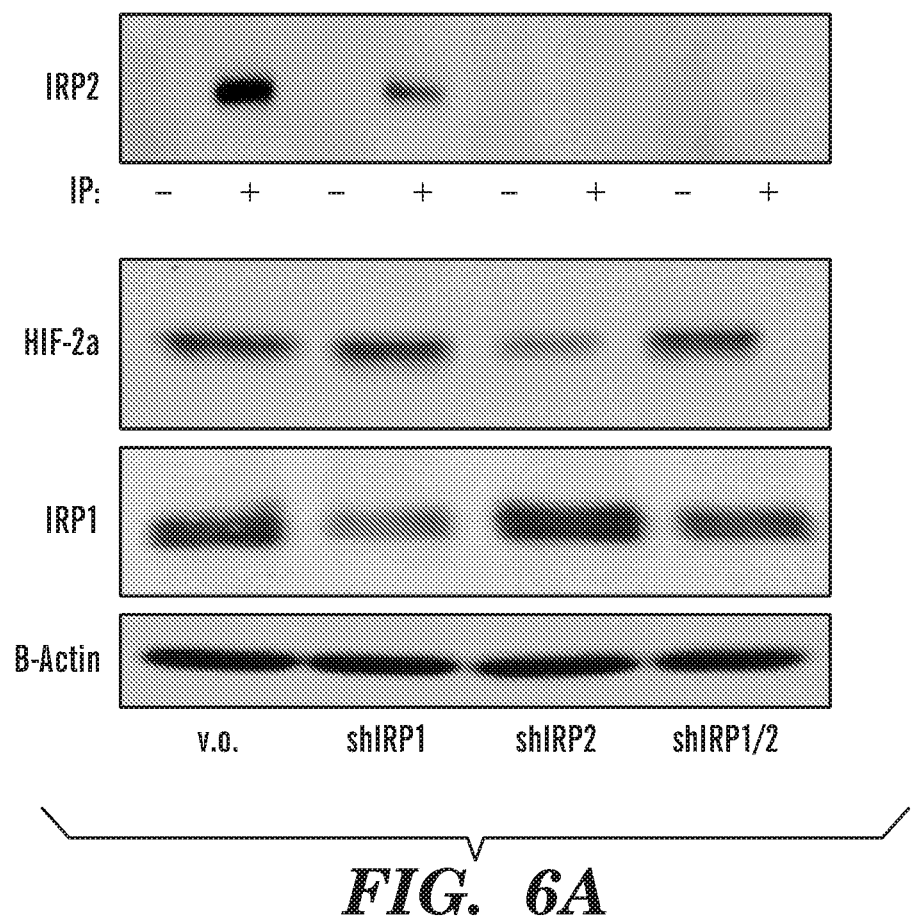
FIGS. 6A-6C show that Hypoxic de-repression of HIF-2a translation and compound induced repression are mediated solely by IRP1.
Figure 6B:
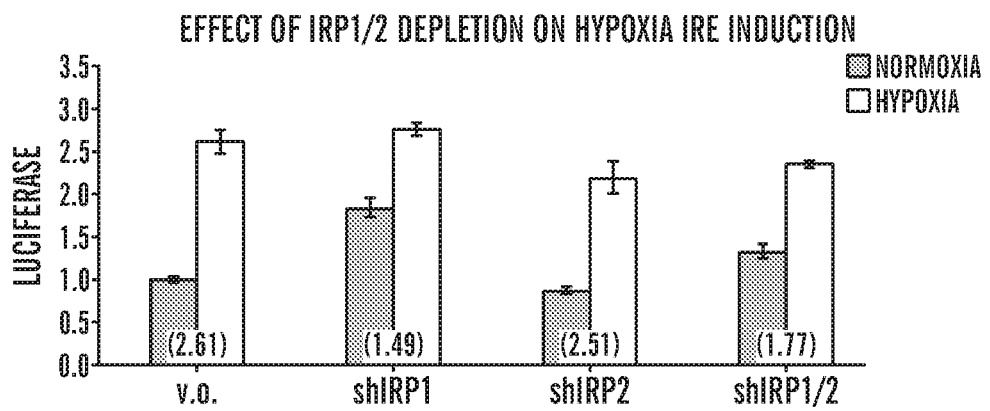

The inventors generated wild-type IRE luciferase reporter lines in which the expression of each isoform individually or both isoforms together was acutely knocked down by RNA interference. Depletion of IRP1 resulted in slight enhancement of IRP2 expression. IRP1 depletion increased HIF-2a expression whereas IRP2 depletion decreased it (FIG. 6A). These lines were subjected to 24 hours normoxia versus hypoxia and tested by luciferase. The inventors discovered that inhibition of only IRP1 attenuated the hypoxic de-repression of HIF-2a translation, while inhibition of IRP2 had little effect (FIG. 6B). This attenuation of hypoxic response by IRP1 shRNA was the result of increased basal translation in the IRP1 knock down line in normoxia, as the relative luciferase activities between the vector only and IRP1 knock down line in hypoxia were similar. It is likely that the residual increase in hypoxia-induced translation in the IRP1 knock down line is due to residual IRP1 expression in this line, as the effect of IRP1 and IRP2 double knock down is similar to that of knocking down IRP1 alone. Basal luciferase activity in the IRP2 knock down line is decreased relative to that of vector only control, which is compatible with the hypothesis that depletion of IRP2 results in a compensatory increase in IRP1 expression and activity.

Example 14

Inhibition IRP1 is Sufficient to Inhibit the Effect of Compounds on HIF-2a

Figure 6C:
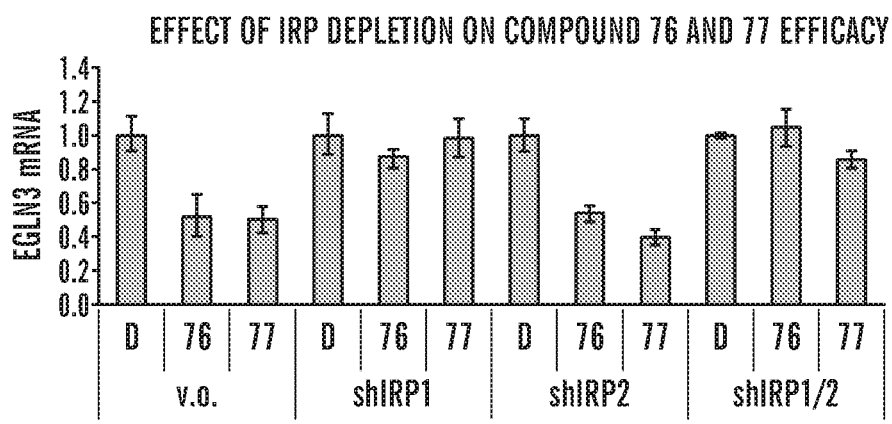

Quantitative RT-PCR for the HIF-2a target gene EGLN3 showed that inhibition of IRP1 blocked the effect of the compounds on HIF-2a activity, whereas knocking down the expression of IRP2 had no effect. Knocking down the expression of both IRP1 and IRP2 together likewise rendered the compounds ineffective (FIG. 6C).

Example 15

Compounds Increase and Hypoxia Decreases IRP1 Binding to HIF-2a IRE

Figures 7A, 7B:
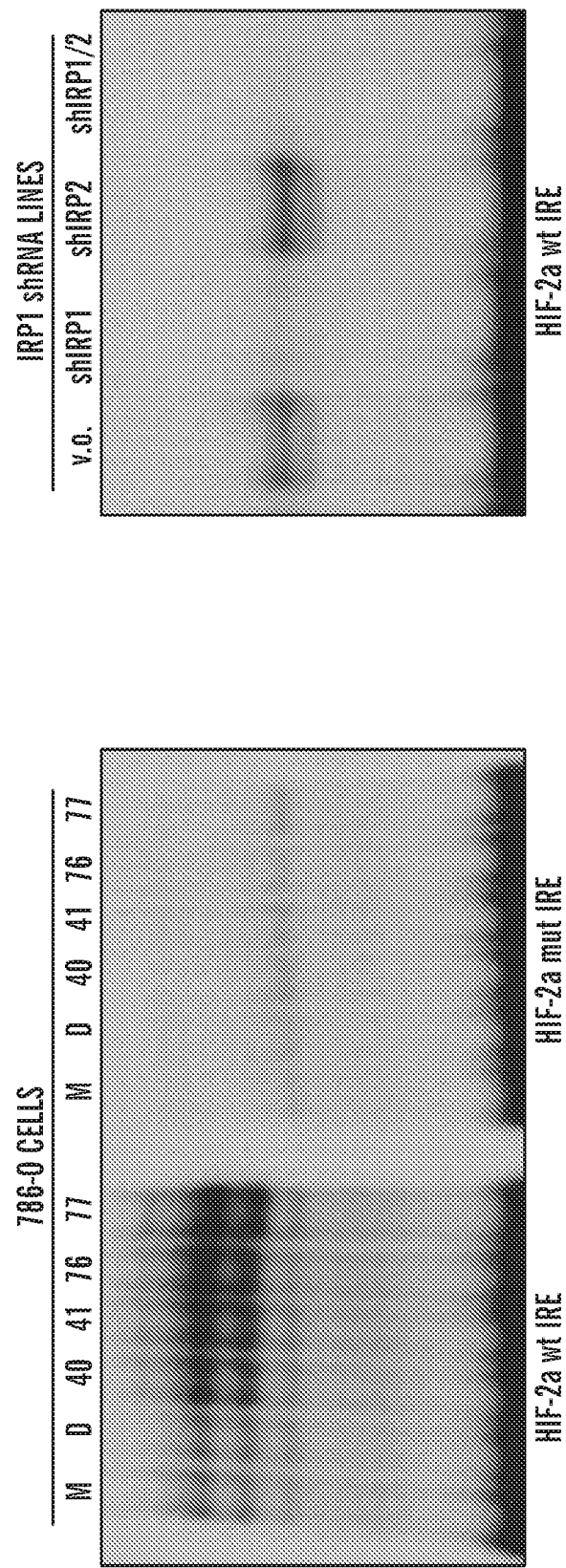
Figure 7D:
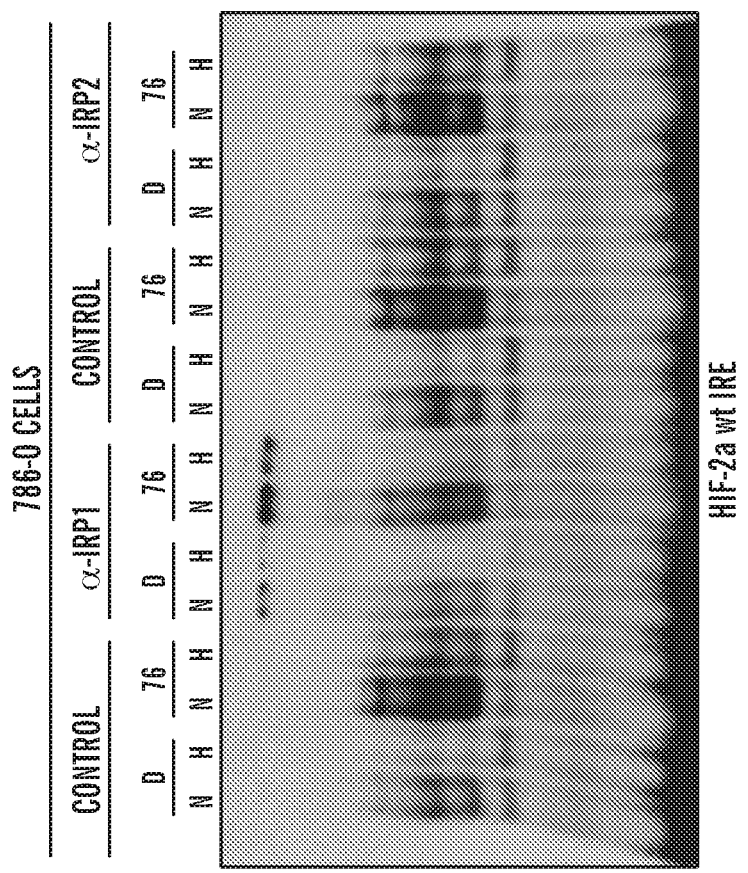
Figure 7C:
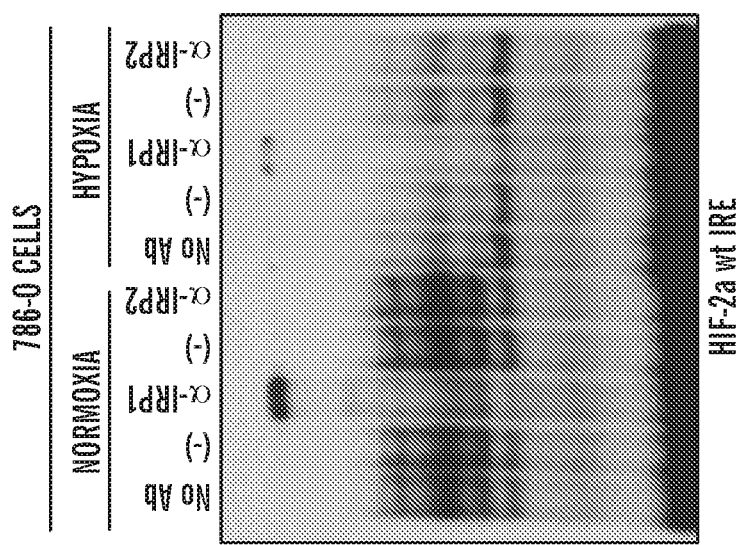

Electrophoretic mobility shift assays (EMSAs) show that compound application increased the binding of IRP1 to radiolabeled wild type by not mutant HIF-2a IRE probe (FIG. 7A). EMSA using lysates of the IRP knock down lines suggest that IRP1 is the predominant species involved in HIF-2a IRE binding and corroborates the observation that depletion of IRP2 leads to enhanced IRP1 activity (FIG. 7B). The inventors next tested the effect of hypoxia on the binding of IRP1 to the HIF-2a wild-type IRE. Consistent with our luciferase reporter assays, hypoxia dramatically decreased the intensity of the shifted IRP bands. This is due to decreased mRNA binding, as western blots confirm that neither compound application nor hypoxia affects IRP1 protein expression. The involvement of IRP1 was further confirmed with super-shifting experiments with IRP1 antibody (FIG. 7C). No supershifted bands were observed using IRP2 antibody.

Figure 7E:
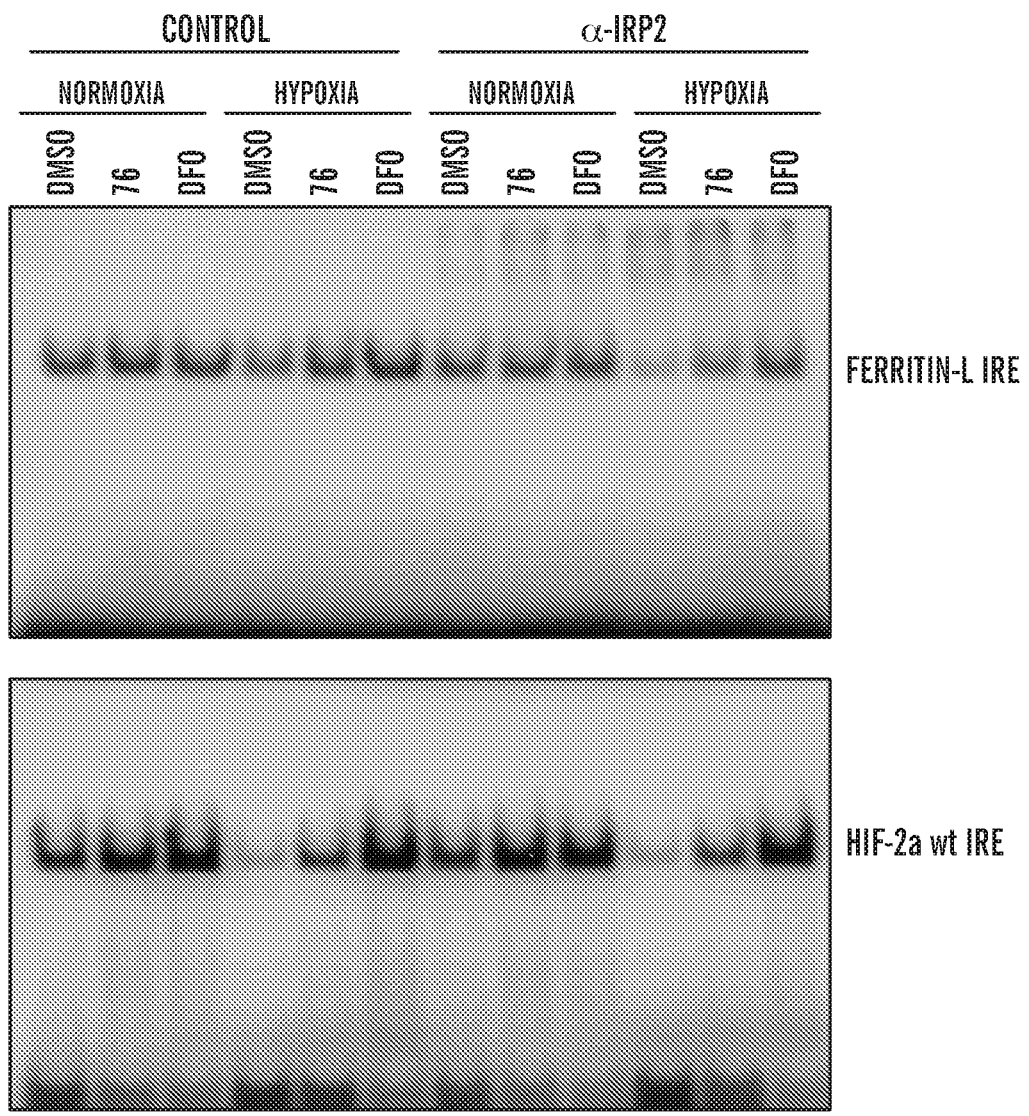

In order to determine if tested compounds increased binding of IRP1 to the HIF-2a IRE, even in conditions of hypoxia, 786-O cells were treated with compound 76 followed by 24 hour exposure to normoxia or hypoxia. Inventors discovered that compound 76 increased the residual amount of IRP1 bound to the HIF-2a IRE in hypoxia, although not to the same extent as that observed in normoxic cells. The involvement of IRP1 in the effect of the compounds was further demonstrated by super shift experiments (FIG. 7D). Lastly, to further investigate the involvement of IRP2 in HIF-2a IRE, the inventors compared side by side IRP2 binding to HIF-2a and Ferritin-L IRE in 786-O cells, in conditions of normoxia or hypoxia and after treatment with compound 76 or DFO (FIG. 7E). While IRP2 binding was clearly detected on Ferritin IRE, the inventors were not able to detect measurable IRP2 binding on HIF-2a IRE. This observation supports the functional data obtained in 786-O cells and indicates that the effect of IRP2 on HIF-2a IRE is likely indirect.

Example 16

Connectivity Map Analysis Links HIF2a Inhibitors to $PGJ_2$

Figure 15A:
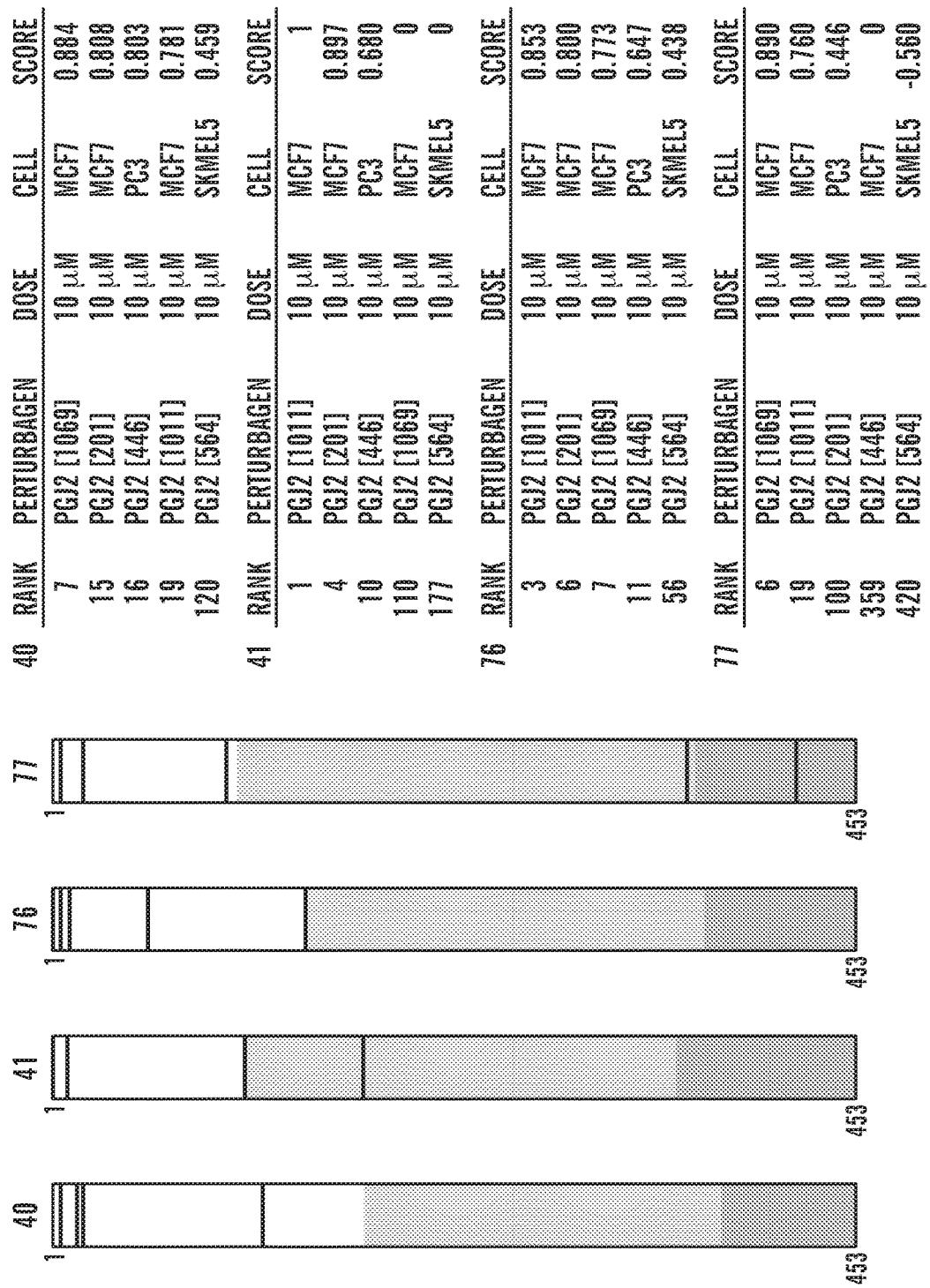
FIGS. 15A-15D show inhibition of HIF activity is linked to 15-deoxy-$\Delta^{12,14}$-Prostaglandin $J_2$.

To gain insight into the molecular target of HIF2 inhibitors and/or the signaling pathways linked to their function, the inventors generated gene expression signatures for these compounds in the renal cell carcinoma cell line 786-O and subjected these signatures to Connectivity Map analysis. 786-O cells are deficient of the von Hippel-Lindau (VHL) disease gene and they therefore constitutively expressed HIF2a. Comparison of gene expression changes induced by the small molecule HIF2a inhibitors to the profiles included in the Connectivity Map database strongly suggested that three out of four compounds (40,41 and 76) shared a functional similarity with the anti-inflammatory $PGJ_2$ (FIG. 15A).

Example 17

$PGJ_2$ Decreases HIF2a Activity in a Dose-Dependent Manner

Figure 15B:
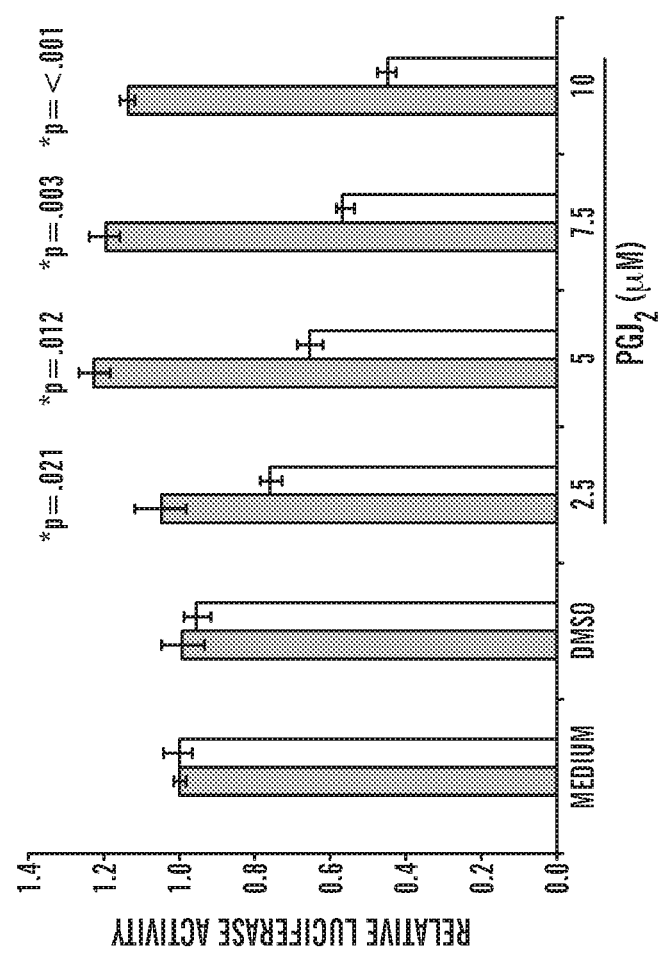
Figure 15C:
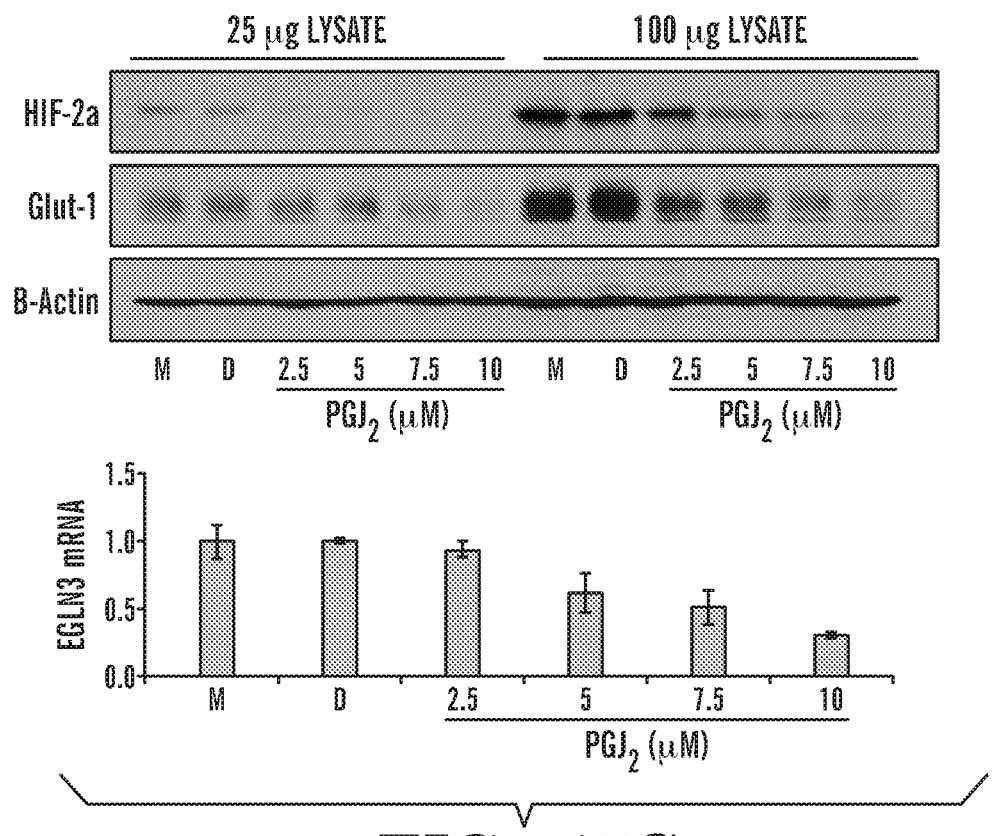
Figure 15D:
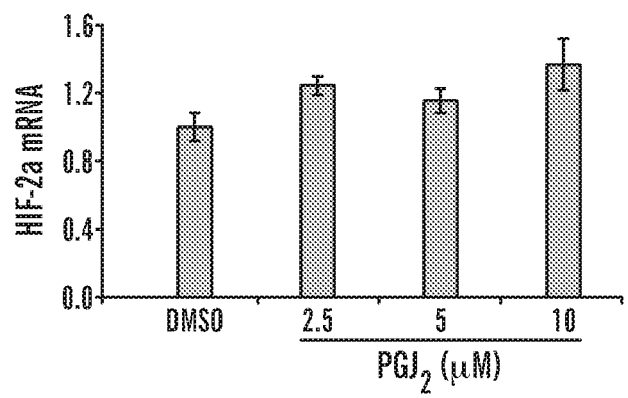

To validate the connectivity map-derived prediction that $PGJ_2$ is involved in HIF signaling, the inventors treated HRE-luciferase expressing 786-O cells (7H4) and SV40-luciferase expressing control cells (7SV) with increasing doses of $PGJ_2$. Fresh medium containing the indicated concentrations of $PGJ_2$ or vehicle-only DMSO control was applied to cells at 24-hour intervals. Luciferase activity was measured at 48 hours. $PGJ_2$ decreased HRE-driven luciferase activity (FIG. 15B) in a dose dependent manner, with an $IC50_{app}$ of 5 uM, while SV40-driven luciferase activity was not affected. This action of $PGJ_2$ appears to be independent of NFkB activation. Application of IKK inhibitor BMS-345541 did not alter the HRE-luciferase activity in 786-O cells (FIGS. 20A and 20B). Moreover, this appears also to be a PPAR gamma-independent function of $PGJ_2$; the $PGJ_2$/HIF inhibitor linkage holds strong even in Connectivity Map comparisons using expression profiles obtained from PPAR-gamma negative cells (MCF7) and application of a PPAR-gamma inhibitor, GW9662, did not block the effect of $PGJ_2$ on HIF2a activity (data not shown). This decrease in HRE-mediated luciferase activity closely matched the decrease in HIF2a protein expression as well as that of the HIF2a target genes Glut-1, as measured by Western blot and EGLN3, as measured by quantitative real time PCR (qRT-PCR; FIG. 15C). To investigate whether the effect of $PGJ_2$ on HIF2a protein expression is due to decreased transcription of the HIF2a gene, the inventors performed qRT-PCR to examine HIF2a mRNA expression in $PGJ_2$ or vehicle-only DMSO treated 786-O cells. The inventors observed no concomitant decrease in HIF2a mRNA expression, indicating that the transcription of HIF2a mRNA was not affected (FIG. 15D). To investigate whether $PGJ_2$ alters the stability of HIF2a protein, the inventors examined the half-life of HIF2a in $PGJ_2$ or vehicle-only DMSO treated 786-O cells following the addition of cycloheximide. These results show no indication that $PGJ_2$ affects HIF2a protein half-life (FIGS. 21A and 21B).

The effect of PGJ2 on HIF2a expression and activity is not a cell line specific phenomenon; treatment of several VHL-deficient human renal cell carcinoma cell lines with PGJ2 similarly resulted in decreased HIF2a protein expression (FIG. 22 shows additional cell lines as an example).

Example 18

$PGJ_2$ Inhibits HIF Translation in an mTOR-Independent Manner

Figure 16A:
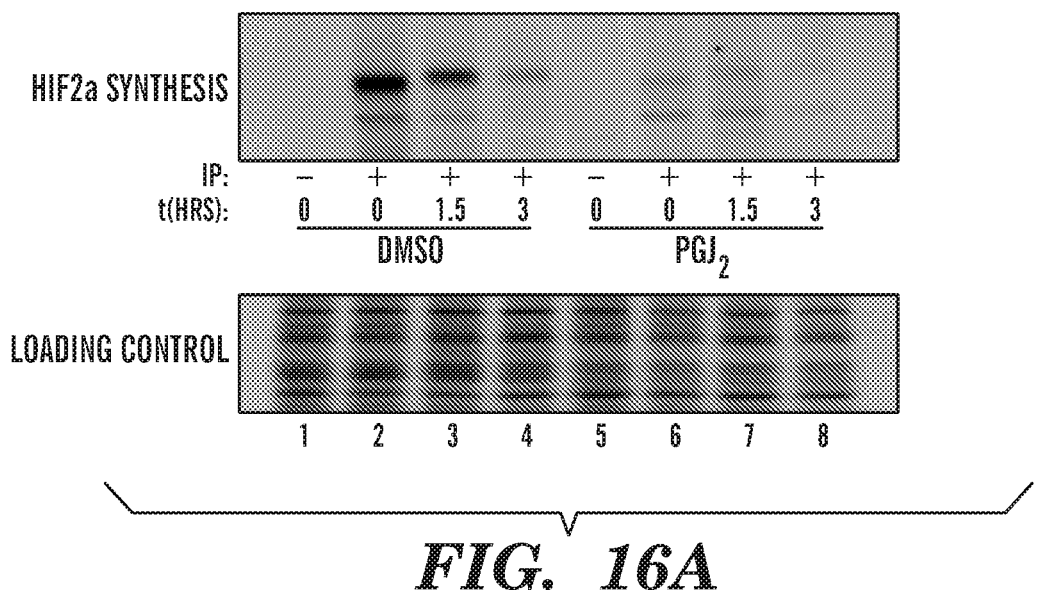
Figure 16B:
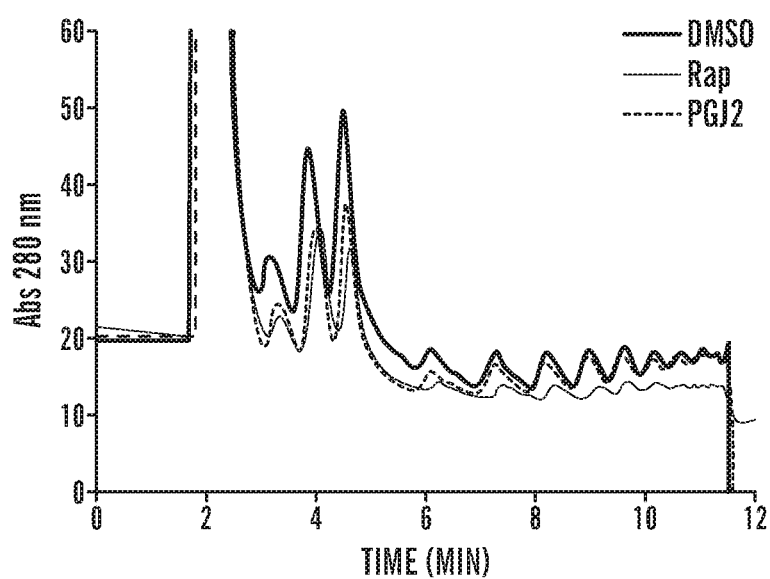

To determine if $PGJ_2$ decreases translation of the HIF2a message, the inventors evaluated the synthesis rate and stability of the newly synthesized HIF2a by an $^{35}$S-methionine pulse chase experiment on $PGJ_2$ or vehicle only DMSO treated 786-O cells. $PGJ_2$ was found to significantly decrease the amount of protein translated from the mRNA without decreasing the half-life of the protein (FIG. 16A, upper panel). Loading control is $1/1000^{th}$ of the cell lysate used in the respective immunoprecipitation directly loaded into an SDS-PAGE gel. This loading control demonstrates not only that equal protein was used in each immunoprecipitation but also that $PGJ_2$ does not globally decrease cellular translation (FIG. 16A, lower panel). Consistent with the interpretation that $PGJ_2$ does not affect global translation, polysome analysis was performed on vehicle-only DMSO, rapamycin or $PGJ_2$ treated 786-O. These experiments show that $PGJ_2$ had little effect on the number of ribosomes actively engaged in translation while rapamycin attenuated it. However, $PGJ_2$, like rapamycin, did appear to slightly decrease the monosome fraction (FIG. 16B).

It has been shown before that mTOR inhibits HIF translation as part of a global effect on translation (Zimmer et al., 2008; Hudson et al., 2002; Majumder et al., 2004; and Brugarolas et al., 2004). The inventors therefore examined whether the effect of $PGJ_2$ on HIF2a translation could be attributed to inhibition of mTOR activity. 786-O cells were treated with medium only, DMSO (vehicle only), rapamycin or $PGJ_2$ and the effect of these treatments on mTOR activity was monitored by detecting phospho-S6, p70S6K and phospho-p70S6K levels, as measured by Western blot using total or phospho-specific antibodies. HIF2a protein expression and HRE activity were decreased by both $PGJ_2$ and rapamycin. However, only rapamycin decreased phosphorylation of the downstream mTOR targets p70S6K and rpS6 (FIG. 16C).

Example 19

The 5'-UTR of HIF2a mRNA is Necessary and Sufficient for the Inhibitory Effect of $PGJ_2$ Since $PGJ_2$ inhibits translation of the HIF2a message in an mTOR independent manner, the inventors next examined whether the 5'-UTR of the HIF2a message might be involved in mediating its effect. The inventors therefore generated two luciferase reporter constructs, the first driven by the endogenous HIF2a promoter alone (HIF) and the second driven by the HIF2a promoter containing the 5'-UTR (HIF-UTR). These constructs were stably transfected into 786-O cells. Treatment with $PGJ_2$ decreased the luciferase activity derived from the UTR-containing plasmid but not the plasmid driven by the HIF promoter alone. Moreover, this effect was equal in magnitude to the effect on HRE-driven reporter activity. The ratio of normalized HRE-luciferase over SV40-luciferase reporter activities is shown compared to the ratio of normalized HIF-UTR-luciferase over HIF-luciferase activities in vehicle only DMSO versus $PGJ_2$ treated cells (FIG. 16D, upper panel). These experiments indicate that HIF2a 5'-UTR is necessary for the inhibitory effect of $PGJ_2$ on HIF2a translation, and corroborate the qRT-PCR findings that the effect of $PGJ_2$ on HIF is not transcriptional.

The inventors next wanted to test if the HIF2a 5'-UTR is sufficient for conferring sensitivity to $PGJ_2$. For this test, the inventors generated a luciferase reporter construct (SV-UTR) in which the entire 488 base pair HIF2a 5'-UTR was cloned between the SV40 promoter and the luciferase gene of the same SV40-luciferase reporter (SV) used as a HIF/hypoxia-independent control in the previously discussed experiments. The inventors compared this set of luciferase reporters to second matched set, consisting of a CMV-luciferase reporter by itself and the same CMV-luciferase into which a synthetic stem loop was cloned between the CMV promoter and the start of the luciferase gene (CMV-SL; kind gifts of Michele Pagano). This luciferase reporter set serves as a random 5'-UTR control that might capture possible effects on RNA helicase activity (Yang et al., 2004). Shown are the ratios of normalized CMV-SL over CMV and SV-UTR over SV luciferase reporter activities from vehicle only DMSO versus $PGJ_2$ treated cells. The results indicate that the effect of $PGJ_2$ that is mediated through the HIF2a 5'-UTR element is indeed heterologously transferable to a different promoter element, whereas $PGJ_2$ had no effect on the synthetic 5'-UTR element (FIG. 16D, lower panel).

Example 20

Figure 17A:
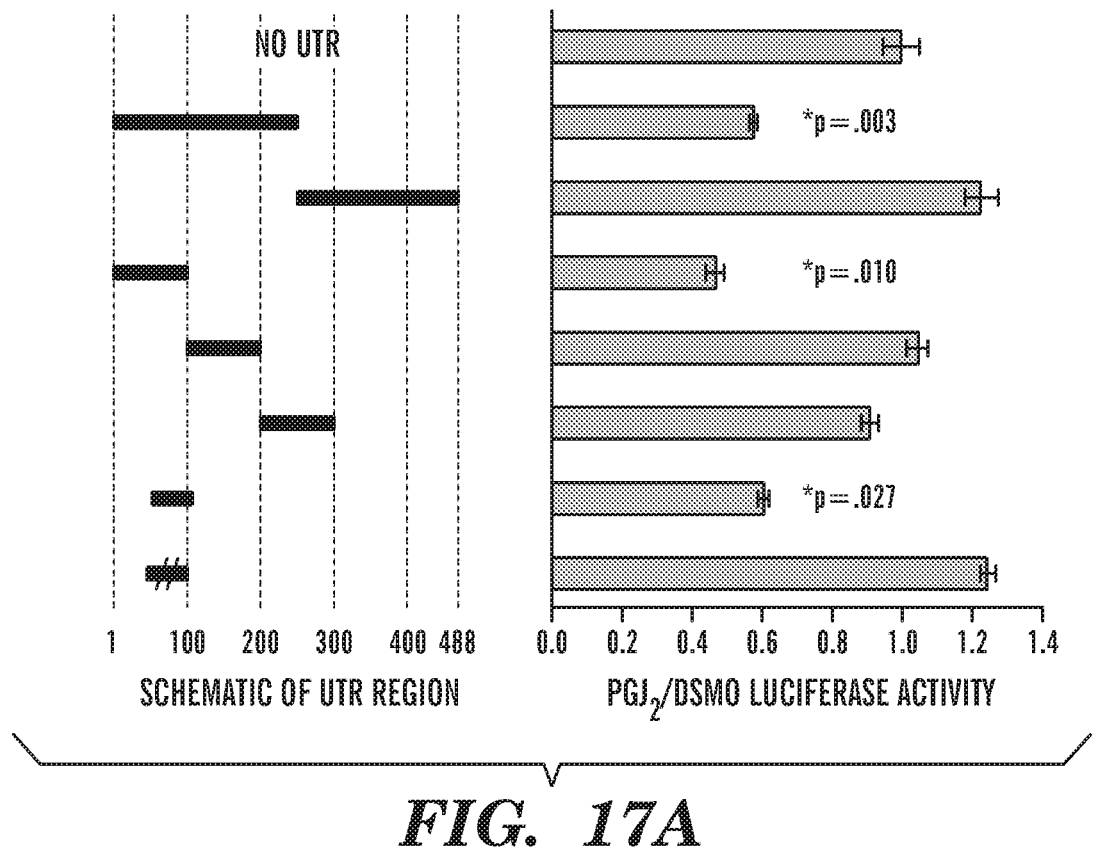
FIGS. 17A-17B show $PGJ_2$ enhances the cellular IRE activity.

The Iron Responsive Element (IRE) Within the HIF2a 5'-UTR is Responsible for the Effect of $PGJ_2$ on HIF Translation To map the domain responsible for mediating the effect of $PGJ_2$ on translation of the HIF2a message, the inventors created several reporter constructs in which different segments of the HIF2a 5'-UTR were cloned between the HIF2a promoter and the start of the luciferase gene and used these constructs to generate stable 786-O derived cell lines. These lines were then treated with vehicle-only DMSO or $PGJ_2$. The inventors found that the effect of $PGJ_2$ maps to a 50 base pair segment of the 5'-UTR that contains a recently reported Iron Responsive Element (IRE) (Zimmer et al., 2008). A mutation in the IRE consensus loop completely abolished $PGJ_2$ sensitivity. These results are summarized in FIG. 17A, where the normalized ratio of luciferase activities from $PGJ_2$ over vehicle-only DMSO treated cells is shown.

Example 21

IRP1 is Necessary for the Effect of $PGJ_2$ on HIF-2a

Figure 17B:
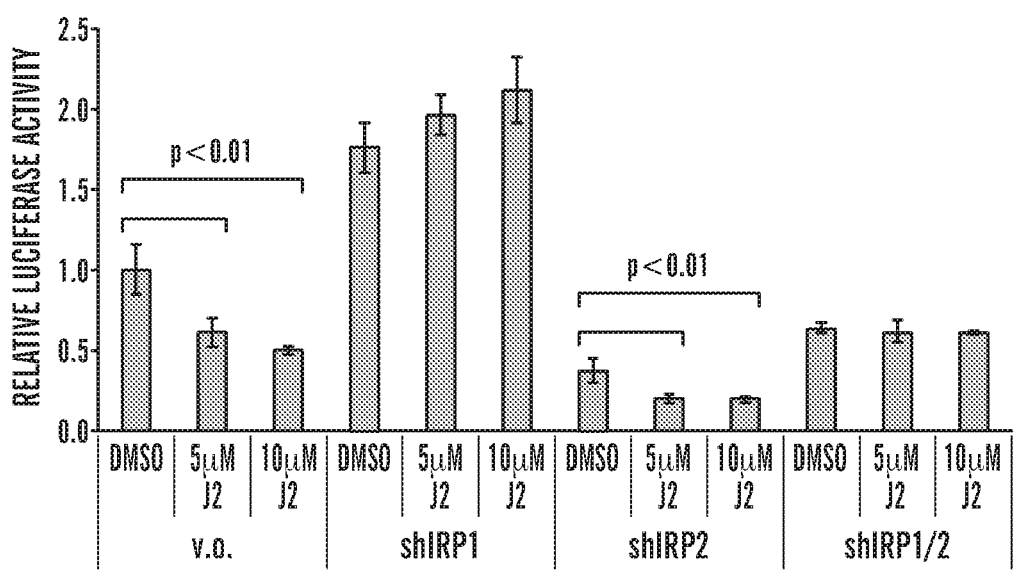

The IREs are the mRNA target sequences for the binding of both Iron Regulatory Proteins IRP1 and IRP2 (Rouault, 2006). Nevertheless, slight variations in the IRE sequences can result in higher affinity for one of the two isoforms (Ke et al., 1998). Inventors demonstrated before that it is mainly the IRP1 and not IRP2 that can measurably bound to the HIF2a IRE element, under normoxic conditions, when expressed in endogenous levels (Zimmer et al., 2008). The inventors therefore examined whether PGJ2 requires the expression of IRP1 and/or IRP2 for repressing HIF2a translation through its IRE element (FIG. 17B). In keeping with inventors' previous observation that HIF2a IRE translation is primarily repressed through IRP1, knocking down the expression of IRP1 resulted in increased activity of HIF2a, consistent with the observation that IRP1 represses HIF2a translation (FIG. 17B). More importantly, down regulation of IRP1 abolished the ability of PGJ2 to repress HIF2a activity, while inactivation of IRP1 still permitted HIF2a repression by PGJ2 (FIG. 17B). These findings are consistent with the model by which PGJ2 represses HIF2a translation by enhancing endogenous IRP1 activity.

Example 22

$PGJ_2$ Directly Enhances the Binding of Iron Regulatory Protein-1 to the HIF2a IRE The inventors next sought to determine if $PGJ_2$ affects the expression of IRP1 and/or IRP2 and we found that, as is the case for the 3 small molecule HIF inhibitors that linked to $PGJ_2$ in the Connectivity Map, IRP1 expression is not affected by $PGJ_2$ treatment while IRP2 expression is minimally increased (data not shown). However, IRP2 contributes very little—if at all—to the total IRP bound to the HIF2a IRE (Zimmer et al., 2008). Without wishing to be bound by theory, the effect of PGJ2 on HIF2a IRE is due to the enhanced binding of IRP1.

To examine this latter possibility the inventors performed an electrophoretic mobility shift assay (EMSA) using a radiolabeled wild type or mutant IRE probe to determine if IRP1 binding is increased (FIG. 18A). Pre-treatment of cells with $PGJ_2$ increased the specific IRE binding activity of cell lysates under conditions of both normoxia and hypoxia. This shifted band can be supershifted with IRP1 but not IRP2 antibodies (data not shown). To further examine the ability of PGJ2 to enhance IRP1 activity under conditions of normoxia and hypoxia the inventors tested its effect at various concentrations of ambient oxygen, corresponding to physiologic or extreme conditions of tissue oxygenation. The results indicate that PGJ2 has the ability to repress HIF2a activity at a wide range of oxygen concentrations spanning the range of physiologic tissue oxygenation (FIG. 17B).

Example 23

Inhibition of Vascularization in Fish Embryo

Fli1-GFP fish embryo were treated at 20 hpf and imaged 48-50 hpf. Results are tabulated in Table 7.

TABLE 7

|  | Animal | 0.1% DMSO | 250 nm Su5412 | 3microM-J2 |
|---|---|---|---|---|
|  | 1 | 21 of 22 | 11 of 16 | 6 of 17 |
|  | 2 | 15 of 17 | 0 of 18 | 6 of 17 |
|  | 3 | 13 of 17 | 2 of 16 | 17 of 18 |
|  | 4 | 17 of 17 | 9 of 18 | 9 of 17 |
|  | 5 |  | 3 of 16 | 9 of 17 |
| Totals |  |  |  |  |
| Completed |  | 66 | 25 | 47 |
| stalled |  | 7 | 59 | 39 |

Fisher Exact Test Results:
DMSO v. SU5412 p < 0.0001;
DMSO v. J2 p < 0.0001;
DMSO v. SU5412 p = 0.001

REFERENCES

1. Aden, D. P., Fogel, A., Plotkin, S., Damjanov, I., and Knowles, B. B. (1979). Controlled synthesis of HBsAg in a differentiated human liver carcinoma-derived cell line. Nature 282, 615-616.
2. Arsham, A. M., Howell, J. J., and Simon, M. C. (2003). A novel hypoxia-inducible factor-independent hypoxic response regulating mammalian target of rapamycin and its targets. J Biol Chem 278, 29655-29660.
3. Bell-Parikh L C, Ide T, Lawson J A, McNamara P, Reilly M, FitzGerald G A. Biosynthesis of 15-deoxy-delta12,14-PGJ2 and the ligation of PPARgamma. J Clin Invest 2003; 112: 945-55.
4. Bert, A. G., Grepin, R., Vadas, M. A., and Goodall, G. J. (2006). Assessing IRES activity in the HlF1alpha and other cellular 5' UTRs. Rna 12, 1074-1083.
5. Blais, J. D., Filipenko, V., Bi, M., Harding, H. P., Ron, D., Koumenis, C., Wouters, B. G., and Bell, J. C. (1994). Activating transcription factor 4 is translationally regulated by hypoxic stress. Mol Cell Biol 24, 7469-7482.
6. Brugarolas, J., Lei, K., Hurley, R. L., Manning, B. D., Reiling, J. H., Hafen, E., Witters, L. A., Ellisen, L. W., and Kaelin, W. G. (2004). Regulation of mTOR function in response to hypoxia by REDD1 and the TSC1/TSC2 tumor suppressor complex. Genes Dev 18, 2893-2904.
7. Brugarolas, J. B., Vazquez, F., Reddy, A., Sellers, W. R., and Kaelin, W. G. (2003). TSC2 regulates VEGF through mTOR-dependent and -independent pathways. Cancer Cell 4, 147-158.
8. Bruick, R. K., and McKnight, S. L. (2001). A conserved family of prolyl-4-hydroxylases that modify HIF. Science 294, 1337-1340.
9. Chang, H., Shyu, K. G., Lee, C. C., Tsai, S. C., Wang, B., Hsien Lee, Y., and Lin, S. (2003). GL331 inhibits HIF-1alpha expression in a lung cancer model. Biochem Biophys Res Commun 302, 95-100.
10. Cramer T, Yamanishi Y, Clausen B E, et al. HIF-1alpha is essential for myeloid cell-mediated inflammation. Cell 2003; 112: 645-57.
11. DeYoung, M. P., Horak, P., Sofer, A., Sgroi, D., and Ellisen, L. W. (2008). Hypoxia regulates TSC1/2-mTOR signaling and tumor suppression through REDD1-mediated 14-3-3 shuttling. Genes Dev 22, 239-25 1.
12. Dull, T., Zufferey, R., Kelly, M., Mandel, R. J., Nguyen, M., Trono, D., and Naldini, L. (1998). A third-generation lentivirus vector with a conditional packaging system. J Virol 72, 8463-8471.
13. Epstein, A. C., Gleadle, J. M., McNeill, L. A., Hewitson, K. S., O'Rourke, J., Mole, D. R., Mukherji, M., Metzen, E., Wilson, M. I., Dhanda, A., et al. (2001). C. elegans EGL-9 and mammalian homologs define a family of dioxygenases that regulate HIF by prolyl hydroxylation. Cell 107, 43-54.
14. Fillebeen, C., Chahine, D., Caltagirone, A., Segal, P., and Pantopoulos, K. (2003). A phosphomimetic mutation at Ser-138 renders iron regulatory protein 1 sensitive to iron-dependent degradation. Mol Cell Biol 23, 6973-6981.
15. Fleming R E. Iron and inflammation: cross-talk between pathways regulating hepcidin. J Mol Med 2008; 86: 491-4.
16. Fukuda R, Kelly B, Semenza G L. Vascular endothelial growth factor gene expression in colon cancer cells exposed to prostaglandin E2 is mediated by hypoxia-inducible factor 1. Cancer Res 2003; 63: 2330-4.
17. Giaccia A, Siim B G, Johnson R S. HIF-1 as a target for drug development. Nat Rev Drug Discov 2003; 2: 803-11.
18. Gilroy D W, Colville-Nash P R, McMaster S, Sawatzky D A, Willoughby D A, Lawrence T. Inducible cyclooxygenase-derived 15-deoxy(Delta)12-14PGJ2 brings about acute inflammatory resolution in rat pleurisy by inducing neutrophil and macrophage apoptosis. Faseb J 2003; 17: 2269-71.
19. Giard, D. J., Aaronson, S. A., Todaro, G. J., Arnstein, P., Kersey, J. H., Dosik, H., and Parks, W. P. (1973). In vitro cultivation of human tumors: establishment of cell lines derived from a series of solid tumors. J Natl Cancer Inst 51, 1417-1423.
20. Golub, T. R., Slonim, D., Tamayo, P., Huard, C., Gaasenbeek, M., Mesirov, J., Coller, H., Loh, M., Downing, J. R., Caligiuri, M. A., et al. (1999). Molecular classification of cancer: class discovery and class prediction by gene expression monitoring. Science 286, 531-537.
21. Gordan, J. D., and Simon, M. C. (2007). Hypoxia-inducible factors: central regulators of the tumor phenotype. Curr Opin Genet Dev 17, 71-77.
22. Grossman, H. B., Wedemeyer, G., and Ren, L. Q. (1985). Human renal carcinoma: characterization of five new cell lines. J Surg Oncol 28, 237-244.
23. Hanahan, D., and Folkman, J. (1996). Patterns and emerging mechanisms of the angiogenic switch during tumorigenesis. Cell 86, 353-364.
24. Hanson, E. S., Foot, L. M., and Leibold, E. A. (1999). Hypoxia post-translationally activates iron-regulatory protein 2. J Biol Chem 274, 5047-5052.

25. Herman, J. G., Latif, F., Weng, Y., Lerman, M. I., Zbar, B., Liu, S., Samid, D., Duan, D.-S. R., Gnarra, J. R., Linhean, W. M., and Baylin, S. B. (1994). Silencing of the VHL tumor-suppressor gene by DNA methylation in renal carcinoma. Proc Natl Acad Sci (USA) 91, 9700-9704.

26. Hudson, C. C., Liu, M., Chiang, G. G., Otterness, D. M., Loomis, D. C., Kaper, F., Giaccia, A. J., and Abraham, R. T. (2002). Regulation of hypoxia-inducible factor 1alpha expression and function by the mammalian target of rapamycin. Mol Cell Biol 22, 7004-70 14.

27. Iliopoulos, O., Kibel, A., Gray, S., and Kaelin, W. G. (1995). Tumor Suppression by the Human von Hippel-Lindau Gene Product. Nature Medicine 1, 822-826.

28. Iliopoulos O. Molecular biology of renal cell cancer and the identification of therapeutic targets. J Clin Oncol 2006; 24: 5593-600.

29. Ivan, M., Kondo, K., Yang, H., Kim, W., Valiando, J., Ohh, M., Salic, A., Asara, J. M., Lane, W. S., and Kaelin, W. G. (2001). HIF1a targeted for VHL-mediated destruction by proline hydroxylation: implications for oxygen sensing. Science 292, 464-468.

30. Jaakkola, P., Mole, D., Tian, Y. M., Wilson, M. I., Gielbert, J., Gaskel, l. S. J., Kriegsheim, A. A., Hebestreit, H. F., Mukherji, M., Schofield, C. J., et al. (2001). Targeting of HIF-alpha to the von Hippel-Lindau Ubiquitylation Complex by O2-Regulated Prolyl Hydroxylation. Science 292, 468-472.

31. Ke Y, Wu J, Leibold E A, Walden W E, Theil E C. Loops and bulge/loops in iron-responsive element isoforms influence iron regulatory protein binding. Fine-tuning of mRNA regulation? J Biol Chem 1998; 273: 23637-40.

32. Kim E H, Surh Y J. 15-deoxy-Delta12,14-prostaglandin J2 as a potential endogenous regulator of redox-sensitive transcription factors. Biochem Pharmacol 2006; 72: 1516-28.

33. Kim W J, Kim J H, Jang S K. Anti-inflammatory lipid mediator 15d-PGJ2 inhibits translation through inactivation of eIF4A. Embo J 2007; 26: 5020-32.

34. Kondo K, Klco J, Nakamura E, Lechpammer M, Kaelin W G. Inhibition of HIF is necessary for tumor suppression by the von Hippel-Lindau protein. Cancer Cell 2002; 1: 237-46.

35. Kondo, K., Kim, W. Y., Lechpammer, M., and Kaelin, W. G. (2003). Inhibition of HIF2alpha Is Sufficient to Suppress pVHL-Defective Tumor Growth. PLoS Biol 1, 83.

36. Kondo, K., Klco, J., Nakamura, E., Lechpammer, M., and Kaelin, W. G. (2002). Inhibition of HIF is necessary for tumor suppression by the von Hippel-Lindau protein. Cancer Cell 1, 237-246.

37. Koumenis, C., Naczki, C., Koritzinsky, M., Rastani, S., Diehl, A., Sonenberg, N., Koromilas, A., and Wouters, B. G. (2002). Regulation of protein synthesis by hypoxia via activation of the endoplasmic reticulum kinase PERK and phosphorylation of the translation initiation factor eIF2alpha. Mol Cell Biol 22, 7405-7416.

38. Kubo, T., Maezawa, N., Osada, M., Katsumura, S., Funae, Y., and Imaoka, S. (2004). Bisphenol A, an environmental endocrine-disrupting chemical, inhibits hypoxic response via degradation of hypoxiainducible factor 1alpha (HIF-1alpha): structural requirement of bisphenol A for degradation of HIF-1alpha. Biochem Biophys Res Commun 318, 1006-1011.

39. Kung, A. L., Zabludoff, S. D., France, D. S., Freedman, S. J., Tanner, E. A., Vieira, A., Cornell- 40. Kennon, S., Lee, J., Wang, B., Wang, J., et al. (2004). Small molecule blockade of transcriptional coactivation of the hypoxia-inducible factor pathway. Cancer Cell 6, 33-43.

41. Lamb, J., Crawford, E. D., Peck, D., Modell, J. W., Blat, I. C., Wrobel, M. J., Lerner, J., Brunet, J. P., Subramanian, A., Ross, K. N., et al. (2006). The Connectivity Map: using gene-expression signatures to connect small molecules, genes, and disease. Science 313, 1929-1935.

42. Lando, D., Peet, D. J., Gorman, J. J., Whelan, D. A., Whitelaw, M. L., and Bruick, R. K. (2002a). FIH1 is an asparaginyl hydroxylase enzyme that regulates the transcriptional activity of hypoxia-inducible factor. Genes Dev 16, 1466-1471.

43. Lando, D., Peet, D. J., Whelan, D. A., Gorman, J. J., and Whitelaw, M. L. (2002b). Asparagine hydroxylation of the HIF transactivation domain a hypoxic switch. Science 295, 858-861.

44. Lang, K. J., Kappel, A., and Goodall, G. J. (2002). Hypoxia-inducible factor-1alpha mRNA contains an internal ribosome entry site that allows efficient translation during normoxia and hypoxia. Mol Biol Cell 13, 1792-1801.

45. Laughner, E., Taghavi, P., Chiles, K., Mahon, P. C., and Semenza, G. L. (2001). HER2 (neu) signaling increases the rate of hypoxia-inducible factor 1alpha (HIF-1alpha) synthesis: novel mechanism for HIF-1-mediated vascular endothelial growth factor expression. Mol Cell Biol 21, 3995-4004.

46. Lin, S., Tsai, S. C., Lee, C. C., Wang, B. W., Liou, J. Y., and Shyu, K. G. (2004). Berberine inhibits HIF-1alpha expression via enhanced proteolysis. Mol Pharmacol 66, 612-619.

47. Liu, L., Cash, T. P., Jones, R. G., Keith, B., Thompson, C. B., and Simon, M. C. (2006). Hypoxiainduced energy stress regulates mRNA translation and cell growth. Mol Cell 21, 521-53 1.

48. Liu, L., and Simon, M. C. (2004). Regulation of transcription and translation by hypoxia. Cancer Biol Ther 3, 492-497.

49. Liu X H, Kirschenbaum A, Lu M, et al. Prostaglandin E2 induces hypoxia-inducible factor-1alpha stabilization and nuclear localization in a human prostate cancer cell line. J Biol Chem 2002; 277: 50081-6.

50. Mabjeesh, N. J., Post, D. E., Willard, M. T., Kaur, B., Van Meir, E. G., Simons, J. W., and Zhong, H. (2002). Geldanamycin induces degradation of hypoxia-inducible factor 1alpha protein via the proteosome pathway in prostate cancer cells. Cancer Res 62, 2478-2482.

51. Mabjeesh, N. J., Escuin, D., LaVallee, T. M., Pribluda, V. S., Swartz, G. M., Johnson, M. S., Willard, M. T., Zhong, H., Simons, J. W., and Giannakakou, P. (2003). 2ME2 inhibits tumor growth and angiogenesis by disrupting microtubules and dysregulating HIF. Cancer Cell 3, 363-375.

52. Mahon, P. C., Hirota, K., and Semenza, G. L. (2001). FIH-1: a novel protein that interacts with HIF1alpha and VHL to mediate repression of HIF-1 transcriptional activity. Genes Dev 15, 2675-2686.

53. Majumder, P. K., Febbo, P. G., Bikoff, R., Berger, R., Xue, Q., McMahon, L. M., Manola, J., Brugarolas, J., McDonnell, T. J., Golub, T. R., et al. (2004). mTOR inhibition reverses Akt-dependent prostate intraepithelial neoplasia through regulation of apoptotic and HIF-1-dependent pathways. Nat Med 10, 594-601.

54. Maranchie, J. K., Vasselli, J. R., Riss, J., Bonifacino, J. S., Linehan, W. M., and Klausner, R. D. (2002). The 55. Maxwell, P. H., Pugh, C. W., and Ratcliffe, P. J. (2001). Activation of the HIF pathway in cancer. Current Opinion in Genetics and Development 11, 293-299.
56. Maxwell, P. H., Wiesener, M. S., Chang, G. W., Clifford, S. C., Vaux, E. C., Cockman, M. E., Wykoff, C. C., Pugh, C. W., Maher, E. R., and Ratcliffe, P. J. (1999). The tumour suppressor protein VHL targets hypoxia-inducible factors for oxygen-dependent proteolysis. Nature 399, 271-275.
57. Mootha, V. K., Lindgren, C. M., Eriksson, K. F., Subramanian, A., Sihag, S., Lehar, J., Puigserver, P., Carlsson, E., Ridderstrale, M., Laurila, E., etal. (2003). PGC-1alpha-responsive genes involved in oxidative phosphorylation are coordinately downregulated in human diabetes. Nat Genet 34, 267-273.
58. Murakawa H, Bland C E, Willis W T, Dallman P R. Iron deficiency and neutrophil function: different rates of correction of the depressions in oxidative burst and myeloperoxidase activity after iron treatment. Blood 1987; 69: 1464-8.
59. Ohh, M., Park, C. W., Ivan, M., Hoffman, M. A., Kim, T. Y., Huang, L. E., Pavletich, N., Chau, V., and Kaelin, W. G. (2000). Ubiquitination of hypoxia-inducible factor requires direct binding to the beta-domain of the von Hippel-Lindau protein. Nat Cell Biol 2, 423-427.
60. Pai R, Soreghan B, Szabo I L, Pavelka M, Baatar D, Tarnawski A S. Prostaglandin E2 transactivates EGF receptor: a novel mechanism for promoting colon cancer growth and gastrointestinal hypertrophy. Nat Med 2002; 8: 289-93.
61. Pantopoulos K. Iron metabolism and the IRE/IRP regulatory system: an update. Ann N Y Acad Sci 2004; 1012: 1-13.
62. Ponten, J., and Saksela, E. (1967). Two established in vitro cell lines from human mesenchymal
63. tumours. Int J Cancer 2, 434-447.
64. Rajakariar R, Hilliard M, Lawrence T, et al. Hematopoietic prostaglandin D2 synthase controls the onset and resolution of acute inflammation through PGD2 and 15-deoxyl)elta12 14 PGJ2. Proc Natl Acad Sci USA 2007; 104: 20979-84.
65. Rapisarda, A., Uranchimeg, B., Scudiero, D. A., Selby, M., Sausville, E. A., Shoemaker, R. H., and Melillo, G. (2002). Identification of small molecule inhibitors of hypoxia-inducible factor 1
66. transcriptional activation pathway. Cancer Res 62(15):, 4316-4324.
67. Raval, R. R., Lau, K. W., Tran, M. G., Sowter, H. M., Mandriota, S. J., Li, J. L., Pugh, C. W., Maxwell, P. H., Harris, A. L., and Ratcliffe, P. J. (2005). Contrasting properties of hypoxia-inducible factor 1 (HIF-1) and HIF-2 in von Hippel-Lindau-associated renal cell carcinoma. Mol Cell Biol 25, 5675-5686.
68. Rius J, Guma M, Schachtrup C, et al. NF-kappaB links innate immunity to the hypoxic response through transcriptional regulation of HIF-1alpha. Nature 2008; 453: 807-11.
69. Rouault T A. The role of iron regulatory proteins in mammalian iron homeostasis and disease. Nat Chem Biol 2006; 2: 406-14
70. Sambrook, Fritsch, Maniatis, and edts. (1989). Molecular Cloning: a Laboratory Manual. CSHL Press. Sanchez, M., Galy, B., Muckenthaler, M. U., and Hentze, M. W. (2007). Iron-regulatory proteins limit hypoxia-inducible factor-2alpha expression in iron deficiency. Nat Struct Mol Biol 14, 420-426.
71. Sanchez M, Galy B, Muckenthaler M U, Hentze M W. Iron-regulatory proteins limit hypoxia-inducible factor-2alpha expression in iron deficiency. Nat Struct Mol Biol 2007; 14: 420-6.
72. Schepens, B., Tinton, S. A., Bruynooghe, Y., Beyaert, R., and Cornelis, S. (2005). The polypyrimidine tract-binding protein stimulates HIF-1 alpha IRE S-mediated translation during hypoxia. Nucleic Acids Res 33, 6884-6894.
73. Schofield, C., and Ratcliffe, P. (2004). Oxygen sensing by the HIF hydroxylases. Nature Reviews Molecular Cell Biology 5, 343-3 54.
74. Semenza, G. L. (2000). HIF-1: mediator of physiological and pathophysiological responses to hypoxia. J Appl Physiol 88, 1747-1480.
75. Sonoshita M, Takaku K, Sasaki N, et al. Acceleration of intestinal polyposis through prostaglandin receptor EP2 in Apc(Delta 716) knockout mice. Nat Med 2001; 7: 1048-51.
76. Spicher, A., Guicherit, O. M., Duret, L., Aslanian, A., Sanjines, E. M., Denko, N. C., Giaccia, A. J., and Blau, H. M. (1998). Highly conserved RNA sequences that are sensors of environmental stress. Mol Cell Biol 18, 7371-73 82.
77. Tan, C., de Noronha, R. G., Roecker, A. J., Pyrzynska, B., Khwaja, F., Zhang, Z., Zhang, H., Teng, Q., Nicholson, A. C., Giannakakou, P., et al. (2005). Identification of a novel small-molecule inhibitor of the hypoxia-inducible factor 1 pathway. Cancer Res 65, 605-612.
78. Thomas, J. D., and Johannes, G. J. (2007). Identification of mRNAs that continue to associate with polysomes during hypoxia. Rna 13, 1116-1131.
79. Toth, I., Yuan, L., Rogers, J. T., Boyce, H., and Bridges, K. R. (1999). Hypoxia alters iron-regulatory protein-1 binding capacity and modulates cellular iron homeostasis in human hepatoma and erythroleukemia cells. J Biol Chem 274, 4467-4473.
80. Wang, J., Buss, J. L., Chen, G., Ponka, P., and Pantopoulos, K. (2002). The prolyl 4-hydroxylase inhibitor ethyl-3,4-dihydroxybenzoate generates effective iron deficiency in cultured cells. FEBS Lett 529, 309-3 12.
81. Wang D, Wang H, Shi Q, et al. Prostaglandin E(2) promotes colorectal adenoma growth via transactivation of the nuclear peroxisome proliferator-activated receptor delta. Cancer Cell 2004; 6: 285-95.
82. Wang D, Buchanan F G, Wang H, Dey S K, DuBois R N. Prostaglandin E2 enhances intestinal adenoma growth via activation of the Ras-mitogen-activated protein kinase cascade. Cancer Res 2005; 65: 1822-9.
83. Wang, W., Di, X., D'Agostino, R. B., Jr., Torti, S. V., and Torti, F. M. (2007). Excess capacity of the iron regulatory protein system. J Biol Chem 282, 24650-24659.
84. Welsh, S., Williams, R., Kirkpatrick, L., Paine-Murrieta, G., and Powis, G. (2004). Antitumor activity and pharmacodynamic properties of PX-478, an inhibitor of hypoxia-inducible factor-1alpha. Mol Cancer Ther 3, 233-244.
85. Williams, R. D., Elliott, A. Y., Stein, N., and Fraley, E. E. (1978). In vitro cultivation of human renal cell cancer. II. Characterization of cell lines. In Vitro 14, 779-786.
86. Wouters, B. G., van den Beucken, T., Magagnin, M. G., Koritzinsky, M., Fels, D., and Koumenis, C. (2005). Control of the hypoxic response through regulation of mRNA translation. Semin Cell Dev Biol 16, 487-501.

87. Yang, H. S., Cho, M. H., Zakowicz, H., Hegamyer, G., Sonenberg, N., and Colburn, N. H. (2004). A novel function of the MA-3 domains in transformation and translation suppressor Pdcd4 is essential for its binding to eukaryotic translation initiation factor 4A. Mol Cell Biol 24, 3894-3906.
88. Yeo, E. J., Chun, Y. S., Cho, Y. S., Kim, J., Lee, J. C., Kim, M. S., and Park, J. W. (2003). YC-1: a potential anticancer drug targeting hypoxia-inducible factor 1. J Natl Cancer Inst 95, 516-525.
89. Zhang P, Wang Y, Hui Y, et al. Inhibition of VEGF expression by targeting HIF-1 alpha with small interference RNA in human RPE cells. Ophthalmologica 2007; 221: 411-7.
90. Zimmer, M., Doucette, D., Siddiqui, N., and Iliopoulos, O. (2004). Inhibition of Hypoxia Inducible Factor is Sufficient for Growth Suppression of VHL-/- Tumors. Mol Cancer Res 2, 89-95.
91. Zimmer M, Ebert B L, Neil C, et al. Small-molecule inhibitors of HIF-2a translation link its 5'UTR iron-responsive element to oxygen sensing. Mol Cell 2008; 32: 838-48.
92. Zundel, W., Schindler, C., Haas-Kogan, D., Koong, A., Kaper, F., Chen, E., Gottschalk, A. R., Ryan, H. E., Johnson, R. S., Jefferson, A. B., et al. (2000). Loss of PTEN facilitates HIF-1-mediated gene expression. Genes Dev 14, 39 1-396.

What is claimed:

1. A pharmaceutical composition for inhibiting angiogenesis comprising a HIF inhibitor and a pharmaceutically acceptable carrier, wherein the HIF inhibitor is a compound of Formula III having the formula of:

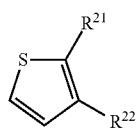

Formula (III)

$R^{21}$ is $C(O)R^{24}$;

$R^{22}$ is $N(R^{25})_2$;

$R^{23}$ is independently for each occurrence H, or $C_1$-$C_6$ alkyl;

$R^{24}$ is alkoxy, which can be optionally substituted;

$R^{25}$ is $N=R^{26}$ for a first occurrence and H for a second occurrence or $N=R^{26}$ for a first and a second occurrence;

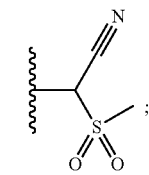 [SMILES: *C(C#N)S(C)(=O)=O]

$R^{26}$ is $C(SO_2R^{23})CN$ or and pharmaceutically acceptable salts and combinations thereof.

2. The pharmaceutical composition of claim 1, wherein $R^{25}$ is $N=R^{26}$ for the first occurrence and H for the second occurrence.

3. The pharmaceutical composition of claim 1, wherein $R^{26}$ is

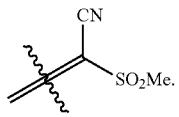

4. The pharmaceutical composition of claim 1, wherein $R^{21}$ is $C(O)R^{24}$, wherein $R^{24}$ is a substituted alkoxy.

5. The pharmaceutical composition of claim 1, wherein $R^{26}$ is $C(SO_2R^{23})CN$.

6. The pharmaceutical composition of claim 1, wherein $R^{21}$ is $C(O)R^{24}$, wherein $R^{24}$ is a substituted alkoxy; wherein $R^{22}$ is $N(R^{25})_2$, wherein $R^{25}$ is $N=R^{26}$

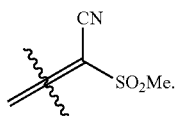 [SMILES: *=C(C#N)S(C)(=O)=O]

and wherein $R^{26}$ is.

* * * * *

SEQUENCE LISTING

```
<160> NUMBER OF SEQ ID NOS: 26

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
tttcatccat ccgacattga                                                  20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
atcttcaaac ctccatgatg                                                  20

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ggatcagcgc acagagttc                                                   19

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gtactgggtg gcgtagcact                                                  20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
```

```
                    primer

<400> SEQUENCE: 5
aagcggttct tggtaccagc                                              20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ggataatctg tgtcctcgca                                              20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gctacgattg ctaacatgtg                                              20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gaggcctttt gggtccacta                                              20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
tgtgattctg gagaactagg                                              20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ccctaaacca ttcaccatcg                                              20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 11
atcagcttcc tcctgtccct                                                   20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gggctgcact tcgtgtgggt                                                   20

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
agacggtgga ctccgcca                                                     18

<210> SEQ ID NO 14
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ttaaagggag gggtacac                                                     18

<210> SEQ ID NO 15
<211> LENGTH: 6
<212> TYPE: RNA
<213> ORGANISM: Unknown
<220> FEATURE:
<223> OTHER INFORMATION: Description of Unknown: IRE consensus loop
      sequence

<400> SEQUENCE: 15 cagugu                                                                   6

<210> SEQ ID NO 16
<211> LENGTH: 6
<212> TYPE: RNA
<213> ORGANISM: Unknown
<220> FEATURE:
<223> OTHER INFORMATION: Description of Unknown: IRE consensus loop
      sequence

<400> SEQUENCE: 16 caaagu                                                                   6

<210> SEQ ID NO 17
<211> LENGTH: 30
<212> TYPE: RNA
<213> ORGANISM: Unknown
<220> FEATURE:
<223> OTHER INFORMATION: Description of Unknown: HIF-2a IRE
      sequence
```

<400> SEQUENCE: 17
uacaauccuc ggcagugucc ugagacugua                                    30

<210> SEQ ID NO 18
<211> LENGTH: 30
<212> TYPE: RNA
<213> ORGANISM: Unknown
<220> FEATURE:
<223> OTHER INFORMATION: Description of Unknown: HIF-1a IRE
      sequence

<400> SEQUENCE: 18
ucgucgcuuc ggccagugug ucgggcuggg                                    30

<210> SEQ ID NO 19
<211> LENGTH: 6
<212> TYPE: RNA
<213> ORGANISM: Unknown
<220> FEATURE:
<223> OTHER INFORMATION: Description of Unknown: IRE consensus loop
      sequence

<400> SEQUENCE: 19 cagwgh                                                               6

<210> SEQ ID NO 20
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
tgaccttcca ggctgtcatg aggttcaaga gacctcatga cagcctggaa ggtcttttt    60 c                                                                   61

<210> SEQ ID NO 21
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
tcgagaaaaa agaccttcca ggctgtcatg aggtctcttg aacctcatga cagcctggaa   60
ggtca                                                               65

<210> SEQ ID NO 22
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
tgccatcaca cagggagacc ttgttcaaga gacaaggtct ccctgtgtga tggctttttt   60
c                                                                   61

<210> SEQ ID NO 23
<211> LENGTH: 65
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 23
tcgagaaaaa agccatcaca cagggagacc ttgtctcttg aacaaggtct ccctgtgtga      60
tggca                                                                 65

<210> SEQ ID NO 24
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
tggattctgg ggtgggggt ctcttcaccc cccacccag aatccttttt tc               52

<210> SEQ ID NO 25
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
tcgagaaaaa aggattctgg ggtggggggt gaagagaccc cccacccag aatcca          56

<210> SEQ ID NO 26
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
ccacagtgca tacgtgggct ccaacaggtc ctcttccctc ccatgca                   47
```